(12) United States Patent
Gilbert et al.

(10) Patent No.: US 7,722,888 B2
(45) Date of Patent: May 25, 2010

(54) STREPTOCOCCUS PNEUMONIAE PROTEINS AND NUCLEIC

(75) Inventors: Christophe Francois Guy Gilbert, Villeurbanne cedex (FR); Philip Michael Hansbro, Newcastle (AU)

(73) Assignee: Sanopi Pasteur Limited, Toronto, Ontario (CA)

( * ) Notice: Subject to any disclaimer, the term of this patent is extended or adjusted under 35 U.S.C. 154(b) by 0 days.

(21) Appl. No.: 11/785,517

(22) Filed: Apr. 18, 2007

(65) Prior Publication Data

US 2008/0089899 A1 Apr. 17, 2008

Related U.S. Application Data

(60) Division of application No. 10/873,528, filed on Jun. 23, 2004, now abandoned, which is a division of application No. 09/769,787, filed on Jan. 26, 2001, now Pat. No. 6,936,252, which is a continuation of application No. PCT/GB99/02451, filed on Jul. 27, 1999.

(60) Provisional application No. 60/125,164, filed on Mar. 19, 1999.

(30) Foreign Application Priority Data

Jul. 27, 1998 (GB) ................................ 9816337.1

(51) Int. Cl.
*A61K 39/09* (2006.01)
*C07H 21/04* (2006.01)
*C12P 21/04* (2006.01)
*C07K 14/195* (2006.01)
*C07K 14/315* (2006.01)

(52) U.S. Cl. .............. 424/244.1; 424/190.1; 424/185.1; 424/184.1; 530/300; 530/350; 435/69.1; 435/69.5; 435/69.7; 435/252.3; 435/320.1; 536/23.1; 536/23.5; 536/23.7

(58) Field of Classification Search ........................ None
See application file for complete search history.

(56) References Cited

U.S. PATENT DOCUMENTS

| | | | |
|---|---|---|---|
| 6,420,135 B1 | 7/2002 | Kunsch et al. | |
| 6,573,082 B1 * | 6/2003 | Choi et al. ............... | 435/252.3 |
| 6,699,703 B1 * | 3/2004 | Doucette-Stamm et al. ........................ | 435/252.3 |
| 6,800,744 B1 | 10/2004 | Doucette-Stamm et al. | |
| 6,936,252 B2 | 8/2005 | Gilbert et al. | |

FOREIGN PATENT DOCUMENTS

| | | |
|---|---|---|
| EP | 0622081 | 11/1994 |
| WO | WO 95/06732 | 3/1995 |
| WO | WO 97/09994 | 3/1997 |
| WO | WO 97/37026 | 10/1997 |
| WO | WO 97/43303 | 11/1997 |
| WO | WO 98/18930 | 5/1998 |
| WO | WO 98/18931 | 5/1998 |
| WO | WO 98/26072 | 6/1998 |
| WO | WO 98/31786 | 7/1998 |
| WO | WO 99/15675 | 4/1999 |

OTHER PUBLICATIONS

Houghten et al. (Vaccines, 1986, Edited by Fred Brown: Cold Spring Harbor Laboratory).*
Lederman et al (Molecular Immunology 28:1171-1181, 1991).*
Li et al (Proc. Natl. Acad. Sci. USA 77:3211-3214, 1980).*
Holmes (Exp. Opin.Invest. Drugs, 2001, 10(3):511-519).*
Greenspan et al (Nature Biotechnology, 1999, 7:936-937).*
Ellis (vaccine, 1988, Saunders company.*
Boslego et al, Chapter 17 in Vaccines and Immunotherapy 1991.*
Anderson et al. (1996) "Immune Response in mice following immunization with DNA encoding fragment C of tetanus toxin." Infection and Immunity 64: 3168-3173.
Angel, et al. (1994) "Degradation of C3 by *Streptococcus pneumoniae*." Journal of Infectious Disease 170(3): 600-608.
Alonsodevelasco, et al. (Dec. 1995) "*Streptococcus pneumoniae*: Virulence Factors, Pathogenesis, and Vaccines." Microbiological Reviews 59(4): 591-603.
Breiman et al. (1990) Arch. Intern. Med. 150: 1401.
Breiman et al. (1994) J. Am. Med. Assoc. 271: 1831.
Bowie (1990) Science 257: 1306-1310.
Burgess, et al. (1990) The Journal of Cell Biology 111: 2129-2136.
Donnelly et al. (1997) Ann. Rev. Immunol. 15: 617-648.
Dougall et al. (Sep. 1994) Tibtech 12: 372-379.
Ellis (1988) Vaccines Chapter 29: 568-575.
Greenspan, et al. (1999) Nature Biotechnology 7: 936-937.
Herbert, et al. (1985) The Dictionary of Immunology (Academic Press) 3$^{rd}$ Ed. pp. 58-59.
Holmes, et al. (2001) Exp. Opin. Invest. Drugs 10(3): 511-519.
Jobling et al. (1991) Mol. Microbiol 5(7): 1755-67.
Kohler & Milstein (1975) Nature 256.
Kolkman et al. (1996) 178: 3736-3741.
Kovacevic et al. (1985) J. Bacteriol. 162: 521-528.
Kurar and Splitter (1997) Vaccine 15: 1851-57.
Lange et al. (Sep. 3, 1999) Gene 237(1): 223-234.
Lazar et al. (1988) Molecular and Cellular Biology 8(3): 1247-1252.
Le Loir et al. (1994) J. Bacteriol. 176: 5135-5139.
LeBlanc et al. (1978) PNAS USA 75: 3484-3487.
Li et al. (1997) PNAS 94: 13251-13256.
Liebl et al. (1992) J. Bacteriol. 174: 1854-1861.
Marck (1988) Nucleic Acids Research 16: 1829-1836.
Miller et al. (1987) J. Bacteriol. 169: 3508-3514.
Morrison et al. (1984) PNAS 81: 6851-6855.
Nanidwada, et al. (1996) "Genetic Analysis of a C3 degrading proteinase in *Steptococcus pneumoniae*." Abstracts of the General Meeting of the American Society for Microbiology vol. 96 p. 177 (Abstract B-134).

(Continued)

*Primary Examiner*—Robert B Mondesi
*Assistant Examiner*—Padma V Baskar
(74) *Attorney, Agent, or Firm*—Hunton & Williams LLP

(57) ABSTRACT

Protein antigens from *Streptococcus pneumoniae* are disclosed, together with nucleic acid sequences encoding them. Their use in vaccines and in screening methods is also described.

5 Claims, 2 Drawing Sheets

OTHER PUBLICATIONS

Oultram and Klaenhammer (1985) FEMS Microbiological Letters 27: 129-134.
Pearson et al. (1988) "Improved tools for biological sequence comparison," Proc. Natl. Acad. Sci. USA, vol. 85, 2444-2448.
Poquet et al. (1998) J. Bacteriol. 180: 1904-1912.
Roitt, et al. (1993) Immunology p. 7.7-7.8.
Rudinger et al. (Jun. 1976) "Peptide Hormones" p. 6.
Schappert (1992) Vital and Health Statistics of the Centres for Disease Control/National Centre for Health Statistics 214: 1.
Shortle (1983) Gene 22: 181-189.
Siber (Sep. 1994) "Pneumococcal Disease: Prospects for a New Generation of Vaccines" Science vol. 265, pp. 1385-1387.
Simon and Chopin (1988) Biochimie 70: 559-567.
Stansfield (1987) "Acute respiratory infections in the developing world: strategies for prevention, treatment and control," Pediatric Infect Dis. Journal, vol. 6, 622-629.

Takeda et al. (1985) Nature 314: 452-454.
Taber's Cyclopedic Medical Dictionary (1985) $16^{th}$ Ed. p. 1354.
van der Vossen, et al. (1985) Applied and Environmental Microbiology 50: 540-542.
Waterfield et al. (1995) Gene 165: 9-15.
Wells and Schoefield (1996) In Current advances in metabolism, genetics, and applications-NATO ASI Series H 98: 37-62.
Wells et al. (1993) J. Appl. Bacteriol. 74: 629-636.
Zhang et al. (1997) Infection and Immunity 176: 1035-1040.
Nandiwada, et al. (1996) "Genetic Analysis of a C3 degrading proteinase in *Steptococcus pneumoniae*." Abstracts of the General Meeting of the American Society for Microbiology vol. 96 p. 177 (Abstract B-134).

* cited by examiner

STREPTOCOCCUS PNEUMONIAE PROTEINS AND NUCLEIC

This application is a divisional of U.S. patent application Ser. No. 10/873,528, filed Jun. 23, 2004, now abandoned, which is a divisional of U.S. patent application Ser. No. 09/769,787, filed Jan. 26, 2001, now U.S. Pat. No. 6,936,252, which is a continuation of PCT/GB99/02451, filed Jul. 27, 1999, which claims benefit of U.S. Provisional Application No. 60/125,164, filed Mar. 19, 1999, and which also claims benefit of United Kingdom 9816337.1, filed Jul. 27, 1998, the disclosures of which are all hereby incorporated by reference.

The present invention relates to proteins derived from *Streptococcus pneumoniae*, nucleic acid molecules encoding such proteins, the use of the nucleic acid and/or proteins as antigens/immunogens and in detection/diagnosis, as well as methods for screening the proteins/nucleic acid sequences as potential anti-microbial targets.

*Streptococcus pneumoniae*, commonly referred to as the pneumococcus, is an important pathogenic organism. The continuing significance of *Streptococcus pneumoniae* infections in relation to human disease in developing and developed countries has been authoritatively reviewed (Fiber, G. R., *Science,* 265:1385-1387 (1994)). That indicates that on a global scale this organism is believed to be the most common bacterial cause of acute respiratory infections, and is estimated to result in 1 million childhood deaths each year, mostly in developing countries (Stansfield, S. K., *Pediatr. Infect. Dis.,* 6:622 (1987)). In the USA it has been suggested (Breiman et al., *Arch. Intern. Med.,* 150:1401 (1990)) that the pneumococcus is still the most common cause of bacterial *pneumoniae*, and that disease rates are particularly high in young children, in the elderly, and in patients with predisposing conditions such as asplenia, heart, lung, and kidney disease, diabetes, alcoholism, or with immunosuppressive disorders, especially AIDS. These groups are at higher risk of pneumococcal septicaemia and hence meningitis and therefore have a greater risk of dying from pneumococcul infection. The pneumococcus is also the leading cause of otitis media and sinusitis, which remain prevalent infections in children in developed countries, and which incur substantial costs.

The need for effective preventative strategies against pneumococcal infection is highlighted by the recent emergence of penicillin-resistant pneumococci. It has been reported that 6.6% of pneumoccal isolates in 13 US hospitals in 12 states were found to be resistant to penicillin and some isolates were also resistant to other antibiotics including third generation cyclosporins (Schappert, S. M., *Vital and Health Statistics of the Centres for Disease Control/National Centre for Health Statistics,* 214:1 (1992)). The rates of penicillin resistance can be higher (up to 20%) in some hospitals (Breiman et al, J. Am. Med. Assoc., 271: 1831 (1994)). Since the development of penicillin resistance among pneumococci is both recent and sudden, coming after decades during which penicillin remained an effective treatment, these findings are regarded as alarming.

For the reasons given above, there are therefore compelling grounds for considering improvements in the means of preventing, controlling, diagnosing or treating pneumococcal diseases.

Various approaches have been taken in order to provide vaccines for the prevention of pneumococcal infections. Difficulties arise for instance in view of the variety of serotypes (at least 90) based on the structure of the polysaccharide capsule surrounding the organism. Vaccines against individual serotypes are not effective against other serotypes and this means that vaccines must include polysaccharide antigens from a whole range of serotypes in order to be effective in a majority of cases. An additional problem arises because it has been found that the capsular polysaccharides (each of which determines the serotype and is the major protective antigen) when purified and used as a vaccine do not reliably induce protective antibody responses in children under two years of age, the age group which suffers the highest incidence of invasive pneumococcal infection and meningitis.

A modification of the approach using capsule antigens relies on conjugating the polysaccharide to a protein in order to derive an enhanced immune response, particularly by giving the response T-cell dependent character. This approach has been used in the development of a vaccine against *Haemophilus influenzae*. There are issues of cost concerning both the multi-polysaccharide vaccines and those based on conjugates.

A third approach is to look for other antigenic components which offer the potential to be vaccine candidates.

BACKGROUND OF THE INVENTION

In the present application we provide a group of proteins antigens which are secreted/exported proteins.

BRIEF SUMMARY OF THE INVENTION

Thus, in a first aspect the present invention provides a *Streptococcus pneumoniae* protein or polypeptide having a sequence selected from those shown in Table 2 herein.

A protein or polypeptide of the present invention may be provided in substantially pure form. For example, it may be provided in a form which is substantially free of other proteins.

In a preferred embodiment, a protein or polypeptide having an amino acid sequence as shown in Table 3 is provided.

The invention encompasses any protein coded for by a nucleic acid sequence as shown in Table 1 herein.

DETAILED DESCRIPTION OF THE INVENTION

As discussed herein, the proteins and polypeptides of the invention are useful as antigenic material. Such material can be "antigenic" and/or "immunogenic". Generally, "antigenic" is taken to mean that the protein or polypeptide is capable of being used to raise antibodies or indeed is capable of inducing an antibody response in a subject. "Immunogenic" is taken to mean that the protein or polypeptide is capable of eliciting a protective immune response in a subject.

Thus, in the latter case, the protein or polypeptide may be capable of not only generating an antibody response and in addition non-antibody based immune responses.

The skilled person will appreciate that homologues or derivatives of the proteins or polypeptides of the invention will also find use in the context of the present invention, ie as antigenic/immunogenic material. Thus, for instance proteins or polypeptides which include one or more additions, deletions, substitutions or the like are encompassed by the present invention.

In addition, it may be possible to replace one amino acid with another of similar "type". For instance replacing one hydrophobic amino acid with another. One can use a program such as the CLUSTAL program to compare amino acid sequences. This program compares amino acid sequences and finds the optimal alignment by inserting spaces in either sequence as appropriate.

It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention.

In the case of homologues and derivatives, the degree of identity with a protein or polypeptide as described herein is less important than that the homologue or derivative should retain its antigenicity or immunogenicity to *Streptoccocus pneumoniae*. However, suitably, homologues or derivatives having at least 60% similarity (as discussed above) with the proteins or polypeptides described herein are provided.

Preferably, homologues or derivatives having at least 70% similarity, more preferably at least 80% similarity are provided. Most preferably, homologues or derivatives having at least 90% or even 95% similarity are provided.

In an alternative approach, the homologues or derivatives could be fusion proteins, incorporating moieties which render purification easier, for example by effectively tagging the desired protein or polypeptide. It may be necessary to remove the "tag" or it may be the case that the fusion protein itself retains sufficient antigenicity to be useful.

In an additional aspect of the invention there are provided antigenic fragments of the proteins or polypeptides of the invention, or of homologues or derivatives thereof.

For fragments of the proteins or polypeptides described herein, or of homologues or derivatives thereof, the situation is slightly different. It is well known that is possible to screen an antigenic protein or polypeptide to identify epitopic regions, i.e., those regions which are responsible for the protein or polypeptide's antigenicity or immunogenicity. Methods for carrying out such screening are well known in the art. Thus, the fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a protein or polypeptide, homologue or derivative as described herein. The key issue, once again, is that the fragment retains the antigenic/immunogenic properties.

Thus, what is important for homologues, derivatives and fragments is that they possess at least a degree of the antigenicity/immunogenicity of the protein or polypeptide from which they are derived.

Gene cloning techniques may be used to provide a protein of the invention in substantially pure form, These techniques are disclosed, for example, in J. Sambrook et al *Molecular Cloning* 2nd Edition, Cold Spring Harbor Laboratory Press (1989). Thus, in a fourth aspect, the present invention provides a nucleic acid molecule comprising or consisting of a sequence which is:

(i) any of the DNA sequences set out in Table 1 or their RNA equivalents;
(ii) a sequence which is complementary to any of the sequences of (i);
(iii) a sequence which codes for the same protein or polypeptide, as those sequences of (i) or (ii);
(iv) a sequence which is has substantial identity with any of those of (i), (ii) and (iii);
(v) a sequence which codes for a homologue, derivative or fragment of a protein as defined in Table 1.

In a fifth aspect the present invention provides a nucleic acid molecule comprising or consisting of a sequence which is:

(i) any of the DNA sequences set out in Table 4 or their RNA equivalents;
(ii) a sequence which is complementary to any of the sequences of (i);
(iii) a sequence which codes for the same protein or polypeptide, as those sequences of (i) or (ii);
(iv) a sequence which is has substantial identity with any of those of (i), (ii) and (iii);
(v) a sequence which codes for a homologue, derivative or fragment of a protein as defined in Table 4.

The nucleic acid molecules of the invention may include a plurality of such sequences, and/or fragments. The skilled person will appreciate that the present invention can include, novel variants of those particular novel nucleic acid molecules which are exemplified herein. Such variants are encompassed by the present invention. These may occur in nature, for example because of strain variation. For example, additions, substitutions and/or deletions are included. In addition, and particularly when utilising microbial expression systems, one may wish to engineer the nucleic acid sequence by making use of known preferred codon usage in the particular organism being used for expression. Thus, synthetic or non-naturally occurring variants are also included within the scope of the invention.

The term "RNA equivalent" when used above indicates that a given RNA molecule has a sequence which is complementary to that of a given DNA molecule (allowing for the fact that in RNA "U" replaces "T" in the genetic code).

When comparing nucleic acid sequences for the purposes of determining the degree of homology or identity one can use programs such as BESTFIT and GAP (both from the Wisconsin Genetics Computer Group (GCG) software package) BESTFIT, for example, compares two sequences and produces an optimal alignment of the most similar segments. GAP enables sequences to be aligned along their whole length and finds the optimal alignment by inserting spaces in either sequence as appropriate. Suitably, in the context of the present invention compare when discussing identity of nucleic acid sequences, the comparison is made by alignment of the sequences along their whole length.

Preferably, sequences which have substantial identity have at least 50% sequence identity, desirably at least 75% sequence identity and more desirably at least 90 or at least 95% sequence identity with said sequences. In some cases the sequence identity may be 99% or above.

Desirably, the term "substantial identity" indicates that said sequence has a greater degree of identity with any of the sequences described herein than with prior art nucleic acid sequences.

It should however be noted that where a nucleic acid sequence of the present invention codes for at least part of a novel gene product the present invention includes within its scope all possible sequence coding for the gene product or for a novel part thereof.

The nucleic acid molecule may be in isolated or recombinant form. It may be incorporated into a vector and the vector may be incorporated into a host. Such vectors and suitable hosts form yet further aspects of the present invention.

Therefore, for example, by using probes based upon the nucleic acid sequences provided herein, genes in *Streptococcus pneumoniae* can be identified. They can then be excised using restriction enzymes and cloned into a vector. The vector can be introduced into a suitable host for expression.

Nucleic acid molecules of the present invention may be obtained from *S. pneumoniae* by the use of appropriate probes complementary to part of the sequences of the nucleic acid molecules. Restriction enzymes or sonication techniques can be used to obtain appropriately sized fragments for probing.

Alternatively PCR techniques may be used to amplify a desired nucleic acid sequence. Thus the sequence data provided herein can be used to design two primers for use in PCR so that a desired sequence, including whole genes or fragments thereof, can be targeted and then amplified to a high degree. One primer will normally show a high degree of specificity for a first sequence located on one strand of a DNA molecule, and the other primer will normally show a high degree of specificity for a second sequence located on the complementary strand of the DNA sequence and being spaced from the complementary sequence to the first sequence.

Typically primers will be at least 15-25 nucleotides long.

As a further alternative chemical synthesis may be used. This may be automated. Relatively short sequences may be chemically synthesised and ligated together to provide a longer sequence.

In yet a further aspect the present invention provides an immunogenic/antigenic composition comprising one or more proteins or polypeptides selected from those whose sequences are shown in Tables 24, or homologues or derivatives thereof, and/or fragments of any of these. In preferred embodiments, the immunogenic/antigenic composition is a vaccine or is for use in a diagnostic assay.

In the case of vaccines suitable additional excipients, diluents, adjuvants or the like may be included. Numerous examples of these are well known in the art.

It is also possible to utilise the nucleic acid sequences shown in Table 1 in the preparation of so-called DNA vaccines. Thus, the invention also provides a vaccine composition comprising one or more nucleic acid sequences as defined herein. The use of such DNA vaccines is described in the art. See for instance, Donnelly et al, *Ann. Rev. Immunol.*, 15:617-648 (1997).

As already discussed herein the proteins or polypeptides described herein, their homologues or derivatives, and/or fragments of any of these, can be used in methods of detecting/diagnosing *S. pneumoniae*. Such methods can be based on the detection of antibodies against such proteins which may be present in a subject. Therefore the present invention provides a method for the detection/diagnosis of *S. pneumoniae* which comprises the step of bringing into contact a sample to be tested with at least one protein, or homologue, derivative or fragment thereof, as described herein. Suitably, the sample is a biological sample, such as a tissue sample or a sample of blood or saliva obtained from a subject to be tested.

In an alternative approach, the proteins described herein, or homologues, derivatives and/or fragments thereof, can be used to raise antibodies, which in turn can be used to detect the antigens, and hence *S. pneumoniae*. Such antibodies form another aspect of the invention. Antibodies within the scope of the present invention may be monoclonal or polyclonal.

Polyclonal antibodies can be raised by stimulating their production in a suitable animal host (e.g. a mouse, rat, guinea pig, rabbit, sheep, goat or monkey) when a protein as described herein, or a homologue, derivative or fragment thereof, is injected into the animal. If desired, an adjuvant may be administered together with the protein. Well-known adjuvants include Freund's adjuvant (complete and incomplete) and aluminium hydroxide. The antibodies can then be purified by virtue of their binding to a protein as described herein.

Monoclonal antibodies can be produced from hybridomas. These can be formed by fusing myeloma cells and spleen cells which produce the desired antibody in order to form an immortal cell line. Thus the well-known Kohler & Milstein technique (*Nature* 256 (1975)) or subsequent variations upon this technique can be used.

Techniques for producing monoclonal and polyclonal antibodies that bind to a particular polypeptide/protein are now well developed in the art. They are discussed in standard immunology textbooks, for example in Roitt et al, *Immunology* second edition (1989), Churchill Livingstone, London.

In addition to whole antibodies, the present invention includes derivatives thereof which are capable of binding to proteins etc as described herein. Thus the present invention includes antibody fragments and synthetic constructs. Examples of antibody fragments and synthetic constructs are given by Dougall et al in *Tibtech* 12 372-379 (September 1994).

Antibody fragments include, for example, Fab, F(ab')$_2$ and Fv fragments. Fab fragments (These are discussed in Roitt et al [supra]). Fv fragments can be modified to produce a synthetic construct known as a single chain Fv (scFv) molecule. This includes a peptide linker covalently joining $V_h$ and $V_l$ regions, which contributes to the stability of the molecule. Other synthetic constructs that can be used include CDR peptides. These are synthetic peptides comprising antigen-binding determinants. Peptide mimetics may also be used. These molecules are usually conformationally restricted organic rings that mimic the structure of a CDR loop and that include antigen-interactive side chains.

Synthetic constructs include chimaeric molecules. Thus, for example, humanized (or primatized) antibodies or derivatives thereof are within the scope of the present invention. An example of a humanized antibody is an antibody having human framework regions, but rodent hypervariable regions. Ways of producing chimaeric antibodies are discussed for example by Morrison et al in PNAS, 81, 6851-6855 (1984) and by Takeda et al in Nature. 314, 452454 (1985).

Synthetic constructs also include molecules comprising an additional moiety that provides the molecule with some desirable property in addition to antigen binding. For example the moiety may be a label (e.g., a fluorescent or radioactive label). Alternatively, it may be a pharmaceutically active agent.

Antibodies, or derivatives thereof, find use in detection/diagnosis of *S. pneumoniae*. Thus, in another aspect the present invention provides a method for the detection/diagnosis of *S. pneumoniae* which comprises the step of bringing into contact a sample to be tested and antibodies capable of binding to one or more proteins described herein, or to homologues, derivatives and/or fragments thereof.

In addition, so-called AFFIBODIES may be utilised. These are binding proteins selected from combinatorial libraries of an alpha-helical bacterial receptor domain (Nord et al) Thus, Small protein domains, capable of specific binding to different target proteins can be selected using combinatorial approaches.

It will also be clear that the nucleic acid sequences described herein may be used to detect/diagnose *S. pneumoniae*. Thus, in yet a further aspect, the present invention provides a method for the detection/diagnosis of *S. pneumoniae* which comprises the step of bringing into contact a sample to be tested with at least one nucleic acid sequence as described herein. Suitably, the sample is a biological sample, such as a tissue sample or a sample of blood or saliva obtained from a subject to be tested. Such samples may be pre-treated before being used in the methods of the invention. Thus, for example, a sample may be treated to extract DNA. Then, DNA probes based on the nucleic acid sequences described herein (i.e., usually fragments of such sequences) may be used to detect nucleic acid from *S. pneumoniae*.

In additional aspects, the present invention provides:

(a) a method of vaccinating a subject against *S. pneumoniae* which comprises the step of administering to a subject a protein or polypeptide of the invention, or a derivative, homologue or fragment thereof, or an immunogenic composition of the invention;

(b) a method of vaccinating a subject against *S. pneumoniae* which comprises the step of administering to a subject a nucleic acid molecule as defined herein;

(c) a method for the prophylaxis or treatment of *S. pneumoniae* infection which comprises the step of administering to a subject a protein or polypeptide of the invention, or a derivative, homologue or fragment thereof, or an immunogenic composition of the invention;

(d) a method for the prophylaxis or treatment of *S. pneumoniae* infection which comprises the step of administering to a subject a nucleic acid molecule as defined herein;

(e) a kit for use in detecting/diagnosing *S. pneumoniae* infection comprising one or more proteins or polypeptides of the invention, or homologues, derivatives or fragments thereof, or an antigenic composition of the invention; and (f) a kit for use in detecting/diagnosing *S. pneumoniae* infection comprising one or more nucleic acid molecules as defined herein.

Given that we have identified a group of important proteins, such proteins are potential targets for anti-microbial therapy. It is necessary, however, to determine whether each individual protein is essential for the organism's viability. Thus, the present invention also provides a method of determining whether a protein or polypeptide as described herein represents a potential anti-microbial target which comprises inactivating said protein and determining whether *S. pneumoniae* is still viable, in vitro or in vivo.

A suitable method for inactivating the protein is to effect selected gene knockouts, ie prevent expression of the protein and determine whether this results in a lethal change. Suitable methods for carrying out such gene knockouts are described in Li et al, *P.N.A.S.*, 94:13251-13256 (1997).

In a final aspect the present invention provides the use of an agent capable of antagonizing, inhibiting or otherwise interfering with the function or expression of a protein or polypeptide of the invention in the manufacture of a medicament for use in the treatment or prophylaxis of *S. pneumoniae* infection.

The invention will now be described with reference to the following examples, which should not be construed as in any way limiting the invention. The examples refer to the figures in which:

EXAMPLE 1

Figure 1:
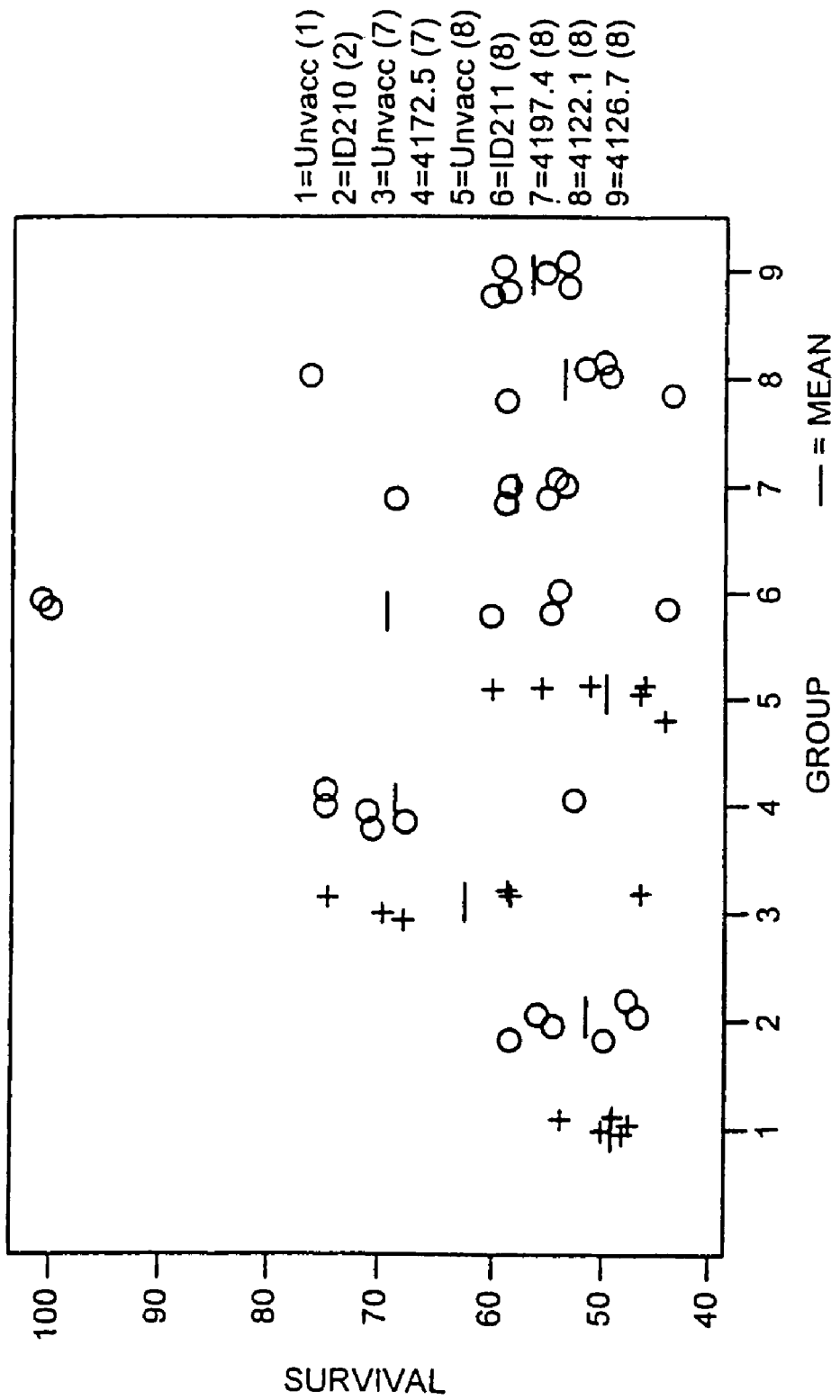
FIG. 1: shows the results of various DNA vaccine trials.

The Genome sequencing of *Streptococcus pneumoniae* type 4 is in progress at the Institute for Genomic Research (TIGR, Rockville, Md., USA). Up to now, the whole sequence has not been completed or published. On Nov. 21, 1997, the TIGR centre released some DNA sequences as contigs which are not accurate reflections of the finished sequence. These contigs can be downloaded from their website. We downloaded these contigs and created a local database using the application GCGToBLAST (Wisconsin Package Version 9.1, Genetics Computer Group (GCG), Madison, USA). This database can be searched with the FastA and TfastA procedures (using the method of Pearson and Lipman (*PNAS USA*, 85:2444-2448 (1988)).

Using FastA and TfastA procedures, the local pneumococcus database was searched for putative leader sequence or anchor sequence features. Relevant sequences were used to interrogate for comparative novel sequences. These were:

(i) already described leader sequences of *Streptococcus pneumoniae* (from proteins NanA, NanB, LytA, PapA, pcpA, PsaA and PspA);

(ii) the leader sequence of Usp45, a secreted protein from *Lactococcus lactis*;

(iii) new hypothetical leader sequences derived from the searches in (i) and (ii);

(iv) the anchor motif LPxTG (SEQ ID NO: 364), a feature common to many Gram-positive bacteria surface proteins which are anchored by a mechanism involving the Sortase complex proteins.

Provided below is an example of this approach, with reference to the sequences derived from the database (see table 1).

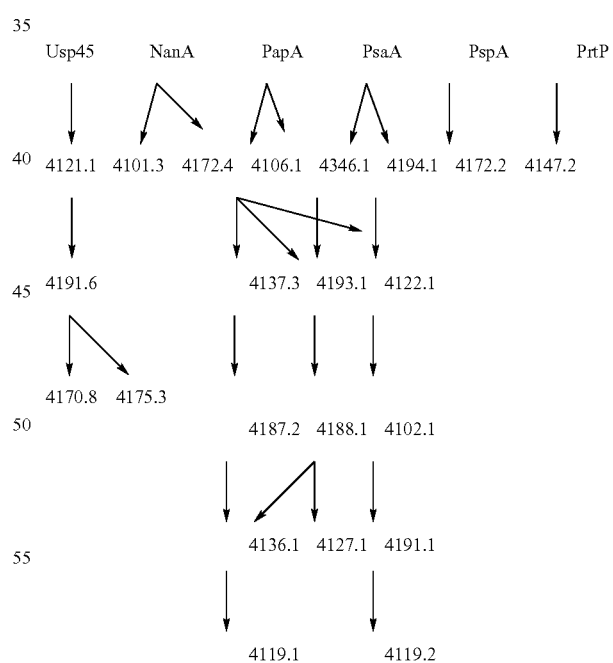

The protein leader sequences of different known exported proteins were used as a starting point for a search of the local pneumococcus database described above. The hypothetical proteins found with this search were then submitted to a Blast search in general databases such as EMBL, Swissprot etc. Proteins remaining unknown in the pneumococcus are kept and annotated. Then the search is performed again using the new potential protein leader sequence as a probe, using the TfastA procedure.

EXAMPLE 2

DNA Vaccine Trials pcDNA3.1+ as a DNA Vaccine Vector pcDNA3.1+

The vector chosen for use as a DNA vaccine vector was pcDNA3.1 (Invitrogen) (actually pcDNA3.1+, the forward orientation was used in all cases but may be referred to as pcDNA3.1 here on). This vector has been widely and successfully employed as a host vector to test vaccine candidate genes to give protection against pathogens in the literature (Zhang, et al., Kurar and Splitter, Anderson et al.). The vector was designed for high-level stable and non-replicative transient expression in mammalian cells. pcDNA3.1 contains the ColE1 origin of replication which allows convenient high-copy number replication and growth in E. coli. This in turn allows rapid and efficient cloning and testing of many genes. The pcDNA3.1 vector has a large number of cloning sites and also contains the gene encoding ampicillin resistance to aid in cloning selection and the human cytomegalovirus (CMV) immediate-early promoter/enhancer which permits efficient, high-level expression of the recombinant protein. The CMV promoter is a strong viral promoter in a wide range of cell types including both muscle and immune (antigen presenting) cells. This is important for optimal immune response as it remains unknown as to which cells types are most important in generating a protective response in vivo. A T7 promoter upstream of the multiple cloning site affords efficient expression of the modified insert of interest and which allows in vitro transcription of a cloned gene in the sense orientation.

Zhang, D., Yang, X., Berry, J. Shen, C., McClarty, G. and Brunham, R. C. (1997) "DNA vaccination with the major outer-membrane protein genes induces acquired immunity to *Chlamydia trachomatis* (mouse pneumonitis) infection". *Infection and Immunity*, 176, 1035-40.

Kurar, E. and Splitter, G. A. (1997) "Nucleic acid vaccination of *Brucella abortus* ribosomal L7/L12 gene elicits immune response". *Vaccine*, 15, 1851-57.

Anderson, R., Gao, X.-M., Papakonstantinopoulou, A., Roberts, M. and Dougan, G. (1996) "Immune response in mice following immunisation with DNA encoding fragment C of tetanus toxin". *Infection and Immunity*, 64, 3168-3173.

Preparation of DNA Vaccines

Oligonucleotide primers were designed for each individual gene of interest derived using the LEEP system. Each gene was examined thoroughly, and where possible, primers were designed such that they targeted that portion of the gene thought to encode only the mature portion of the gene protein. It was hoped that expressing those sequences that encode only the mature portion of a target gene protein, would facilitate its correct folding when expressed in mammalian cells. For example, in the majority of cases primers were designed such that putative N-terminal signal peptide sequences would not be included in the final amplification product to be cloned into the pcDNA3.1 expression vector. The signal peptide directs the polypeptide precursor to the cell membrane via the protein export pathway where it is normally cleaved off by signal peptidase I (or signal peptidase II if a lipoprotein). Hence the signal peptide does not make up any part of the mature protein whether it be displayed on the surface of the bacteria surface or secreted. Where a N-terminal leader peptide sequence was not immediately obvious, primers were designed to target the whole of the gene sequence for cloning and ultimately, expression in pcDNA3.1.

Having said that, however, other additional features of proteins may also affect the expression and presentation of a soluble protein. DNA sequences encoding such features in the genes encoding the proteins of interest were excluded during the design of oligonucleotides.

These features included:
1. LPXTG (SEQ ID NO: 364) cell wall anchoring motifs.
2. LXXC ipoprotein attachment sites.
3. Hydrophobic C-terminal domain.
4. Where no N-terminal signal peptide or LXXC was present the start codon was excluded.
5. Where no hydrophobic C-terminal domain or LPXTG (SEQ ID NO: 364) motif was present the stop codon was removed.

Appropriate PCR primers were designed for each gene of interest and any and all of the regions encoding the above features was removed from the gene when designing these primers. The primers were designed with the appropriate enzyme restriction site followed by a conserved Kozak nucleotide sequence (in all cases) GCCACC was used. The Kozak sequence facilitates the recognition of initiator sequences by eukaryotic ribosomes) and an ATG start codon upstream of the insert of the gene of interest. For example the forward primer using a BamHI site the primer would begin GCGG-GATCCGCCACCATG (SEQ ID NO: 365) followed by a small section of the 5' end of the gene of interest. The reverse primer was designed to be compatible with the forward primer and with a NotI restriction site at the 5' end in all cases (this site is TTGCGGCCGC) (SEQ ID NO:366).

PCR Primers

The following PCR primers were designed and used to amplify the truncated genes of interest.

```
ID210
                                            (SEQ ID NO: 367)
Forward Primer
5' CGGATCCGCCACCATGTCTTCTAATGAATCTGCCGATG 3'

(SEQ ID NO: 368)
Reverse Primer
5' TTGCGGCCGCCTGTTTAGATTGGATATCTGTAAAGACTT 3'

4172.5
                                            (SEQ ID NO: 369)
Forward Primer
5' CGCGGATCCGCCACCATGGATTTTCCTTCAAATTTGGAGG 3'

(SEQ ID NO: 370)
Reverse Primer
5' TTGCGGCCGCACCGTACTGGCTGCTGACT 3'

ID211
                                            (SEQ ID NO: 371)
Forward Primer
5' CGGATCCGCCACCATGAGTGAGATCAAAATTATTAACGC 3'

(SEQ ID NO: 372)
Reverse Primer
5' TTGCGGCCGCCGTTCCATGGTTGACTCCT 3'

4197.4
                                            (SEQ ID NO: 373)
Forward Primer
5' CGCGGATCCGCCACCATGTGGGACATATTGGTGGAAAC 3'
```

-continued

Reverse Primer (SEQ ID NO: 374)
5' TTGCGGCCGCTTCACTTGAGCAAACTGAATCC 3'

4122.1
Forward Primer (SEQ ID NO: 375)
5' CGCGGATCCGCCACCATGTCACAAGAAAAAACAAAAAATGAA 3'

Reverse Primer (SEQ ID NO: 376)
5' TTGCGGCCGCATCGACGTAGTCTCCGCC 3'

4126.7
Forward Primer (SEQ ID NO: 377)
5' CGCGGATCCGCCACCATGCTGGTTGGAACTTTCTACTATCAAT 3'

Reverse Primer (SEQ ID NO: 378)
5' TTGCGGCCGCAACTTTCGTCCCTTTTGG 3'

4188.11
Forward Primer (SEQ ID NO: 379)
5' CGCGGATCCGCCACCATGGGCAATTCTGGCGGAA 3'

Reverse Primer (SEQ ID NO: 380)
5' TTGCGGCCGCTTGTTTCATAGCTTTTTTGATTGTT 3'

ID209
Forward Primer (SEQ ID NO: 381)
5' CGCGGATCCGCCACCATGCTATTGATACGAAATGCAGGG 3'

Reverse Primer (SEQ ID NO: 382)
5' TTGCGGCCGCAACATAATCTAGTAAATAAGCGTAGCC 3'

ID215
Forward Primer (SEQ ID NO: 383)
5' CGCGGATCCGCCACCATGACGGCGACGAATTTTC 3'

Reverse Primer (SEQ ID NO: 384)
5' TTGCGGCCGCTTAATTCGTTTTTGAACTAGTTGCT 3'

4170.4
Forward Primer (SEQ ID NO: 385)
5' CGCGGATCCGCCACCATGGCTGTTTTTCTTCGCTATCATG 3'

Reverse Primer (SEQ ID NO: 386)
5' TTGCGGCCGCTTTCTTCAACAAACCTTGTTCTTG 3'

4193.1
Forward Primer (SEQ ID NO: 387)
5' CGCGGATCCGCCACCATGGGTAACCGCTCTTCTCGTAAC 3'

Reverse Primer (SEQ ID NO: 388)
5' TTGCGGCCGCGCTTCCATCAAGGATTTTAGC 3'

Cloning

The insert along with the flanking features described above was amplified using PCR against a template of genomic DNA isolated from type 4 *S. pneumoniae* strain 11886 obtained from the National Collection of Type Cultures. The PCR product was cut with the appropriate restriction enzymes and cloned in to the multiple cloning site of pcDNA3.1 using conventional molecular biological techniques. Suitably mapped clones of the genes of interested were cultured and the plasmids isolated on a large scale (>1.5 mg) using Plasmid Mega Kits (Qiagen). Successful cloning and maintenance of genes was confirmed by restriction mapping and sequencing ~700 base pairs through the 5' cloning junction of each large scale preparation of each construct.

Strain Validation

A strain of type 4 was used in cloning and challenge methods which is the strain from which the *S. pneumoniae* genome was sequenced. A freeze dried ampoule of a homogeneous laboratory strain of type 4 *S. pneumoniae* strain NCTC 11886 was obtained from the National Collection of Type Strains. The ampoule was opened and the cultured re suspended with 0.5 ml of tryptic soy broth (0.5% glucose, 5% blood). The suspension was subcultured into 10 ml tryptic soy broth (0.5% glucose, 5% blood) and incubated statically overnight at 37° C. This culture was streaked on to 5% blood agar plates to check for contaminants and confirm viability and on to blood agar slopes and the rest of the culture was used to make 20% glycerol stocks. The slopes were sent to the Public Health Laboratory Service where the type 4 serotype was confirmed.

A glycerol stock of NCTC 11886 was streaked on a 5% blood agar plate and incubated overnight in a CO2 gas jar at 37° C. Fresh streaks were made and optochin sensitivity was confirmed.

Pneumococcal Challenge

A standard inoculum of type 4 *S. pneumoniae* was prepared and frozen down by passaging a culture of pneumococcus 1× through mice, harvesting from the blood of infected animals, and grown up to a predetermined viable count of around $10^9$ cfu/ml in broth before freezing down. The preparation is set out below as per the flow chart.

Streak pneumococcal culture and confirm identity
↓
Grow over-night culture from 4-5 colonies on plate above
↓
Animal passage pneumococcal culture
(i.p. injection of cardiac bleed to harvest)
↓
Grow over-night from animal passaged pneumococcus
↓
Grow day culture (to pre-determined optical density) from over-night of animal passage and freeze down at -70° C. - This is standard minimum
↓
Thaw one aliquot of standard inoculum to viable count
↓
Use standard inoculum to determine effective dose
(called Virulence Testing)
↓
All subsequent challenges - use standard inoculum to effective dose An aliquot of standard inoculum was diluted 500× in PBS and used to inoculate the mice.

Mice were lightly anaesthetized using halothane and then a dose of $1.4 \times 10^5$ cfu of pneumococcus was applied to the nose of each mouse. The uptake was facilitated by the normal breathing of the mouse, which was left to recover on its back.

S. pneumoniae Vaccine Trials

Vaccine trials in mice were carried out by the administration of DNA to 6 week old CBA/ca mice (Harlan, UK). Mice to be vaccinated were divided into groups of six and each group was immunised with recombinant pcDNA3.1+ plasmid DNA containing a specific target-gene sequence of interest. A total of 100 μg of DNA in Dulbecco's PES (Sigma) was injected intramuscularly into the tibialis anterior muscle of both legs (50 μl in each leg). A boost was carried using the same procedure 4 weeks later. For comparison, control groups were included in all vaccine trials. These control groups were either unvaccinated animals or those administered with non-recombinant pcDNA3.1+DNA (sham vaccinated) only, using the same time course described above. 3 weeks after the second immunisation, all mice groups were challenged intranasally with a lethal dose of S. pneumoniae serotype 4 (strain NCTC 11886). The number of bacteria administered was monitored by plating serial dilutions of the inoculum on 5% blood agar plates. A problem with intranasal immunizations is that in some mice the inoculum bubbles out of the nostrils, this has been noted in results table and taken account of in calculations. A less obvious problem is that a certain amount of the inoculum for each mouse may be swallowed. It is assumed that this amount will be the same for each mouse and will average out over the course of inoculations. However, the sample sizes that have been used are small and this problem may have significant effects in some experiments. All mice remaining after the challenge were killed 3 or 4 days after infection. During the infection process, challenged mice were monitored for the development of symptoms associated with the onset of S. pneumoniae induced-disease. Typical symptoms in an appropriate order included piloerection, an increasingly hunched posture, discharge from eyes, increased lethargy and reluctance to move. The latter symptoms usually coincided with the development of a moribund state at which stage the mice were culled to prevent further suffering. These mice were deemed to be very close to death, and the time of culling was used to determine a survival time for statistical analysis. Where mice were found dead, the survival time was taken as the last time point when the mouse was monitored alive.

Interpretation of Results

A positive result was taken as any DNA sequence that was cloned and used in challenge experiments as described above which gave protection against that challenge. Protection was taken as those DNA sequences that gave statistically significant protection (to a 95% confidence level ($p<0.05$)) and also those which were marginal or close to significant using Mann-Whitney or which show some protective features for example there were one or more outlying mice or because the time to the first death was prolonged. It is acceptable to allow marginal or non-significant results to be considered as potential positives when it is considered that the clarity of some of the results may be clouded by the problems associated with the administration of intranasal infections.

Results for vaccine trials 2, 7 and 8 (see FIG. 1)

| Mouse number | Mean survival times (hours) | | | | | | | | |
|---|---|---|---|---|---|---|---|---|---|
| | Unvacc control (2) | ID210 (2) | Unvacc control (7) | 4172.5 (7) | Unvacc control (8) | ID211 (8) | 4197.4 (8) | 4122.1 (8) | 4126.7 (8) |
| 1 | 49.0 | 55.0 | 59.6 | 72.6 | 45.1 | 102.3T | 60.1 | 50.6 | 60.0 |
| 2 | 51.0 | 46.5 | 47.2 | 67.9 | 50.8 | 55.5 | 54.9 | 77.2 | 60.0 |
| 3 | 49.0 | 49.0 | 59.6 | 54.4 | 60.4 | 60.6* | 68.4 | 60.3 | 54.8 |
| 4 | 55.0 | 59.0 | 70.9 | 75.3 | 55.2 | 45.3 | 60.1 | 50.6 | 52.6 |
| 5 | 49.0 | 55.0 | 68.6* | 70.9 | 45.1 | 55.5 | 54.9 | 50.6* | 54.8 |
| 6 | 49.0 | 49.0 | 76.0 | 75.3 | 45.1 | 102.3T | 52.7 | 44.9 | 60 |
| Mean | 50.3 | 52.3 | 63.6 | 69.4 | 50.2 | 70.2 | 58.5 | 55.7 | 57.0 |
| sd | 2.4 | 4.8 | 10.3 | 7.9 | 6.4 | 25.3 | 5.7 | 11.6 | 3.4 |
| p value 1 | — | 0.3333 | — | 0.2104 | — | 0.0215 | 0.0621 | 0.4038 | 0.0833 |

*bubbled when dosed so may not have received full inoculum.
Tterminated at end of experiment having no symptoms of infection.
Numbers in brackets - survival times disregarded assuming incomplete dosing
p value 1 refers to significance tests compared to unvaccinated controls Statistical Analyses.

Trial 2—The group vaccinated with ID210 also had a longer mean survival time than the unvaccinated controls but the results are not statistically significant.

Trial 7—The group vaccinated with 4172.5 showed much greater survival times than unvaccinated controls although the differences were not statistically significant.

Trial 8—The group vaccinated with ID211 survived significantly longer than unvaccinated controls. 4197.4, 4122.1 and 4126.7 vaccinated groups showed longer mean survival times than the unvaccinated group but the results were not statistically significant. The 4197.4 and 4126.7 groups also showed a prolonged time to the first death and the 4122.1 group showed 1 outlying result.

Figure 2:
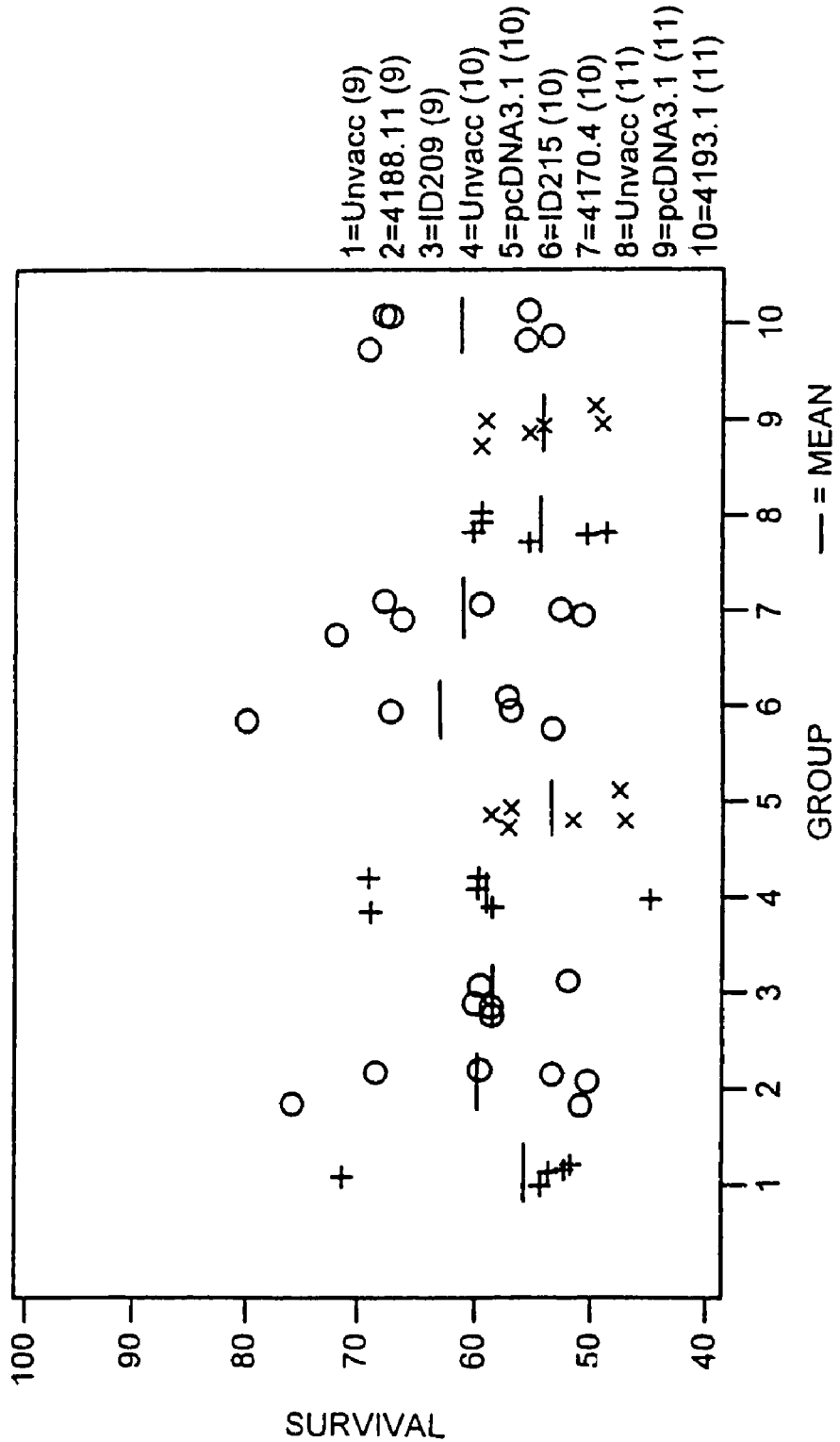
FIG. 2: shows the results of further DNA vaccine trials.

Results of pneumococcal challenge DNA vaccination trials 9-11 (see FIG. 2)

Mean survival times (hours)

| Mouse number | Unvacc control (9) | 4188.11 (9) | ID209 (9) | Unvacc control (10) | pcDNA3.1 + (10) | ID215 (10) | 4170.4 (10) | Unvacc control (11) | pcDNA3.1 + (11) | 4193.1 (11) |
|---|---|---|---|---|---|---|---|---|---|---|
| 1 | (98.5)T | 69.4 | 60.2 | 68.4 | 58.6 | 79.2 | 68.1 | 60.0 | 53.2 | 54.8 |
| 2 | 53.4 | 53.7 | 60.2 | 59.0 | 58.6 | 54.2 | 58.6 | 50.0 | 50.4 | 54.8 |
| 3 | 53.4 | 51.2 | 60.2 | 59.0 | 50.8 | (103.2)*T | 50.9 | 60.0 | 55.4 | 68.7* |
| 4 | 53.4 | 75.0 | (98.0)*T | 45.1* | 58.6 | 58.8 | 72.1 | 55.0 | 60.6 | 54.8 |
| 5 | 70.8 | 51.2 | 60.2 | 68.4 | 46.5 | 68.3 | 68.1 | 60.0 | 50.4 | 68.7 |
| 6 | 53.4 | 61.2 | 52.9 | 59.0 | 48.9 | 58.8 | 54.0 | 50.0 | 60.6 | 68.7* |
| Mean | 56.9 | 60.3 | 58.8 | 59.8 | 53.6 | 63.9 | 62.0 | 55.8 | 55.1 | 61.7 |
| Sd | 7.8 | 10.0 | 3.3 | 8.5 | 5.6 | 10.0 | 8.7 | 5.0 | 4.6 | 7.6 |
| p value 1 | — | 0.3894 | 0.2519 | — | 0.0307 | <30.0 | <39.0 | — | — | 0.1837 |
| p value 2 | — | — | — | — | — | 0.0168 | 0.0316 | — | — | 0.0829 |

*bubbled when dosed so may not have received full inoculum.
Tterminated at end of experiment having no symptoms of infection.
Numbers in brackets - survival times disregarded assuming incomplete dosing
p value 1 refers to significance tests compared to unvaccinated controls
p value 2 refers to significance tests compared to pcDNA3.1 + vaccinated controls Statistical Analyses.
Trial 9—Although not statistically significant the groups vaccinated with 4188.11 and ID209 did have noticeably higher mean survival times than unvaccinated controls.
Trial 10—The unvaccinated control group survived for a significantly longer period than the pcDNA3.1+ vaccinated group. The groups vaccinated with ID215 and 4170.4 showed statistically significant longer survival times compared to the sham vaccinated group (p=0.0168 and 0.0316) but not compared to the unvaccinated group.
Trial 11—The group vaccinated with 4193.1 was the most promising and survived an average of 6.5 hours longer than the pcDNA3.1+ vaccinated group and 6 hours longer than the unvaccinated group although the results were not statistically significant.

TABLE 1

4101.1 (SEQ. ID. NO. 208)
ATGGAAGAGTTAGTGACCTTAGATTGTTTGTTTATTGACAGAACTAAGAT

TGAAGCCAATGCCAACAAGTATAGTTTTGTGTGGAAGAAAACGACAGAGA

AATTCTCCGCCAAACTTCAAGAACAGATACAGGTCTATTTTCAAGAAGAA

ATCACTCCCCTTCTGATTAAATATGCCATGTTTGATAAGAAACAAAAGAG

AGGGTATAAAGAGTCAGCTAAAAACTTAGCGAATTGGCACTATAATGACA

AGGAGGATAGCTACACACATCCTGATGGCTGGTATTATCGTTTTCACCAT

ACCAAATATCAGAAAACACAGACAGACTTTCAACAAGAAATCAAGGTTTA

CTACGCCGACGAACCTGAATCAGCCCCTCAAAAGGGACTGTATATGAACG

AACGCTATCAAAACTTGAAAGCTAAAGAATGTCAGGCGCTTTTATCTCCC

CAAGGTAGACAGATTTTCGCTCAACGCAAGATTGATGTGGAACCTGTCTT

TGGGCAGATAAAGGCTTCTTTGGGTTACAAGAGATGTAATCTGAGAGGGA

AGCGTCAAGTGAGAATTGACATGGGATTGGTACTTATGGCCAATAACCTC

CTAAAATATAGTAAAATGAAATAA 4101.3 (SEQ. ID. NO. 209)
ATGGGGAAAGGCCATTGGAATCGGAAAAGAGTTTATAGCATTCGTAAGTT

TGCTGTGGGAGCTTGCTCAGTAATGATTGGGACTTGTGCAGTTTTATTAG

TABLE 1-continued

GAGGAAATATAGCTGGAGAATCTGTAGTTTATGCGGATGAAACACTTATT

ACTCATACTGCTGAGAAACCTAAAGAGGAAAAAATGATAGTAGAAGAAAA

GGCTGATAAAGCTTTGGAAACTAAAAATATAGTTGAAAGGACAGAACAAA

GTGAACCTAGTTCAACTGAGGCTATTGCATCTGAGAAGAAAGAAGATGAA

GCCGTAACTCCAAAAGAGGAAAAAGTGTCTGCTAAACCGGAAGAAAAAGC

TCCAAGGATAGAATCACAAGCTTCAAATCAAGAAAAACCGCTCAAGGAAG

ATGCTAAAGCTGTAACAAATGAAGAAGTGAATCAAATGATTGAAGACAGG

AAAGTGGATTTTAATCAAAATTGGTACTTTAAACTCAATGCAAATTCTAA

GGAAGCCATTAAACCTGATGCAGACGTATCTACGTGGAAAAAATTAGATT

TACCGTATGACTGGAGTATCTTTAACGATTTCGATCATGAATCTCCTGCA

CAAAATGAAGGTGGACAGCTCAACGGTGGGGAAGCTTGGTATCGCAAGAC

TTTCAAACTAGATGAAAAAGACCTCAAGAAAAATGTTCGCCTTACTTTTG

ATGGCGTCTACATGGATTCTCAAGTTTATGTCAATGGTCAGTTAGTGGGG

CATTATCCAAATGGTTATAACCAGTTCTCATATGATATCACCAAATACCT

TCAAAAAGATGGTCGTGAGAATGTGATTGCTGTCCATGCAGTCAACAAAC

AGCCAAGTAGCCGTTGGTATTCAGGAAGTGGTATCTATCGTGATGTGACT

TTACAAGTGACAGATAAGGTGCATGTTGAGAAAAATGGGACAACTATTTT

AACACCAAAACTTGAAGAACAACAACATGGCAAGGTTGAAACTCATGTGA

CCAGCAAAATCGTCAATACGGACGACAAAGACCATGAACTTGTAGCCGAA

TATCAAATCGTTGAACGAGGTGGTCATGCTGTAACAGGCTTAGTTCGTAC

AGCGAGTCGTACCTTAAAAGCACATGAATCAACAAGCCTAGATGCGATTT

TAGAAGTTGAAAGACCAAAACTCTGGACTGTTTTAAATGACAAACCTGCC

TTGTACGAATTGATTACGCGTGTTTACCGTGACGGTCAATTGGTTCATGC

TAAGAAGGATTTGTTTGGTTACCGTTACTATCACTGGACTCCAAATGAAG

GTTTCTCTTTGAATGGTGAACGTATTAAATTCCATGGAGTATCCTTGCAC

TABLE 1-continued

```
CACGACCATGGGGCGCTTGGAGCAGAAGAAAACTATAAAGCAGAATATCG
CCGTCTCAAACAAATGAAGGAGATGGGAGTTAACTCCATCCGTACAACCC
ACAACCCTGCTAGTGAGCAAACCTTGCAAATCGCAGCAGAACTAGGTTTA
CTCGTTCAGGAAGAGGCCTTTGATACGTGGTATGGTGGCAAGAAACCTTA
TGACTATGGACGTTTCTTTGAAAAAGATGCCACTCACCCAGAAGCTCGAA
AAGGTGAAAATGGTCTGATTTTGACCTACGTACCATGGTCGAAAGAGGC
AAAAACAACCCTGCTATCTTCATGTGGTCAATTGGTAATGAAATAGGTGA
AGCTAATGGTGATGCCCACTCTTTAGCAACTGTTAAACGTTTGGTTAAGG
TTATCAAGGATGTTGATAAGACTCGCTATGTTACCATGGGAGCAGATAAA
TTCCGTTTCGGTAATGGTAGCGGAGGGCATGAGAAAATTGCTGATGAACT
CGATGCTGTTGATTTAACTATTCTGAAGATAATTACAAAGCCCTTAGAG
CTAAGCATCCAAAATGGTTGATTTATGGATCAGAAACATCTTCAGCTACC
CGTACACGTGGAAGTTACTATCGCCCTGAACGTGAATTGAAACATAGCAA
TGGACCTGAGCGTAATTATGAACAGTCAGATTATGGAAATGATCGTGTGG
GTTGGGGGAAAACAGCAACCGCTTCATGGACTTTTGACCGTGACAACGCT
GGCTATGCTGGACAGTTTATCTGGACAGGTACGGACTATATTGGTGAACC
TACACCATGGCACAACCAAAATCAAACTCCTGTTAAGAGCTCTTACTTTG
GTATCGTAGATACAGCCGGCATTCCAAAACATGACTTCTATCTCTACCAA
AGCCAATGGGTTTCTGTTAAGAAGAAACCGATGGTACACCTTCTTCCTCA
CTGGAACTGGGAAAACAAAGAATTAGCATCCAAAGTAGCTGACTCAGAAG
GTAAGATTCCAGTTCGTGCTTATTCGAATGCTTCTAGTGTAGAATTGTTC
TTGAATGGAAAATCTCTTGGTCTTAAGACTTTCAATAAAAAACAAACCAG
CGATGGGCGGACTTACCAAGAAGGTGCAAATGCTAATGAACTTTATCTTG
AATGGAAAGTTGCCTATCAACCAGGTACCTTGGAAGCAATTGCTCGTGAT
GAATCTGGCAAGGAAATTGCTCGAGATAAGATTACGACTGCTGGTAAGCC
AGCGGCAGTTCGTCTTATTAAGGAAGACCATGCGATTGCAGCAGATGGAA
AAGACTTGACTTACATCTACTATGAAATTGTTGACAGCCAGGGGAATGTG
GTTCCAACTGCTAATAATCTGGTTCGCTTCCAATTGCATGGCCAAGGTCA
ACTGGTCGGTGTAGATAACGGAGAACAAGCCAGCCGTGAACGCTATAAGG
CGCAAGCAGATGGTTCTTGGATTCGTAAAGCATTTAATGGTAAAGGTGTT
GCCATTGTCAAATCAACTGAACAAGCAGGGAAATTCACCCTGACTGCCCA
CTCTGATCTCTTGAAATCGAACCAAGTCACTGTCTTTACTGGTAAGAAAG
AAGGACAAGAGAAGACTGTTTTGGGGACAGAAGTGCCAAAAGTACAGACC
ATTATTGGAGAGGCACCTGAAATGCCTACCACTGTTCCGTTTGTATACAG
TGATGGTAGCCGTGCAGAACGTCCTGTAACCTGGTCTTCAGTAGATGTGA
GCAAGCTGGTATTGTAACGGTGAAAGGTATGGCTGACGGACGAGAAGTA
GAAGCTCGTGTAGAAGTGATTGCTCTTAAATCAGAGCTACCAGTTGTGAA
ACGTATTGCTCAAATACTGACTTGAATTCTGTAGACAAATCTGTTTCCT
ATGTTTTGATTGATGGAAGTGTTGAAGAGTATGAAGTGGACAAGTGGGAG
ATTGCCGAAGAAGATAAAGCTAAGTTAGCAATTCCAGGTTCTCGTATTCA
AGCGACCGGTTATTTAGAAGGTCAACCAATTCATGCAACCCTTGTGGTAG
AAGAAGGCAATCCTGCGGCACCTGCAGTACCAACTGTAACGGTTGGTGGT
GAGGCAGTAACAGGTCTTACTAGTCAAAAACCAATGCAATACCGCACTCT
TGCTTATGGAGCTAAGTTGCCAGAAGTCACAGCAAGTGCTAAAAATGCAG
CTGTTACAGTTCTTCAAGCAAGCGCAGCAAACGGCATGCGTGCGAGCATC
TTTATTCAGCCTAAAGATGGTGGCCCTCTTCAAACCTATGCAATTCAATT
CCTTGAAGAAGCGCCAAAAATTGCTCACTTGAGCTTGCAAGTGGAAAAAG
CTGACAGTCTCAAAGAAGACCAAACTGTCAAATTGTCGGTTCGAGCTCAC
TATCAAGATGGAACGCAAGCTGTATTACCAGCTGATAAAGTAACCTTCTC
TACAAGTGGTGAAGGGGAAGTCGCAATTCGTAAAGGAATGCTTGAGTTGC
ATAAGCCAGGAGCAGTCACTCTGAACGCTGAATATGAGGGAGCTAAAGAC
CAAGTTGAACTCACTATCCAAGCCAATACTGAGAAGAAGATTGCGCAATC
CATCCGTCCTGTAAATGTAGTGACAGATTTGCATCAGGAACCAAGTCTTC
CAGCAACAGTAACAGTTGAGTATGACAAAGGTTTCCCTAAAACTCATAAA
GTCACTTGGCAAGCTATTCCGAAAGAAAAACTAGACTCCTATCAAACATT
TGAAGTACTAGGTAAAGTTGAAGGAATTGACCTTGAAGCGCGTGCAAAAG
TCTCTGTAGAAGGTATCGTTTCAGTTGAAGAAGTCAGTGTGACAACTCCA
ATCGCAGAAGCACCACAATTACCAGAAAGTGTTCGGACATATGATTCAAA
TGGTCACGTTTCATCAGCTAAGGTTGCATGGGATGCGATTCGTCCAGAGC
AATACGCTAAGGAAGGTGTCTTTACAGTTAATGGTCGCTTAGAAGGTACG
CAATTAACAACTAAACTTCATGTTCGCGTATCTGCTCAAACTGAGCAAGG
TGCAAACATTTCTGACCAATGGACCGGTTCAGAATTGCCACTTGCCTTTG
CTTCAGACTCAAATCCAAGCGACCCAGTTTCAAATGTTAATGACAAGCTC
ATTTCCTACAATAACCAACCAGCCAATCGTTGGACAAACTGGAATCGTAC
TAATCCAGAAGCTTCAGTCGGTGTTCTGTTTGGAGATTCAGGTATCTTGA
GCAAACGCTCCGTTGATAATCTAAGTGTCGGATTCCATGAAGACCATGGA
GTTGGTGTACCGAAGTCTTATGTGATTGAGTATTATGTTGGTAAGACTGT
CCCAACAGCTCCTAAAAACCCTAGTTTTGTTGGTAATGAGGACCATGTCT
TTAATGATTCTGCCAACTGGAAACCAGTTACTAATCTAAAAGCCCCTGCT
CAACTCAAGGCTGGAGAAATGAACCACTTTAGCTTTGATAAAGTTGAAAC
CTATGCTGTTCGTATTCGCATGGTTAAAGCAGATAACAAGCGTGGAACGT
CTATCACAGAGGTACAAATCTTTGCGAAACAAGTTGCGGCAGCCAAGCAA
GGACAAACAAGAATCCAAGTTGACGGCAAAGACTTAGCAAACTTCAACCC
TGATTTGACAGACTACTACCTTGAGTCTGTAGATGGAAAAGTTCCGGCAG
TCACAGCAAGTGTTAGCAACAATGGTCTCGCTACCGTCGTTCCAAGCGTT
CGTGAAGGTGAGCCAGTTCGTGTCATCGCGAAAGCTGAAAATGGCGACAT
CTTAGGAGAATACCGTCTGCACTTCACTAAGGATAAGAGCTTACTTTCTC
ATAAACCAGTTGCTGCGGTTAAACAAGCTCGCTTGCTACAAGTAGGTCAA
GCACTTGAATTGCCGACTAAGGTTCCAGTTTACTTCACAGGTAAAGACGG
```

TABLE 1-continued

CTACGAAACAAAAGACCTGACAGTTGAATGGGAAGAAGTTCCAGCGGAAA
ATCTGACAAAAGCAGGTCAATTTACTGTTCGAGGCCGTGTCCTTGGTAGT
AACCTTGTTGCTGAGATCACTGTACGAGTGACAGACAAACTTGGTGAGAC
TCTTTCAGATAACCCTAACTATGATGAAAACAGTAACCAGGCCTTTGCTT
CAGCAACCAATGATATTGACAAAAACTCTCATGACCGCGTTGACTATCTC
AATGACGGAGATCATTCAGAAAATCGTCGTTGGACAAACTGGTCACCAAC
ACCATCTTCTAATCCAGAAGTATCAGCGGGTGTGATTTTCCGTGAAAATG
GTAAGATTGTAGAACGGACTGTTACACAAGGAAAAGTTCAGTTCTTTGCA
GATAGTGGTACGGATGCACCATCTAAACTCGTTTTAGAACGCTATGTCGG
TCCAGAGTTTGAAGTGCCAACCTACTATTCAAACTACCAAGCCTACGACG
CAGACCATCCATTCAACAATCCAGAAAATTGGGAAGCTGTTCCTTATCGT
GCGGATAAAGACATTGCAGCTGGTGATGAAATCAACGTAACATTTAAAGC
TATCAAAGCCAAAGCTATGAGATGGCGTATGGAGCGTAAAGCAGATAAGA
GCGGTGTTGCGATGATTGAGATGACCTTCCTTGCACCAAGTGAATTGCCT
CAAGAAAGCACTCAATCAAAGATTCTTGTAGATGGAAAAGAACTTGCTGA
TTTCGCTGAAAATCGTCAAGACTATCAAATTACCTATAAAGGTCAACGGC
CAAAAGTCTCAGTTGAAGAAAACAATCAAGTAGCTTCAACTGTGGTAGAT
AGTGGAGAAGATAGCTTTCCAGTACTTGTTCGCCTCGTTTCAGAAAGTGG
AAAACAAGTCAAGGAATACCGTATCCACTTGACTAAGGAAAAACCAGTTT
CTGAGAAGACAGTTGCTGCTGTACAAGAAGATCTTCCAAAAATCGAATTT
GTTGAAAAAGATTTGGCATACAAGACAGTTGAGAAAAAAGATTCAACACT
GTATCTAGGTGAAACTCGTGTAGAACAAGAAGGAAAAGTTGGAAAAGAAC
GTATCTTTACAGCGATTAATCCTGATGGAAGTAAGGAAGAAAAACTCCGT
GAAGTGGTAGAAGTTCCGACAGACCGCATCGTCTTGGTTGGAACCAAACC
AGTAGCTCAAGAAGCTAAAAAACCACAAGTGTCAGAAAAAGCAGATACAA
AACCAATTGATTCAAGTGAAGCTAGTCAAACTAATAAAGCCCAGTTACCA
AGTACAGGTAGTGCGGCAAGCCAAGCAGCAGTAGCAGCAGGTTTAACTCT
TCTAGGTTTGAGTGCAGGATTAGTAGTTACTAAAGGTAAAAAAGAAGACT
AG 4101.5 (SEQ. ID. NO. 210)
ATGGATGCAATCTTTGACCTAATCGGAAAGGTTTTCAATCCCATCTTAGA
AATGGGTGGACCTGTCATCATGTTAATCATTTTGACAGTATTGGCTTTAC
TTTTTGGAGTGAAATTCTCCAAAGCGCTTGAAGGTGGTATCAAACTTGCC
ATCGCTCTTACAGGTATCGGTGCTATCATCGGTATGCTAAACACTGCTTT
CTCAGCATCACTAGCAAAATTCGTTGAAAACACTGGTATCCAATTGAGTA
TTACCGACGTTGGTTGGGCACCACTTGCTACAATCACTTGGGGTTCTGCT
TGGACACTATACTTCTTGCTCATCATGTTGATTGTCAACATAGTGATGCT
AGCTATGAAGAAAACAGATACACTTGATGTCGATATCTTTGATATCTGGC
ACTTGTCTATCACAGGTCTCTTGATTAAATGGTATGCTGATAACAATGGT
GTGAGTCAAGGGGTTTCACTCTTTATTGCTACAGCAGCTATCGTCCTTGT

CGGTGTGTTGAAAATTATCAACTCTGACTTGATGAAACCTACATTTGATG
ACCTTCTTAACGCCCCAAGTTCATCACCAATGACATCAACTCACATGAAC
TACATGATGAACCCAGTTATCATGGTTTTGGATAAGATTTTTGAAAAATT
CTTCCCAGGCCTTGATAAATATGACTTTGATGCTGCTAAATTGAACAAGA
AAATCGGTTTCTGGGGATCTAAATTCTTCATCGGTTTCATCCTTGGTATC
GTTATCGGTATTATGGGAACTCCACATCCAATTGCAGGTGTTGCAGATGC
AGATAAATGGCGTCTTGTTATCAAAGGATGGTTGTCTCTTGGTTTGACTG
CCGGTGTATCTTTGGAACTCTTCTCACTTATCGGTTCATGGTTCATCGCA
GCCGTAGAACCACTATCACAAGGTATTACAAACGTTGCTACTAAACGTCT
TCAAGGACGTAAATTCAATATCGGTCTTGACTGGCCATTCATCGCTGGTC
GTGCTGAAATCTGGGCTTGTGCCAACGTACTTGCACCAATCATGTTGATT
GAAGCAGTGCTTCTTTCAAAAGTTGGAAATGGTATCTTGCCACTTGCAGG
TATCATCGCTATGGGTGTTACTCCAGCTCTCTTGGTTGTAACTCGTGGTA
AATTGCTCCGTATGATTATCTTCGGAACACTCTTGTTGCCACTCTTCCTT
CTTTCAGGTACACTTATTGCACCATTTGCAACAGAACTTGCTAAAGGTGT
AGGTGCCTTCCCAGAAGGTGTGAGCCAAACTCAATTGATTACTCACTCTA
CTCTTGAAGGACCAATCGAAAAACTTCTTGGTTGGACAATTGGTAACACT
ACAACTGGTGATATCAAAGCAATCCTTGGTGCAGTAGTCTTCCTTGTATT
CTATATCGGTATCTTTGCTTGGTACAGAAAACAAATGATCAAACGTAACG
AAGAGTACGCAGCAAAAGCAAAATAA 4102.1 (SEQ. ID. NO. 211)
ATGAAGATTATGAAAAAAAATATTGGACTTTAGCGATATTATTCTTTTG
TTTGTTCAATAATTCTGTTACTGCTCAAGAAATACCTAAAAATCTTGATG
GCAATATAACTCACACTCAGACTAGCGAAAGTTTTTCTGAATCTGATGAA
AAACAGGTTGACTATTCTAATAAAAATCAAGAAGAAGTAGACCAAAATAA
ATTTCGTATTCAAATCGATAAGACAGAATTATTTGTAACAACAGATAAAC
ATTTAGAAAAAAACTGTTGTAAATTGGAACTTGAACCACAAATAAATAAC
GATATTGTTAACTCTGAAAGTAATAATTTACTAGGCGAAGATAATTTAGA
TAATAAAATTAAGGAAATGTTTCTCATCTAGATAATAGAGGAGGAAATA
TAGAGCATGACAAAGATAACTTAGAATCGTCGATTGTAAGAAAAATATGAA
TGGGATATAGATAAAGTTACTGGTGGAGGCGAAAGTTATAAATTATATTC
TAAAAGTAATTCTAAAGTTTCAATTGCTATTTTAGATTCAGGAGTCGATT
TACAAAATACTGGATTACTGAAAATCTTTCAAATCACTCAAAAAACTAT
GTCCCCAATAAAGGATATTTAGGAAAAGAGGAGGGAGAGGAAGGAATAAT
ATCAGATATTCAAGATAGATTAGGTCATGGTACGGCTGTTGTAGCTCAAA
TTGTAGGGGATGACAATATTAATGGAGTAAATCCTCACGTTAATATTAAC
GTCTATAGAATATTTGGTAAGTCGTCAGCTAGTCCAGATGGATTGTAAA
AGCAATTTTTGATGCTGTAGATGATGGCAATGATATTATCAATCTTAGTA
CTGGACAATATTTAATGATTGATGGAGAATATGAGGACGGAACAAATGAT
TTTGAAACATTTTTGAAGTATAAAAAGGCTATTGATTACGCGAATCAAAA

TABLE 1-continued

AGGAGTAATTATAGTAGCTGCATTAGGGAATGACTCCCTAAATGTATCAA

ATCAGTCAGATTTATTGAAACTTATTAGTTCACGCAAAAAAGTAAGAAAA

CCAGGATTAGTAGTTGATGTTCCAAGTTATTTCTCATCTACAATTTCGGT

CGGAGGCATAGATCGCTTAGGTAATTTATCAGATTTTAGCAATAAAGGGG

ATTCTGATGCAATATATGCGCCTGCAGGCTCAACATTATCTCTTTCAGAA

TTAGGACTTAATAACTTTATTAATGCAGAAAAATATAAAGAAGATTGGAT

TTTTTCGGCAACACTAGGAGGATATACGTATCTTTATGGAAACTCATTTG

CTGCTCCTAAAGTTTCTGGTGCGATTGCAATGATTATTGATAAATACAAA

TTAAAAGATCAGCCCTATAATTATATGTTTGTAAAAAAATTCTGGAAGAA

ACATTACCAGTAA 4106.1 (SEQ. ID. NO. 212)
ATGAAGAAAACATGGAAAGTGTTTTTAACGCTTGTAACAGCTCTTGTAGC

TGTTGTGCTTGTGGCCTGTGGTCAAGGAACTGCTTCTAAAGACAACAAAG

AGGCAGAACTTAAGAAGGTTGACTTTATCCTAGACTGGACACCAAATACC

AACCACACAGGGCTTTATGTTGCCAAGGAAAAAGGTTATTTCAAAGAAGC

TGGAGTGGATGTTGATTTGAAATTGCCACCAGAAGAAAGTTCTTCTGACT

TGGTTATCAACGGAAAGGCACCATTTGCAGTGTATTTCCAAGACTACATG

GCTAAGAAATTGGAAAAGGAGCAGGAATCACTGCCGTTGCAGCTATTGT

TGAACACAATACATCAGGAATCATCTCTCGTAAATCTGATAATGTAAGCA

GTCCAAAAGACTTGGTTGGTAAGAAATATGGGACATGGAATGACCCAACT

GAACTTGCTATGTTGAAAACCTTGGTAGAATCTCAAGGTGGAGACTTTGA

GAAGGTTGAAAAAGTACCAAATAACGACTCAAACTCAATCACACCGATTG

CCAATGGCGTCTTTGATACTGCTTGGATTTACTACGGTTGGGATGGTATC

CTTGCTAAATCTCAAGGTGAGATGCTAACTTCATGTACTTGAAAGACTAT

GTCAAGGAGTTTGACTACTATTCACCAGTTATCATCGCAAACAACGACTA

TCTGAAAGATAACAAAGAAGAAGCTCGCAAAGTCATCCAAGCCATCAAAA

AAGGCTACCAATATGCCATGGAACATCCAGAAGAAGCTGCAGATATTCTC

ATCAAGAATGCACCTGAACTCAAGGAAAAACGTGACTTTGTCATCGAATC

TCAAAAATACTTGTCAAAAGAATACGCAAGCGACAAGGAAAAATGGGGTC

AATTTGACGCAGCTCGCTGGAATGCTTTCTACAAATGGGATAAAGAAAAT

GGTATCCTTAAAGAAGACTTGACAGACAAAGGCTTCACCAACGAATTTGT

GAAATAA 4106.4 (SEQ. ID. NO. 213)
ATGATAAAAAATCCTAAATTATTAACCAAGTCTTTTTTAAGAAGTTTTGC

AATTCTAGGTGGTGTTGGTCTAGTCATTCATATAGCTATTTATTTGACCT

TTCCTTTTTATTATATTCAACTGGAGGGGAAAAGTTTAATGAGAGCGCA

AGAGTGTTTACGGAGTATTTAAAGACTAAGACATCTGATGAAATTCCAAG

CTTACTCCAGTCTTATTCAAAGTCCTTGACCATATCTGCTCACCTTAAAA

GAGATATTGTAGATAAGCGGCTCCCTCTTGTGCATGACTTGGATATTAAA

GATGGAAAGCTATCAAATTATATCGTGATGTTAGATATGTCTGTTAGTAC

AGCAGATGGTAAACAGGTAACCGTGCAATTTGTTCACGGGGTGGATGTCT

ACAAAGAAGCAAAGAATATTTTGCTTTTGTATCTCCCATATACATTTTTG

GTTACAATTGCTTTTTCCTTTGTTTTTTCTTATTTTTATACTAAACGCTT

GCTCAATCCTCTTTTTTACATTTCAGAAGTGACTAGTAAAATGCAAGATT

TGGATGACAATATTCGTTTTCATCAAACTAGGAAAGATGAAGTTGGTGAA

GTTGGAAAACAGATTAATGGTATGTATGAGCACTTGTTGAAGGTTATTTA

TGAGTTGGAAAGTCTGTAATGAGCAAATTGTAAAATTGCAAAATCAAAAG

GTTTCCTTTGTCCGCGGAGCATCACATGAGTTGAAAACCCCTTTAGCCAG

TCTTAGAATTATCCTAGAGAATATGCAGCATAATATTGGAGATTACAAAG

ATCATCCAAAATATATTGCAAAGAGTATAAATAAGATTGACCAGATGAGC

CACTTATTAGAAGAAGTACTGGAGTCTTCTAAATTCCAAGAGTGGACAGA

GTGTCGTGAGACCTTGACTGTTAAGCCAGTTTTAGTAGATATTTTATCAC

GTTATCAAGAATTAGCTCATTCAATAGGTGTTACAATTGAAAATCAATTG

ACAGATGCTACCAGGGTCGTCATGAGTCTTAGGGCATTGGATAAGGTTTT

GACAAACCTGATTAGTAATGCAATTAAATATTCAGATAAAAATGGGCGTG

TAATCATATCCGAGCAAGATGGCTATCTCTCTATCAAAAATACATGTGCG

CCTCTAAGTGACCAAGAACTAGAACATTTATTTGATATATTCTATCATTC

TCAAATCGTGACAGATAAGGATGAAAGTTCCGGTTTGGGTCTTTACATTG

TGAATAATATTTTAGAAAGCTATCAAATGGATTATAGTTTTCTCCCTTAT

GAACACGGTATGGAATTTAAGATTAGCTTGTAG 4106.6 (SEQ. ID. NO. 214)
ATGTATTTAGGAGATTTGATGGAGAAAGCCGAGTGTGGTCAATTTTCAAT

ACTTTCCTTTCTATTACAAGAGTCTCAGACGACCGTCAAGGCTGTAATGG

AAGAAACAGGATTTTCAAAAGCAACCCTAACCAAATATGTCACCCTGCTC

AATGACAAGGCTTTGGATAGTGGCTTAGAGCTGGCTATTCACTCAGAAGA

TGAAAATCTGCGTCTGTCTATCGGTGCAGCTACCAAGGGGAGAGATATTC

GGAGCTTGTTTTGGAGAGTGCTGTTAAATACCAGATTTGGTTTATCTT

CTCTACCACCAACAGTTTTTAGCCCATCAGCTGGCTCAAGAATTGGTGAT

TAGCGAGGCTACGCTTGGTCGTCACTTGGCTGGTTTAAATCAGATTTTGT

CAGAATTTGATTTATCCATCCAAAATGGCCGTTGGCGAGGTCCAGAGCAT

CAGATTCACTATTTCTATTTCTGTCTTTTCCGAAAGGTCTGGTCGAGTCA

GGAATGGAAGGTCACATGCAGAAACCAGAGAGAAAACAGGAGATTGCCA

ATTTAGAGGAAATCTGCGGTCAAGTTTGTCTGCGGGGCAGAAATTGGAC

TTGGTTCTCTGGGCTCACATCAGTCAACAACGTCTTCGGGTCAATGCTTG

TCAGTTTCAAGTCATAGAAGAGAAATGCGAGGGTATTTTGACAATATCT

TTTATCTTCGTTTGCTGAGAAAGGTTCCGTCCTTTTTTGCTGGGCAACAT

ATTCCACTAGGAGTTGAGGATGGTGAGATGATGATATTCTTCTCTTTTCT

CCTATCTCATCGCATTCTTCCTCTTCATACTATGGAGTATATTCTTGGTT

TTGGAGGGCAGTTGGCAGATTTACTGACGCAATTGATTCAAGAAATGAAG

AAGGAGGAACTATTGGGGGATTATACAGAGGACCATGTCACCTATGAACT

TABLE 1-continued

CAGTCAGCTTTGTGCTCAAGTCTATCTCTATAAGGGCTATATTTTACAGG
ATCGCTACAAGTACCAGTTAGAGAATCGTCATCCATATTTACTGATGGAA
CATGATTTTAAAGAGACAGCAGAGGAGATTTTTCATGCTCTACCTGCTTT
TCAACAGGGGACAGATTTAGATAAGAAGATTCTCTGGGAATGGCTCCAGT
TAATCGAATATATGGCTGAAAACGGTGGCCAGCATATGCGGATTGGTCTG
GATTTGACATCTGGTTTTCTTGTCTTTTCAAGGATGGCAGCCATTTTGAA
ACGGTATTTGGAATACAATCGTTTTATTACCATTGAAGCTTATGACCCTA
GTCGGCATTATGATTTGCTGGTTACCAATAACCCGATTCATAAGAAGGAA
CAGACACCAGTCTATTATTTAAAAAATGACTTGGATATGGAGGATTTGGT
AGCGATTCGCCAGTTATTATTCACTTAA 4106.7 (SEQ. ID. NO. 215)
ATGGAATTTTCAAAAGAAAACACGTGAATTGTCAATTAAAAAAATGCAGG
AACGTACCCTGGACCTCTTGATTATCGGTGGAGGAATCACAGGAGCTGGT
GTAGCCTTGCAGGCGGCAGCTAGCGGTCTTGAGACTGGTTTGATTGAAAT
GCAAGACTTTGCAGAAGGAACATCTAGTCGTTCAACAAAATTGGTTCACG
GAGGACTTCGTTACCTCAAACAATTTGACGTAGAAGTGGTCTCAGATACG
GTTTCTGAACGTGCAGTGGTTCAACAAATCGCTCCACACATTCCAAAATC
AGATCCAATGCTCTTACCAGTTTACGATGAAGATGGAGCAACCTTTAGCC
TCTTCCGTCTTAAAGTAGCCATGGACTTGTACGACCTCTTGGCAGGTGTT
AGCAACACACCAGCTGCGAACAAGGTTTTGAGCAAGGATCAAGTCTTGGA
ACGCCAGCCAAACTTGAAGAAGGAAGGCTTGGTAGGAGGTGGAGTGTATC
TTGACTTCCGTAACAACGATGCGCGTCTCGTGATTGAAAACATCAAACGT
GCCAACCAAGACGGTGCCCTCATTGCCAACCACGTGAAGGCAGAAGGCTT
CCTCTTTGACGAAAGTGGCAAGATTACAGGTGTTGTAGCTCGTGATCTCT
TGACAGACCAAGTGTTTGAAATCAAGGCCCGTCTGGTTATTAATACAACA
GGTCCTTGGAGTGATAAAGTACGTAATTTGTCTAATAAGGGAACGCAATT
CTCACAAATGCGCCCAACTAAGGGAGTTCACTTGGTAGTAGATTCAAGCA
AAATCAAGGTTTCACAGCCAGTTTACTTCGACACAGGTTTGGGTGACGGT
CGTATGGTCTTTGTTCTCCCACGTGAAAACAAGACTTACTTTGGTACAAC
TGATACAGACTACACAGGTGATTTGGAGCATCCAAAAGTAACTCAAGAAG
ATGTAGATTATCTACTTGGCATTGTCAACAACCGCTTCCCAGAATCCAAC
ATCACCATTGATGATATCGAAAGCAGCTGGGCAGGTCTTCGTCCATTGAT
TGCAGGGAACAGTGCCTCTGACTATAATGGTGGAAATAACGGTACCATCA
GTGATGAAAGCTTTGACAACTTGATTGCGACTGTTGAATCTTATCTCTCC
AAAGAAAAAACACGTGAAGATGTTGAGTCTGCTGTCAGCAAGCTTGAAAG
TAGCACATCTGAGAAACATTTGGATCCATCTGCAGTTTCTCGTGGGTCTA
GCTTGGACCGTGATGACAATGGTCTCTTGACTCTTGCTGGTGGTAAAATC
ACAGACTACCGTAAGATGGCTGAAGGAGCTATGGAGCGCGTGGTTGACAT
CCTCAAAGCAGAATTTGACCGTAGCTTTAAATTGATCAATTCTAAACTTT
ACCCTGTTTAGGTGGAGAATTGAACCCAGCAAATGTGGATTCAGAAATCG

AAGCCTTTGCGCAACTTGGAGTATCACGTGGTTTGGATAGCAAGGAAGCT
CACTATCTGGCAAATCTTTACGGTTCAAATGCACCGAAAGTCTTTGCACT
TGCTCACAGCTTGGAACAAGCGCCAGGACTCAGCTTGGCAGATACTTTGT
CCCTTCACTATGCAATGCGCAATGAGTTGACTCTTAGCCCAGTTGACTTC
CTTCTTCGTCGTACCAATCACATGCTCTTTATGCGTGATAGCTTGGATAG
TATCGTTGAGCCAATTTTGGATGAAATGGGACGATTCTATGACTGGACAG
AAGAAGAAAAAGCAACTTACCGTGCTGATGTCGAAGCAGCTCTCGCTAAC
AACGATTTAGCAGAATTAAAAAATTAA 4106.8 (SEQ. ID. NO. 216)
ATGATGAATGAATTATTTGGAGAATTTCTAGGGACTTTAATCCTGATTCT
TCTAGGAAATGGTGTTGTTGCAGGTGTGGTTCTTCCTAAAACCAAGAGCA
ATAGCTCAGGTTGGATTGTGATTACTATGGGTTGGGGGATTGCAGTTGCG
GTTGCAGTCTTTGTATCTGGCAAGCTCAGTCCAGCTTATTTAAACCCAGC
TGTGACCATCGGTGTGGCCTTAAAAGGTGGTTTGCCTTGGGCTTCCGTTT
TGCCTTATATCTTAGCCCAGTTCGCAGGGGCCATGCTGGGTCAGATTTTG
GTTTGGTTGCAATTCAAACCTCACTATGAGGCAGAAGAAAATGCAGGCAA
TATCCTGGCAACCTTCAGTACTGGACCAGCCATCAAGGATACTGTATCAA
ACTTGATTAGCGAAATCCTTGGAACTTTTGTTTTGGTGTTGACAATCTTT
GCTTTGGGTCTTTACGACTTTCAGGCAGGTATCGGAACCTTTGCAGTGGG
AACTTTGATTGTCGGTATCGGTCTATCACTAGGTGGGACAACAGGTTATG
CCTTGAACCCAGCTCGTGACCTTGGACCTCGTATCATGCACAGCATCTTG
CCAATTCCAAACAAGGGAGACGGAGACTGGTCTTACGCTTGGATTCCTGT
TGTAGGCCCTGTTATCGGAGCAGCCTTGGCAGTGCTTGTATTCTCACTTT
TCTAG 4106.10 (SEQ. ID. NO. 217)
ATGAAAAGGACCTGGAGGAACTCATTCGTGACAAATCTTAATACACCTTT
TATGATTGGCAATATTGAGATTCCCAATCGTACCGTTTTAGCGCCTATGG
CTGGCGTGACCAACTCAGCCTTTCGTACTATCGCAAAGGAGCTCGGAGCT
GGACTCGTTGTAATGGAAATGGTCTCTGACAAGGGAATCCAATACAACAA
CGAAAAAACCCTGCACATGCTTCATATCGATGAGGGCGAAAACCCTGTCT
CTATCCAACTTTTTGGTAGCGATGAAGACAGCCTAGCACGCGCAGCAGAA
TTCATCCAAGAAAACACCAAGACCGATATCGTCGATATCAACATGGGCTG
CCCTGTCAACAAAATCGTGAAGAACGAAGCTGGTGCTATGTGGCTCAAGG
ATCCAGACAAGATTTACTCCATCATCAACAAGGTCCAGTCTGTCCTTGAT
ATCCCACTTACTGTCAAAATGCGTACCGGCTGGGCGGACCCATCTCTTGC
AGTAGAAAATGCTCTCGCTGCTGAAGCTGCAGGTGTTTCTGCCCTCGCCA
TGCATGGCCGTACCCGTGAACAAATGTATACTGGCCACGCAGACCTTGAG
ACCCTTTACAAGGTTGCCCAAGCTCTAACCAAGATTCCATTCATCGCCAA
CGGTGATATCCGTACTGTCCAAGAAGCCAAGCAACGCATCGAAGAAGTTG
GTGCTGACGCAGTCATGATTGGCCGAGCTGCCATGGGAAATCCTTACCTC
TTCAACCAAATCAACCATTACTTTGAAACAGGAGAAATCCTACCTGATTT

TABLE 1-continued

GACCTTTGAAGACAAGATGAAGATCGCCTAGGAACACTTGAAACGATTGA

TTAACCTCAAAGGAGAAAACGTCGCAGTTCGTGAATTCCGCGGTCTCGCT

CCTCACTATCTCCGTGGAACATCTGGCGCTGCCAAACTCCGTGGAGCCAT

TTCGCAAGCCAGCACCCTGGCAGAGATTGAAACCCTCTTGCAATTGGAGA

AGGCTTAA 4107.1 (SEQ. ID. NO. 218)
ATGACAAAGAAGAAAATTGAGCGTATTTCTGTAATACACCGAGAAAAGAT

TTTATGGCTCAAGTGGTATTTCATGCGAGATAAAGAACAACCTAAGTATA

GTGTCCTTGAGCGTAAAATGTTTGATGCTGCTAAAAATCAAGATATGCTA

GCTTATCAAAAATACGCAACTATCAAGCAGATAACAGATATTAGGGTACA

AACAAGTGAGGCTGACATTTTAGAGGCTGTAAAAGAGGTTTATGTGTACA

ATCACATGAATGTTATCGGAGCTTGTCAGCGGATATTATTTATCAGTCAA

TCACCAGCTTATGATAAGTTAAATAAGTGGTTTAATATCTATTCTGATTT

GTATTTTAGCGTTGTACCCTTGCCCAAAATGGGGGTATATCATGAGATGG

TAGGTATCTAG 4107.2 (SEQ. ID. NO. 219)
ATGAAAAATTCCAACGAGGCTGAGATGAAATTACTTTATACTGATATTCG

GACTTCTTTGACAGAAATTCTAACAAGAGAGGCAGAAGAGCTAGTTGCAG

CTGGCAAGCGGGTCTTCTACATTGCCCCCAACTCTCTTTCTTTTGAAAAG

GAACGCGCCGTGCTGGAATACTTGTCCCAGCAGGCTTCTTTTTCGATTAC

CGTCACGCGCTTTGCTCAAATGGCTCGCTATCTGGTCTTGAATGATTTAC

CAGCTAAAACTACTCTTGATGATATCGGTCTTGGGTTGGCCTTTTACAAA

TGCCTTGCCGAACTCGATCCCAAGGACTTGCGTGTTTATGGCGCTATTAA

GCAGGATCCTCAATTGATCCAGCAGTTAATTGAGCTTTACCATGAGATGA

CCAAATCTCAGATGAGTTTTTTGGACTTGGAGAATTTAACAGATGAGGAT

AAGAGGGCGGATTTACTCTTGATTTTTGAGAAAGTAACAGCCTATCTTAA

TCAAGGTCAGTTAGCCCAGGAAAGTCAGTTGTCCCATTTGATTGAGGCTA

TTGAGAATGACAAGGTAAGTAGTGATTTTAATCAAATCGCCTTGGTCATT

GACGGCTTTACTCGTTTTTCTGCTGAGGAAGAGCGGGTTGTGGACTTACT

TCACGGCAAAGGTGTTGAGATTGTTATCGGGGCTTATGCTAGTAAGAAAG

CCTATACCAGTCCTTTTAGCGAGGCAATCTCTACCAAGCCAGCGTAAAA

TTTCTCCATCATCTGGCTTCTAAATACCAAACGCCTGCTCAGGACTGTTC

TCAAACTCATGAGAAGATGGATAGTTTTGACAAGGCCTCTCGTTTGTTGG

AGTCTTCTTATGACTTTTCAGAACTCGCTTTGGATGTCGATGAGAAAGAC

CGTGAAAATTTACAAATCTGGTCTTGTTTGACGCAAAAGGAGGAGTTGGA

GCTAGTAGCCCGTAGTATTCGTCAGAAATTACATGAGAACTCAGACCTGA

GCTACAAGCATTTTCGTATTCTCTTGGGGGATGTAGCTTCTTACCAGTTA

TCTCTCAAAACCATTTTTGACCAGTATCAGATTCCTTTTTATCTTGGTAG

AAGCGAAGCCATGGCTCATCATCCCTTGACTCAGTTTGTCGAGTCTATTT

TAGCTTTAAAACGTTACCGTTTTCGTCAGGAGGATTTGATTAATCTTCTT

AGAACTGATTTGTATACTGACCTCAGTCAGTCTGATATTGATGCTTTTGA

GCAATATATCCGCTATCTTGGTATCAATGGCTTGCCAGCCTTTCAGCAAA

CCTTCACCAAATCCCACCATGGAAAATTTAATCTTGAGCGTTTGAATGTC

CTCCGCCTGAGAATTTTAGCACCTCTTGAAACCCTCTTTGCCAGCCGAAA

ACAAAAGGCTGAAAAACTCCTACAAAAATGGAGTGTCTTTCTAAAAGAAG

GAGCTGTGACCAAGCAGTTACAAGATTTGACAACCACTTTGGAAGCTGTA

GAACAGGAAAGACAAGCCGAAGTTTGGAAGGCTTTCTGCCATGTTTTAGA

ACAATTTGCGACTGTTTTTGCTGGTTCACAGGTTAGTCTGGAAGACTTCC

TAGCCTGCTCCATTCTGGAATGAGTTTGTCCCAATACCGTACCATTCCAG

CAACAGTGGACACTGTTCTGGTGCAGCGTTACGATTTGATTGCACCATTG

ACTGCTGACTTTGTCTATGCTATTGGACTAACTCAGGACCATTTACCCAAA

AATTTCTCAAAACACCAGTCTTCTGACAGATGAAGAAAGGCAAAACCTAA

ACCAAGCGACCGAAGAAGGCGTTCAATTACTGATTGCCAGCAGTGAAAAT

CTCAAGAAAAATCGCTACACTATGCTTTCCTTGGTCAATTCTGCTCGTAA

GCAGTTGTTCTTGTCGGCTCCAAGCCTTTTTAACGAAAGTGAAAGTAAGG

AATCTGCCTATCTTCAAGAGTTGATCCATTTTGGATTTAGGCGGAGAGAG

AAGAGGATGAATCACAAAGGACTGTCTAAGGAGGATATGGGGTCCTATCA

CAGTCTTTTGTCTAGTCTGGTTGCCTATCACCAGCAGGGTGAGATGAGCG

ATACTGAGCAAGATTTGACTTTTGTCAAGGTTCTGTCGCGTGTCATAGGT

AAAAAAACTAGATCAGCAAGGTCTGGAAAATCCAGCTATCCCAACCAGTCC

AAGCAGCAAGACCTTAGCCAAGGACACCTTGCAAGCTCTCTATCCTGCCA

AACAGGAGTTTTACCTGTCTACGTCGGGTTTGACAGAGTTTTATCGCAAT

GAATACAGTTATTTCCTACGCTACGTTTTAGGCTTGCAGGAGGAATTACG

TTTGCATCCTGATGCCCGTAGTCACGGGAATTTCTTGCATCGTATCTTTG

AACGCGCCTTACAGTTGCCTAATGAAGATTCCTTTGACCAACGTCTAGAA

CAAGCTATTCAAGAAACCAGTCAAGAACGCGAATTTGAAGCTATTTATCA

AGAAACTTTGGAAGCCCAGTTTACCAAGGAAGTTTTGCTTGATGTTGCAC

GGACAACTGGACATATTCTCCGACACAATCCAGCCATCGAAACCATCAAA

GAAGAAGCAAATTTTGGTGGAAAAGACCAAGCCTTTATTCAATTAGACAA

TGGACGCAGTGTCTTTGTACGAGGCAAGGTGGACCGGATTGACCGTTTGA

AAGCTAATGGAGCGATAGGAGTAGTAGACTACAAATCCAGTCTGACTCAG

TTCCAGTTTCCTCATTTCTTTAATGGGCTCAATTCTCAGTTACCAACCTA

TCTTGCTGCCCTAAAAAGAGAAGGGGAGCAGAACTTTTTCGGCGCCATGT

ACTTGGAAATGGCTGAACCTGTCCAATCTCTGATGGCGGTAAAAAGTCTG

GCAGGAGCAGTGGTAGAAGCCAGCAAATCTATGAAATACCAAGGGCTCTT

CTTGGAAAAGAAAGCAGTTATTTAGGCGAATTTTATAACAAAAACAAGG

CTAATCAACTGACAGATGAGGAATTTCAGCTCCTACTGGACTACAATGCC

TATCTTTACAAGAAAGCTGCTGAGAAGATTTTAGCAGGCCGGTTCGCCAT

CAATCCTTATACTGAAAATGGCAGAAGCATTGCCCCATACGTCCAGCAAC

ATCAGGCTATTACAGGCTTTGAAGCCAATTACCATCTGGGCCAAGCCCGT

TABLE 1-continued

TTCCTAGAAAAGTTGGACCTAGCTGATGGCAAGCGTCTGGTCGGAGAAAA

ACTCAAGCAAGCTTGGCTTGAAAAAATAAGAGAGGAGTTGAATCGATGA 4107.3 (SEQ. ID. NO. 220)
ATGAAGCTTATTCCCTTTTTAAGTGAGGAGGAGATTCAAAAACTGCAAGA

AGCAGAAGCAAATTCGAGCAAGGAACAGAAGAAAACTGCCGAGCAAATCG

AAGCTATCTACACTTCTGCCCAGAATATCCTGGTCTCAGCATCGGCTGGT

TCTGGAAAGACCTTTGTCATGGCAGAGCGCATTCTGGACCAATTGGCGCG

TGGTGTCGAAATTTCTCAACTCTTTATCTCAACCTTTACCGTCAAGGCTG

CAACTGAACTTAAAGAACGTTTAGAGAAAAAAATCAGCAAGAAAATCCAA

GAAACAGATGATGTCGACCTCAAACAACACTTGGGTCGCCAGTTGGCAGA

CCTACCCAACGCTGCCATTGGAACCATGGATTCTTTCACACAAAAATTCC

TTGGCAAACATGGTTATCTGCTTGATATTGCACCTAATTTCCGTATTTTA

CAAAACCAAAGCGAGCAACTTATTCTCGAAAACGAAGTCTTTCATGAGGT

CTTTGAAGCGCATTACCAAGGTAAACAGAAAGAGACCTTTAGTCATTTGC

TGAAAAACTTTGCTGGGCGTGGCAAGGACGAACGGGGTCTGCGCCAGCAG

GTCTATAAAATCTATGACTTCCTCCAATCCACCAGTAATCCTCAAAAGTG

GCTGAGTGAATCTTTCCTCAAAGGATTTGAGAAAGCTGATTTTACCAGTG

AAAAAGAAAACTGACCGAGCAAATCAAACAAGCCCTTTGGGATTTGGAA

AGCTTTTTCCGTTACCATCTGGATAACGATGCCAAGGAGTTTGCAAAGGC

TGCCTATTTAGAAAATGTTCAGTTAATTCTGGATGAAATTGGCTCCCTAA

ATCAGGAGTCCGATAGTCAGGCTTATCAGGCAGTGCTTGCGCGTGTTGTC

GCCATCTCTAAGGAGAAAAACGGTCGAGCTCTGACTAATGCCAGCCGTAA

GGCTGATTTGAAGCCCCTGGCTGATGCCTACAACGAAGAGAGAAAGACCC

AGTTTGCTAAACTAGGACAATTATCAGACCAGATAGCGATTCTCGACTAT

CAAGAACGTTATCATGGAGACACTTGGAAACTAGCTAAAACCTTCCAATC

TTTCATGAGCGATTTTGTAGAGGCTTATCGTCAGAGAAAACGACAGGAAA

ATGCCTTCGAATTCGCTGATATCAGCCATTACACCATTGAGATTTTAGAG

AATTTCCCACAAGTTCGTGAGTCTTATCAGGAGCGCTTCCATGAAGTCAT

GGTCGATGAGTATCAGGATACCAACCATATTCAAGAACGGATGCTGGAAT

TGTTGTCTAATGGCCACAATCGCTTTATGGTGGGAGATATCAAGCAATCC

ATCTATCGTTTCCGTCAGGCAGACCCGCAGATTTTCAATGAGAAATTCCA

ACGCTATGCGCAAAATCCCCAAGAAGGCAGGCTCATTATCCTCAAGGAAA

ATTTCCGTAGTAGTTCAGAAGTGCTGTCAGCAACCAATGATGTCTTTGAA

CGTCTCATGGACCAAGAGGTCGGCGAAATCAACTATGATAACAAGCACCA

GCTTGTTTTGCCAATACCAAACTGACTCCCAATCCAGCAACAAGGCAG

CATTTCTCCTCTACGACAAGGACGATACAGGTGAGGAAGAAGAGAGTCAA

ACAGAAACGAAACTAACAGGCGAAATGCGCTTAGTTATCAAGGAGATTCT

GAAACTTCATCAAGAAAAAGGTGTTGCCTTTAAGGAAATTGCCCTTCTGA

CCTCCAGCCGCAGTCGTAATGACCAGATTCTCCTCGCCCTGTCTGAGTAC

GGAATTCCTGTCAAAACTGACGGAGAGCAAAACAATTATCTCCAATCCCT

AGAAGTGCAAGTCATGCTAGACACTCTTCGTGTCATTCACAATCCCCTGC

AAGACTACGCCTTGGTTGCCCTTATGAAGTCTCCAATGTTTGGTTTTGAT

GAGGATGAGCTAGCACGTTTGTCCCTTCAGAAAGCAGAGGATAAAGTCCA

CGAAAATCTCTATGAGAAACTGGTCAATGCACAAAAAATGGCAAGTAGTC

AAAAAGGCTTGATTCACACAGCTCTAGCTGAAAACTAAAGCAATTCATG

GATATCCTAGCTTCTTGGCGCTTGTATGCCAAAACCCACTCTCTCTATGA

CTTGATTTGGAAGATTTACAACGACCGTTTTTATTATGACTATGTTGGGG

CTTTGCCGAATGGTCCTGCTAGGCAGGCCAATCTCTATGCCCTAGCACTG

CGTGCTGATCAATTTGAAAAGAGCAATTTCAAAGGTTTGTCGCGTTTTAT

TCGTATGATTGACCAAGTCTTAGAAGCCCAGCACGATTTGGCAAGCGTGG

CCGTCGCACCGCCAAAAGATGCAGTAGAGCTCATGACCATCCACAAGAGT

AAAGGGCTGGAGTTTCCTTACGTCTTTATCCTCAATATGGATCAAGATTT

CAACAAGCAAGACTCTATGTCAGAAGTCATTCTCAGTCGTCAGAATGGTC

TTGGTGTCAAATATATTGCCAAGATGGAGACAGGGGCAGTAGAAGACCAC

TATCCTAAAACCATCAAACTCTCCATTCCTAGTCTGACCTATAGGCAGAA

CGAAGAGGAATTACAGCTAGCAAGCTATTCTGAGCAGATGCGTTTGCTGT

ATGTTGCTATGACGCGGGCTGAGAAAAAGCTCTATCTTGTCGGCAAGGGT

TCTCGTGAAAAGCTGGAATCCAAGGAATACCCAGCAGCCAAAAATGGGAA

ACTAAATAGCAATACTAGACTGCAAGCACGGAATTTCCAAGATTGGCTTT

GGGCTATCAGTAAAGTGTTTACTAAGGACAAGCTCAACTTTAGTTATCGT

TTTATTGGCGAAGATCAGTTGACCAGAGAAGCTATCGGAGAGTTGGAAAC

CAAGAGTCCTCTCCAAGATAGCTCCCAAGCAGACAATCGTCAGTCAGATA

CCATCAAAGAAGCTCTGGAAATGCTGAAGGAGGTGGAAGTTTATAATACT

CTTCACCGCGCAGCTATTGAACTTCCTAGTGTTCAAACCCCAAGTCAAAT

CAAGAAATTCTACGAACCAGTTATGGATATGGAAGGTGTCGAGATTGCTG

GTCAAGGTCAGTCAGTAGGCAAGAAAATCAGCTTCGATTTGCCAGATTTT

TCAACCAAAGAAAAGGTAACTGGAGCTGAGATTGGTAGTGCTACTCACGA

ACTCATGCAGAGAATTGACCTCAGCCAGCAACTAACCCTTGCTAGCCTAA

CAGAAACACTCAAACAAGTTCAAACTAGCCAAGCTGTCAGAGACAAGATC

AATCTTGATAAAATTCTTGCTTTCTTTGACACAGTACTCGGTCAGGAAAT

TCTTGCTAATACCGACCATCTTTATCGCGAGCAACCTTTCTCCATGCTCA

AACGAGACCAAAAGAGTCAGGAAGACTTTGTTGTCCGTGGTATCCTTGAT

GGCTATCTGCTTTACGAAAACAAAATTGTTCTGTTCGACTACAAGACAGA

CCGCTATGATGAACCAAGTCAACTCGTAGACCGCTATCGTGGTCAGTTAG

CTCTATACGAAGAGGCTTTATCACGAGCCTATTCGATTGAAAATATTGAA

AAATACTTGATTTTACTCGGTAAAGACGAGGTTCAAGTTGTAAAGTATA
A 4109.1 (SEQ. ID. NO. 221)
ATGGAACTTGCTCGCCATGCTGAAACGTTGGGAGTAGATGCTATTGCAAC

GATTCCACCAATTTATTTCCGCTTGCCAGAATACTCAGTTGCCAAATACT

TABLE 1-continued

GGAACGATATCAGTTCTGCAGCTCCAAACACAGACTACGTGATTTACAAC

ATTCCTCAATTGGCAGGGGTTGCTTTGACTCCAAGCCTTTACACAGAAAT

GTTGAAAAATCCTCGTGTTATCGGTGTGAAGAACTCTTCTATGCCAGTTC

AAGATATCCAAACCTTTGTCAGCCTTGGTGGAGAAGACCATATCGTCTTT

AATGGTCCTGATGAGCAGTTCCTAGGAGGACGCCTCATGGGGGCTAGGGC

TGGTATCGGTGGTACTTATGGTGCTATGCCAGAACTCTTCTTGAAACTCA

ATCAGTTGATTGCGGATAAGGACCTAGAAACAGCGCGTGAATTGCAGTAT

GCTATCAACGCAATCATTGGTAAACTCACTTCTGCTCATGGAAATATGTA

CGGTGTCATCAAAGAAGTCTTGAAAATCAATGAAGGCTTGAATATTGGAT

CTGTTCGTTCACCATTGACACCAGTGACTGAAGAAGATCGTCCAGTTGTA

GAAGCGGCTGCTGCCTTGATTCGTGAAACCAAGGAGCGCTTCCTCTAA 4110.2 (SEQ. ID. NO. 222)
ATGTATAAGACAAAGTGTTTACGAGAGAAGTTAGTATTATTTTTAAAAAT

TTTCTTCCCAATCCTGATCTACCAATTTGCCAATTATTCTGCCTCTTTTG

TTGATACTGCAATGACAGGTCAATACAACACTATGGACTTGGCTGGTGTA

TCTATGGCAACCAGTATCTGGAATCCTTTCTTTACATTTCTAACAGGGAT

TGTGTCAGCCTTGGTGCCTATCATTGGTCACCATCTTGGTCGAGGCAAAA

AGGAAGAAGTTGCGTCTGATTTTTACCAATTTATTTATTTGGCCTTGGGC

CTATCTGTGGTCTTGCTGGGGATGGTACTTTTCTTGGCACCAATAATCTT

GAATCATATTGGGTTAGAAGCAGCAGTAGCGGCAGTAGCGGTTCGCTATC

TTTGGTTTTTATCTATCGGGATTATCCCCTTGTTGCTCTTTAGCGTCATT

CGTTCCTTGCTGGATTCGCTGGGCTTGACCAAACTGTCCATGTACCTCAT

GCTTTTCTTACTCCCTCTCAATAGCGGATTTAACTATCTCTTGATTTACG

GTGCCTTTGGTGTTCCACAACTGGGAGGGGCTGGTGCTGGTTTAGGAACA

TCCTTGGCCTACTGGGTCTTGCTTGGGATTTCTGTTCTGGTTTTATTTAA

ACAGGAGAAGCTCAAAGCCTTACACCTTGAGAAACGAATTCCACTTAATA

TGGATAAAATTAAGGAAGGAGTTCGTTTAGGTCTGCCTATTGGGGGAACT

GTCTTCGCGGAAGTGGCTATCTTTTCAGTGGTTGGCTTGATTATGGCTAA

GTTTTCGCCCTTGATTATAGCTAGTCACCAGTCAGCTATGAACTTTTCAA

GTCTTATGTACGCCTTTCCTATGAGTATCTCATCGGCTATGGCTATTGTC

GTTTCCTATGAAGTGGGAGCCAAGCGATTTGATGATGCGAAAACCTATAT

TGGTCTAGGAAGATGGACTGCCCTCATTTTTGCGGCCTTCACCTTAACCT

TCCTTTACATTTTTAGGGGAAATGTGGCCAGTCTTTATGGTAACGACCCA

AAATTTATCGATTTGACAGTGCGTTTTTAACTTATAGTCTTTTCTTCCA

GTTAGCAGATACCTTTGCGGCGCCGCTTCAGGGAATTTTGCGGGGGTATA

AGGATACAGTTATTCCTTTTTACCTTGGTTTGCTTGGTTATTGGGGCGTA

GCAATCCCTGTGTACGCTATTTGA 4112.2 (SEQ. ID. NO. 223)
ATGAGTACTTTAGCAAAAATAGAAGCGCTCTTGTTTGTAGCGGGTGAAGA

TGGGATTCGGGTCCGCCAGTTAGCTGAACTCCTCTCTCTGCCACCGACAG

GCATCCAGCAAAGTTTAGGAAAATTAGCCCAGAAGTATGAAAAGGACCCA

GATTCCAGTTTGGCTTTGATTGAGACAAGTGGTGCTTATAGATTGGTGAC

CAAGCCTCAATTTGCAGAGATTTTGAAGGAATACTCTAAGGCGCCTATCA

ACCAGAGCTTGTCTCGGGCTGCCCTTGAGACCTTGTCCATTATTGCCTAC

AAACAGCCGATTACGCGGATAGAAATTGATGCCATCCGTGGAGTTAACTC

GAGTGGAGCCTTGGCAAAGTTGCAGGCTTTTGACCTGATAAAGGAAGACG

GGAAAAAGGAAGTATTGGGGCGCCCCAACCTCTATGTGACTACGGATTAT

TTCCTAGATTACATGGGGATAAACCATTTAGAAGAATTACCAGTGATTGA

TGAGCTTGAGATTCAAGCCCAAGAAAGCCAATTATTTGGTGAAAGGATAG

AAGAAGATGAGAATCAATAA 4113.1 (SEQ. ID. NO. 224)
ATGGATACGATGATTAGTAGATTTTTTCGCCATTATTTGAAGCCTTAAA

AAGTTTGAAACGAAATGGTTGGATGACAGTAGCTGCTGTCAGTTCAGTCA

TGATTACTTTGACCTTGGTGGCAATATTTGCATCTGTTATTTTCAATACA

CGAAAACTAGCTACAGATATTGAAAATAATGTCCGTGTAGTAGTTTATAT

CCGAAAGGATGTGGAAGATAATAGTCAGACAATTGAAAAAGAAGGTCAAA

CTGTTACAAATAATGACTACCACAAGGTATATGATTCTTTGAAGAACATG

TCTACGGTTAAAAGTGTTACCTTTTCAAGTAAAGAAGAACAATATGAAAA

ATTAACCGAGATAATGGGAGATAACTGGAAAATCTTTGAAGGAGATGCCA

ATCCTCTCTATGATGCCTATATTGTAGAGGCAAACACTCCAAATGATGTA

AAAACTATAGCCGAAGATGCTAAAAAAATTGAAGGTGTCTCTGAGGTTCA

AGATGGCGGTGCCAATACAGAAAGACTCTTCAAGTTAGCTTCATTTATCC

GTGTTTGGGGACTAGGGATTGCTGCTTTGTTAATTTTTATCGCAGTTTTC

TTGATTTCAAATACCATTCGTATTACCATTATTTCCCGCAGTCGCGAAAT

TCAAATCATGCGCTTGGTCGGAGCTAAAAACAGTTATATCCGTGGACCGT

TCTTGTTAGAAGGAGCCTTTATCGGTTTATTGGGAGCTATCGCACCATCT

GTTTTGGTCTTTATTGTTTATCAAATTGTTTACCAATCTGTCAACAAATC

GTTGGTAGGGCAAAATCTATCCATGATTAGTCCAGATTTATTTAGTCCGT

TGATGATTGCCCTACTATTTGTGATTGGGGTTTTCATTGGTTCATTGGGA

TCAGGAATATCCATGCGCCGATTCTTGAAGATTTAG 4117.1 (SEQ. ID. NO. 225)
ATGAAGAAAGTAAGATTTATTTTTTTAGCTCTGCTATTTTTCTTAGCTAG

TCCAGAGGGTGCAATGGCTAGTGATGGTACTTGGCAAGGAAAACAGTATC

TGAAAGAAGATGGCAGTCAAGCAGCAAATGAGTGGGTTTTTGATACTCAT

TATCAATCTTGGTTCTATATAAAAGCAGATGCTAACTATGCTGAAAATGA

ATGGCTAAAGCAAGGTGACGACTATTTTTACCTCAAATCTGGTGGCTATA

TGGCCAAATCAGAATGGGTAGAAGACAAGGGAGCCTTTTATTATCTTGAC

CAAGATGGAAAGATGAAAAGAAATGCTTGGGTAGGAACTTCCTATGTTGG

TGCAACAGGTGCCAAAGTAATAGAAGACTGGGTCTATGATTCTCAATACG

ATGCTTGGTTTTATATCAAAGCAGATGGACAGCACGCAGAGAAAGAATGG

CTCCAAATTAAAGGGAAGGACTATTATTTCAAATCCGGTGGTTATCTACT

TABLE 1-continued

```
GACAAGTCAGTGGATTAATCAAGCTTATGTGAATGCTAGTGGTGCCAAAG
TACAGCAAGGTTGGCTTTTTGACAAACAATACCAATCTTGGTTTTACATC
AAAGAAAATGGAAACTATGCTGATAAAGAATGGATTTTCGAGAATGGTCA
CTATTATTATCTAAAATCCGGTGGCTACATGGCAGCCAATGAATGGATTT
GGGATAAGGAATCTTGGTTTTATCTCAAATTTGATGGGAAAATGGCTGAA
AAAGAATGGGTCTACGATTCTCATAGTCAAGCTTGGTACTACTTCAAATC
CGGTGGTTACATGACAGCCAATGAATGGATTTGGGATAAGGAATCTTGGT
TTTATCTCAAATCTGATGGGAAAATAGCTGAAAAAGAATGGGTCTACGAT
TCTCATAGTCAAGCTTGGTACTACTTCAAATCCGGTGGTTACATGACAGC
CAATGAATGGATTTGGGATAAGGAATCTTGGTTTTACCTCAAATCTGATG
GGAAAATAGCTGAAAAAGAATGGGTCTACGATTCTCATAGTCAAGCTTGG
TACTACTTCAAATCTGGTGGCTACATGGCGAAAAATGAGACAGTAGATGG
TTATCAGCTTGAAGCGATGGTAAATGGCTTGGAGGAAAAACTACAAATG
AAAATGCTGCTTACTATCAAGTAGTGCCTGTTACAGCCAATGTTTATGAT
TCAGATGGTGAAAAGCTTTCCTATATATCGCAAGGTAGTGTCGTATGGCT
AGATAAGGATAGAAAAAGTGATGACAAGCGCTTGGCTATTACTATTTCTG
GTTTGTCAGGCTATATGAAAACAGAAGATTTACAAGCGCTAGATGCTAGT
AAGGACTTTATCCCTTATTATGAGAGTGATGGCCACCGTTTTTATCACTA
TGTGGCTCAGAATGCTAGTATCCCAGTAGCTTCTCATCTTTCTGATATGG
AAGTAGGCAAGAATATTATTCGGCAGATGGCCTGCATTTTGATGGTTTT
AAGCTTGAGAATCCCTTCCTTTTCAAAGATTTAACAGAGGCTACAAACTA
CAGTGCTGAAGAATTGGATAAGGTATTTAGTTTGCTAAACATTAACAATA
GCCTTTTGGAGAACAAGGGCGCTACTTTTAAGGAAGCCGAAGAACATTAC
CATATCAATGCTCTTTATCTCCTTGCCCATAGTGCCCTAGAAAGTAACTG
GGGAAGAAGTAAAATTGCCAAAGATAAGAATAATTTCTTTGGCATTACAG
CCTATGATACGACCCCTTACCTTTCTGCTAAGACATTTGATGATGTGGAT
AAGGGAATTTTAGGTGCAACCAAGTGGATTAAGGAAAATTATATCGATAG
GGGAAGAACTTTCCTTGGAAACAAGGCTTCTGGTATGAATGTGGAATATG
CTTCAGACCCTTATTGGGGCGAAAAAATTGCTAGTGTGATGATGAAAATC
AATGAGAAGCTAGGTGGCAAAGATTAG
```

4119.2 (SEQ. ID. NO. 226)
```
ATGAAAAAGTATTACAAAATATTGGGCATGGGCTTTTGTGGTCATCCC
CCTCTTGTTACAAGCAATTTTCTTCTATGTGCCGATGTTTCAAGGAGCCT
TTTACAGTTTTACCAACTGGACAGGATTGACTTATAACTACAAATTTGTT
GGCTTAAACAACTTTAAGCTCCTCTTCATGGATCCAAATTCATGAATGC
GATTGGCTTTACCGCAATCATTGCGATTGCCATGGTGGTTGGTGAGATTG
CACTCGGGATCTTCATTGCGCGTGTCTTGAATTCTAAAATCAAAGGCCAA
ACCTTCTTCCGTGCTTGGTTCTTCTTCCCAGCTGTTTTATCTGGTTTGAC
AGTGGCTTTGATCTTCAAGCAAGTCTTCAACTACGGTCTTCCAGCGATTG
GAAATGCCCTTCATATTGAATTTTTCCAAACCAGTCTTTTAGGGACTAAG
```

```
TGGGGAGCAATCTTTGCGGCTGTCTTTGTCCTTCTTTGGCAAGGGGTGGC
TATGCCCATCATCATCTTCCTAGCTGGTTTGCAATCTATTCCAACTGAGA
TTACAGAGGCAGCAAGGATTGATGGTGCGACTAGCAAGCAAGTTTTCTGG
AACATTGAATTGCCTTACTTGCTACCAAGTGTCTCTATGGTCTTTATCCT
AGCCTAAAAGGTGGGCTGACTGCCTTTGACCAAGTCTTTGCCATGACCGG
TGGTGGTCCAAACAATGCCACAACCTCACTTGGGCTCTTGGTTTATAACT
ATGCCTTTAAAAACAACCAATTCGGTTATGCCAATGCCATTGCCGTAATC
TTGTTCTTCTTAATTGTAGTGATTTCGATCATCCAATTGAGAGTATCTAA
GAAATTTGAAATTTAA
```

4119.3 (SEQ. ID. NO. 227)
```
ATGATGAAACAAGATGAAAGAAAAGCCCTGATTGGCAAATACATTCTATT
GATTCTAGGATCGGTTCTGATTTTAGTGCCGCTCCTTGCTACCCTCTTTA
GTTCCTTCAAACCCACTAAGGATATTGTAGATAATTTCTTTGGCTTTCCA
ACCAACTTCACATGGGACAACTTTAGCCGTCTCTTAGCTGATGGGATTGG
AGGCTATTATTGGAACTCTGTCGTCATCACTGTCTTGTCTTTACTTGCAG
TAATGATCTTTATCCCTATGGCAGCGTACTCCATCGCTCGCAATATGAGT
AAAAGAAAAGCCTTTACCATCATGTATACCCTCTTAATCCTCGGAATCTT
CGTACCTTTCCAAGTCATCATGATTCCGATTACGGTTATGATGAGTAAAC
TCGGTTTGGCTAATACCTTTGGTTTGATCTTGCTCTACTTGACCTATGCG
ATTCCACAGACCCTCTTTCTCTATGTGGCTATATCAAAATCTCGATTCC
AGAAAGTCTGGATGAAGCAGCAGAGATCGATGGGCTAATCAATTTACAA
CCTATTTCCGCATCATCTTCCCAATGATGAAACCGATGCATGCGACAACC
ATGATCATCAATGCCCTTTGGTTCTGGAATGACTTCATGTTGCCACTCCT
TGTCTTGAACCGGGATTCCAAAATGTGGACTCTGCCTTTGTTCCAATACA
ACTACGCAGGCCAATATTTCAACGACTACGGACCAAGCTTTGCCTCTTAC
GTGGTCGGCATTATCAGTATCACCATTGTCTATCTCTTCTTCCAACGCCA
TATCATTTCAGGAATGAGCAACGGGGCAGTGAAGTAA
```

4119.4 (SEQ. ID. NO. 228)
```
ATGAAAAGTATTCTTCAGAAAATGGGGAGCATCCGATGCTGCTTCTTTT
TCTTAGCTATAGTACTGTTATATCCATTCTTGCACAAAATTGGATGGGTC
TTGTGGCTTCAGTAGGAATGTTTCTATTTACTATTTTCTTTTTGCACTAT
CAGTCGATTTATCCCATAAATTCTTTCGATTGATTTTGCAGTTTGTCTT
GTTTGGTAGTGTCTTGTCAGCTGCTTTTGCCAGTTTAGAACATTTCCAAA
TTGTGAAGAAATTTAACTATGCTTTTCTTCACCCAATATGCAGGTGTGG
CATCAGAACCGGGCAGAAGTGACCTTCTTTAATCCTAATTATTATGGAAT
TATTTGTTGTTTCTGTATTATGATTGCTTTCTATCTGTTTACAACGACCA
AGTTGAATTGGTTGAAAGTATTCTGTGTGATTGCAGGCTTTGTTAATCTC
TTTGGTTTGAACTTTACTCAAAATCGAACTGCCTTTCCTGCTATTATCGC
TGGAGCAATTATCTATCTCTTTACGACTATTAAAAACTGGAAGGCCTTTT
GGCTTAGTATTGGGGTCTTCGCGATTGGTTTGAGTTTCCTCTTTTCTAGT
```

TABLE 1-continued

GATTTGGGAGTTCGAATGGGTACTTTAGACTCTTCTATGGAAGAACGCAT

TTCTATCTGGGATGCTGGGATGGCCTTGTTTAAGCAAAATCCTTTTTGGG

GTGAAGGGCCATTGACCTATATGAACTCTTATCCTCGGATACATGCTCCT

TATCATGAACATGCCCACAGTCTTTATATTGATACGATTCTGAGTTACGG

AATTGTGGGGACTATTTTATTAGTTTTGTCTTCTGTTGCTCCTGTTCGCT

TGATGATGGATATGAGTCAGGAGTCGGGGAAACGTCCGATTATCGGCCTT

TATCTATCTTTCCTTACAGTGGTTGCTGTGCACGGAATTTTTGACTTGGC

TCTCTTCTGGATTCAGTCAGGCTTTATTTTCTTGCTAGTTATGTGCAGTA

TTCCATTGGAGCATCGAATGTTGGTATCGGACATGACGGATTAA 4120.1 (SEQ. ID. NO. 229)
ATGTCAAAGATGGATGTTCAGAAAATCATTGCACCGATGATGAAGTTTGT

GAATATGCGTGGCATTATAGCTCTAAAAGATGGGATGTTAGCAATTTTGC

CATTGACAGTAGTTGGTAGTTTGTTCTTGATTATGGGACAATTGCCGTTC

GAAGGATTAAATAAGAGCATTGCTAGTGTTTTTGGAGCTAATTGGACAGA

GCCGTTTATGCAAGTATATTCAGGAACTTTTGCTATTATGGGTCTAATTT

CTTGTTTTTCAATTGCCTATTCTTATGCTAAGAATAGCGGCGTAGAGGCT

TTACCAGCTGGACTTCTATCTGTATCTGCATTCTTTATTTTGCTAAGATC

ATCTTATATCCCTAAACAAGGTGAGGCGATTGGGGACGCTATTAGTAAAG

TTTGGTTTGGAGGCCAAGGAATTATCGGTGCTATCATTATAGGTTTGGTA

GTAGGAAGTATTTATACCTTCTTTATAAAGAGAAAAATTGTTATTAAGAT

GCCAGAACAAGTTCCACAAGCTATTGCCAAACAGTTTGAAGCAATGATTC

CAGCATTTGTAATTTTCTTATCTTCTATGATTGTATATATTTTAGCGAAG

TCATTGACTAATGGCGGAACATTCATAGAAATGATTTATTCTGCTATTCA

AGTTCCGTTGCAAGGTTTAACTGGATCTTTGTATGGTGCTATTGGAATTG

CATTCTTTATATCATTTTTGTGGTGGTTTGGTGTTCATGGGCAATCGGTA

GTAAATGGAGTAGTGACAGCTCTGCTTTTATCTAATCTTGATGCTAATAA

AGCTATGTTAGCCTCTGCTAATCTATCATTAGAAAATGGTGCACATATTG

TTACTCAACAATTTTTAGATTCATTTTTAATTCTATCAGGTTCAGGGATT

ACGTTTGGTCTTGTAGTTGCCATGCTTTTTGCAGCAAAATCAAAACAATA

CCAAGCCTTAGGAAAAGTTGCAGCTTTTCCAGCAATATTTAACGTAAATG

AGCCAGTTGTATTTGGATTTCCGATTGTCATGAATCCAGTTATGTTTGTA

CCTTTCATTCTTGTTCCTGTACTTGCAGCTGTGATAGTATATGGAGCTAT

TGCAACAGGTTTCATGCAGCCATTCTCAGGGGTAACATTGCCTTGGAGTA

CACCAGCTATTTTATCAGGATTTTTGGTGGTGGATGGCAAGGAGTTATT

ACTCAGCTGGTGATATTAGCGATGTCTACATTGGTTTATTTTCCATTCTT

TAAAGTACAGGATCGTTTAGCTTACCAAAATGAAATCAAACAATCTTAG 4121.2 (SEQ. ID. NO. 230)
ATGAAGAAAAGGACTTAGTAGACCAACTAGTGTCAGAGATCGAGACGGG

GAAAGTCAGGACACTGGGAATATACGGTCATGGAGCTTCAGGTAAATCAA

CCTTTGCACAGGAATTGTACCAAGCTTTAGATTCTACTACAGTAAATTTG

CTAGAGACAGATCCTTATATCACCTCAGGACGCCATCTGGTACTACCCAA

GGACGCGCCGAATCAAAAGGTGACAGCCAGTCTGCCAGTGGCGCATGAAC

TGGAGAGTTTGCAGAGAGATATCCTTgCTTGCAGGCGGGTATGGATGTCT

TGA 4122.1 (SEQ. ID. NO. 231)
ATGAAGAAAAGATACCTAGTCTTGACAGCTTTGCTAGCCTTGAGTCTAGC

AGCTTGTTCACAAGAAAAAACAAAAAATGAAGATGGAGAAACTAAGACAG

AACAGACAGCCAAAGCTGATGGAACAGTCGGTAGTAAGTCTCAAGGAGCT

GCCCAGAAGAAAGCAGAAGTGGTCAATAAAGGTGATTACTACAGCATTCA

AGGGAAATACGATGAAATCATCGTAGCCAACAAACACTATCCATTGTCTA

AAGACTATAATCCAGGGGAAAATCCAACAGCCAAGGCAGAGTTGGTCAAA

CTCATCAAAGCGATGCAAGAGGCAGGTTTCCCTATTAGTGATCATTACAG

TGGTTTTAGAAGTTATGAAAACTCAGACCAAGCTCTATCAAGATTATGTC

AACCAAGATGGAAAGGCAGCAGCTGACCGTTACTCTGCCCGTCCTGGCTA

TAGCGAACACCAGACAGGCTTGGCCTTTGATGTGATTGGGACTGATGGTG

ATTTGGTGACAGAAGAAAAAGCAGCCCAATGGCTCTTGGATCATGCAGCT

GATTATGGCTTTGTTGTCCGTTATCTCAAAGGCAAGGAAAAGGAAACAGG

CTATATGGCTGAAGAATGGCACCTGCGTTATGTAGGAAAAGAAGCTAAAG

AAATTGCTGCAAGTGGTCTCAGTTTGGAAGAATACTATGGCTTTGAAGGC

GGAGACTACGTCGATTAA 4125.6 (SEQ. ID. NO. 232)
ATGCGTAAATTCTTAATTATTTTGTTGCTACCAAGTTTTTTGACCATTTC

AAAAGTCGTTAGCACAGAAAAAGAAGTCGTCTATACTTCGAAAGAAATTT

ATTACCTTTCACAATCTGACTTTGGTATTTATTTTAGAGAAAAATTAAGT

TCTCCCATGGTTTATGGAGAGGTTCCTGTTTATGCGAATGAAGATTTAGT

AGTGGAATCTGGGAAATTGACTCCCAAAACAAGTTTTCAAATAACCGAGT

GGCGCTTAAATAAACAAGGAATTCCAGTATTTAAGCTATCAAATCATCAA

TTTATAGCTGCGGACAAACGATTTTTATATGATCAATCAGAGGTAACTCC

AACAATAAAAAAGTATGGTTAGAATCTGACTTTAAACTGTACAATAGTC

CTTATGATTTAAAAGAAGTGAAATCATCCTTATCAGCTTATTCGCAAGTA

TCAATCGACAAGACCATGTTTGTAGAAGGAAGAGAATTTCTACATATTGA

TCAGGCTGGATGGGTAGCTAAAGAATCAACTTCTGAAGAAGATAATCGGA

TGAGTAAAGTTCAAGAAATGTTATCTGAAAAATATCAGAAAGATTCTTTC

TCTATTTATGTTAAGCAACTGACTACTGGAAAAGAAGCTGGTATCAATCA

AGATGAAAAGATGTATGCAGCCAGCGTTTTGAAACTCTCTTATCTCTATT

ATACGCAAGAAAAATAAATGAGGGTCTTTATCAGTTAGATACGACTGTA

AAATACGTATCTGCAGTCAATGATTTTCCAGGTTCTTATAAACCAGAGGG

AAGTGGTAGTCTTCCTAAAAAAGAAGATAATAAAGAATATTCTTTAAAGG

ATTTAATTACGAAAGTATCAAAAGAATCTGATAATGTAGCTCATAATCTA

TTGGGATATTACATTTCAAACCAATCTGATGCCACATTCAAATCCAAGAT

GTCTGCCATTATGGGAGATGATTGGGATCCAAAAGAAAAATTGATTTCTT

TABLE 1-continued

CTAAGATGGCCGGGAAGTTTATGGAAGCTATTTATAATCAAAATGGATTT
GTGCTAGAGTCTTTGACTAAAACAGATTTTGATAGTCAGCGAATTGCCAA
AGGTGTTTCTGTTAAAGTAGCTCATAAAATTGGAGATGCGGATGAATTTA
AGCATGATACGGGTGTTGTCTATGCAGATTCTCCATTTATTCTTTCTATT
TTCACTAAGAATTCTGATTATGATACGATTTCTAAGATAGCCAAGGATGT
TTATGAGGTTCTAAAATGA 4125.7 (SEQ. ID. NO. 233)
ATGAAAAAACAAATAATGGTTTAATTAAAAATCCTTTTCTATGGTTATT
ATTTATCTTTTTCCTTGTGACAGGATTCCAGTATTTCTATTCTGGGAATA
ACTCAGGAGGAAGTCAGCAAATCAACTATACTGAGTTGGTACAAGAAATT
ACCGATGGTAATGTAAAAGAATTAACTTACCAACCAAATGGTAGTGTTAT
CGAAGTTTCTGGTGTCTATAAAAATCCTAAAACAAGTAAAGAAGAAACAG
GTATTCAGTTTTTCACGCCATCTGTTACTAAGGTAGAGAAATTTACCAGC
ACTATTCTTCCTGCAGATACTACCGTATCAGAATTGCAAAAACTTGCTAC
TGACCATAAAGCAGAAGTAACTGTTAAGCATGAAAGTTCAAGTGGTATAT
GGATTAATCTACTCGTATCCATTGTGCCATTTGGAATTCTATTCTTCTTC
CTATTCTCTATGATGGGAAATATGGGAGGAGGCAATGGCCGTAATCCAAT
GAGTTTTGGACGTAGTAAGGCTAAAGCAGCAAATAAAGAAGATATTAAAG
TAAGATTTTCAGATGTTGCTGGAGCTGAGGAAGAAAAACAAGAACTAGTT
GAAGTTGTTGAGTTCTTAAAAGATCCAAAACGATTCACAAAACTTGGAGC
CCGTATTCCAGCAGGTGTTCTTTTGGAGGGACCTCCGGGGACAGGTAAAA
CTTTGCTTGCTAAGGCAGTCGCTGGAGAAGCAGGTGTTCCATTCTTTAGT
ATCTCAGGTTCTGACTTTGTAGAAATGTTTGTCGGAGTTGGAGCTAGTCG
TGTTCGCTCTCTTTTTGAGGATGCCAAAAAAGCAGCACCAGCTATCATCT
TTATCGATGAAATTGATGCTGTTGGACGTCAACGTGGAGTCGGTCTCGGC
GGAGGTAATGACGAACGTGAACAAACCTTGAACCAACTTTTGATTGAGAT
GGATGGTTTTGAGGGAAATGAAGGGATTATCGTCATCGCTGCGACAAACC
GTTCAGATGTACTTGACCCTGCCCTTTTGCGTCCAGGACGTTTTGATAGA
AAAGTATTGGTTGGTCGTCCTGATGTTAAAGGTCGTGAAGCAATCTTGAA
AGTTCACGCTAAGAATAAGCCTTTAGCAGAAGATGTTGATTTGAAATTAG
TGGCTCAACAAACTCCAGGCTTTGTTGGTGCTGATTTAGAGAATGTCTTG
AATGAAGCAGCTTTAGTTGCTGCTCGTCGCAATAAATCGATAATTGATGC
TTCAGATATTGATGAAGCAGAAGATAGAGTTATTGCTGGACCTTCTAAGA
AAGATAAGACAGTTTCACAAAAAGAACGAGAATTGGTTGCTTACCATGAG
GCAGGACATACCATTGTTGGTCTAGTCTTGTCGAATGCTCGCGTTGTCCA
TAAGGTTACAATTGTACCACGCGGCCGTGCAGGCGGATACATGATTGCAC
TTCCTAAAGAGGATCAAATGCTTCTATCTAAAGAAGATATGAAAGAGCAA
TTGGCTGGCTTAATGGGTGGACGTGTAGCTGAAGAAATTATCTTTAATGT
CCAAACCACAGGAGCTTCAAACGACTTTGAACAAGCGACACAAATGGCAC
GTGCAATGGTTACAGAGTACGGTATGAGTGAAAAACTTGGCCCAGTACAA

TATGAAGGAAACCATGCTATGCTTGGTGCACAGAGTCCTCAAAAATCAAT
TTCAGAACAAACAGCTTATGAAATTGATGAAGAGGTTCGTTCATTATTAA
ATGAGGCACGAAATAAAGCTGCTGAAATTATTCAGTCAAATCGTGAAACT
CACAAGTTAATTGCAGAAGCATTATTGAAATACGAAACATTGGATAGTAC
ACAAATTAAAGCTCTTTACGAAACAGGAAAGATGCCTGAAGCAGTAGAAG
AGGAATCTCATGCACTATCCTATGATGAAGTAAAGTCAAAAATGAATGAC
GAAAAATAA 4125.10 (SEQ. ID. NO. 234)
ATGAGGGAACCAGATTTTTTAAATCATTTTCTCAAGAAGGGATATTTCAA
AAAGCATGCTAAGGCGGTTCTAGCTCTTTCTGGTGGATTAGATTCCATGT
TTCTATTTAAGGTATTGTCTACTTATCAAAAAGAGTTAGAGATTGAATTG
ATTCTAGCTCATGTGAATCATAAGCAGAGAATTGAATCAGATTGGGAAGA
AAAGGAATTAAGGAAGTTGGCTGCTGAAGCAGAGCTTCCTATTTATATCA
GCAATTTTTCAGGAGAATTTTCAGAAGCGCGTGCACGAAATTTTCGTTAT
GATTTTTTTCAAGAGGTCATGAAAAAGACAGGTGCGACAGCTTTAGTCAC
TGCCCACCATGCTGATGATCAGGTGGAAACGATTTTTATGCGCTTGATTC
GAGGAACTCGCTTGCGCTATCTATCAGGAATTAAGGAGAAGCAAGTAGTC
GGAGAGATAGAAATCATTCGTCCCTTCTTGCATTTTCAGAAAAAAGACTT
TCCATCAATTTTTCACTTTGAAGATACATCAAATCAGGAGAATCATTATT
TTCGAAATCGTATTCGAAATTCTTACTTACCAGAATTGGAAAAAGAAAAT
CCTCGATTTAGGGATGCAATCTTAGGCATTGGCAATGAAATTTTAGATTA
TGATTTGGCAATAGCTGAATTATCTAACAATATTAATGTGGAAGATTTAC
AGCAGTTATTTTCTTACTCTGAGTCTACACAAAGAGTTTTACTTCAAACT
TATCTGAATCGTTTTCCAGATTTGAATCTTACAAAAGCTCAGTTTGCTGA
AGTTCAGCAGATTTTAAAATCTAAAAGCCAGTATCGTCATCCGATTAAAA
ATGGCTATGAATTGATAAAAGAGTACCAACAGTTTCAGATTTGTAAAATC
AGTCCGCAGGCTGATGAAAAGGAAGATGAACTTGTGTTACACTATCAAAA
TCAGGTAGCTTATCAAGGATATTTATTTTCTTTTGGACTTCCATTAGAAG
GTGAATTAATTCAACAAATACCTGTTTCACGTGAAACATCCATACACATT
CGTCATCGAAAAACAGGAGATGTTTTGATTAAAAATGGGCATAGAAAAAA
ACTCAGACGTTTATTTATTGATTTGAAAATCCCTATGGAAAAGAGAAACT
CTGCTCTTATTATTGAGCAATTTGGTGAAATTGTCTCAATTTTGGGAATT
GCGACCAATAATTTGAGTAAAAAAACGAAAAATGATATAATGAACACTGT
ACTTTATATAGAAAAAATAGATAGGTAA 4126.1 (SEQ. ID. NO. 235)
ATGAAGCGTTCTTCTCTTTTAGTTAGAATGGTTATTTCCATCTTTCTGGT
CTTTCTCATTCTCCTAGCTCTGGTTGGAACTTTCTACTATCAATCAAGTT
CTTCAGCCATTGAGGCCACCATTGAGGGCAACAGCCAAACGACCATCAGC
CAGACTAGCCACTTTATTCAGTCTTATATCAAAAAACTAGAAACCACCTC
GACTGGTTTGACCCAGCAGACGGATGTTCTGGCCTATGCTGAGAATCCCA
GTCAAGACAAGGTCGAGGGAATCCGAGATTTGTTTTTGACCATCTTGAAG

TABLE 1-continued

TCAGATAAGGACTTGAAAACTGTTGTGCTGGTGACCAAATCTGGTCAGGT

CATTTCTACAGATGACAGTGTGCAGATGAAAACTTCCTCTGATATGATGG

CTGAGGATTGGTACCAAAAGGCCATTCATCAGGGAGCTATGCCTGTTTTG

ACTCCAGCTCGTAAATCAGATAGTCAGTGGGTCATTTCTGTCACTCAAGA

ACTTGTTGATGCAAAGGGAGCCAATCTTGGTGTGCTTCGTTTGGATATTT

CTTATGAAACTCTGGAAGCCTATCTCAATCAACTCCAGTTGGGGCAGCAG

GGCTTTGCCTTCATTATCAATGAAAACCATGAATTTGTCTACCATCCTCA

ACACACAGTTTATAGTTCGTCTAGCAAAATGGAGGCTATGAAACCCTACA

TCGATACAGGTCAGGGTTATACTCCTGGTCACAAATCCTACGTCAGTCAA

GAGAAGATTGCAGGAACTGATTGGACGGTGCTTGGCGTGTCATCATTGGA

AAAGTTAGACCAGGTTCGGAGTCAGCTCTTGTGGACCTTGCTTGGGGCCA

GTGTCACATCTCTTCTTGTCTGTCTCTGCTTAGTGTGGTTCAGTCTTAAA

CGCTGGATTGCTCCTTTGAAGGATTTGAGAGAAACCATGTTGGAAATTGC

TTCTGGTGCTCAAAATCTTCGTGCCAAGGAAGTTGGTGCCTATGAACTGA

GAGAAGTAACTCGCCAATTTAATGCTATGTTGGATCAGATTGATCAGTTG

ATGGTAGCTATTCGTAGCCAGGAAGAAACGACCCGTCAGTACCAACTTCA

AGCCCTTTCGAGCCAGATTAATCCACATTTCCTCTATAACACTTTGGACA

CCATCATCTGGATGGCTGAATTTCATGATAGTCAGCGAGTGGTGCAGGTG

ACCAAGTCCTTGGCAACCTATTTCCGCTTGGCGCTCAATCAAGGCAAGGA

CTTGATTTGTCTCTCTGACGAAATCAATCATGTCCGCCAGTATCTCTTTA

TCCAGAAACAACGCTATGGAGATAAGCTTGGAATACGAAATTAATGAAAA

TGTTGCCTTTGATAATTTAGTCTTACCCAAGCTGGTCCTACAACCCCTTG

TAGAAAATGCTCTTTACCATGGCATTAAGGAAAAGGAAGGTCAGGGCCAT

ATTAAACTTTCTGTCCAGAAACAGGATTCGGGATTGGTCATCCGTATTGA

GGATGATGGCGTTGGCTTCCAAGATGCTGGTGATAGTAGTCAAAGTCAAC

TCAAACGTGGGGAGTTGGTCTTCAAAATGCGATCAACGGCTCAAACTTC

ATTTTGGAGCCAATTACCATATGAAGATTGATTCTAGACCCCAAAAGGG

ACGAAAGTTGAAATATATATAAATAGAATAGAAACTAGCTAA 4126.7 (SEQ. ID. NO. 236)
ATGAAGCGTTCTTCTCTTTTAGTTAGAATGGTTATTTCCATCTTTCTGGT

CTTTCTCATTCTCCTAGCTCTGGTTGGAACTTTCTACTATCAATCAAGTT

CTTCAGCCATTGAGGCCACCATTGAGGGCAACAGCCAAACGACCATCAGC

CAGACTAGCCACTTTATTCAGTCTTATATCAAAAAACTAGAAACCACCTC

GACTGGTTTGACCCAGCAGACGGATGTTCTGGCCTATGCTGAGAATCCCA

GTCAAGACAAGGTCGAGGGAATCCGAGATTGTTTTTGACCATCTTGAAG

TCAGATAAGGACTTGAAAACTGTTGTGCTGGTGACCAAATCTGGTCAGGT

CATTTCTACAGATGACAGTGTGCAGATGAAAACTTCCTCTGATATGATGG

CTGAGGATTGGTACCAAAAGGCCATTCATCAGGGAGCTATGCCTGTTTTG

ACTCCAGCTCGTAAATCAGATAGTCAGTGGGTCATTTCTGTCACTCAAGA

ACTTGTTGATGCAAAGGGAGCCAATCTTGGTGTGCTTCGTTTGGATATTT

CTTATGAAACTCTGGAAGCCTATCTCAATCAACTCCAGTTGGGGCAGCAG

GGCTTTGCCTTCATTATCAATGAAAACCATGAATTTGTCTACCATCCTCA

ACACACAGTTTATAGTTCGTCTAGCAAAATGGAGGCTATGAAACCCTACA

TCGATACAGGTCAGGGTTATACTCCTGGTCACAAATCCTACGTCAGTCAA

GAGAAGATTGCAGGAACTGATTGGACGGTGCTTGGCGTGTCATCATTGGA

AAAGTTAGACCAGGTTCGGAGTCAGCTCTTGTGGACCTTGCTTGGGGCCA

GTGTCACATCTCTTCTTGTCTGTCTCTGCTTAGTGTGGTTCAGTCTTAAA

CGCTGGATTGCTCCTTTGAAGGATTTGAGAGAAACCATGTTGGAAATTGC

TTCTGGTGCTCAAAATCTTCGTGCCAAGGAAGTTGGTGCCTATGAACTGA

GAGAAGTAACTCGCCAATTTAATGCTATGTTGGATCAGATTGATCAGTTG

ATGGTAGCTATTCGTAGCCAGGAAGAAACGACCCGTCAGTACCAACTTCA

AGCCCTTTCGAGCCAGATTAATCCACATTTCCTCTATAACACTTTGGACA

CCATCATCTGGATGGCTGAATTTCATGATAGTCAGCGAGTGGTGCAGGTG

ACCAAGTCCTTGGCAACCTATTTCCGCTTGGCGCTCAATCAAGGCAAGGA

CTTGATTTGTCTCTCTGACGAAATCAATCATGTCCGCCAGTATCTCTTTA

TCCAGAAACAACGCTATGGAGATAAGCTTGGAATACGAAATTAATGAAAA

TGTTGCCTTTGATAATTTAGTCTTACCCAAGCTGGTCCTACAACCCCTTG

TAGAAAATGCTCTTTACCATGGCATTAAGGAAAAGGAAGGTCAGGGCCAT

ATTAAACTTTCTGTCCAGAAACAGGATTCGGGATTGGTCATCCGTATTGA

GGATGATGGCGTTGGCTTCCAAGATGCTGGTGATAGTAGTCAAAGTCAAC

TCAAACGTGGGGAGTTGGTCTTCAAAATGCGATCAACGGCTCAAACTT

CATTTTGGAGCCAATTACCATATGAAGATTGATTCTAGACCCCAAAAGG

GACGAAAGTTGAAATATATATAAATAGAATAGAAACTAGCTAA 4127.4 (SEQ. ID. NO. 237)
ATGTTTTTAAATTATTAAGAGAAGCTCTTAAAGTCAAGCAGGTTCGATC

AAAAATTTTATTTACAATTTTTATCGTTTTGGTCTTTCGTATCGGAACTA

GCATTACAGTTCCTGGTGTGAATGCCAATAGCTTGAATGCTTTAAGTGGA

TTATCCTTCTTAAACATGTTGAGCTTGGTGTCGGGGAATGCCCTAAAAAA

CTTTTCGTTTTTTGCCCTAGGAGTTAGTCCCTATATCACCGCTTCTATTG

TTGTCCAACTCTTGCAAATGGATATTTTACCCAAGTTTGTAGAGTGGGT

AAACAAGGGGAAGTAGGTCGAAGAAAATTGAATCAAGCTACTCGTTATAT

TGCTCTAGTTCTCGCTTTTGTGCAATCTATCGGGATTACAGCTGGTTTTA

ATACCTTGGCTGGAGCTCAATTGATTAAAACTGCTTTAACTCCACAAGTT

TTTCTGACGATTGGTATCATCTTAACAGCTGGTAGTATGATTGTCACTTG

GTTGGGTGAGCAAATTACAGATAAGGGATACGGAAACGGTGTTTCCATGA

TTATCTTTGCCGGGATTGTTTCCTCAATTCCAGAGATGATTCAGGGCATC

TATGTGGACTACTTTGTGAACGTCCCAAGTAGCCGTATCACTTCATCTAT

CATTTTCGTAATCATTTTGATTATTACTGTATTGTTGATTATTTACTTTA

CAACTTATGTTCAACAAGCAGAATACAAAATTCCAATCCAATATACTAAG

GTTGCACAAGGTGCTCCATCTAGCTCTTACCTTCCGTTAAAAGTAAACCC

TABLE 1-continued

TGCTGGAGTTATCCCTGTTATCTTTGCCAGTTCGATTACTGCAGCGCCTG
CGGCTATTCTTCAGTTTTTGAGTGCCACAGGTCATGATTGGGCTTGGGTA
AGGGTAGCACAAGAGATGTTGGCAACTACTTCTCCAACTGGTATTGCCAT
GTATGCTTTGTTGATTATTCTCTTTACATTCTTCTATACGTTTGTACAGA
TTAATCCTGAAAAAGCAGCAGAGACCTACAAAAGAGTGGTGCCTATATCC
ATGGAGTTCGTCCTGGTAAAGGTACAGAAGAATATATGTCTAAACTTCTT
CGTCGTCTTGCAACTGTTGGTTCCCTCTTCCTTGGTGTGA 4127.5 (SEQ. ID. NO. 238)
ATGGATATTAGACAAGTTACTGAAACCATCGCCATGATTGAGGAGCAAAA
CTTCGATATTAGAACCATTACCATGGGGATTTCTCTTTTGGACTGTATCG
ATCCAGATATCAATCGTGCTGCGGAGAAAATCTATCAAAAAATTACGACA
AAGGCGGCTAATTTAGTAGCTGTTGGTGATGAAATTGCGGCTGAGTTGGG
AATTCCTATCGTTAATAAGCGTGTATCGGTGACACCTATTTCTCTGATTG
GGGCAGCGACAGATGCGACGGACTACGTGGTTCTGGCAAAAGCGCTTGAT
AAGGCTGCGAAAGAGATTGGTGTGGACTTTATTGGTGGTTTTTCTGCCTT
AGTACAAAAAGGTTATCAAAAGGGAGATGAGATTCTCATCAATTCCATTC
CTCGCGCTTTGGCTGAGACGGATAAGGTCTGCTCGTCAGTCAATATCGGC
TCAACCAAGTCTGGTATTAATATGACGGCTGTGGCAGATATGGGACGAAT
TATCAAGGAAACAGCAAATCTTTCAGATATGGGAGTGGCCAAGTTGGTTG
TATTCGCTAATGCTGTTGAGGACAATCCATTTATGGCGGGTGCCTTTCAT
GGTGTTGGGGAAGCAGATGTTATCATCAATGTCGGAGTTTCTGGTCCTGG
TGTTGTGAAACGTGCTTTGGAAAAAGTTCGTGGACAGAGCTTTGATCTAG
TAGCCGAAACAGTTAAGAAAACTGCCTTTAAAATCACTCGTATCGGTCAA
TTGGTTGGTCAAATGGCCAGTGAGAGACTGGGTGTGGAGTTTGGTATTGT
GGACTTGAGTTTGGCACCAACCCCTGCGGTTGGAGACTCTGTGGCACGTG
TCCTTGAGGAAATGGGGCTAGAAACAGTTGGCACGCATGGAACGACGGCT
GCCTTGGCCCTCTTGAACGACCAAGTTAAAAAGGGTGGAGTGATGGCCTG
CAACCAAGTCGGTGGTTTATCTGGTGCCTTTATCCCTGTTTCTGAGGATG
AAGGAATGATTGCTGCAGTGCAAAATGGCTCTCTTAATTTAGAAAAACTA
GAAGCTATGACGGCTATCTGTTCTGTTGGATTGGATATGATTGCCATCCC
AGAAGATACGCCTGCTGAAACTATTGCGGCTATGATTGCGGATGAAGCAG
CAATCGGTGTTATCAACATGAAAACAACAGCTGTTCGTATCATTCCCAAA
GGAAAAGAAGGCGATATGATTGAGTTTGGTGGTCTATTAGGAACTGCACC
CGTTATGAAGGTTAATGGGGCTTCGTCTGTCGACTTCATCTCTCGCGGTG
GACAAATCCCAGCACCAATTCATAGTTTTAAAAATTAA 4128.1 (SEQ. ID. NO. 239)
ATGACACAGATTATTGATGGGAAAGCTTTAGCGGCCAAATTGCAGGGGCA
GTTGGCTGAAAAGACTGCAAAATTAAAGGAAGAAACAGGTCTAGTGCCTG
GTTTGGTAGTGATTTTGGTTGGGGACAATCCAGCCAGCCAAGTCTACGTT
CGCAACAAGGAGAGGTCAGCCCTTGCGGCTGGTTTCCGTAGCGAAGTAGT
ACGGGTTCCAGAGACCATTACTCAAGAGGAATTCTTAGACCTGATTGCTA
AATACAATCAGGATCCAGCTTGGCATGGGATTTTGGTTCAGTTGCCATTA
CCAAAACACATTGATGAAGAGGCGGTTCTATTGGCTATTGACCCAGCAAA
AGGATGTGGATGGTTTCCATCCTCTAAACATGGGGCGTCTTTGGTCTGGT
CATCCAGTCATGATTCCTTCGACACCGGCAGGAATTATGGAAATGTTCCA
TGAATATGGGATTGACT6TGGAAGGTAAAAATGCAGTCGTCATCGGTCGA
TCCAATATTGTCGGAAAACCTATGGCCCAGCTTCTTTTGGCAAAGAATGC
AACAGTAACCTTGACTCACTCACGTACTCATAATCTTTCCAAGGTGGCTG
CAAAAGCAGATATTCTGGTTGTTGCAATCGGTCGTGCCAAGTTTGTGACT
GCTGACTTTGTCAAACCAGGTGCGGTAGTCATTGACGTTGGGATGAACCG
CGATGAAAATGGTAAGCTCTGTGGGGATGTTGATTATGAGGCGGTTGCCC
CACTTGCTAGCACATTACGCCAGTCCCTGGAGGTGTCGGTCCTATGACC
ATTACTATGCTGATGGAGCAAACCTATCAGGCAGCACTTAGGACATTGGA
TAGAAAATAA 4128.2 (SEQ. ID. NO. 240)
ATGTCTAAATTTAATCGTATTCATTTGGTGGTACTGGATTCTGTAGGAAT
CGGTGCAGCACCAGATGCTAATAACTTTGTCAATGCAGGGGGTTCCAGATG
GAGCTTCTGACACACTGGGACACATTTCAAAAACAGTTGGTTTGAATGTC
CCAAACATGGCTAAAATAGGTCTTGGAAATATTCCTCGTGAAACTCCTCT
TAAGACTGTAGCAGCTGAAAGCAATCCAACTGGATATGCAACAAAATTAG
AGGAAGTATCTCTTGGTAAGGATACTATGACTGGACACTGGGAAATCATG
GGACTCAACATTACTGAGCCTTTCGATACTTTCTGGAACGGATTCCCAGA
AGAAATCCTGACAAAAATCGAAGAATTCTCAGGACGCAAGGTTATTCGTG
AAGCCAACAAACCTTATTCAGGAACGGCTGTTATCTATGATTTTGGACCA
CGTCAGATGGAAACTGGAGAGTTGATTATCTATACTTCAGCTGACCCTGT
TTTGCAGATTGCTGCCCACGAAGACATTATTCCTTTGGATGAATTGTACC
GTATCTGTGAATACGCTCGTTCGATTACCCTTGAGCGTCCTGCCCTTCTT
GGTCGCATCATTGCTCGCCCTTATGTAGGTGAACCAGGTAACTTCACTCG
TACGGCAAACCGTCGTGACTTGGCTGTATCTCCATTTTTCCCAACTGTTT
TGGATAAATTGAATGAGGCTGGTATCGATACTTATGCTGTGGGTAAAATC
AACGATATCTTTAACGGTGCTGGTATCAACCATGACATGGGTCACAACAA
GTCAAATAGTCATGGAATTGATACACTATTGAAGACTATGGGACTTGCTG
AGTTTGAAAAGGATTCTCATTCACAAACCTAGTTGACTTTGATGCCCTT
TACGGCCATCGTCGTAATGCTCACGGTTACCGTGATTGCTTGCATGAGTT
TGATGAACGCTTACCTGAAATTATCGCAGCTATGAGAGAGAATGACCTTC
TCTTGATTACTGCGGACCATGGAAATGACCCAACGTATGCAGGAACGGAT
CACACTCGGGAATATATTCCATTGTTGGCCTATAGCCCTGCCTTTAAAGG
AAATGGTCTCATTCCAGTAGGACATTTTGCAGATATTTCAGCGACTGTTG
CCGATAACTTTGGTGTGGAAACTGCTATGATTGGGGAAAGTTTCTTAGAT
AAATTGGTATAA

TABLE 1-continued 4129.2 (SEQ. ID. NO. 241)
ATGTTTATTTCCATCAGTGCTGGAATTGTGACATTTTTACTAACTTTAGT
AGAAATTCCGGCCTTTATCCAATTTTATAGAAAGGCGCAAATTACAGGCC
AGCAGATGCATGAGGATGTCAAACAGCATCAGGCAAAAGCTGGGACTCCT
ACAATGGGAGGTTTGGTTTTCTTGATTACTTCTGTTTTGGTTGCTTTCTT
TTTCGCCCTATTTAGTAGCCAATTCAGCAATAATGTGGGAATGATTTTGT
TCATCTTGGTCTTGTATGGCTTGGTCGGATTTTTAGATGACTTTCTCAAG
GTCTTTCGTAAAATCAATGAGGGGCTTAATCCTAAGCAAAAATTAGCTCT
TCAGCTTCTAGGTGGAGTTATCTTCTATCTTTTCTATGAGCGCGGTGGCG
ATATCCTGTCTGTCTTTGGTTATCCAGTTCATTTGGGATTTTTCTATATT
TTCTTCGCTCTTTTCTGGCTAGTCGGTTTTTCAAACGCAGTAAACTTGAC
AGACGGTGTTGACGGTTTAGCTAGATTTCCGTTGTGATTAGTTTGTCTGC
CTATGGAGTTATTGCCTATGTGCCAGGTCAGATGGATATTCTTCTAGTAA
TTCTTGCCATGATTGGTGGTTTGCTCGGTTTCTTCATCTTTAACCATAAG
CCTGCCAAGGTCTTTATGGGTGATGTGGGAAGTTTGGCCCTAGGTGGGAT
GCTGGCAGCTATCTCTATGGCTCTCCACCAAGAATGGACTCTCTTGATTA
TCGGAATTGTGTATGTTTTGAAACAACTTCTGTTATGATGCAAGTCAGT
TATTTCAAACTGACAGGTGGTAAACGTATTTTCCGTATGACGCCTGTACA
TCACCATTTTGAGCTTGGGGGATTGTCTGGTAAAGGAAATCCTTGGAGC
GAGTGGAAGGTTGACTTCTTCTTTTGGGGAGTGGGACTTCTAGCAAGTCT
CCTGACCCTAGCAATTTTATATTTGATGTAA 4133.1 (SEQ. ID. NO. 242)
TTGTTTAAGAAAAATAAAGACATTCTTAATATTGCATTGCCAGCTATGGG
TGAAAACTTTTTGCAGATGCTAATGGGAATGGTGGACAGTTATTTGGTTG
CTCATTTAGGATTGATAGCTATTTCAGGGGTTTCAGTAGCTGGTAATATT
ATCACCATTTATCAGGCGATTTTCATCGCTCTGGGAGCTGCTATTTCCAG
TGTTATTTCAAAAAGCATAGGGCAGAAAGACCAGTCGAAGTTGGCCTATC
ATGTGACTGAGGCGTTGAAGATTACCTTACTATTAAGTTTCCTTTTAGGA
TTTTTGTCCATCTTCGCTGGGAAAGAGATGATAGGACTTTTGGGGACGGA
GAGGGATGTAGCTGAGAGTGGTGGACTGTATCTATCTTTGGTAGGCGGAT
CGATTGTTCTCTTAGGTTTAATGACTAGTCTAGGAGCCTTGATTCGTGCA
ACGCATAATCCACGTCTGCCTCTCTATGTTAGTTTTTTATCCAATGCCTT
GAATATTCTTTTTCAAGTCTAGCTATTTTTGTTCTGGATATGGGGATAG
CTGGTGTTGCTTGGGGACAATTGTGTCTCGTTTGGTTGGTCTTGTGATT
TTGTGGTCACAATTAAAACTGCCTTATGGAAGCCAACTTTTGGTTTAGA
TAAGGAACTGTTGACCTTGGCTTTACCAGCAGCTGGAGAGCGACTTATGA
TGAGGGCTGGAGATGTAGTGATCATTGCCTTGGTCGTTTCTTTTGGGACG
GAGGCAGTTGCTGGGAATGCAATCGGAGAAGTCTTGACCCAGTTTAACTA
TATGCCTGCCTTTGGCGTCGCTACGGCAACGGTCATGCTGTTGGCCCGAG
CAGTTGGAGAGGATGATTGGAAAAGAGTTGCTAGTTTGAGTAAACAAACC
TTTTGGCTTTCTCTGTTCCTCATGTTGCCCCTGTCCTTTAGTATATATGT CTTGGGTGTACCATTAACTCATCTCTATACGACTGATTCTCTAGCGGTGG
AGGCTAGTGTTCTAGTGACACTGTTTTCACTACTTGGGACCCCTATGACG
ACAGGAACAGTCATCTATACGGCAGTCTGGCAGGGATTAGGAAATGCACG
CCTCCCTTTTTATGCGACAAGTATAGGAATGTGGTGTATCCGCATTGGGA
CAGGATATCTGATGGGATTGTGCTTGGTTGGGCTTGCCTGGTATTTGG
GCAGGGTCTCTCTTGGATAATGGTTTTCGCTGGTTATTTCTACGCTATCG
TTACCAGCGCTATATGAGCTTGAAAGGATAG 4135.2 (SEQ. ID. NO. 243)
ATGCAAACCAAGAAAAACACTCGCAAGCAGCCGTTCTTGGCTTGCAGCAC
TTACTAGCCATGTACTCAGGATCTATCCTGGTTCCCATCATGATTGCGAC
AGCCCTTGGCTATTCAGCTGAGCAGTTGACCTACCTGATTTCTACAGATA
TCTTCATGTGTGGGGTGGCAACCTTCCTCCAACTCCAACTCAACAAATAC
TTTGGGATTGGACTCCCAGTCGTTCTTGGAGTTGCATTCCAGTCGGTCGC
TCCCTTGATTATGATTGGGCAAAGCCATGGTAGTGGCGCTATGTTTGGTG
CCCTTATCGCATCTGGGATTTACGTGGTTCTTGTTTCAGGCATCTTCTCA
AAAGTAGCCAATCTCTTCCCATCTATCGTAACAGGATCTGTTATTACCAC
GATTGGTTTAACCTTGATCCCTGTCGCTATTGGAAATATGGGAAATAACG
TTCCAGAGCCAACTGGTCAAAGTCTCTTGCTTGCAGCTATTACTGTTCTG
ATTATCCTCTTGATCAACATCTTTACCAAAGGATTTATCAAGTCTATCTC
TATTTTGATTGGTCTGGTTGTTGGAACTGCCATTGCTGCTACTATGGGCT
TGGTGGACTTCTCTCCTGTTGCGGTAGCTCCACTTGTCCATGTCCCAACT
CCACTCTACTTTGGGATGCCAACCTTTGAAATCTCATCTATTGTCATGAT
GTGTATCATCGCAACGGTGTCTATGGTTGAGTCAACTGGTGTTTATCTGG
CCTTGTCTGATATCACAAAGGAATCCAATCGACAGCACGCGCCTTCGCAA
CGGATACCGCGCAGAAGGTTTGGCCGTACTTCTCGGAGGAATCTTTAACA
CCTTCCCTTACACCGGATTTTCACAAAACGTTGTTTGGTTAAATTGTCA
GGCATCAAAAAACGCCTGCCAATCTACTACGCAGCTGGTTTCCTGGTTCT
CCTTGGACTGCTTCCTAAGTTTGGCGCCCTTGCCCAAATCATTCCAAGCT
CCGTCCTCGGTGGTGCCATGCTGGTAATGTTTGGTTTTGTATCAATTCAA
GGGATGCAAATCCTCGCCCGTGTTGACTTTGCTAACAATGAACACAACTT
CCTTATCGCAGCTGTTCAATCGCTGCAGGTGTCGGTCTCAACAACAGTA
ATCTCTTTGTCAGCATGCCGACAGCCTTCCAAATGTTCTTCTCAAACGGA
ATCGTCGTAGCCAGCCTACTCGCTATTGTCCTCAATGCCGTATTAAATCA
TAAAAAGAAATAA 4136.2 (SEQ. ID. NO. 244)
ATGAAAGATAGAAATAAAAGAATATTTACAAGACAAGGGAAAGGTGACTG
TTAATGATTTGGCTCAGGCTTGGGAAAAGACAGTTCCAAGGATTTTCGTG
AGTTGATTAAAACCTTGTCCTTAATGGAAAGAAAGCACCAAATTCGTTTT
GAAGAAGATGGTAGTCTGACATTAGAAATTAAGAAAAAACATGAGATTAC
CCTCAAGGGGATTTTTCATGCCCATAAAAATGGCTTTGGCTTTGTTAGTC TABLE 1-continued TGGAAGGCGAGGAGGACGACCTTTTTGTAGGGAAAAATGATGTCAACTAT
GCTATTGATGGTGATACCGTCGAGGTAGTGATTAAGAAAGTCGCTGACCG
CAATAAGGGAACAGCAGCAGAAGCCAAAATTATTGATATCCTAGAACACA
GTTTGACAACAGTTGTCGGGCAAATCGTTCTGGATCAGGAAAAACCTAAG
TATGCTGGCTATATTCGTTCAAAAAATCAGAAAATCAGTCAACCGATTTA
TGTTAAGAAACCAGCCCTAAAATTAGAAGGAACAGAAGTTCTCAAAGTCT
TTATCGATAAATACCCAAGCAAGAAACATGATTTCTTTGTCGCGAGTGTT
CTCGATGTAGTGGGACACTCAACGGATGTCGGAATTGATGTTCTTGAGGT
CTTGGAATCAATGGACATTGTATCCGAGTTTCCAGAAGCTGTTGTTAAGG
AAGCAGAAAGTGTGCCTGATGCTCCGTCTCAAAAGGATATGGAAGGTCGT
CTGGATCTAAGAGATGAAATTACCTTTACCATTGACGGTGCGGATGCCAA
GGACTTGGACGATGCAGTGCATATCAAGGCTCTGAAAAATGGCAATCTGG
AGTTTGGGGTTCACATCGCAGATGTTTCTTATTATGTGACCGAGGGGTCT
GCCCTTGACAAGGAAGCCCTTAACCGTGCGACTTCTGTTTACGTGACAGA
CCGAGTGGTGCCAATGCTTCCAGAACGACTATCAAATGGCATCTGCTCTC
TCAATCCCCAAGTTGACCGCCTGACCCAGTCTGCTATTATGGAGATTGAT
AAACATGGTCGTGTGGTCAACTATACCATTACACAAACAGTTATCAAGAC
CAGTTTTCGTATGACCTATAGCGATGTCAATGATATCCTAGCTGGCGATG
AAGAAAAGAGAAAAGAATATCATAAAATTGTATCAAGTATCGAACTCATG
GCCAAGCTTCATGAAACTTTAGAAAACATGCGTGTGAAACGTGGAGCTCT
CAATTTTGATACCAATGAAGCGAAGATTTTAGTGGATAAACAAGGTAAGC
CTGTTGATATCGTTCTTCGGCAGCGTGGTATTGCCGAGCGGATGATTGAG
TCTTTTATGTTGATGGCTAATGAAACAGTTGCCGAACATTTCAGCAAGTT
GGATTTGCCTTTTATCTATCGAATTCACGAGGAGCCTAAGGCTGAAAAGG
TTCAGAAGTTTATTGATTATGCTTCGAGTTTTGGCTTGCGCATTTATGGA
ACTGCCAGTGAGATTAGTCAGGAGGCACTTCAAGACATCATGCGTGCTGT
TGAGGGAGAACCTTATGCAGATGTATTGTCCATGATGCTTCTTCGCTCTA
TGCAGCAGGCTCGTTATTCGGAGCACAATCACGGCCACTATGGACTAGCT
GCTGACTATTATACTCACTTTACCAGTCCAATTCGTCGTTATCCAGACCT
TCTTGTTCACCGTATGATTCGGGATTACGGCCGTTCTAAGGAAATAGCAG
AGCATTTTGAACAAGTGATTCCAGAGATTGCGACCCAGTCTTCCAACCGT
GAACGTCGTGCCATAGAAGCTGAGCGTGAAGTCGAAGCCATGAAAAGGC
TGAGTATATGGAAGAATACGTGGGTGAAGAGTATGATGCAGTTGTATCAA
GTATTGTCAAATTCGGTCTCTTTGTCGAATTGCCAAACACAGTTGAAGGC
TTGATTCACATCACTAATCTGCCTGAATTTTATCATTTCAATGAGCGTGA
TTTGACTCTTCGTGGAGAAAAATCAGGTATCACTTTCCGAGTGGGTCAGC
AGATCCGTATCCGTGTTGAAAGAGCGGATAAAATGACTGGAGAGATTGAT
TTTTCATTCGTACCTAGTGAGTTTGATGTGATTGAAAAAGGCTTGAAACA
GTCTAGTCGTAGTGGCAGAGGGCGTGATTCAAATCGTCGTTCGGATAAGA
AGGAAGACAAGAGAAAATCAGGACGCTCAAATGATAAGCGTAAGCATTCA CAAAAAGACAAGAAGAAAAAAGGAAAGAAACCTTTTTCACCGGAAGTAGC
TAAGAAAGGAGCCAAGCATGGCAAAGGGCGAGGGAAAGGTCGTCGCACAA
AATAA 4137.2 (SEQ. ID. NO. 245)
ATGGGCACAACAGGATTTACAATAATTGACTTAATTATCTTGATTGTTTA
TTTACTTGCGGTGTTGGTTGCAGGTATCTATTTCTCTAAAAAAGAGATGA
AAGGAAAAGAGTTCTTTAAAGGAGATGGTTCGGTTCCTTGGTATGTTACT
TCGGTATCCATTTTTGCCACAATGCTCAGTCCGATTTCCTTCTTGGGACT
CGCTGGTAGCTCTTATGCAGGTAGCTGGATTTTATGGTTTGCTCAATTAG
GGATGGTAGTAGCTATTCCACTGACAATTCGTTTTATCTTACCTATCTTT
GCACGGATAGACATCGATACGGCATATGATTACTTGGATAAACGTTTTAA
TTCTAAAAGCACTTCGTATTATTTCAGCACTCTTGTTTATTATTTATCAA
TTGGGACGTATGTCTATCATTATGTACCTCCCATCAGCTGGTTTATCAGT
ATTGACAGGAATTGACATCAATATTTTGATTATTTTGATGGGTGTAGTTG
CAATTGTTTATTCTTATACTGGTGGTCTAAAATCCGTATTATGGACAGAC
TTTATTCAAGGTGTGATTCTGATTAGTGGTGTCGTTTTAGCTTTATTTGT
ACTGATTGCTAATATTAAAGGTGGCTTTGGTGCAGTAGCAGAAACATTAG
CAAACGGGAAATTCCTTGCTGCAAATGAAAAACTTTTCGATCCTAACTTG
CTTTCAAACTCCATCTTTTTAATTGTGATGGGTTCAGGCTTTACAATCTT
GTCTTCCTATGCTTCATCTCAAGATTTGGTTCAACGTTTTACTACAACAC
AAAATATTAAGAAACTTAATAAGATGTTGTTCACAAACGGTGTTTTGTCA
CTTGCAACTGCAACAGTCTTTTACTTGATTGGTACAGGCTTGTACGTATT
CTATCAAGTACAAAATGCAGATAGTGCAGCTAGCAATATCCCTCAAGACC
AAATCTTTATGTACTTTATTGCATACCAGTTACCAGTAGGTATCACAGGT
TTGATCTTGGCAGCGATTTATGCAGCATCTCAATCAACTATTTCAACAGG
TTTGAACTCTGTTGCAACTTCATGGACATTGGATATTCAAGATGTCATTT
CTAAAAATATGTCAGACAATCGTCGTACGAAAATTGCACAATTCGTATCT
CTAGCAGTAGGTTTATTCTCAATTGGTGTTTCCATTGTCATGGCTCACTC
AGATATTAAATCTGCATACGAATGGTTCAATAGTTTCATGGGACTTGTAC
TTGGTCTACTTGGTGGTGTATTTATTCTTGGATTTGTTTCTAAAAAAGCA
AATAAACAAGGTGCTTATGCAGCGCTGATTGTATCAACCATCGTCATGGT
ATTTATTAAATACTTCCTTCCTCCAACAGCTGTTAGCTACTGGGCATATT
CATTGATTTCAATCTCTGTATCAGTAGTTTCAGGTTATATTGTATCTGTT
CTTACTGGAAATAAAGTATCTGCACCTAAATATACAACGATTCATGATAT
TACAGAAATTAAAGCGGATTCAAGTTGGGAAGTTCGTCACTAA 4138.1 (SEQ. ID. NO. 246)
ATGAAATTTAGTAAAAAATATATAGCAGCTGGATCAGCTGTTATCGTATC
CTTGAGTCTATATGCCTATGCACTAAACCAGCATCGTTCGCAGGAAAATA
AGGACAATAATCGTGTCTCTTATGTGGATGGCAGCCAGTCAAGTCAGAAA
AGTGAAAACTTGACACCAGACCAGGTTAGCCAGAAAGAAGGAATTCAGGC TABLE 1-continued TGAGCAAATTGTAATCAAAATTACAGATCAGGGCTATGTAACGTCACACG
GTGACCACTATCATTACTATAATGGGAAAGTTCCTTATGATGCCCTCTTT
AGTGAAGAACTCTTGATGAAGGATCCAAACTATCAACTTAAAGACGCTGA
TATTGTCAATGAAGTCAAGGGTGGTTATATCATCAAGGTCGATGGAAAAT
ATTATGTCTACCTGAAAGATGCAGCTCATGCTGATAATGTTCGAACTAAA
GATGAAATCAATCGTCAAAAACAAGAACATGTCAAAGATAATGAGAAGGT
TAACTCTAATGTTGCTGTAGCAAGGTCTCAGGGACGATATACGACAAATG
ATGGTTATGTCTTTAATCCAGCTGATATTATCGAAGATACGGGTAATGCT
TATATCGTTCCTCATGGAGGTCACTATCACTACATTCCCAAAAGCGATTT
ATCTGCTAGTGAATTAGCAGCAGCTAAAGCACATCTGGCTGGAAAAAATA
TGCAACCGAGTCAGTTAAGCTATTCTTCAACAGCTAGTGACAATAACACG
CAATCTGTAGCAAAAGGATCAACTAGCAAGCCAGCAAATAAATCTGAAAA
TCTCCAGAGTCTTTTGAAGGAACTCTATGATTCACCTAGCGCCCAACGTT
ACAGTGAATCAGATGGCCTGGTCTTTGACCCTGCTAAGATTATCAGTCGT
ACACCAAATGGAGTTGCGATTCCGCATGGCGACCATTACCACTTTATTCC
TTACAGCAAGCTTTCTGCCTTAGAAGAAAGATTGCCAGAATGGTGCCTA
TCAGTGGAACTGGTTCTACAGTTTCTACAAATGCAAAACCTAATGAAGTA
GTGTCTAGTCTAGGCAGTCTTTCAAGCAATCCTTCTTCTTTAACGACAAG
TAAGGAGCTCTCTTCAGCATCTGATGGTTATATTTTTAATCCAAAAGATA
TCGTTGAAGAAACGGCTACAGCTTATATTGTAAGACATGGTGATCATTTC
CATTACATTCCAAAATCAAATCAAATTGGGCAACCGACTCTTCCAAACAA
TAGTCTAGCAACACCTTCTCCATCTCTTCCAATCAATCCAGGAACTTCAC
ATGAGAAACATGAAGAAGATGGATACGGATTTGATGCTAATCGTATTATC
GCTGAAGATGAATCAGGTTTTGTCATGAGTCACGGAGACCACAATCATTA
TTTCTTCAAGAAGGACTTGACAGAAGAGCAAATTAAGGTGCGCAAAAACA
TTTAG 4139.1 (SEQ. ID. NO. 247)
ATGAAAAAAAGAGCAATAGTGGCAGTCATTGTACTGCTTTTGATTGGGCT
GGATCAGTTGGTCAAATCCTATATCGTCCAGCAGATTCCACTGGGTGAAG
TGCGCTCCTGGATCCCCAATTTCGTTAGCTTGACCTACCTGCAAAATCGA
GGTGCAGCCTTTTCTATCTTACAAGATCAGCAGCTGTTATTCGCTGTCAT
TACTCTGGTTGTCGTGATAGGTGCCATTTGGTATTTACATAAAACACATG
GAGGACTCATTCTGGATGGTCTTGGGTTTGACTCTAATAATCGCGGGTGG
TCTTGGAAACTTTATTGACAGGGTCAGTCAGGGCTTTGTTGTGGATATGT
TCCACCTTGACTTTATCAACTTTGCAATTTTCAATGTGGCAGATAGCTAT
CTGACGGTTGGAGTGATTATTTTATTGATTGCAATGCTAAAAGAGGAAAT
AAATGGAAATTAA 4139.5 (SEQ. ID. NO. 248)
ATGAATACAAATCTTGCAAGTTTTATCGTTTGGACTGATCATCGATGAAA
ACGACCGTTTTTACTTTGTGCAAAAGGATGGTCAAACCTATGCTCTTGCT
AAGGAAGAAGGCCAACATACAGTAGGGGATACGGTCAAAGGTTTTGCATA CACGGATATGAAGCAAAAACTCCGCCTGACAACCTTAGAAGTGACTGCCA
CTCAGGACCAATTTGGTTGGGGACGTGTCACAGAGGTTCGTAAGGACTTG
GGTGTCTTTGTGGATACAGGCCTTCCTGACAAGGAAATCGTTGTGTCACT
CGATATTCTCCCTGAGCTCAAGGAACTCTGGCCTAAGAAGGGCGACCAAC
TCTACATCCGTCTTGAAGTGGATAAGAAAGACCGTATCTGGGGCCTCTTG
GCTTATCAAGAAGACTTCCAACGTCTTGCTCGTCCTGCCTACAACAACAT
GCAGAACCAAAACTGGCCAGCCATTGTTTACCGTCTCAAGCTGTCAGGAA
CTTTTGTTTACCTACCAGAAAATAATATGCTTGGTTTTATTCATCCTAGC
GAGCGTTACGCAGAGCCACGTTTGGGGCAAGTATTAGATGCGCGCGTTAT
TGGTTTCCGTAAGTGGACCGCACTCTGAACCTCTCCCTCAAACCACGCTC
CTTTGAAATGTTGGAAAACGATGCTCAGATGATTTTGACTTATTTGGAAA
GCAATGGCGGTTTCATGACCTTAAATGACAAGTCATCTCCAGACGACATC
AAGGCAACCTTTGGCATTTCTAAAGGTCAGTTCAAGAAAGCTTTAGGTGG
TCTTATGAAGGCTGGTAAAATCAAGCAGGACCAGTTTGGGACAGAGTTGA
TTTAG 4139.8 (SEQ. ID. NO. 249)
ATGAAAGATGTTAGTCTATTTTTATTGAAAAAAGTTTTCAAAAGCCGCTT
AAACTGGATTGTCTTAGCTTTATTTGTATCTGTACTCGGTGTTACCTTTT
ATTTAAATAGTCAGACTGCAAACTCACACAGCTTGGAGAGCAGGTTGGAA
AGTCGCATTGCAGCCAACGAGAGGGCTATCAATGAAAATGAAGAGAAACT
CTCCCAAATGTCTGATACCAGCTCGGAGGAATACCAGTTTGCTAAAAATA
ATTTAGACGTGCAAAAAAATCTTTTGACGCGAAAGACAGAAATTCTGACT
TTATTAAAAGAAGGGCGCTGGAAAGAAGCCTACTATTTGCAGTGGCAAGA
TGAAGAGAAGAATTATGAATTTGTATCAAATGACCCGACTGCTAGCCCTG
GCTTAAAAATGGGGGTTGACCGCGAACGGAAGATTTACCAAGCCCTGTAT
CCCTTGAACATAAAAGCACATACTTTGGAGTTTCCGACCCACGGGATTGA
TCAGATTGTCTGGATTTTAGAGGTTATCATCCCAAGTTTGTTTGTGGTTG
CTATTATTTTTATGCTAACACAACTATTTGCAGAAAGATATCAAAATCAT
CTGGACACAGCTCACTTATATCCTGTTTCAAAAGTGACATTTGCAATATC
CTCTCTTGGAGTTGGAGTGGGATATGTAACTGTGCTGTTTATCGGAATCT
GTGGCTTTTCTTTTCTAGTGGGAAGTCTGATAAGTGGTTTTGGACAGTTA
GATTATCCCTACCCAATTTATAGCTTAGTGAATCAAGAAGTAACTATTGG
GAAAATACAAGATGTATTATTTCCTGGCTTGCTCTTAGCTTTCTTAGCCT
TTATCGTCATTGTGGAAGTTGTGTACTTGATTGCTTACTTTTTCAAGCAA
AAAATGCCTGTCCTCTTTCTTCACTCATTGGGATTGTTGGCTTATTGTT
TGGTATCCAAACCATTCAGCCTCTTCAAAGGATTGCACATCTGATTCCCT
TTACTTACTTGCGTTCAGTGGAGATTTTATCTGGAAGATTACCTAAGCAG
ATTGATAATGTCGATCTAAATTGGAGCATGGGAATGGTCTTACTTCCTTG
CCTGATTATCTTTTTGCTATTGGGAATTCTATTTATTGAAAGATGGGGAA
GTTCACAGAAAAAAGAATTTTTTAATAGATTCTAG TABLE 1-continued 4141.1 (SEQ. ID. NO. 250)
ATGATGAAGTTCATATTGGATATTGTTAGTACACCAGCTATTTTAGTAGC
TTTAATTGCAATCTTAGGATTAGTTCTTCAGAAGAAGAAATTACCTGATA
TTATTAAAGGTGGAATTAAGACCTTTGTTGGTTTCTTAGTTGTATCTGGT
GGTGCAGGAATTGTACAAAATTCTTTAAATCCATTTGGTACCATGTTTGA
GCATGCTTTTCATTTATCTGGCGTTGTGCCGAATAATGAAGCAATTGTAG
CTGTAGCTTTAACAACATATGGCTCAGCTACTGCAATGATTATGTTTGCA
GGCATGGTGTTCAATATCTTAATCGCTCGTTTTACTCGATTTAAATATAT
TTTTTTAACAGGGCACCACACTCTATATATGGCATGTATGATTGCGGTCA
TTTTATCAGTTGCTGGCTTTACTAGCTTGCCTCTCATCTTACTAGGAGGA
TTAGCACTCGGTATTATTATGAGTATTTCCCCAGCATTTGTGCAAAAATA
TATGGTTCAATTAACTGGAAATGACAAGGTAGCTTTAGGTCATTTCAGTT
CTTTGGGATATTGGTTGAGTGGTTTTACTGGTAGCCTTATCGGTGACAAA
TCAAAATCAACAGAGGACATTAAATTTCCAAAGAGTTTAGCTTTTTTACG
TGATAGTACTGTTAGTATTACTTTATCCATGGCAGTTATTTACATTATTG
TAGCTATCTTTGCAGGGTCAGAATATATAGAAAAAGAAATCAGTAGTGGT
ACAAGTGGTCTAGTTTATGCTTTACAATTAGCAGGTCAATTTGCAGCAGG
GGTATTTGTTATTTTAGCAGGTGTTCGCCTTATTTTGGGCGAAATTGTTC
CAGCCTTTAAAGGTATTTCAGAGCGTCTTGTACCTAATTCAAAACCTGCT
TTGGATTGTCCGATTGTTTATACTTATGCACCCAATGCAGTTCTAATTGG
ATTTATCTCTAGTTTTGTTGGTGGTTTAGTAAGTATGGTAATTATGATTG
CTTCAGGAACGGTTGTTATCTTACCAGGTGTTGTGCCTCATTTCTTCTGT
GGAGCGACTGCAGGTGTCATTGGGAATGCATCTGGTGGTGTTCGTGGAGC
CACTATTGGAGCATTTTTACAAGGTATTTTAATCAGTTTTCTTCCAGTCT
TTTTAATGCCAGTTTTGGGAGGACTTGGTTTCCAAGGATCAACTTTCTCA
GATGCAGATTTTGGTCTATCAGGAATTATTTTAGGAATGTTAAATCAATT
TGGCTCACAAGCAGGCATTGTGATTGGTCTTGTTCTTATTCTAGCAGTTA
TGTTTGGAGTATCCTTTATTAAAAAGCCATCTGCAACGGAGGAATAA 4142.3 (SEQ. ID. NO. 251)
ATGATTAAAACATTTCTCTCTGCCCTTTCGGTCATTCTCTTTTCTATCCC
TATCATAACTTATTCTTTTTTCCCATCTTCTAATCTTAACATTTGGCTAT
CTACCCAACCTATCTTGGCACAGATTTATGCCTTCCCCTTAGCTACTGCA
ACTATGGCTGCTATTTTAAGTTTCTTATTTTTTTTCCTATCTTTTTACAA
GAAAAATAAACAAATACGGTTTTACTCTGGCATTTTGCTCTTACTATCGC
TCATATTACTATTATTCGGAACAGATAAAACCCTTTCTTCTGCATCAAAT
AAGACTAAAAACTTAAAATTAGTAACTTGGAACGTCGCTAATCAAATAGA
AGCACAACATATTGAGCGAATTTTTAGCCATTTTGACGCCGATATGGCTA
TATTCCCTGAACTAGCTACCAATATCAGAGGTGAGCAAGAAAACCAGAGA
ATCAAACTATTGTTTCATCAAGTTGGACTTTCTATGCCAACTATGATAT
TTTCACTTCTCCACCTACCAATAGTGGAATAGCTCCTGTGACTGTGATTG TCAAGAAAAGTTATGGTTTCTATACAGAAGCTAAAACTTTTCATACAACA
CGGTTCGGGACAATTGTATTACATTCGAGAAAACAAAATATACCAGATAT
CATTGCCTTGCATACTGCGCCTCCTCTGCCAGGTTTAATGGAAATCTGGA
AGCAAGACTTAAACATCATTCATAATCAATTGGCTTCAAAATATCCAAAG
GCTATTATTGCAGGTGATTTTAATGCAACTATGCGTCATGGAGCACTTGC
AAAAATAAGCTCTCATAGGGACGCATTAAATGCACTGCCACCTTTTGAAA
GAGGAACTTGGAATAGCCAAAGTCCAAAACTTTTTAATGCAACAATAGAT
CATATTTTATTGCCTAAAAACCACTACTATGTTAAAGATTTAGACATTGT
AAGTTTTCAAAACTCTGATCATAGATGTATTTTTACAGAAATCACATTTT
AA 4142.4 (SEQ. ID. NO. 252)
ATGAATCCAATCCAAAGATCTTGGGCTTATGTCAGCAGAAAGCGACTGAG
AAGTTTTATTTTATTTCTGATTTATTGGTCTTATTGGCCGGAATTTCAG
CCTGTTTGACTCTGATGAAGTCCAACAAAACAGTAGAAAGCAATCTTTAT
AAATCACTCAATACATCTTTTTCTATTAAGAAGATAGAGAATGGTCAGAC
ATTCAAGTTGTCAGACCTAGCATCTGTAAGCAAGATTAAGGGGCTGGAAA
ATGTCTCTCCTGAACTTGAGACGGTCGCAAAACTAAAAGACAAGGAAGCA
GTGACTGGCGAGCAGAGCGTGGAGCGTGATGATTATCAGCTGCAGACAA
TAACTTGGTTAGCTTAACGGCTCTTGAGGATTCATCCAAGGATGTAACCT
TTACCAGTTCGGCTTTCAATCTAAAAGAAGGGCGACACCTTCAAAAAGGG
GATTCCAAGAAAATCCTTATCCACGAAGAATTGGCTAAGAAGAACGGTCT
TTCGCTTCATGACAAGATTGGCTTGGATGCTGGTCAGTCTGAATCTGGAA
AAGGACAAACAGTAGAGTTTGAGATTATCGGCATCTTTTCTGGTAAAAAA
CAAGAGAAATTCACAGGCTTGTCTTCTGACTTCAGTGAAAATCAAGTCTT
TACAGACTATGAAAGTAGCCAAACCCTTTTGGGCAATAGTGAAGCTCAAG
TCAGTGCAGCACGCTTCTATGTAGAAAATCCTAAGGAAATGGACGGACTC
ATGAAGCAGGTAGAAAACTTGGCCTTGGAAAATCAAGGCTACCAAGTCGA
AAAGGAAAACAAGGCTTTTGAACAAATCAAAGACTCAGTTGCAACTTTCC
AAACCTTCCTGACCATCTTCCTTTATGGGATGTTGATAGCAGGAGCTGGA
GCCTTAATTCTGGTTTTGTCTCTCTGGTTGAGAGAACGGGTCTATGAAGT
GGGGATTTACTTGCACTTGGAAAAGGCAAGAGCTCGATCTTCCTACAAT
TCTGTTTAGAGGTAGTTTTGGTATCTCTTGGAGCTTTGCTTCCAGCATTT
GTTGCAGGAAACGCAATCACAACTTACCTACTCCAAACTCTACTAGCAAG
TGGAGATCAGGCAAGCTTACAAGATACACTAGCCAAAGCAAGCAGTTTAT
CAACTAGCATCTTATCTTTTGCAGAATCCTATGTTTTTCTAGTTCTGCTT
AGTTGCTTATCTGTAGCCCTTTGTTTCCTATTCTTATTTAGAAAATCACC
GAAAGAAATTTATCATCTATTAGTTAA 4142.5 (SEQ. ID. NO. 253)
ATGTTACACAACGCATTTGCCTATGTTACAAGGAAGTTTTTCAAATCGAT
TGTCATCTTCCTGATTATTCTCCTCATGGCGAGCTTGAGTTTGGTCGGCT
TGTCAATCAAGGGAGCTACTGCCAAGGCTTCTCAGGAGACCTTTAAAAAT ATCACCAATAGCTTCTCCATGCAAATCAATCGTCGCGTCAACCAAGGAAC
GCCTCGTGGTGCTGGGAATATCAAGGGTGAAGACATCAAAAAAATCACCG
AAAACAAGGCCATTGAGTCTTATGTCAAACGTATCAACGCTATCGGAGAT
TTGACTGGATATGACCTGATTGAAACGCCAGAAACCAAGAAGAATCTCAC
TGCTGATCGTGCCAAGCGTTTTGGAAGTAGCTTGATGATTACAGGTGTCA
ATGACTCCTCTAAAGAAGACAAGTTTGTCTCTGGTTCTTATAAACTAGTC
GAAGGAGAGCACTTAACCAACGACGACAAGGATAAAATCCTCTTGCACAA
GGACTTGGCAGCCAAACACGGCTGGAAAGTAGGGGACAAGGTTAAACTGG
ACTCTAATATCTACGATGCAGATAATGAAAAAGGAGCCAAGGAAACAGTT
GAAGTGACAATCAAGGGACTCTTTGATGGTCATAATAAGTCAGCAGTAAC
CTACTCACAAGAACTTTACAGAAACACAGCTATTACAGACATTCACACTG
CTGCAAAACTTTATGGATACACAGAAGACACAGCCATTTATGGGGACGCA
ACCTTCTTTGTAACAGCAGACAAGAACTTGGATGATGTTATGAAAGAGTT
GAATGGCATCAGTGGTATCAACTGGAAGAGCTACACACTCGTCAAGAGCT
CCTCTAACTACCCAGCTCTTGAGCAATCTATCTCTGGTATGTACAAGATG
GCCAACCTCCTCTTCTGGGGTAGCTTGAGCTTCTCAGTTCTCCTCCTTGC
CCTCTTGCTCAGCCTTTGGATCAACGCCCGTCGCAAGGAAGTGGGAATTC
TCCTCTCTATCGGCCTCAAGCAGGCAAGTATCTTGGGTCAATTCATCACC
GAATCTATCTTGATTGCTATCCCTGCTCTAGTTTCTGCTTACTTCCTAGC
TAATTACACTGCCCGTGCAATTGGAAACACTGTCCTTGCCAATGTGACTT
CAGGTGTTGCCAAACAGGCTAGTAAGGCGGCTCAAGCCTCTAACCTTGGT
GGTGGTGCAGAAGTAGATGGCTTTAGCAAGACCTTGTCGAGCCTAGACAT
TTCCATTCAGACATCAGACTTTATCATCATTTTTGTCCTTGCCTTGGTTC
TAGTGGTTCTCGTTATGGCGCTTGCTTCAAGCAATCTCCTTAGAAAACAA
CCAAAAGAGCTCTTGCTGGATGGTGAATAA 4144.1 (SEQ. ID. NO. 254)
ATGTCACAGGATAAACAAATGAAAGCTGTTTCTCCCCTTCTGCAGCGAGT
TATCAATATCTCATCGATTGTCGGTGGGGTTGGGAGTTTGATTTTCTGTA
TTTGGGCTTATCAGGCTGGGATTTTACAATCCAAGGAAACCCTCTCTGCC
TTTATCCAGCAGGCAGGCATCTGGGGTCCACCTCTCTTTATCTTTTTACA
GATTTTACAGACTGTCGTCCCTATCATTCCAGGGGCCTTGACCTCGGTGG
CTGGGGTCTTTATCTACGGGCACATCATCGGGACTATCTACAACTATATC
GGCATCGTGATTGGCTGTGCCATTATCTTTTATCTAGTGCGCCTATACGG
AGCTGCCTTTGTCCAGTCTGTCGTCAGCAAGCGCACCTACGACAAGTACA
TCGACTGGCTAGATAAGGGCAATCGTTTTGACCGCTTCTTTATTTTTATG
ATGATTTGGCCCATTAGCCCAGCTGACTTTCTCTGTATGCTGGCTGCCCT
GACCAAGATGAGCTTCAAGCGCTACATGACCATCATCATTCTGACCAAAC
CCTTTACCCTCGTGGTTTATACCTACGGTCTGACCTATATTATTGACTTT
TTCTGGCAAATGCTTTGA 4144.2 (SEQ. ID. NO. 255)
ATGAGAAATATGTGGGTTGTAATCAAGGAAACCTATCTTCGACATGTCGA
GTCATGGAGTTTCTTCTTTATGGTGATTTCGCCGTTCCTCTTTTTAGGAA
TCTCTGTAGGAATTGGGCATCTCCAAGGTTCTTCTATGGCTAAAAATAAT
AAAGTGGCAGTAGTGACAACAGTGCCATCTGTAGCAGAAGGACTGAAGAA
TGTAAATGGTGTTAACTTCGACTATAAAGACGAAGCAAGTGCCAAAGAAG
CAATTAAAGAAGAAAAATTAAAAGGTTATTTGACCATTGATCAAGAAGAT
AGTGTTCTAAAGGCAGTTTATCATGGCGAAACATCGCTTGAAAATGGAAT
TAAATTTGAGGTTACAGGTACACTCAATGAACTGCAAAATCAGCTTAATC
GTTCAACTGCTTCCTTGTCTCAAGAGCAGGAAAAACGCTTAGCGCAGACA
ATTCAATTCACAGAAAAGATTGATGAAGCCAAGGAAAATAAAAAGTTTAT
TCAAACAATTGCAGCAGGTGCCTTAGGATTCTTTCTTTATATGATTCTGA
TTACCTATGCGGGTGTAACAGCTCAGGAAGTTGCCAGTGAAAAAGGCACC
AAAAATTATGGAAGTCGTTTTTCTAGCATAAGGGCAAGTCACTATTTCTA
TGCGCGGATGATGGCTCTGTTTCTAGTGATTTTAACGCATATTGGGATCT
ATGTTGTAGGTGGTCTGGCTGCCGTTTTGCTCTTTAAAGATTTGCCATTC
TTGGCTCAGTCTGGTATTTTGGATCACTTGGGAGATGCTATCTCACTGAA
TACCTTGCTCTTTATTTTGATCAGTCTTTTCATGTACGTAGTCTTGGCAG
CCTTCCTAGGATCTATGGTTTCTCGTCCTGAGGACTCAGGGAAAGCCTTG
TCGCCTTTGATGATTTTGATTATGGGTGGTTTTTTTGGAGTGACAGCTCT
AGGTGCAGCTGGTGACAATCTCCTCTTGAAGATTGGTTCTTATATTCCCT
TTATTTCGACCTTCTTTATGCCGTTTCGAACGATTAATGACTATGCGGGG
GGAGCAGAAGCATGGATTTCACTTGCTATTACAGTGATTTTTGCGGTGGT
AGCAACAGGATTTATCGGACGCATGTATGCTAGTCTCGTTCTTCAAACGG
ATGATTAGGGATTTGGAAAACCTTTAAACGTGCCTTATCTTATAAATAG 4144.3 (SEQ. ID. NO. 256)
ATGACAGAAACCATTAAATTGATGAAGGCTCATACTTCAGTGCGCAGGTT
TAAAGAGCAAGAAATTCCCCAAGTAGACTTAAATGAGATTTTGACAGCAG
CCCAGATGGCATCATCTTGGAAGAATTTCCAATCCTACTCTGTGATTGTG
GTACGAAGTCAAGAGAAGAAAGATGCCTTGTATGAATTGGTACCTCAAGA
AGCCATTCGCCAGTCTGCTGTTTTCCTTCTCTTTGTCGGAGATTTGAACC
GAGCAGAAAGGGAGCCCGACTTCATACCGACACCTTCCAACCCCAAGGT
GTGGAAGGTCTCTTGATTAGTTCGGTCGATGCAGCTCTTGCTGGACAAAA
CGCCTTGTTGGCAGCTGAAAGCTTGGGCTATGGTGGTGTGATTATCGGTT
TGGTTCGATACAAGTCTGAAGAAGTGGCAGAGCTCTTTAACCTACCTGAC
TACACCTATTCTGTCTTTGGGATGGCACTGGGTGTGCCAAATCAACATCA
TGATATGAAACCGAGACTGCCACTAGAGAATGTTGTCTTTGAGGAAGAAT
ACCAAGAACAGTCAACTGAGGCAATCCAAGCTTATGACCGTGTTCAGGCT
GACTATGCTGGGGCGCGTGCGACCACAAGCTGGAGTCAGCGCCTAGCAGA 4146.1 (SEQ. ID. NO. 257)
ATGTTAAAACTTATTGCTATTGTTGGAACAAATTCAAAACGTTCTACAAA
CCGTCAATTGCTTCAATACATGCAAAAACACTTTACTGACAAAGCTGAAA
TTGAACTTGTTGAAATCAAGGCCATTCCTGTCTTCAACAAACCAGCTGAC
AAGCAAGTACCTGCTGAAATATTGGAAATTGCTGCTAAAATCGAAGAGGC
AGATGGCGTTATTATCGGTACTCCTGAGTATGATCACTCTATTCCAGCTG
TTTTGATGAGCGCTCTTGCTTGGTTGTCTTATGGTATTTACCCACTTTTG
AACAAACCAATCAGTATTACAGGTGCTTCTTACGGTACGCTTGGTTCATC
TCGTGCCCAATTGCAACTTCGTCAAATCTTGAATGCTCCTGAAATCAAGG
CAAATGTTCTTCCAGATGAATTCTTGCTCTCACACTCTCTTCAAGCATTT
AACCCAAGTGGCGACTTGGTTGACCTTGATGTTATCAAGAAATTGGATGC
CATCTTTGATGACTTCCGTATCTTTGTAAAAATCACAGAAAAATTACGTA
ATGCACAAGAATTACTTCGCAAAGATGCTGAAGACTTTGACTGGGAAAAT
TTGTAA 4146.2 (SEQ. ID. NO. 258)
ATGAATACCTATCAATTAAATAATGGAGTAGAAATTCCAGTATTGGGATT
TGGAACTTTTAAGGCTAAGGATGGAGAAGAAGCCTATCGTGCAGTGTTAG
AAGCCTTGAAGGCTGGTTATCGTCATATTGATACGGCGGCGATTTATCAG
AATGAAGAAAGTGTTGGTCAAGCAATCAAAGATAGCGGAGTTCCACGTGA
AGAAATGTTCGTAACTACCAAGCTTTGGAATAGTCAGCAAACCTATGAGC
AAACTCGTCAAGCTTTGGAAAAATCTATAGAAAAACTGGGCTTGGATTAT
TTGGATTTGTATTTGATTCATTGGCCGAACCCAAAACCGCTCAGAGAAAA
TGACGCATGGAAAACTCGCAATGCGGAAGTTTGGAGAGCGATGGAAGACC
TCTATCAAGAAGGGAAAATCCGTGCTATCGGCGTTAGCAATTTTCTTCCC
CATCATTTGGATGCCTTGCTTGAAACTGCAACTATCGTTCCTGCGGTCAA
TCAAGTTCGCTTGGCGCCAGGTGTGTATCAAGATCAAGTCGTAGCTTACT
GTCGTGAAAGGGAATTTTATTGGAAGCTTGGGGCCTTTTGGACAAGGA
GAACTGTTTGATAGCAAGCAAGTCCAAGAAATAGCAGCAAATCACGGAAA
ATCGGTTGCTCAGATAGCCTTGGCCTGGAGCTTGGCAGAAGGATTTTTAC
CACTTCCAAAATCTGTCACAACCTCTCGTATTCAAGCTAATCTTGATTGC
TTTGGAATTGAACTGAGTCATGAGGAGAGAGAAACCTTAAAAACGATTGC
TGTTCAATCGGGTGCTCCACGAGTTGATGATGTGGATTTCTAG 4147.1 (SEQ. ID. NO. 259)
ATGAGGTGCAAAATGCTTGATCCAATTGCTATTCAACTAGGACCCCTAGC
CATTCGTTGGTATGCCTTATGTATTGTGACAGGCTTGATTCTTGCGTTTT
ATTTGACCATGAAAGAAGCACCTAGAAAGAAGATCATACCAGACGATATT
TTAGATTTTATCTTAGTAGCCTTTCCCTTGGCTATTTTAGGAGCTCGTCT
CTACTATGTTATTTTCCGATTTGATTACTATAGTCAGAATTTAGGAGAGA
TTTTTGCCATTTGGAATGGTGGTTTGGCCATTTACGGTGGTTTGATAACT
GGGGCTCTTGTGCTCTATATCTTTGCTGACCGTAAACTCATCAATACTTG
GGATTTTCTAGATATTGCGGCGCCTAGCGTTATGATTGCTCAAAGTTTGG
GGCGTTGGGGTAATTTCTTTAACCAAGAAGCTTATGGTGCAACAGTGGAT
AATCTGGATTATCTACCTGGCTTTATCCGTGACCAGATGTATATTGAGGG
GAGCTACCGTCAACCGACTTTCCTTTATGAGTCTCTATGGAATCTGCTTG
GCTTTGCCTTGATTCTGATTTTTAGACGGAAATGGAAGAGTCTCAGACGA
GGTCATATCACGGCCTTTTACTTGATTTGCTATGGTTTCGGTCGTATGGT
TATCGAAGGTATGCGAACAGATAGTCTCATGTTCTTCGGCTTTCGAGTGT
CCCAATGGCTGTCAGTTGTCCTTATCGGTCTCGGTATAATGATCGTTATT
TATCAAAATCGAAAGAAGGCCCCTTACTATATTACAGAGGAGGAAAACTA
A 4147.2 (SEQ. ID. NO. 260)
ATGGGTAAATTATCCTCAATCCTTTTAGGAACCGTTTCAGGTGCAGCTCT
TGCCTTGTTTTTAACAAGTGATAAGGGCAAACAAGTTTGCAGTCAGGCTC
AAGATTTTCTAGATGATTTGAGAGAAGATCCGGAGTATGCCAAGGAGCAA
GTCTGTGAAAAACTGACGAAGTTAAGGAGCAGGCTACAGATTTTGTTCT
GAAAACAAAAGAACAGGTTGAGTCAGGTGAAATCACTGTGGACAGTATAC
TTGCTCAAACTAAATCCTATGCTTTTCAAGCGACAGAAGCATCAAAAAAT
CAATTAAATAATCTCAAGGAGCAATGGCAAGAAAAAGCCGAAGCTCTTGA
TGACTCAGAAGAGATTGTGATTGATATAACAGAAGAATAA 4147.3 (SEQ. ID. NO. 261)
ATGAAAACTAAATTGATCTTTTGGGGCTCTATGCTCTTTCTCCTCTCCCT
CTCCATCCTTCTGACCATTTATCTGGCTTGATTTTCTATCCTATGGAGAT
TCAGTGGCTAAACTTAACGAATCGAGTCTATCTAAAACCAGAAACCATTC
AATACAATTTTCATATCTTGATGAATTATCTGACCAATCCTTTTAGTCAG
GTCTTACAGATGCCTGATTTTCGTTCGTCAGCAGCTGGTCTGCACCATTT
CGCAGTGGTCAAGAATCTCTTTCATTTGGTTCAGCTAGTAGCTCTAGTGA
CACTGCCAAGTTTCTATGTCTTTGTCAATAGGATTGTGAAAAAGGACTTT
TTGTCTCTTTATCGAAAAGTCTCCTGGCTCTAGTAGTCTTACCTGTGAT
GATTGGACTTGGGGGAGTTTTCATTGGTTTTGACCAATTCTTTACTCTTT
TCCATCAAATTCTCTTTGTGGGAGATGATACCTGGCTTTTTGATCCAGCC
AAGGATCCTGTTATTATGATTTTGCCAGAGACCTTCTTTCTTCATGCCTT
CCTCCTCTTTTTTGCCCTCTATGAAAACTTCTTGGCTATCTGTATCTGA
AAAGTCGTAGGAAGTGA 4149.1 (SEQ. ID. NO. 262)
ATGACTTATCATTTTACTGAAGAATACGATATTATTGTAATTGGTGCGGG
ACACGCTGGGGTTGAGGCTTCCTTGGCCGCTAGCCGTATGGGCTGTAAGG
TCCTGCTTGCGACCATCAATATTGAAATGCTGGCTTTCATGCCTTGTAAT
CCCTCTATCGGTGGTTCTGCCAAGGGGATTGTCGTGCGTGAAGTCGATGC
CCTCGGTGGCGAGATGGCCAAAACCATTGACAAGACTTACATCCAGATGA
AGATGCTAAACACAGGGAAGGGGCCAGCTGTCCGTGCCCTTCGTGCGCAG TABLE 1-continued

GCTGACAAGGAACTTTACTCTAAGGAGATGCGCAAGACGGTTGAAAACCA

AGAAAATCTGACCCTTCGTCAAACCATGATTGATGAGATTTTGGTGGAAG

ATGGCAAGGTTGTCGGTGTGTCGTACAGCCACCCATCAAGAATATGCTGC

TAAGGCTGTTATTGTGACGACAGGGACTGCTCTCCGTGGGGAAATTATCA

TCGGAGACCTCAAGTACTCATCAGGTCCTAACCACAGCTTGGCTTCTATT

AACCTAGCTGACAATCTCAAGGAACTGGGTCTCGAAATCGGTCGTTTCAA

GACAGGACCCCTCCACGTGTCAAGGCTTCTTCTATCAATTACGATGTGAC

AGAAATTCAGCCAGGAGACGAAGTGCCTAATCATTTCTCATACACTTCAC

GTGATGAGGATTATGTCAAGGACCAAGTACCATGCTGGTTGACCTATACC

AATGGTACCAGTCATGAGATTATCCAAAACAACCTCCACCGTGCGCCTAT

GTTTACAGGTGTGGTCAAGGGAGTGGGGCCTCGTTACTGTCCGTCGATTG

AAGACAAGATTGTGCGCTTTGCGGACAAGGAACGTCACCAACTCTTCCTT

GAGCCAGAAGGGCGCATTACTGAGGAAGTCTATGTGCAAGGACTTTCAAC

CAGTCTGCCTGAGGATGTCCAGCGTGACTTGGTGCATTCCATCAAAGGTT

TGGAAAATGCAGAGATGATGCGGACAGGTTATGCTATTGAGTATGATATG

GTCTTGCCTCATCAGTTGCGTGCGACTTTGGAAACCAAGAAAATCTCAGG

TCTCTTCACTGCTGGTCAGACAAATGGAACATCAGGTTACGAAGAGGCAG

CAGGCCAAGGGATTATCGCGGGTATCAATGCGGCTCTGAAAATCCAAGGC

AAGCCTGAATTGATTTTGAAGCGCAGTGATGGTTATATCGGGGTGATGAT

CGACGACTTGGTGACCAAGGGAACCATTGAACCCTACCGTCTCTTGACCA

GTCGTGCTGAATACCGTCTCATTCTTCGTCATGACAATGCTGATATGCGC

TTGACTGAGATGGGACGCGAGATTGGCCTTGTGGACGATGAACGCTGGGC

TCGTTTTGAAATCAAGAAAATCAATTTGATAATGAGATGAAGCGCCTAG

ACAGTATCAAACTCAAGCCAGTCAAGGAAACCAATGCCAAGGTTGAGGAG

ATGGGCTTCAAACCCTTGACCGATGCAGTGACAGCCAAGGAATTCCTTCG

CCGTCCAGAAGTTTCTTACCAAGATGTGGTGGCCTTCATCGGACCAGCTG

CAGAAGACTTGGATGACAAGATTATCGAATTGATTGAAACAGAAATCAAG

TATGAAGGCTATATTTCCAAAGCCATGGACCAGGTTGCCAAGATGAAACG

CATGGAAGAAAACGCATTCCGGCCAATATCGACTGGGATGACATTGATT

CTATCGCAACCGAAGCCCGTCAGAAGTTCAAACTCATCAATCCAGAAACC

ATCGGCCAAGCCAGCCGTATTTCGGGAGTAAACCCAGCAGATATTTCTAT

TTTGATGGTGTATCTGGAAGGTAAAAATCGTAGTATTTCTAAAACTCTTC

AAAAATCAAATGA 4149.2 (SEQ. ID. NO. 263)
ATGAAAGTATTAGCTTTTGATACGTCCAGCAAGGCTCTTTCTCTGGCTAT

TTTAGAGGATAAGCAGGTTCTTGCCGAGACGACGATTAATATTAAGAAAA

ATCACAGTATTACTCTTATGCCTGCCATCGATTTTTTGATGGCAAGTTTG

GATTGGACACCCAAGGATTTGGACCGAATCGTGGTAGCTGAAGGGCCGGG

TAGCTATACAGGCTTGCGAATTGCGGTAGCAACTGCTAAGACCTTAGCTC

ACACCCTGAACATCGAGTTGGTTGGTATGTCGAGTCTCTTGGCTCTGGTG

CCCCATCAACAAGAAGGTTTGTTTGTCCCCTTGATGGATGCGCGTCGCAA

TAATGTTTATGCAGGATTTTATGAAAATGCCAAACCTGTCATGGCAGAAG

CGCACCTATCTTTTGAAGAGGTGCTAGAAAAAGTCAAGGGTACTAGTCAG

GTAACCTTTGTCGGAGAAGTTGGCCCCTTTGTTGAGCAGATTCAAAAACA

CTTGCCAAGGACTGATTACAAAGAAACATTGCCCAATGCAGCTAATCTAG

CTCTTTTGGCCTGGGACAAGGAAGCAGACTCCTTGCATGATTTTGTGCCG

AATTACCTCAAACGAGTCGAGGCTGAGGAAAACTGGCTCAAGAACCATAC

CGAGTCTGGCGAGTCTTACATTAAACGCCTATGA 4149.3 (SEQ. ID. NO. 264)
ATGATAGAAATCAAGCGAATTCAACAACAGCCTGACCTAGCTCAAGCCAT

CTACGCTGTTATGGCAGCTGTTTACCTAGTCAGTCCTTGGACTCTGGAGC

AAATCCAAGCAGATCTGTCCCAAGACCAGACTTGGTATGCATTGGCTTAT

GATGGGGCAGAAGTGATTGGATTTCTAGCTGTGCAGGAGAATCTTTTTGA

AGCAGAAGTCCTGCAAATCGCTGTCAAAGGAGCTTATCAGGGTCAGGGGA

TTGCGTCagCCTTGTTTGCTCAATTGCCGACAGACAAGGAAATTTTCCTC

GAAGTCAGACAGTCAAATCAACGAGCGCAAGCATTTTACAAGAAAGAAAA

GATGACAGTTATCGCTGAGCGAAAGGCCTACTACCATGACCCAGTCGAGG

ACGCCATTATCATGAAGAGAGAAATAGATGAAGGATAG 4152.2 (SEQ. ID. NO. 265)
ATGACAAAACAAGTCTTATTAGTGGATGATGAAGAACACATTCTGAAATT

GCTTGACTACCATTTAAGTAAGGAAGGCTTTTCTACTCAATTGGTGACAA

ATGGACGGAAGGCCTTAGCTTTGGCAGAAACAGAACCCTTTGATTTTATC

TTGCTTGATATCATGTTACCACAATTAGATGGCATGGAAGTTTGTAAGCG

GCTGAGAGCCAAAGGCGTCAAAACTCCAATTATGATGGTTTCTGCGAAAA

GTGATGAATTTGATAAGGTTTTGGCCTTGGAATTAGGGGCTGATGACTAC

CTGACCAAGCCTTTTAGCCCTAGAGAATTGCTGGCGGCGTGCAAGGCTGT

CCTCAGGCGAACTAAAGGAGAACAAGAAGGAGATGATTCAGATAATATCG

CTGACGATTCTTGGCTATTTGGGACCTTGAAAGTATACCCTGAGCGTCAT

GAAGTCTACAAGGCGAATAAGTTACTGAGTTTGACCCCAAAAGAATTTTG

AAAGCGATAAAAATCCGTTTTTTGAAGTTTTCAAAGTTTCGAAAGTAACC

GCCCAATAA 4154.1 (SEQ. ID. NO. 266)
ATGACTACTTTTAAAGATGGATTTTTATGGGTGGTGCTGTTGCTGCTCA

TCAACTTGAAGGTGGATGGCAAGAAGGTGGCAAGGGAATTAGTGTTGCTG

ATGTTATGACTGCTGGTCGTCATGGAGTAGCTCGTGAAATACTTTGGGAG

TTTTAGAGGGTAAATATTATCCAAATCATGAGGCGATAGATTTTATCAC

CGTTATAAAGAAGATATAGCACTTTTTGCTGAAATGGGATTCAAGTGCTT

CCGTACCTCTATTGCATGGACACGTATCTTCCAAAAGGTGATGAGTTAGA

GCCGAATGAAGAAGGATTACAGTTTTATGATAATCTTTTTGATGAATGCT

TAAAGAATGGTATTGAACCTGTCATCACTCTATCTCATTTTGAAATGCCT

TATCACTTAGTGACCGAATATGGTGGTTGGAAAAATAGGAAATTGATTGA

TABLE 1-continued

TTTCTTTGCTCGTTTTGCAGAAGTCGTATTTAAACGTTACAAAGATAAGG
TTAAATATTGGATGACTTTCAATGAAATCAATAATCAAGCGAATTATCAG
GAAGATTTTGCACCATTTACTAACTCAGGTATTGTATATGAGGAAGGTGA
TAATAGAGAAGCAATTTATGTATCAAGCAGCACATTACGAATTAGTTGCT
TCTGCACGAGCTGTAAAAATTGGTCATGAGATTAATCCAGATTTTCAAAT
AGGTTGTATGATTGCGATGTGTCCAATTTATCCAGTTACTTGCAATCCTA
AGGATATCTTAATGGCAATGAAAGCTATGCAGAAGCGTTATTATTTTGCT
GATGTGCATGTTTTAGGTAAATATCCTGAGCATATTTTCAAGTATTGGGA
ACGAAAAGGTATTTCAGTTGATTTTACTGCCCAGGATAAAGAAGATTTAC
TTGGTGGGACTGTAGATTACATTGGTTTCAGTTACTATATGTCCTTTGCT
ATCGACTCTCATCGTGAAAATAATCCTTATTTTGATTATCTTGAAACAGA
AGATTTAGTGAAAAATAATTATGTTAAGGCTTCTGAATGGGAGTGGCAAA
TTGATCCAGAAGGTTTGCGTTATGCGTTAAATTGGTTTACAGACCACTAT
CACTTACCACTCTTTATTGTTGAAAATGGTTTTGGAGCTATAGATCAAGT
TGCAGCAGATGGTATGGTACATGATGATTATAGAATTGAATATCTAGGTG
CCCATATTCGTGAAATGAAAAAGGCTGTAGTTGAAGATGGTGTTGATTTA
ATGGGTTATACTCCATGGGGATGTATTGATTTGGTTTCAGCTGGTACCGG
TGAAATGCGGAAACGTTATGGCTTTATTTATGTAGATAAAGATGATAATG
GGAAGGGAAGTTATAATCGTTCCCCGAAAAAATCTTTTGGCTGGTATAAG
GAAGTTATTTCATCTAACGGTGAATCAGTAGAATAG 4154.2 (SEQ. ID. NO. 267)
ATGGATCAACAAAACGGGTTGTTTGGTTTTCTTGAAAACCATGTTATGGG
ACCAATGGGCAAACTTGCTCAGTTTAAAGTAGTACGTGCTATCACGGCTG
CAGGTATGGCTGCTGTACCATTTACTATTGTAGGATCAATGTTTTGGTAT
TCAGTATTTTGCCACAAGCTTTCTCATTTTGGCCAATTGTGGCAGATATT
TTCTCTGCTTCATTTGATAAATTCACATCACTTTACATGGTTGCAAACTA
TGCGACTATGGGTTCTCTATCTCTTTATTTCGTTCTATCACTTGCATATG
AATTGACAAAAATTTATGCAGAGGAAGAAGAACTCAATATGAATCCTCTT
AATGGTGCCTTGCTTGCCTTGATGGCTTTTGTCATGACAGTACCGCAAAT
CATTTTTGATGGTGGAATGATGAAGACTGTGACAAGTCTAAAAGAAGGTG
CAGTAATTGCAGATGGATGGGCAATGGGAAATGTCGTCGCACGTTTTGGG
ACAACAGGGATTTTTACCGCAATCATTATGGCAATTGTGACTGTTCTTAT
TTATCGTATGTGTGTTAAACATAATTGGGTTATTAAAATGCCTGAAGCTG
TTCCAGAAGGAGTTCTCGTGGATTTACCGCTTTGGTTCCGGGATTTGTTG
TTGCATTTGTTGTTATCTTTATCAACGGTCTTCTTGTAGCAATGGGAACA
GATATTTTAAAGTCATTGCAATTCCATTTGGTTTTGTATCCAATCTGAC
TAATTCGTGGATTTGGTTTAATGATTATTTATCTATTGACTCAACTACTT
TGGATTGTAGGTATCCACGGTGCGAACATTGTTTTTGCATTTGTTAGTCC
AATTGCTCTTGCTAACATGGCTGAAAATGCTGCTGGCGGGCACTTCGCTG
TTGCAGGTGAATTTTCTAATATGTTTGTAATTGCAGGTGGTTCTGGTGCA

ACTTTAGGACTATGTTTATATATTGCTTTTGCCTCTAAATCTGAACAGCT
TAAAGCAATAGGACGAGCATCTGTAGTTCCAGCCTTATTTAATATTAATG
AACCATTAATTTTTGGATTACCTATTATCTATAATCCAGCCTTGGCTATA
CCATTTATTTTAGCACCAATGGTTACTGCTACTATTTATTACGTAGCGAA
TTCTCTAAACTTTATTAAGCCAATTATCGCACAGGTTCCATGGCCAACTC
CAGTAGGGATTGGAGCTTTCTTAGGGACAGCAGATCTTCGAGCTGTATTA
GTTGCTCTAGTATGTGCATTTGCAGCATTCCTAGTCTATCTTCCATTCAT
CCGTGTATATGATCAAAAATTGGTGAAAGAAGAGCAAGGTATCTAA 4155.1 (SEQ. ID. NO. 268)
ATGAAAAAATTTTATGTAAGTCCAATTTTTCCTATTCTAGTAGGATTGAT
TGCGTTTGGAGTCTTATCCACTTTCATTATTTTTGTTAATAATAATCTGT
TGACGGTTTTAATTTTGTTTCTTTTTGTAGGAGGCTATGTTTTTTTATTT
AAGAAACTGAGAGTGCATTATACAAGGAGTGATGTAGAACAGATACAGTA
TGTAAACCACCAAGCGGAAGAAAGTTTGACAGCTCTATTGGAACAGATGC
CTGTAGGTGTTATGAAATTGAATTTATCTTCTGGAGAGGTTGAGTGGTTT
AATCCCTATGCTGAATTGATTTTGACCAAGGAAGATGGTGATTTTGATTT
AGAAGCTGTTCAAACGATTATCAAGGCTTCAGTAGGAAATCCGTCTACTT
ATGCCAAGCTTGGTGAGAAGCGTTATGCTGTTCATATGGATGCTTCTTCC
GGTGTTTTGTATTTTGTAGATGTATCCAGGGAACAAGCCATAACAGATGA
ATTGGTAACAAGTAGACCAGTGATTGGGATTGTCTCTGTGGATAATTATG
ATGATTTGGAGGATGAAACTTCTGAGTCAGATATTAGTCAAATCAATAGT
TTTGTAGCTAATTTTATATCAGAGTTTTCAGAAAAACACATGATGTTTTC
TCGTCGGGTAAGTATGGATCGATTTTATCTATTTACTGACTACACGGTGC
TTGAGGGCTTGATGAATGATAAATTTCTGTTATTGATGCTTTCAGAGAA
GAGTCGAAACAGAGACAGTTGCCCTTGACCTAAGTATGGGATTTTCTTA
TGGCGATGGAAATCATGATGAGATAGGGAAAGTTGCTTTGCTCAATTTGA
ACTTGGCTGAAGTACGTGGTGGCGACCAGGTGGTTGTTAAGGAAAACGAC
GAAACGAAAAATCCAGTTTATTTTGGTGGTGGGTCTGCTGCTTCAATCAA
GCGTACACGGACTCGTACGCGCGCTATGATGACAGCTATTTCAGATAAGA
TTCGGAGTGTAGATCAGGTTTTTGTAGTCGGTCACAAAAATTTAGACATG
GATGCTTTGGGCTCTGCTGTAGGTATGCAGTTGTTCGCCAGCAATGTGAT
TGAAAATAGCTATGCTCTTTATGATGAAGAACAAATGTCTCCAGATATTG
AACGAGCTGTTTCATTCATAGAAAAAGAAGGAGTTACGAAGTTGTTGTCT
GTTAAGGATGCAATGGGGATGGTGACCAATCGTTCTTTGTTGATTCTTGT
AGACCATTCAAAGACAGCCTTAACATTATCAAAGAATTTTATGATTTAT
TTACCCAAACCATTGTTATTGACCACCATAGAAGGGATCAGGATTTTCCA
GATAATGCGGTTATTACTTATATCGAAAGTGGTGCAAGTAGTGCCAGTGA
GTTGGTAACGAATTGATTCAGTTCCAGAATTCTAAGAAAAATCGTTTGA
GTCGTATGCAAGCAAGTGTCTTGATGGCTGGTATGATGTTGGATACTAAA
AATTTCACCTCGCGAGTAACTAGTCGGACATTTGATGTTGCTAGCTATCT

TABLE 1-continued

CAGAACGCGCGGAAGTGATAGTATTGCTATCCAGGAAATCGCTGCGACAG

ATTTTGAAGAATATCGTGAGGTCAATGAACTTATTTTACAGGGGCGTAAA

TTAGGTTCAGATGTACTAATAGCAGAGGCTAAGGACATGAAATGCTATGA

TACAGTTGTTATTAGTAAGGCAGCAGATGCCATGTTAGCCATGTCAGGTA

TTGAAGCGAGTTTTGTTCTTGCGAAGAATACACAAGGATTTATCTCTATC

TCAGCTCGAAGTCGTAGTAAACTGAATGTACAACGGATTATGGAAGAGTT

AGGCGGTGGAGGCCACTTTAATTTGGCAGCAGCTCAAATTAAAGATGTAA

CCTTGTCAGAAGCAGGTGAAAAACTGACAGAAATTGTATTAAATGAAATG

AAGGAAAAGGAGAAAGAAGAATGA 4156.1 (SEQ. ID. NO. 269)
ATGAAAGAGAAAAATATGTGGAAAGAATTGTTGAATCGTGCAGGCTGGAT

TTTGGTCTTTTTACTTGCCGTCCTTTTATATCAGGTTCCCCTAGTGGTTA

CCTCTATTTTGACTTTAAAAGAAGTAGCCCTGCTACAGTCAGGGCTGATA

GTTGCTGGCCTTTCAATTGTGGTTCTGGCTCTATTTATTATGGGAGCTCG

TAAAACCAAGTTAGCTAGTTTTAATTTTTCTTTTTTTAGAGCTAAAGATT

TGGCACGTTTGGGCTTGAGTTATCTAGTTATTGTCGGGTCAAATATACTT

GGTTCCATTTTATTGCAACTGTCAAATGAGACGACAACAGCTAACCAGTC

TCAGATTAATGATATGGTTCAAAATAGTTCGTTGATTTCCAGTTTCTTCT

TGCTAGCCTTGCTTGCTCCGATTTGTGAGGAAATCTTGTGTCGTGGGATT

GTTCCTAAAAAGATTTTCCGAGGCAAGGAGAACTTGGGATTTGTAGTCGG

TACGATTGTGTTTGCTTTATTGCATCAACCAAGTAATTTACCTTCTTTAT

TGATTTATGGAGGTATGTCGACAGTTCTATCTTGGACAGCCTACAAGACC

CAACGTTTGGAAATGTCGATCTTGCTTCACATGATTGTTAATGGGATTGC

TTTCTGTTTGTTGGCTCTTGTGGTGATTATGAGTCGGACATTAGGAATTT

CTGTTTAAATGAAAGAGAAAAATATGTGGAAAGAATTGTTGAATCGTGCA

GGCTGGATTTTGGTCTTTTTACTTGCCGTCCTTTTATATCAGGTTCCCCT

AGTGGTTACCTCTATTTTGACTTTAAAAGAAGTAGCCCTGCTACAGTCAG

GGCTGATAGTTGCTGGCCTTTCAATTGTGGTTCTGGCTCTATTTATTATG

GGAGCTCGTAAAACCAAGTTAGCTAGTTTTAATTTTTCTTTTTTTAGAGC

TAAAGATTTGGCACGTTTGGGCTTGAGTTATCTAGTTATTGTCGGGTCAA

ATATACTTGGTTCCATTTTATTGCAACTGTCAAATGAGACGACAACAGCT

AACCAGTCTCAGATTAATGATATGGTTCAAAATAGTTCGTTGATTTCCAG

TTTCTTCTTGCTAGCCTTGCTTGCTCCGATTTGTGAGGAAATCTTGTGTC

GTGGGATTGTTCCTAAAAAGATTTTCCGAGGCAAGGAGAACTTGGGATTT

GTAGTCGGTACGATTGTGTTTGCTTTATTGCATCAACCAAGTAATTTACC

TTCTTTATTGATTTATGGAGGTATGTCGACAGTTCTATCTTGGACAGCCT

ACAAGACCCAACGTTTGGAAATGTCGATCTTGCTTCACATGATTGTTAAT

GGGATTGCTTTCTGTTTGTTGGCTCTTGTGGTGATTATGAGTCGGACATT

AGGAATTTCTGTTTAA 4156.4 (SEQ. ID. NO. 270)
ATGGATACACAAAAGATTGAAGCGGCTGTAAAAATGATTATCGAGGCTGT

AGGAGAGGACGCTAATCGCGAGGGCTTGCAGGAAACACCTGCTCGTGTAG

CCCGTATGTATCAAGAGATTTTTTCAGGTCTTGGTCAAACAGCAGAGGAA

CATTTGTCAAAATCCTTTGAAATTATTGACGATAATATGGTGGTAGAAAA

GGATATCTTTTTCCATACCATGTGTGAACACCACTTCTTGCCATTTTATG

GTAGAGCGCACATTGCCTACATTCCAGATGGTCGTGTGGCAGGCTTGTCT

AAGCTAGCCCGTACGGTTGAAGTTTATTTCGAAAAAACCACAAATTCAAG

AACGTTTGAATATCGAAGTGGCCGATGCCTTGATGGACTATCTAGGTGCT

AAAGGAGCCTTTGTTGTCATTGAGGCGGAACATATGTGTATGAGTATGCG

TGGTGTTAGAAAACCAGGCACTGCAACCTTGACGACAGTAGCTCGTGGTC

TATTTGAAACAGATAAGGATCTCCGTGACCAAGCTTATCGTTTAATGGGG

CTATAA 4157.2 (SEQ. ID. NO. 271)
ATGAAAGACTTGTTTTTAAAGAGAAAGCAGGCCTTTCGTAAGGAGTGTCT

TGGTTATCTGCGCTATGTGCTCAATGACCACTTTGTCTTGTTCCTGCTTG

TCCTGTTGGGCTTTCTAGCCTACCAGTACAGTCAACTCTTACAACATTTT

CCTGAAAATCATTGGCCTATCCTTTTGTTTGTAGGAATTACGTCTGTTTT

ACTTTTACTTTGGGGAGGAACTGCCACCTATATGGAGGCTCCAGACAAGC

TCTTTCTCTTAGTTGGAGAAGAGGAAATTAAGCTCCATCTCAAGCGTCAA

ACTGGCATTTCCCTAGTCTTTTGGCTCTTTGTACAGACCCTTTTCTTGCT

GTTATTTGCGCCTTTATTTTTAGCAATGGGTTATGGCTTGCCAGTTTTTC

TGCTCTATGTGCTTTTATTGGGGGTAGGAAAATATTTCCACTTTTGTCAA

AAGGCCAGCAAATTTTTCACTGAAACTGGACTGGACTGGGACTATGTTAT

TTCTCAAGAAAGCAAGCGTAAGCAAGTCTTGCTTCGTTTCTTTGCCCTCT

TTACGCAGGTCAAGGGAATTTCAAACAGCGTTAAGCGTCGTGCCTATCTG

GACTTTATTTTAAAGGCTGTTCAGAAGGTGCCTGGGAAGATTTGGCAAAA

TCTCTATCTGCGTTCTTATCTGCGAAATGGCGACCTCTTTGCTCTCAGTC

TTCGTCTTCTCTTGCTTTGCCTTGCTGGCGCAGGTTTTTATCGAGCAAGC

TTGGATTGCGACAGCAGTGGTAGTTCTCTTTAACTACCTCTTGCTCTTCC

AGTTGCTGGCCCTCTATCATGCCTTTGACTACCAGTATTTGACCCAACTC

TTTCCGCTGGACAAGGGGCAAAAGGAAAAAGGCTTACAGGAGGTAGTTCG

AGGATTGACCAGTTTTGTTTTACTTGTGGAATTAGTTGTTGGGTTGATTA

CCTTCCAAGAAAAACTAGCCCTTCTAGCCTTACTAGGAGCTGGTTTGGTT

TTACTAGTCTTGTATTTGCCTTATCAGGTAAAACGTCAGATGCAGGACTA
A 4258.2 (SEQ. ID. NO. 272)
ATGAGAAAATCAATAGTATTAGCGGCAGATAATGCCTATCTTATTCCTTT

AGAGACGACTATAAAGTCTGTATTGTATCACAATAGAGATGTTGATTTTT

ATATTCTCAACAGTGATATAGCTCCTGAATGGTTTAAATTATTGGGGAGA

AAAATGGAAGTTGTGAATTCTACAATTCGCAGTGTACACATTGATAAAGA

TABLE 1-continued

ACTTTTTGAAAGCTATAAAACAGGACCTCATATAAATTATGCTTCTTACT
TTAGATTTTTTGCGACAGAAGTGGTTGAATCTGATAGGGTATTGTATCTG
GATTCCGATATCATTGTAACTGGGGAACTAGCTACTTTGTTTGAGATAGA
TCTCAAAGGATATTCAATTGGTGCTGTTGATGATGTCTATGCCTATGAAG
GACGAAAATCTGGATTTAATACTGGTATGTTACTAATGGATGTTGCAAAG
TGGAAAGAACATTCTATTGTCAATAGTTTATTGGAATTAGCGGCCGAGCA
GAATCAAGTTGTTCATCTTGGGGATCAGAGTATTTTAAATATTTATTTTG
AGGATAATTGGCTAGCCTTAGATAAAACATATAATTATATGGTGGGTATT
GATATTTATCACCTTGCTCAAGAATGTGAACGTCTAGATGACAATCCACC
TACAATTGTTCACTATGCTAGTCATGATAAACCTTGGAATACATATAGTA
TATCTAGACTACGTGAATTATGGTGGGTTTATAGAGATTTGGATTGGTCA
GAGATTGCTTTTCAACGTTCCGATTTAAATTATTTTGAAAGAAGCAATCA
GTCTAAAAAACAAGTGATGCTTGTGACATGGAGTGCAGATATAAAACATT
TAGAGTATTTAGTACAACGGTTACCTGATTGGCATTTTCATTTGGCTGCA
CCGTGTGATTGTTCTGAGGAGCTGACCTCTCTATCACAGTATACGAATGT
AACAGTATATCAAAATGTATTACATAGTAGAATTGATTGGCTATTGGACG
ATTCTATAGTTTATTTAGATATTAATACAGGTGGAGAGGTTTTTAATGTA
GTTACAAGGGCACAAGAAAGTGGCAAGAAAATCTTCGCTTTTGATATCAC
ACGTAAAAGTATGGATGATGGACTCTATGACGGTATTTTTTCTGTGGAGA
GACCAGATGATTTAGTGGATAGAATGAAGAATATAGAGATAGAGTAA 4158.2 (SEQ. ID. NO. 273)
ATGACTAAGATTTATTCGTCAATAGCAGTAAAAAAAGGACTATTTACCTC
ATTTCTACTGTTTATCTATGTATTGGGAAGTCGTATTATTCTCCCTTTTG
TTGACCTAAATACTAAAGATTTTTAGGAGGTTCAACAGCCTATCTAGCC
TTCTCAGCCGCCCTAACAGGTGGGAATCTAAGAAGTTTATCAATTTTTTC
TGTTGGATTATCCCCTTGGATGTCCGCCATGATTTTATGGCAGATGTTTT
CTTTTTCTAAACGGTTGGGTTTAACATCTACGTCTATAGAAATACAAGAT
CGCCGTAAAATGTACCTGACCTTGCTAATTGCTGTGATTCAATCCTTGGC
AGTTAGCTTGAGACTGCCAGTACAATCCTCCTATTCTGCAATATTGGTTG
TTCTAATGAATACAATATTGCTGATAGCAGGAACATTTTTTCTTGTTTGG
TTGTCAGATTTAAATGCGAGTATGGGGATTGGAGGTTCTATTGTAATCCT
CCTATCCAGTATGGTTTTAAATATTCCTCAGGATGTTTTGGAAACATTTC
AGACAGTACACATTCCAACAGGGATTATTGTGTTACTTGCTTTATTAACC
CTTGTCTTTTCTTATTTACTTGCCCTTATGTATCGAGCTCGCTATTTGGT
TCCTGTTAATAAAATTGGCTTACACAATCGATTTAAACGCTATTCTTATC
TCGAAATCATGTTGAATCCTGCAGGTGGGATGCCTTATATGTATGTGATG
AGTTTTCTTAGTGTACCAGCTTATTTGTTCATCTTGTTGGGATTTATTTT
CCCTAATCATTCAGGGTTAGCGGCTTTATCAAAGGAATTTATGGTTGGAA
AGCCTTTGTGGGTCTAGTTTATATTTCGGTCTTATTTTTATTTAGTATCA
TTTTTGCTTTTGTTACGATGAATGGAGAAGAGATTGCAGACCGTATGAAA

AAATCTGGAGAATACATTTATGGTATTTATCCAGGTGCGGATACTAGTCG
ATTTATTAATCGATTGGTCCTTCGTTTCTCAGTCATAGGTGGTCTCTTTA
ATGTGATTATGGCAGGTGGTCCCATGCTTTTTGTTTTGTTTGATGAAAAG
TTATTACGATTGGCAATGATTCCAGGCTTATTTATGATGTTCGGGGGCAT
GATTTTTACGATTAGAGACGAGGTCAAGGCTTTAAGGCTAAATGAGACCT
ATAGACCTTTGATTTAG 4158.3 (SEQ. ID. NO. 274)
ATGTCCTCTCTTTCGGATCAAGAATTAGTAGCTAAAACAGTAGAGTTTCG
TCAGCGTCTTTCCGAGGGAGAAAGTCTAGACGATATTTTGGTTGAAGCTT
TTGCTGTGGTGCGTGAAGCAGATAAGCGGATTTTAGGGATGTTTCCTTAT
GATGTTCAAGTCATGGGAGCTATTGTCATGCACTATGGAAATGTTGCTGA
GATGAATACGGGGAAGGTAAGACCTTGACAGCTACCATGCCTGTCTATT
TGAACGCTTTTTCAGGAGAAGGAGTGATGGTTGTGACTCCTAATGAGTAT
TTATCAAAGCGTGATGCCGAGGAAATGGGTCAAGTTTATCGTTTTCTAGG
ATTGACCATTGGTGTACCATTTACGGAAGATCCAAAGAAGGAGATGAAAG
CTGAAGAAAAGAAGCTTATCTATGCTTCGGATATCATCTACACAACCAAT
AGTAATTTAGGTTTTGATTATCTAAATGATAACCTAGCCTCGAATGAAGA
AGGTAAGTTTTTACGACCGTTTAACTATGTGATTATTGATGAAATTGATG
ATATCTTGCTTGATAGTGCACAAACTCCTCTGATTATTGCGGGTTCTCCT
CGTGTTCAGTCTAATTACTATGCGATCATTGATACACTTGTAACAACCTT
GGTCGAAGGAGAGGATTATATCTTTAAAGAGGAGAAAGAGGAGGTTTGGC
TCACTACTAAGGGGGCCAAGTCTGCTGAGAATTTCCTAGGGATTGATAAT
TTATACAAGGAAGAGCATGCGTCTTTTGCTCGTCATTTGGTTTATGCGAT
TCGAGCTCATAAGCTCTTTACTAAAGATAAGGACTATATCATTCGTGGAA
ATGAGATGGTACTGGTTGATAAGGGAACAGGGCGTCTAATGGAAATGACT
AAACTTCAAGGAGGTCTCCATCAGGCTATTGAAGCCAAGGAACATGTCAA
ATTATCTCCTGAGACGCGGGCTATGGCCTCGATCACCTATCAGAGTCTTT
TTAAGATGTTTAATAAGATATCTGGTATGACAGGGACAGGTAAGGTCGCG
GAAAAAGAGTTTATTGAAACTTACAATATGTCTGTAGTACGCATTCCAAC
CAATCGTCCGAGACAACGGATTGACTATCCAGATAATCTATATATCACTT
TACCTGAAAAAGTGTATGCATCCTGGAGTACATCAAGCAATACCATGCT
AAGGGAAATCCTTTACTCGTTTTGTAGGCTCAGTTGAAATGTCTCAACT
CTATTCGTCTCTCTTGTTTCGTGAAGGGATTGCCCATAATGTCCTAAATG
CTAATAATGCGGCGCGTGAGGCTCAGATTATCTCCGAGTCAGGTCAGATG
GGGGCTGTGACAGTGGCTACCTCTATGGCAGGACGTGGTACGGATATCAA
GCTTGGTAAAGGAGTCGCAGAGCTTGGGGGCTTGATTGTTATGGGACTGA
GCGGATGGAAAGTCAGCGGATCGACCTACAAATTCGTGGCCGTTCTGGTC
GTCAGGGAGATCCTGGTATGAGTAAATTTTTTGTATCCTTAGAGGATGAT
GTTATCAAGAAATTTGGTCCATCTTGGGTGCATAAAAAGTACAAAGACTA
TCAGGTTCAAGATATGACTCAACCGGAAGTATTGAAAGGTCGTAAATACC

TABLE 1-continued

GGAAACTAGTCGAAAAGGCTCAGCATGCCAGTGATAGTGCTGGACGTTCA
GCACGTCGTCAGACTCTGGAGTATGCTGAAAGTATGAATATACAACGGGA
TATAGTCTATAAAGAGAGAAATCGTCTAATAGATGGTTCTCGTGACTTAG
AGGATGTTGTTGTGGATATCATTGAGAGATATACAGAAGAGGTAGCGGCT
GATCACTATGCTAGTCGTGAATTATTGTTTCACTTTATTGTGACCAATAT
TAGTTTTCATGTTAAAGAGGTTCCAGATTATATAGATGTAACTGACAAAA
CTGCAGTTCGTAGCTTTATGAAGCAGGTGATTGATAAAGAACTTCTGAA
AAGAAAGAATTACGTTAATCAACATGACTTATATGAACAGTTTTTACGAC
TTTCACTGCTTAAAGCCATTGATGACAACTGGGTAGAGCAGGTAGACTAT
CTACAACAGCTATCCATGGCTATCGGTGGTCAATCTGCTAGTCAGAAAAA
TCCAATCGTAGAGTACTATCAAGAAGCCTACGCGGGCTTTGAAGCTATGA
AAGAACAGATTCATGCGGATATGGTGCGTAATCTCCTGATGGGGCTGGTT
GAGGTCACTCCAAAAGGTGAAATCGTGACTCATTTTCCATAA 4158.4 (SEQ. ID. NO. 275)
ATGATAGGGACTTTCGCCGCTGCTCTTGTAGCTGTACTAGCAAATTTCAT
CGTCCCTATTGAAATTACCCCAAATAGTGCCAATACTGAAATTGCACCAC
CAGATGGGATTGGGCAGGTTCTCAGCAACCTCTTGCTCAAACTGGTTGAC
AACCCAGTCAACGCCCTGCTTACTGCTAACTATATTGAATCTTATCTTG
GGCAGTCATTTTTGGAATCGCTATGAGAGAAGCCAGTAAAAATAGTCAAG
AATTGCTAAAAACTATCGCTGACGTGACTTCTAAAATTGTCGAATGGATC
ATCAATCTGGCTCCATTTGGAATCCTTGGTCTTGTTTTAAAACCATTTC
TGACAAGGGAGTCGGAAGCCTTGCCAACTACGGTATTTTATTGGTTCTAT
TAGTAACGACTATGCTTTTGTTGCCCCTGTGGTCAACCCTTTGATTGCC
TTCTTCTTTATGAGACGCAATCCTTACCCTCTAGTTTGGAACTGCCTCCG
TGTCAGCGGTGTGACAGCCTTTTTCACTCGTAGTTCTGCGACTAACATTC
CTGTCAACATGAAACTCTGCCATGACCTTGGACTCAACCCAGATACCTAT
TCTGTTTCTATCCCACTCGGTTCTACTATCAATATGGCTGGAGTAGCGAT
TACCATTAACCTTTTGACCCTTGCTGCAGTTAACACTCTTGGAATTCCTG
TTGACTTTGCCACAGCCTTTGTCCTCAGTGTGGTAGCAGCTATCTCATCC
TGTGATGCTTCAGGTATTGCCGGAGGTTCCCTCCTTCTTATCCCAGTTGC
TTGTAGCCTTTTCGGTATTTCTAACGATATTGCCATACAAATTGTTGGGG
TTGGTTTTGTGATTGGTGTCATCCAAGACTCATGTGAAACAGCCCTTAAC
TCTTCTACAGATGTCCTCTTTACCGCCGTTGCCGAATACGCAGCAACCCG
TAAAAAATAA 4158.5 (SEQ. ID. NO. 276)
ATGTCTATTAGCCAACGTACGACCAAGCTCATCTTAGCTACCTGTCTTGC
CTGCCTGCTTGCTTATTTTCTCAATCTTTCGTCAGCAGTTTCGGCTGAA
TTATCGCTCTCTTGAGCCTATCTGATACGCGTAGAAGTACTTTAAAACTG
GCTCGCAATCGTCTTTTTTCTATGCTTCTAGCTCTGGCTATCGGTGTTCT
AGCTTTTCACTTGAGCGGATTTCATATCTGGAGTCTCGGCCTCTATCTGG

CCTTCTACGTTCCTTTAGCCTACAAGATGGGCTGGGAAATTGGCATCACA
CCAAGCACTGTTTTGGTTAGCCATCTCTTGGTTCAAGAGTCAACCTCTCC
AGACCTTCTAGTCAATGAATTCCTTCTCTTTGCTATTGGTACAGGATTTG
CCTTGCTTGTTAATCTCTATATGCCTTCACGAGAAGAGGAAATCCAGCAC
TACCACACGCTGGTGGAAGAAAAGTTAAAAGATATCCTCCAGCGCTTCAA
ATACTATTTATCCAGAGGAGACGGACGCAACCGAGCACAGCTGGTAGCAG
AATTAGACACGCTTTTGAAAGAAGCCCTCAGACTGGTCTATTTGGATCAC
TCTGACCACCTCTTTCACCAGACAGACTACCATATCCACTACTTTGAGAT
GAGACAGCGACAAATGCGTATCCTGAGAAACATGGCCCAACAGATTAACA
CTTGTCACCTTGCCGCAGTGAAAGCCTGATCTTAGCGCAACTCTTTTCA
AAAATTGCAGGTCAACTGAGCCAGACCAATCCTGCTTCTGATTTGCTAGA
TGAAATTGAACGTTATCTGGAAGTCTTCCGGAACCGCAGTCTGCCCAAGA
CAAGAGAAGAATTTGAAACCCGCGCCACCCTTCTTCAACTCCTACGTGAA
GCCAAAACCTTCATCCAAGTAAAAGTTGATTTTTACCAAAAATATAGACA
GTAA 4158.6 (SEQ. ID. NO. 277)
ATGGAAATCATGTCGCTTGCGATTGCTGTTTTTGCCGTCATCATTGGTTT
AGTCATTGGATATGTCAGCATCTCAGCTAAGATGAAATCATCTCAGGAAG
CTGCAGAGTTGATGCTTTTAAATGCTGAACAAGAAGCAACTAATTTACGT
GGACAAGCTGAGCGTGAAGCGGATTTACTTGTTAATGAAGCCAAACGTGA
AAGCAAGTCTCTTAAAAAGAAGCACTATTGGAGGCCAAAGAAGAAGCCA
GAAAATACCGTGAAGAAGTGGACGCTGAATTCAAATCAGAACGTCAAGAA
CTCAAACAAATCGAAAGTCGTTTGACAGAGAGAGCTACTAGCCTTGACCG
TAAGGACGACAATTTGACGAGTAAAGAACAAACACTTGAACAAAAGAAC
AAAGTATTTCTGATAGAGCGAAAAACCTTGATGCGCGTGAAGAGCAATTA
GAGGAAGTCGAAAGACAAAAAGAAGCAGAACTAGAGCGTATTGGTGCGCT
GTCTCAGGCAGAAGCACGAGATATTATCTTGGCTCAGACAGAGGAAAACT
TGACCAGGGAGATTGCCAGTCGCATTCGCGAAGCTGAGCAAGAGGTCAAG
GAACGTTCTGACAAAATGGCCAAGGACATCTTGGTTCAAGCTATGCAACG
TATCGCTGGTGAATATGTAGCGGAGTCAACAAACTCAACAGTTCATCTGC
CAGACGATACTATGAAGGGACGCATTATTGGTCGTGAAGGTCGTAACATT
CGTACCCTTTGAAAGTTTGACAGGGGTCGATGTGATTATCGACGATACACC
AGAAGTGGTGACCTTGTCAGGATTTGATCCGATTCGTCGTGAGATTGCCC
GTATGACTATGGAAATGTTGCTCAAAGATGGTCGTATACATCCAGCTCGT
ATCGAAGAGTTGGTTGAGAAAAACCGTCAAGAGATTGACAATAAGATTCG
TGAATACGGTGAGGCTGCTGCCTATGAAATTGGTGCGCCAAACCTTCATC
CAGACTTGATGAAGATTATGGACGTTTGCAGTTCCGTACTTCATATGGA
CAAAATGTTTTGCGCCATTCGATTGAGGTTGCTAAGTTGGCTGGTATCAT
GGCGAGCGAACTTGGTGAAAATGCGGCTCTTGCCCCGTCGTGCTGGATTCC
TTCACGATATCGGGAAAGCCATTGACCATGAGGTTGAAGGTAGCCACGTT

TABLE 1-continued

GAAATCGGTATGGAATTGGCCCGTAAGTACAAGGAACCCCCAGTTGTGGT

GAATACGATTGCTAGTCACCACGGAGATGTTGAAGCTGAGAGCGTGATAG

CAGTTATCGTCGCTGCAGCAGATGCCTTGAGCGCAGCCCGTCCAGGTGCT

CGTAGTGAGTCTCTTGAAAGCTACATCAAGCGTCTCCATGATTTGGAAGA

AATTGCTAACGGCTTTGAAGGAGTGCAAACTAGCTTTGCCCCTTCAAGCAG

GACGTGAAATTCGTATCATGGTCAATCCAGGAAAAATCAAGGACGACAAA

GTCACAATCTTGGCTCACAAAGTTCGTAAGAAAATTGAAAACAATCTCGA

TTATCCAGGAAATATCAAGGTAACCGTGATTCGCGAGCTTCGTGCAGTAG

ATTATGCTAAATAA 4158.7 (SEQ. ID. NO. 278)
ATGATGTTAAAACCCTCTATTGATACCTTGCTCGACAAGGTTCCTTCAAA

ATATTCACTCGTAATCTTGGAAGCAAAACGTGCCCACGAATTGGAAGCAG

GTGCCCCAGCAACTCAAGGTTTCAAGTCTGAAAAATCAACTCTTCGCGCT

TTAGAAGAAATCGAATCAGGAAACGTTACAATTCACCCAGATCCAGAAGG

AAAACGTGAAGCAGTGCGTCGCCGTATCGAAGAAGAAAACGCCGCAAAGA

AGAAGAAGAAAAGAAAATCAAAGAGCAAATTGCTAAAGAAAAAGAAGATG

GTGAAAAAATTTAA 4161.1 (SEQ. ID. NO. 279)
ATGTCAGCATATCAATTACCGACCGTATGGCAGGATGAAGCTAGTAATCA

AGGAGCTTTTACGGGGCTAAACAGACCAACAGCAGGTGCCCGTTTCGAAC

AAAACTTGCCAAAAGGAGAACAAGCTTTTCAGCTTTATTCACTGGGAACA

CCAAATGGTGTGAAGGTTACTATCTTATTGGAAGAATTACTAGAAGCTGG

TTTTAAGGAAGCGGCTTACGACTTGTATAAGATTGCTATCATGGATGGGG

ATCAATTCGGATCAGACTTTGTGAAGCTCAATCCAAATTCCAAGATTCCA

GCCTTATTGGACCAGTCAGGTACTGAAAACGTAAGAGTCTTTGAGTCTGC

TCATATTCTTCTTTACCTTGCTGAGAAATTTGGAGCCTTTTTACCAAGTA

ATCCTGTGGAAAAGGTAGAAGTTTTGAATTGGCTATTCTGGCAAGCAGGT

GCAGCACCTTTTCTAGGTGGGGATTTGGACATTTCTTCAATTATGCTCC

TGAAAAATTGGAATATCCTATTAACCGTTTTACGATGGAAGTGAAACGCC

AGTTGGATTTATTGGATAAGGAATTGGCTCAGAAACCTTATATTGCAGGC

AATGACTATACGATTGCAGATATTGCTATCTGGTCTTGGTATGGACAGTT

AGTTCAAGGAAATCTTTACCAAGGTTCTGCAAAATTCTTGGATGCCTCAA

GTTATCAAAATCTAGTAAAATGGGCAGAAAAAATTGCCAATCGTCCAGCT

GTTAAGCGTGGCTTGGAAGTAACTTATACAGAAATTAAATAG 4161.2 (SEQ. ID. NO. 280)
TTGGCAAGCTTGATCACTTCTATCATCATGTTCTATGTCGGTTTCGATGT

TCTAAGAGATACCATTCAAAAGATTCTCAGTCGGGAAGAAACGGTCATTG

ATCCTCTTGGTGCAACTCTAGGAATCATTTCTGCAGCGATTATGTTTGTG

GTCTATCTCTACAATACTCGCCTCAGTAAGAAATCCAACTCCAATGCGCT

GAAGGCAGCTGCTAAGGACAATCTTTCTGACGCTGTTACCTCACTTGGAA

CCGCCATTGCCATCCTAGCTAGTAGTTTCAATTATCCGATTGTGGATAAA

TABLE 1-continued

CTGGTTGCTATCATCATCACTTTCTTTATCTTGAAGACTGCCTATGATAT

CTTCATCGAGTCTTCCTTTAGTCTTTCAGATGGCTTTGACGACCGCCTGC

TCGAGGACTACCAAAAGGCTATCATGGAAATTCCCAAAATCAGCAAGGTC

AAATCGCAAAGAGGTCGCACCTACGGTAGCAACATCTACCTGGATATTAC

ACTAGAGATGAATCCTGACTTGTCTGTTTTTGAAAGCCATGAAATCGCGG

ATCAGGTCGAGTCTATGCTGGAGGAGCGTTTTGGCGTCTTTGATACCGAT

GTCCATATCGAACCAGCACCTATCCCTGAGGATGAAATTTTAGACAATGT

CTATAAAAAATTGCTTATGCGTGAACAATTGATTGACCAAGGAAACCAAC

TAGAAGAACTCTTGACTGATGATTTTGTCTATATTCGCCAAGATGGAGAG

CAGATGGATAAAGAGGCTTATAAGACCAAAAAAGAGTTAAATTCTGCTAT

CAAGGACATTCAAATTACTTCCATCAGTCAAAAAACCAAACTCATCTGCT

ATGAGTTAGATGGTATCATCCATACCAGTATCTGGCGTCGCCACGAAACC

TGGCAAAATATCTTTCATCAAGAAACCAAAAAAGAATAG 4162.1 (SEQ. ID. NO. 281)
ATGACAATTAAACTAGTAGCAACGGATATGGACGGAACCTTCCTAGATGG

GAATGGACGCTTTGATATGGATCGTCTCAAGTCTCTCTTGGTTTCCTACA

AGGAAAAAGGGATTTACTTTGCGGTAGCTTCGGGTCGGGGATTTCTGTCT

CTAGAAAAATTATTTGCTGGTGTTCGTGATGACATTATTTTCATCGCGGA

AAATGGCAGTTTGGTAGAGTATCAAGGTCAGGACTTGTATGAAGCGACTA

TGTCTCGTGACTTTTATCTGGCAACTTTTGAAAAGCTGAAAACTTCACCT

TATGTAGATATCAATAAACTGCTCTTGACGGGTAAGAAGGGTTCATATGT

TCTAGATACGGTTGATGAGACCTATTTGAAAGTGAGTCAGCACTATAATG

AAAAATATCCAAAAAGTAGCGAGTTTGGAAGATATCACAGATGACATTTTC

AAATTTACAACCAACTTCACAGAAGAAACGCTGGAAGATGGGGAGGCTTG

GGTAAACGAAAACGTTCCTGGTGTTAAGGCCATGACAACTGGCTTTGAAT

CCATTGATATTGTTCTGGACTATGTCGATAAGGGAGTGGCCATTGTTGAA

TTAGTTAAAAAACTTGGTATCACAATGGATCAGGTCATGGCTTTTGGAGA

CAATCTTAATGACTTACATATGATGCAGGTTGTGGGACATCCTGTAGCTC

CTGAAAATGCACGACCTGAAATTTAGAATTAGCAAAGACTGTGATTGGTC

ACCATAAGGAACGGTCGGTTATAGCTTATATGGAGGGCTTATAA 4162.2 (SEQ. ID. NO. 282)
ATGGCAGATATAAAATTGATTGCATTGGACTTGGACGGGACCTTGCTGAC

TACTGATAAAGGCTGACGGATCGTACCAAGGAAACCTTGCAAGCTGCGC

GTGATCGTGGTATCAAGGTCGTATTGACAACTGGTCGTCCCTTAAAAGCC

ATGGATTTCTTTCTCCATGAGTTAGGGACTGACGGTCAGGAAGATGAGTA

TACCATTACTTTTAATGGTGGATTAGTTCAGAAAAATACAGGAGAAATCC

TTGATAAAACAGTCTTTTCATATGATGATGTGGCACGTTTGTATGAAGAA

ACAGAGAAATTATCACTGCCTCTTGATGCCATCTCAGAAGGAACAGTTTA

TCAAATCCAATCGGACCAAGAAAGTCTTTATGCCAAATTCAATCCAGCTT

TGACCTTTGTTCCAGTGGACTTTGAAGACTTATCTAGTCAAATGACCTAC

AACAAATGCGTGACTGCCTTTGCTCAAGAACCCTTGGATGCAGCCATTCA

TABLE 1-continued

```
GAAGATTTCTCCAGAATTGTTTGACCAATATGAAATCTTTAAATCACGTG
AAATGTTGCTAGAATGGTCACCAAAGAATGTTCATAAAGCAACAGGTTTG
GCAAAACTAATCAGCCATCTTGGAATCGACCAAAGTCAAGTGATGGCTTG
TGGTGACGAGGCCAATGACCTCTCTATGATTGAATGGGCAGGTCTTGGTG
TTGCTATGCAAAACGCTGTTCCTGAAGTAAAGGCAGCCGCAAATGTAGTG
ACGCCGATGACCAACGATGAGGAAGCTGTCGCCTGGGCTATCGAAGAATA
TGTGCTAAAGGAGAACTAA 4164.2 (SEQ. ID. NO. 283)
ATGGAAAGTTTACTTATTCTATTATTAATTGCCAATCTAGCTGGTCTCTT
TCTGATTTGGCAAAGGCAGGATAGGCAGGAGAAACACTTAAGTAAGAGCT
TGGAGGATCAGGCAGATCATTTGTCAGACCAGTTGGATTACCGCTTTGAC
CAAGCCAGACAAGCCAGCCAGTTAGACCAAAAAGATTTGGAAGTGGTTGT
CAGCGACCGTTTGCAAGAAGTGCGGATTGAATTGCACCAAGGTCTGACCC
AAGTCCGTCAAGAAATGACAGATAATCTCCTCCAAACTAGAGACAAGACA
GACCAACGTCTCCAAGCCTTGCAGGAATCAAATGAGCAACGTTTGGAACA
AATGCGCCAGACGGTCGAGGAAAAACTAGAAAAGACCTTGCAGACACGCT
TACAGGCTTCCTTTGAGACAGTTTCTAAACAACTGGAGTCTGTCAATCGT
GGCCTTGGAGAAATGCAGACAGTTGCCCGTGATGTCGGAGCTCTTAACAA
GGTTCTCTCTGGAACCAAGACGCGAGGGATTCTGGGAGAATTGCAACTGG
GGCAAATTATTGAAGACATCATGACACCTGCCCAGTACGAACGAGAATAC
GCAACGGTTGAAAACTCTAGTGAACGAGTGGAGTATGCCATCAAGTTACC
CGGACAAGGCGACCAAGAATACGTCTATCTGCCAATTGACTCTAAGTTTC
CACTGGCAGATTATTACCGCTTGGAAGAAGCCTATGAGACAGGTGACAAG
GATGAGATTGAACGCTGTCGTAAGTCACTCCTAGCAAGCGTCAAGCGCTT
TGCTAGGGATATTAGGAACAAGTACATAGCACCACCTCGGACGACCAATT
TTGGAGTTTTGTTTGTTCCGACAGAAGGTCTCTACTCAGAAATCGTCCGC
AATCCGGTCTTCTTTGATGATTTGAGACGGGAAGAACAGATTATTGTTGC
AGGACCAAGTACCCTATCAGCCCTTCTTAACTCCCTATCAGTTGGTTTCA
AGACCCTTAATATCCAAAGAGTGCCGACCATATCAGCAAGACTCTTGCC
AGTGTCAAGACCGAGTTTGGCAAGTTTGGTGGTATTCTGGTCAAGGCACA
AAAACATCTCCAACATGCCTCTGGCAATATTGATGAATTATTAAACCGTC
GTACCATAGCTATCGAGCGGACGATCCGTCACATTGAGTTGTCAGAAGGT
GAGCCTGCGCTTGATCTACTCCATTTTCAAGAAAATGAGGAAGAATATGA
AGATTAG 4164.3 (SEQ. ID. NO. 284)
ATGAAGATTAGTCACATGAAAAAGATGAGTTATTTGAAGGCTTTTACCT
AATCAAATCAGCTGACCTGAGGCAAACTCGAGCTGGGAAAAACTACCTAG
CCTTTACCTTCCAAGATGATAGTGGCGAGATTGATGGGAAGCTCTGGGAT
GCCCAACCTCATAAACATTGAGGCCTTTACCGCAGGTAAGGTTGTCCACAT
GAAAGGACGCCGAGAAGTTTATAACAATACCCCTCAAGTCAATCAAATTA
CTCTCCGCCTGCCTCAAGCTGGTGAACCCAATGACCCAGCTGATTTCAAG
GTCAAGTCACCAGTTGATGTCAAGGAAATTCGTGACTACATGTCGCAAAT
GATTTTCAAAATTGAAAATCCTGTCTGGCAACGGATTGTCCGAAATCTCT
ACACCAAGTATGATAAGGAATTCTACTCCTATCCAGCTGCCAAGACCAAC
CACCATGCCTTTGAAACGGGCTTGGCCTATCATACGGCGACCATGGTGCG
TTTGGCAGACGCTATTAGCGAAGTTTATCCTCAGCTCAATAAGAGCCTGC
TCTATGCGGGATTATGTTGCATGACTTAGCTAAGGTCATCGAGTTGACG
GGGCCAGACCAGACAGAGTACACAGTGCGAGGTAATCTTCTTGGACATAT
CGCTCTCATTGATAGCGAAATTACCAAGACAGTTATGGAACTCGGCATCG
ATGATACCAAGGAAGAAGTCGTTTTGCTTCGTCATGTCATCCTCAGTCAC
CACGGCTTGCTTGAGTATGGAAGCCCAGTCCGTCCACGCATTATGGAAGC
AGAGATTATCCATATGATTGACAATCTGGATGCAAGCATGATGATGATGT
CAACAGCTCTTGCTTTGGTGGATAAAGGAGAGATGACCAATAAAATCTTC
GCTATGGATAATCGTTCCTTCTATAAACCAGATTTAGATTAA 4166.2 (SEQ. ID. NO. 285)
ATGAGTGAAAAAGCTAAAAAAGGGTTTAAGATGCCTTCATCTTACACCGT
ATTATTGATAATCATTGCTATTATGGCAGTGCTAACTTGGTTTATCCCTG
CGGGGGCCTTTATAGAAGGTATTTACGAGACTCAGCCTCAAAATCCACAA
GGGATTTGGGATGTCCTGATGGCACCGATTCGGGCTATGCTAGGTACTCA
TCCAGAGGAAGGTTCGCTCATTAAAGAAACGAGCGCAGCGATTGATGTAG
CCTTCTTCATCCTTATGGTTGGTGGTTTCCTTGGCATTGTCAACAAAACT
GGTGCTCTTGACGTAGGGATTGCCTCTATCGTGAAGAAGTATAAGGGCCG
CGAAAAAATGTTAATTTTGGTACTGATGCCTTTGTTTGCCCTCGGTGGTA
CAACTTATGGTATGGGTGAAGAAACAATGGCCTTCTATCCACTCCTTGTG
CCAGTTATGATGGCCGTTGGTTTTGATAGCCTGACTGGTGTTGCAATTAT
TTTGCTCGGTTCTCAAATCGGCTGTTTGGCATCTACTCTGAATCCATTTG
CGACAGGTATTGCTTCAGCGACTGCGGGAGTTGGTACAGGGGACGGTATC
GTACTTCGTCTGATCTTCTGGGTTACCTTGACTGCTCTTAGTACTTGGTT
TGTTTACCGTTATGCGGATAAGATTCAAAAAGATCCGACTAAGTCACTGG
TTTATAGTACTCGCAAAGAAGATTTGAAACACTTTAACGTAGAAGAATCT
TCATCTGTAGAATCTACACTTAGCAGCAAACAAAAATCAGTTCTCTTCTT
ATTTGTGTTGACATTCATCTTGATGGTATTGAGCTTCATTCCATGGACAG
ACCTTGGCGTTACCATTTTTGATGACTTTAATACTTGGTTGACTGGTCTT
CCAGTTATTGGTAATATTGTCGGTTCATCTACTTCTGCACTAGGTACTTG
GTACTTCCCAGAAGGCGCAATGCTCTTTGCCTTTATGGGTATCCTGATTG
GTGTTATTTATGGTCTTAAAGAAGATAAGATTATCTCTTCCTTCATGAAT
GGTGCTGCTGACTTGCTCAGTGTTGCCTTGATCGTAGCGATTGCTCGTGG
TATTCAAGTTATCATGAACGACGGTATGATTACCGATACAATCCTCAACT
GGGGTAAAGAAGGCTTGAGCGGTCTATCTTCACAAGTCTTTATCGTTGTA
ACTTATATCTTCTATCTACCTATGTCATTCTTGATCCCATCTTCATCTGG
```

TABLE 1-continued

```
TCTTGCCAGCGCAACTATGGGTATCATGGCTCCACTTGGAGAATTTGTAA
ATGTCCGTCCTAGCTTGATTATCACTGCTTACCAATCTGCTTCAGGTGTC
TTGAACTTGATTGCACCAACATCTGGTATTGTGATGGGAGCTCTTGCACT
TGGACGTATCAACATTGGTACTTGGTGGAAATTCATGGGCAAACTCGTAG
TCGCTATTATTGTAGTGACCATCGCCCTTCTTCTCCTTGGAACCTTCCTT
CCATTCCTATAA
```

4166.3 (SEQ. ID. NO. 286)
```
ATGAAAATAGATATAACAAATCAAGTTAAAGATGAATTTCTTATATCATT
AAAAACCTTGATTTCCTATCCTTCAGTACTCAATGAAGGAGAAAATGGAA
CACCTTTTGGACAAGCAATCCAAGATGTCCTAGAAAAAACTTTAGAGATT
TGTCGAGACATAGGTTTCACTACCTATCTTGACCCTAAAGGTTATTACGG
ATATGCAGAAATCGGTCAGGGAGCAGAGCTTCTGGCCATTCTCTGTCATT
TGGATGTTGTTCCATCAGGTGATGAAGCAGATTGGCAGACACCGCCATTT
GAAGCAACTATCAAAGACGGCTGGGTATTCGGACGTGGTGTCCAAGATGA
TAAAGGCCCTTCGCTCGCAGCTCTCTATGCAGTAAAAAGCTTGCTGGACC
AAGGTATTCAGTTCAAAAAGCGCGTACGCTTTATCTTTGGTACCGATGAG
GAAACCCTCTGGCGCTGCATGGCACGCTACAATACCATCGAAGAACAGGC
CAGTATGGGCTTTGCACCTGACTCATCTTTTCCTCTGACCTATGCTGAAA
AAGGGCTTCTACAGGTCAAACTTCATGGCCCTGGATCGGATCAACTAGAG
CTTGAAGTAGGAGGCGCCTTTAACGTTGTACCAGACAAGGCCAACTACCA
AGGTCTCCTCTATGAACAGGTTTGTAACGGTCTCAAAGAAGCTGGTTATG
ATTACCAAACCACTGAACAAACCGTAACGGTTCTCGGAGTGCCAAAGCAT
GCTAAGGATGCTAGTCAAGGTATCAATGCTGTCATCCGACTAGCTACCAT
TCTTGCTCCTCTCCAAGAACACCCTGCTCTCAGTTTTCTTGCAACACAAG
CAGGTCAAGACGGCACAGGAAGACAAATCTTTGGTGATATAGCAGATGAA
CCTTCTGGTCACCTATCCTTTAATGTCGCAGGTCTCATGATCAATCATGA
ACGTTCTGAAATCCGTATTGACATTCGGACTCCTGTCTTAGCTGACAAGG
AAGAACTAGTAGAGTTGCTTACAAGATGTGCACAAAACTACCAACTCCGC
TACGAAGAGTTTGACTATCTAGCGCCTCTATACGTCGCAGAAGCAGTAA
ACTCGTTAGCACACTGATGCAAATCTACCAAGAAAAGACTGGCGATAACA
GTCCTGCTATTTCATCCGGTGGTGCCACTTTTGCTCGCACCATGCCAAAT
TGTGTAGCCTTCGGCGCCTTATTCCCAGGAGCGAAGCAGACAGAACATCA
GGCAAATGAATGTGCCGTTCTAGAAGATTTGTACCGTGCTATGGATATTT
ATGCCGAAGCCGTCTATCGACTTGCAACTTAA
```

4169.1 (SEQ. ID. NO. 287)
```
ATGTCTAATTCATTTGTCAAGTTGTTAGTCTCTCAATTATTTGCAAATTT
AGCAGATATTTTCTTTAGAGTAACAATCATTGCTAACATATACATTATTT
CAAAATCAGTAATTGCCACATCACTAGTTCCTATCTTAATAGGAATATCC
TCTTTTGTTGCGAGTCTTTTAGTTCCGTTGGTTACTAAAAGGTTAGCGCT
AAATAGGGTTTTATCTTTATCTCAATTTGGAAAGACTATATTATTGGCGA
TACTGGTAGGAATGTTTACCGTAATGCAATCCGTAGCGCCTTTGGTGACC
TATCTATTTGTTGTTGCAATTTCCATACTAGATGGTTTTGCAGCACCCGT
TTCCTATGCTATTGTGCCACGCTATGCGACCGATTTGGGTAAGGCTAATT
CAGCCTTATCAATGACTGGTGAAGCTGTTCAATTGATAGGTTGGGGATTA
GGTGGACTCTTGTTTGCAACAATTGGTCTGTTACCTACCACGTGTATCAA
TTTAGTCTTGTATATCATTTCTAGCTTTCTGATGTTATTCTTCCTAACG
CTGAAGTGGAGGTGTTAGAGTCAGAAACTAATCTTGAAATTTTGCTCAAA
GGTTGGAAGTTAGTTGCTAGAAATCCTAGATTAAGACTTTTTGTATCAGC
AAATTTATTGGAAATTTTTTCAAATACGATTTGGGTTTCTTCCATTATAC
TTGTTTTTGTAACGGAGTTATTAAATAAAACGGAAAGTTACTGGGGATAT
TCTAATACAGCATACTCTATTGGTATTATAATTAGTGGCTTAATTGCTTT
TAGGCTATCTGAAAAGTTCCTTGCTGCTAAATGGGAAGGGGAATTATTCA
CCCCAAATCTAAAAACCATCCAGAATCCTTGCCTTAGCTTAGATCCTGGA
TGGTTTCTTTTTTCACCCAATGGGTGTTTTTTACTAGACAAAAAAGAGTT
TCCCCTTTATGGTATAAGTGTAGAAAAAAACACAAAAAGAAAGGAAACTC
ACATGAACAGTTTACCAAATCATCACTTCCAAAACAAGTCTTTTTACCAA
CTATCTTTCGATGGAGGTCATTTAACCCAGTATGGTGGTCTTATCTTTTT
TCAGGAACTTTTTTCCCAGTTGAAACTAAAAGAGCGGATTTCTAAGTATT
TAGTAACGAATGACCAACGCCGCTACTGTCGTTATTCGGATTCAGATATC
CTTGTCCAGTTCCTCTTTCAACTGTTAACAGGTTATGGAACGGACTATGC
TTGTAAAGAATTGTCAGCTGATGCCTACTTTCCAAAATTGTTGGAAGGAG
GGCAGCTTGCTTCACAGCCAACCTTATCCCGTTTTCTTTCCAGAACTGAC
GAGGAAACAGTCCATAGTTTGCGATGCCTCAACCTTGAATTGGTCGAATT
CTTTTTACAGTTTCACCAGCTAAACCAACTCATTGTAGATATCGATTCTA
CCCATTTCACAACTTATGGCAAGCAAGAAGGTGTTGCTTATAACGCCCAC
TATCGTGCTCATGGCTATCATCCTCTTATGCTTTCGAGGGGAAGACAGGT
TATTGTTTCAATGCCCAGCTTCGTCCTGGTAATCGTTATTGTTCTGAAGA
GGCAGACAGCTTTATCACACCTGTTTTAGAACGGTTTAATCAACTTCTCT
TTCGAATGGATAGTGGCTTTGCGACCCCAAAATTATACGATTTAATTGAA
AAAACAGGGCAATACTACCTCATAAAACTCAAGAAAAATACTGTTCTGAG
CCGTCTTGGAGACCTTTCCCTCCCTTGCCCACAGGATGAGGACTTAACCA
TCTTGCCCACTCCGCCTACTCAGAAACTCTCTATCAAGCAGGATCTTGG
TCGCACAAGCGTCGTGTCTGCCAGTTCTCTGAACGAAAAGAAGGAAACTT
GTTCTACGATGTTATTTCTCTCGTTACAAATATGACGAGTGGAACAAGCC
AAGACCAGTTTCAGCTTTATCGTGGACGTGGTCAAGCCGAGAATTTCATC
AAGGAGATGAAGGAGGGATTTTTTGGCGATAAAACGGATAGTTCAACCTT
AATCAAAAACGAAGTTCGTATGATGATGAGCTGTATCGCCTACAATCTCT
ATCTTTTTCTCAAACATCTAGCTGGAGGTGACTTCCAAACTTTAACAATC
AAACGCTTCCGCCATCTTTTTCTTCACGTGGTGGGAAAATGTGTTCGAAC
AGGACGCAAGCAGCTCCTCAAATTGTCTAGTCTCTATGCCTATTCCGAAT
```

TABLE 1-continued

TGTTTTCAGCACTTTATTCTAGGATTAGAAAAGTCAACCTGAATCTTCCT

GTTCCTTATGAACCACCTAGAAGAAAAGCGTCGTTAATGATGCATTAA 4169.3 (SEQ. ID. NO. 288)
ATGATGGAGTTTTTTCAACAGCTTCCTCATTTAGAGCCATATGGCAATCC

TCAGTATTTTGTTTATGTGATTGCTGCAACCTTGCCCATCTTTATAGGTC

TCTTTTTCAAGAAACGCTTTGCCTGGTATGAAGTGTTGGTAAGTCTCTTC

TTTATTGTCACCATGTTGGTGGGTGGAAAGACCAATCAACTAGCTGCCTT

GGGTATTTACCTTTGCTGGGAAATATTGCTCCTGCTTTTCTACAAGCATT

ATCGAAAAGCAAGGATGGCAAGTGGGTCTTCTACTTAGTTAGTTTTCTG

TCCCTACTTCCGATTATCTTTGTCAAGGTGCAACCAGCTATCAATGGAAC

GCAGTCTTTGCTTGGGTTCTTGGGAATTTCTTACCTGACCTTTCGTTCGG

TTGGAATTGTCATCGAGCTGAGAGATGGAGTGATTAAGGATTTTACCCTC

TGGGAATTCCTCCGTTTCCTTCTCTTCATGCCAACTTTCTCGAGTGGTCC

AATCGATCGCTTTAAGCGATTTAATGAAAATTATCAGGCTATTCCTGAGC

GAGATGAGTTGATGGATATGCTGGATGAATCTGTCCGCTATATCATGTGG

GGCTTTTTGTATAAGTTTATCCTAGCTCATGTTTAGGAGAGACCTTACT

ACCTCCTCTGAAGAATTTAGCCTTGCAGTCAGGTGGCTTCTTTAATCTCT

ATGCCTTGGCAGTTATGTATACTTTTGGTCTGGAACTCTTCTTTGACTTT

GCAGGTTATTCTATGTTTGCTTTGGCCATCTCAAACTTGATGGGAATCCG

TAGCCCTATCAACTTTAACAAGCCCTTTTTATCAAGGGATTTAAAGGAGT

TTTGGAATCGCTGGCATATGAGTCTGTCCTTCTGGTTCCGTGACTTTGTC

TTTATGCGAATGGTGATGGTGTTAACCAGAAAGAAAGTCTTTAAAAATCG

TAATGTAACCTCAAGCATGGCCTACATTGTAAATATGCTGATTATGGGAT

TTTGGCATGGTGTGACCTGGTACTATATCGCCTATGGACTCTTTCATGGA

CTAGGCTTGGTCATCAATGATGCCTGGGTTCGCAAGAAAAAACGCTCAA

TAAGGAACGGAAAAAAGCAGGGAAGGCTGCCCTACCTGAGAATCGCTGGA

TTCAGTTGCTTGGCATGGTTGTCACTTTCCATGTTGTCATGTTGTCATTC

TTAATCTTTTCTGGATTCTTGAATAATCTATGGTTTAAAAAATAA 4169.4 (SEQ. ID. NO. 289)
ATGCTTAAACGCTTATGGATGATCTTCGGACCGGTCTTGATCGCTGGTTT

GTTGGTTTTTCTGCTCATTTTCTTTTATCCTACTGAGATGCATCATAATC

TAGGAGCTGAAAAGCGTTCAGCAGTGGCTACTACTATCGATAGTTTTAAG

GAGCGAAGTCAAAAAGTCAGAGCACTATCTGATCCAAATGTGCGTTTTGT

TCCCTTCTTTGGCTCTAGTGAATGGCTTCGTTTTGACGGTGCTCATCCTG

CGGTATTAGCTGAGAAATACAATCGTTCCTACCGTCCTTATCTTTTAGGA

CAGGGGGAGCTGCATCGCTTAACCAATATTTGGAATGCAACAGATGTT

ACCACAGCTGGAGAATAAACAAGTTGTGTATGTTATCTCACCTCAGTGGT

TCAGTAAAAATGGCTATGATCCAGCAGCCTTCCAGCAGTATTTTAATGGA

GACCAGTTGACTAGTTTTCTGAAACATCAATCTGGGGATCAGGCTAGTCA

ATATGCAGCGACTCGCTTACTGCAACAGTTCCCAAACGTAGCTATGAAGG

ACCTGGTTCAGAAGTTGGCAAGTAAAGAAGAATTGTCGACAGCAGACAAT

GAAATGATTGAATTATTGGCTCGTTTTAATGAACGCCAAGCTTCCTTTTT

TGGTCAGTTTTCGGTTAGAGGCTATGTTAACTACGATAAGCATGTAGCTA

AGTATTTAAAAATCTTGCCAGACCAGTTTTCTTATCAGGCAATAGAAGAT

GTTGTCAAAGCAGATGCTGAAAAAAATACTTCCAATAATGAGATGGGAAT

GGAAAATTATTTCTATAATGAGCAGATCAAGAAGGATTTGAAGAAATTAA

AGGATTCTCAGAAAAGCTTTACCTATCTCAAGTCGCCAGAGTATAATGAC

TTGCAGTTGGTTTTAACACAGTTTTCTAAATCTAAGGTAAACCCGATTTT

TATCATTCCACCTGTTAATAAAAAATGGATGAACTATGCTGGTCTACGAG

AGGATATGTACCAACAAACGGTGCAGAAGATTCGCTACCAGTTAGAAAGT

CAAGGTTTTACCAATATAGCAGATTTTTCTAAGGACGGCGGGGAGCCTTT

CTTTATGAAGGACACCATTCACCTTGGTTGGTTGGGTTGGTTGGCTTTTG

ACAAGGCAGTTGATCCTTTCCTATCCAATCCCACACCAGCTCCGACTTAC

CATCTGAATGAGCGCTTTTTCAGCAAAGATTGGGCGACTTATGATGGAGA

TGTCAAAGAATTTCAATAG 4169.6 (SEQ. ID. NO. 290)
ATGGAGAAAAACCTCAAGGCTTTGAAACAAACAACAGACCAAGAAGGCCC

AGCAATTGAACCTGAAAAGGCAGAGGATACCAAGACAGTCCAAAATGGTT

ACTTCGAGGATGCAGCTGTCAAGGACCCGCACCTTGAGTGACTATGCAGGT

AACTGGCAATCAGTTTATCCTTTCCTTGAAGACGGCACGTTTGACCAAGT

CTTTGACTACAAGGCTAAGTTGACTGGTAAGATGACCCAGGCTGAGTACA

AGGCTTACTATACAAAAGGCTATCATACAGATGTGACTAAGATTAACATT

ACTGATAATACTATGGAATTTGTTCAAGGTGGACAAAGCAAGAAATACAC

TTACAAGTATGTCGGTAAGAAAATTTTGACTTACAAGAAAAGGCAATCGT

GGCGTGCGTTTCCTCTTTGAAGCCACAGATGCTGACGCTGGACAATTCAA

GTATGTTCAGTTTAGTGACCACAATGTTGCCCCAGTTAAGGCAGAACATT

TCCATATCTTCTTTGGAGGCACAAGCCAAGAAGCCCTCTTTGAAGAAATG

GACAACTGGCCAACCTACTACCCAGATAACCTATCTGGCCAAGAAATCGC

CCAAGAAATGTTGGCGCATTGA 4170.3 (SEQ. ID. NO. 291)
ATGAAAGATGGTCATTTGCTAGCCCATCATATTCGTTTGTTGAATGGGCG

GATTTTTCAAAAGTTACTGAGTCAAGATCCTGAGGCTCTTTATAGGGGTG

AACAGGGCAAGATTTTAGCGGTTTTATGGAATAGTGAAACTGGCTGCGCA

ACTGCGACAGATATCGCGCTTGCGACTGGACTTGCGAATAATACGCTGAC

GACTATGATAAAAAGCTAGAGGAACAAAAGCTTGTAATTGTTAGTCCGT

GTGGAAAGACAAGCGTAAGAAGTATTTAGTTTTAACGGAGTTAGGCAAG

TCCCAGAAAGAAGTGGGGCATCGTGTCAGTCAGAAATTGGATACTATCTT

TTACAAAGGATTTTCAGAGGAAGAAATTCACCAATTTGAAGGTTTTCAAG

AAAGAATTTTGGCGAATCTGAAAGAGAAGGGAAATGAGGTTTAG 4170.4 (SEQ. ID. NO. 292)
ATGACTAATTTAATTGCAACTTTTCAGGATCGTTTTAGTGATTGGTTGAC

AGCTCTATCTCAACATTTGCAGTTGTCGCTTTTGACCTTGTTACTAGCTA

TABLE 1-continued

TTTTGCTTGCGATTCCCTTGGCTGTTTTTCTTCGCTATCATGAGAAGCTG
GCCGACTGGGTCTTGCAGATTGCAGGTATTTTCCAGACCATCCCGTCTCT
GGCCTTGTTGGGGCTCTTTATCCCTTTGATGGGAATTGGGACCTTGCCGG
CTTTGACAGCTCTAGTGATTTATGCGATTTTCCCTATTTTGCAAAATACT
ATCACTGGGCTGAAGGGAATTGATCCGAACCTGCAAGAGGCTGGGATTGC
CTTTGGGATGACCAGATGGGAACGTCTCAAGAAATTTGAAATTCCACTCG
CCATGCCTGTTATCATGTCTGGGATTCGGACGGCAGCTGTTTTGATTATC
GGTACGGCAACCTTGGCGGCCTTGATTGGTGCAGGGGACTAGGTTCCTT
TATTCTTTTGGGAATTGACCGTAATAATGCCAGTTTGATTTTGATTGGGG
CACTTTCTTCTGCAGTGCTAGCCATTGCCTTTAACTTCCTACTAAAAGTG
ATGGAAAAAGCAAAATTACGGACGATTTTCTCAGGTTTTGCCTTGGTGGC
TTTATTACTGGGTCTGTCTTATAGTCCAGCTCTTTTGGTTCAAAAGAGA
AGGAAAACTTGGTTATTGCTGGGAAAATAGGTCCAGAACCAGAAATTTTG
GCCAATATGTATAAGTTGCTGATTGAAGAAATACCAGCATGACTGCGAC
TGTTAAACCGAATTTTGGGAAGACAAGCTTCCTTTATGAAGCTCTGAAAA
AAGGCGATATTGACATCTATCCTGAATTTACTGGTACGGTGACTGAAAGT
TTGCTTCAACCATCACCCAAGGTGAGTCATGAACCAGAACAGGTTTATCA
GGTGGCGCGTGATGGCATTGCTAAGCAGGATCATCTAGCCTATCTCAAAC
CCATGTCTTATCAAACACCTATGCTGTAGCTGTTCCGAAAAAGATTGCT
CAAGAATATGGCTTGAAGACCATTTCAGACTTGAAAAAAGTGGAAGGGCA
GTTGAAGGCAGGTTTTACACTCGAGTTTAACGACCGTGAAGATGGAAATA
AGGGCTTGCAATCAATGTATGGTCTCAATCTCAATGTAGCGACCATTGAG
CCAGCCCTTCGCTATCAGGCTATTCAGTCAGGGGATATTCAAATCACGGA
TGCCTATTCGACTGATGCGAATTGGAGCGTTATGATTTACAGGTCTTGG
AAGATGACAAGCAACTCTTCCCACCTTATCAAGGGGCTCCACTCATGAAA
GAAGCTCTTCTCAAGAAACACCCAGAGTTGGAAAGAGTTCTTAATACATT
GGCTGGTAAGATTACAGAAAGCCAGATGAGCCAGCTCAACTACCAAGTCG
GTGTTGAAGGCAAGTCAGCAAAGCAAGTAGCCAAGGAGTTTCTCCAAGAA
CAAGGTTTGTTGAAGAAATGA 4170.5 (SEQ. ID. NO. 293)
ATGATGCATACTTATTTGCAAAAGAAAATTGAAAATATCAAAACAACCCT
AGGTGAAATGTCAGGTGGTTACCGTCGTATGGTTGCGGCTATGGCTGATT
TAGGATTTTCAGGAACTATGAAGGCTATCTGGGATGACCTCTTTGCCCAT
CGTAGTTTTGCCCAGTGGATTTATTTGCTGGTTTTAGGAAGTTTTCCTCT
CTGGCTGGAGTTGGTTTACGAACATCGTATTGTTGACTGGATTGGGATGA
TTTGTAGCTTGACAGGGATTATCTGTGTAATCTTTGTATCGGAAGGTCGA
GCAAGTAATTATCTTTTGGCTTGATTAACTCTGTTATTTACCTTATTTT
GGCCCTACAGAAAGGCTTTTATGGTGAGGTGCTGACGACACTTTACTTCA
CAGTCATGCAGCCAATTGGACTTCTAGTTTGGATTTATCAGGCACAGTTT
AAGAAGGAAAAGCAGGAGTTTGTCGCGCGTAAACTGGACGGCAAGGGCTG

GACAAAGTATCTTTCCATTAGTGTGCTTTGGTGGTTGGCCTTTGGCTTCA
TTTATCAGTCTATTGGTGCCAATCGTCCCTATCGTGATTCAATCACAGAT
GCAACCAATGGGGTAGGGCAAATCCTCATGACAGCTGTTTACCGTGAACA
GTGGATATTCTGGGCGGCTACCAATGTCTTTTCAATCTATCTCTGGTGGG
GAGAAAGCCTGCAAATTCAAGGGAAATATCTAATTTATCTCATTAACAGT
CTAGTTGGTTGGTATCAATGGAGCAAGGCAGCTAAGCAGAATACTGATTT
ACTTAACTAG 4170.6 (SEQ. ID. NO. 294)
ATGAGAAATATGAAGGCAAAATATGCTGTTTGGGTGGCTTTTTTCTTAAA
TTTGACTTATGCCATTGTTGAGTTTATGCAGGTGGAGTATTTGGTTCTAG
CGCTGTTCTTGCTGACTCTGTGCATGACTTGGGAGATGCGATTGCAATTG
GAATATCAGCTTTTCTAGAAACAATCTCCAATCGTGAAGAAGACAATCAG
TACACCTTGGGCTATAAGCGGTTTAGCCTGCTAGGAGCCTTGGTAACAGC
TGTGATTCTCGTAACGGGCTCTGTTCTAGTCATTTTGGAAAATGTCACGA
AGATTTGCATCCGCAACCAGTCAATGATGAGGGGATTCTCTGGTTAGGAA
TTATTGCGATTACTATCAATCTGTTAGCGAGTCTGGTGGTTGGTAAGGGA
AAGACAAAGAATGAGTCTATTCTGAGTCTGCATTTTCTGGAAGATACGCT
AGGGTGGGTAGCTGTTATCCTGATGGCGATTGTTCTTCGATTTACGGACT
GGTATATCCTAGATCCTCTTTTGTCCCTTGTCATTTCTTTCTTTATTCTT
TCAAAAGCCCTTCCACGTTTTTGGTCTACACTCAAGATTTTCTTGGATGC
TGTGCCAGAAGGTCTTGATATCAAGCAAGTAAAGAGTGGCCTGGAGCGAT
TGGACAATGTGGCCAGCCTTAATCAGCTTAATCTCTGGACTATGGATGCT
TTGGAAAAAAATGCCATTGTCCATGTTTGTCTAAAAGAAATGGAACATAT
GGAAACTTGTAAAGAGTCTATTCGAATTTTCCTAAAAGATTGTGGTTTTC
AAAATATTACCATTGAAATTGATGCTGACCTAGAAACTCACCAAACCCAT
AAGCGAAAGGTGTGTGACTTGGAACGGAGTTATGAGCATCAACATTAG 4170.8 (SEQ. ID. NO. 295)
ATGATTGAATACAAAAATGTAGCACTGCGCTACACAGAAAAGGATGTCTT
GAGAGATGTCAACTTACAGATTGAGGATGGGGAATTTATGGTTTTAGTAG
GGCCTTCTGGGTCAGGTAAGACGACCATGCTCAAGATGATTAACCGTCTT
TTGGAACCAACTGATGGAAATATTTATATGGATGGGAAGCGCATCAAAGA
CTATGATGAGCGTGAACTTCGTCTTTCTACTGGTTATGTTTTACAGGCTA
TTGCTCTTTTTCCAAATCTAACAGTTGCGGAAAATATTGCTCTCATTCCT
GAAATGAAGGGGTGGAGCAAGGAAGAAATTACGAAGAAACAGAAGAGGT
TTTGGCTAAGGTTGGTTTACCAGTAGCCGAGTATGGGCATCGCTTACCTA
GTGAATTATCTGGTGGAGAACAGCAACGGGTCGGTATTGTCCGAGCTATG
ATTGGTCAGCCCAAGATTTTCCTCATGGATGAACCCTTTTCGGCCTTGGA
TGCTATTTCGAGAAAACAGTTGCAGGTTCTGACAAAAGAATTGCATAAAG
AGTTTGGGATGACAACGATTTTTGTAACCCATGATACGGATGAAGCCTTG
AAGTTGGCGGACCGTATTGCTGTCTTGCAGGATGGAGAAATTCGCCAGGT

TABLE 1-continued

AGCGAATCCCGAGACAATTTTAAAAGCGCCTGCAACAGACTTTGTAGCAG

ACTTGTTGGAGGTAGTGTTCATGACTAA 4171.1 (SEQ. ID. NO. 296)
ATGTCAGCAGTTGCTATTTCAGCTATGACCAAGGTTATGCAAGAAACCCA

CGGAAATCCTTCTAGTATTCATGGTCATGGTCGTCAAGCTGGCAAACTCT

TGCGAGAAGCCCGTCAGGAACTAGCCCAGTTACTAAGGACAAAACCTCAA

CATATCTTTTTCACTTCTGGTGGGACTGAAGGCAATAATACTACCATCAT

TGGCTACTGTCTTCGTCACCAAGAACAAGGAAAACATATCATCACAACTG

CCATCGAGCACCATGCTGTCCTTGAAACAATTGATTACTTGGTTCAACAC

TTTGGGTTTGAAGCAACCATTATCCAGCCAGAAAATCAAGAAATCACAGC

CCAGCAAATTCAAAAGGCTTTACGTGACGATACGATTTTGGTTTCTACCA

TGTTTGTCAATAATGAGACAGGAAACCTACTGCCCATCGCTGAAATTGGC

CAAATACTCAAGCAACACCCTGCTGCCTATCATGTTGATGCAGTTCAGGC

TATTGGTAAAATCCCAATTCATTCAGAAGAATTGGGCATTGATTTTCTCA

CTGCTTCTGCCCACAAATTCCATGGTCCTAAGGGAATCGGTTTTCTCTAC

GCATCTAGCATGGACTTTGATTCCTATCTACATGGCGGAGACCAGGAACA

GAAAAAACGTGCAGGAACTGAAAATCTGCCTGCCATTGTAGGCATGGTTG

CAGCCCTAAAAGAAGACCTAGAAAACAAGAAGAACATTTTCAACATGTA

CAAAATCTAGAAACTGCCTTTCTGGCAGAGCTGGAGGGCATTCAGTATTA

CCTGAATAGAGGAAAACATCATCTCCCTTATGTTCTCAATATTGGATTTC

CTGGTCAGAAAAATGACCTCTTACTCCTTCGGCTAGATTTAGCTGGAATT

TCAATCTCTACTGGCTCAGCCTGTACTGCAGGCGTTGTCCAATCCAGCCA

TGTTCTTGAAGCCATGTATGGCGCAAATTCAGAACGCTTGAAGGAATCCC

TTCGCATCAGTTTGTCGCCACAAAATACCGTTGAAGACCTACAAACCCTC

GCAAAAACCTTAAAAGAAATTATCGGAGGTTAG 4172.1 (SEQ. ID. NO. 297)
ATGTTATTCAAATTATCTAAGGAAAAAATAGAGCTAGGCTTATCTCGTTT

ATCGCCAGCCCGTCGTATTTTTTGAGTTTTGCCTTGGTCATTTTACTAG

GCTCTCTTCTTTTGAGCTTGCCCTTTGTCCAAGTTGAAAGCTCACGAGCG

ACTTATTTTGATCATCTTTTCACTGCTGTCTCTGCAGTCTGTGTGACGGG

TCTCTCAACCCTTCCAGTAGCTCACACCTATAATATCTGGGGTCAAATAA

TCTGTTTGCTCTTGATTCAGATCGGTGGTCTAGGGCTCATGACCTTTATT

GGGGTTTTCTATATCCAGAGCAAGCAAAAGCTTAGTCTTCGTAGCCGTGC

AACTATTCAGGATAGTTTTAGTTATGGAGAAACTCGATCTTTGAGAAAGT

TTGTCTATTCTATTTTTCTCACGACCTTTTTGGTTGAGAGCTTGGGAGCT

ATTTTGCTTAGTTTTCGCCTTATTCCTCAACTTGGCTGGGGACGTGGTCT

TTTTAGTTCCATTTTTCTAGCGATCTCAGCCTTCTGTAATGCCGGTTTTG

ATAATTTAGGGAGCACCAGTTTATTTGCTTTTCAGACCGATTTACTGGTC

AATCTGGTGATTGCAGGCTTGATTATTACAGGCGGCCTTGGTTTTATGGT

CTGGTTTGATTTGGCTGGTCATGTAGGAAGAAAGAAAAAAGGACGTCTGC

ACTTTCATACGAAGCTTGTACTATTATTGACTATAGGTTTGTTGTTATTT

GGAACAGCAACTACTCTCTTTCTTGAGTGGAACAATGCTGGAACGATTGG

CAATCTCCCTGTTGCCGATAAGGTTTTAGTTAGCTTTTTTCAAACAGTGA

CGATGCGAACAGCTGGCTTTTCTACGATAGATTATACTCAGGCTCATCCT

GTGACTCTTTTGATTTATATCTTACAGATGTTTCTAGGTGGGGCACCTGG

AGGAACAGCTGGGGGACTCAAGATTACGACATTTTTTGTCCTCTTGGTCT

TTGCACGAAGTGAGCTTCTAGGCTTGCCTCATGCCAATGTTGCGAGACGA

ACGATCGCGCCGCGAACGGTTCAAAAATCCTTTAGTGTCTTTATTATCTT

TTTGATGAGCTTCTTGATAGGATTGATTCTGCTAGGGATAACAGCCAAAG

GCAATCCTCCCTTTATCCACCTCGTATTTGAAACCATTTCAGCTCTTAGT

ACAGTTGGTGTAACGGCAAATCTGACTCCTGACCTTGGGAAATTGGCTCT

CAGTGTTATCATGCCACTTATGTTTATGGGACGAATTGGTCCCTTGACCT

TGTTTGTTAGCTTGGCAGATTACCATCCAGAAAAGAAAGATATGATTCAC

TATATGAAAGCAGATATTAGTATTGGTTAA 4172.2 (SEQ. ID. NO. 298)
ATGTCAGATCGTACGATTGGAATTTTGGGCTTGGGAATTTTTGGGAGCAG

TGTCCTAGCTGCCCTAGCCAAGCAGGATATGAATATTATCGCTATTGATG

ACCACGCAGACGCGATCAATCAGTTTGAGCCAGTTTTGGCGCGTGGAGTG

ATTGGTGACATCACAGATGAAGAATTATTGAGATCAGCAGGGATTGATAC

CTGCGATACCGTTGTAGTCGCGACAGGTGAAAATCTGGAGTCGAGTGTGC

TTGCGGTTATGCACTGTAAGAGTTTGGGGGTACCGACTGTTATTGCTAAG

GTCAAAAGTCAGACCGCTAAGAAAAGTGCTAGAAAAGATTGGAGCTGACT

CGGTTATCTCGCCAGAGTATGAAATGGGCAGTCTCTAGCACAGACCATT

CTTTTCCATAATAGTGTTGATGTCTTTCAGTTGGATAAAAATGTGTCTAT

CGTGGAGATGAAAATTCCTCAGTCTTGGGCAGGTCAAAGTCTGAGTAAAT

TAGACCTCCGTGGCAAATACAATCTGAATATTTTGGGTTTCCGAGAGCAG

GAAAATTCCCCATTGGATGTTGAATTTGGACCAGATGACCTCTTGAAAGC

AGATACCTATATTTTGGCAGTCATCAACAACCAGTATTTGGATACCCTAG

TAGCATTGAATTCGTAA 4172.3 (SEQ. ID. NO. 299)
ATGAAGTTATTGTCTATCGCAATTTCTAGCTATAATGCAGCAGCCTATCT

TCATTACTGTGTGGAGTCGCTAGTGATTGGTGGTGAGCAAGTTGGGATTT

TGATTATCAATGACGGGTCTCAGGATCAGACTCAGGAAATCGCTGAGTGT

TTAGCTAGCAAGTATCCTAATATCGTTAGAGCCATCTATCAGGAAATAA

ATGCCATGGCGGTGCGGTCAATCGTGGCTTGGTAGAGGCTTCTGGGCGCT

ATTTTAAAGTAGTTGACAGTGATGACTGGGTGGATCCTCGTGCCTACTTG

AAAATTCTTGAAACCTTGCAGGAACTTGAGAGCAAAGGTCAAGAGGTGGA

TGTCTTTGTGACCAATTTTGTCTATGAAAAGGAAGGGCAGTCTCGTAAGA

AGAGTATGAGTTACGATTCAGTCTTGCCTGTTCGGCAGATTTTTGGCTGG

GACCAGGTCGGAAATTTCTCCAAAGGCCAGTATACCATGATGCACTCGCT

GATTTATCGGACAGATTTGTTGCGTGCTAGCCAGTTCTAA

TABLE 1-continued 4172.4 (SEQ. ID. NO. 300)
ATGAAATTCAATCCAAATCAAAGATATACTCGTTGGTCTATTCGCCGTCT
CAGTGTCGGTGTTGCCTCAGTTGTTGTGGCTAGTGGCTTCTTTGTCCTAG
TTGGTCAGCCAAGTTCTGTACGTGCCGATGGGCTCAATCCAACCCCAGGT
CAAGTCTTACCTGAAGAGACATCGGGAACGAAAGAGGGTGACTTATCAGA
AAAACCAGGAGACACCGTTCTCACTCAAGCGAAACCTGAGGGCGTTACTG
GAAATACGAATTCACTTCCGACACCTACAGAAAGAACTGAAGTGAGCGAG
GAAACAAGCCCTTCTAGTCTGGATACACTTTTTGAAAAAGATGAAGAAGC
TCAAAAAAATCCAGAGCTAACAGATGTCTTAAAAGAAACTGTAGATACAG
CTGATGTGGATGGGACACAAGCAAGTCCAGCAGAAACTACTCCTGAACAA
GTAAAAGGTGGAGTGAAAGAAAATACAAAAGACAGCATCGATGTTCCTGC
TGCTTATCTTGAAAAAGCTGAAGGGAAAGGTCCTTTCACTGCCGGTGTAA
ACCAAGTAATTCCTTATGAACTATTCGCTGGTGATGGTATGTTAACTCGT
CTATTACTAAAAGCTTCGGATAATGCTCCTTGGTCTGACAATGGTACTGC
TAAAAATCCTGCTTTACCTCCTCTTGAAGGATTAACAAAAGGGAAATACT
TCTATGAAGTAGACTTAAATGGCAATACTGTTGGTAAACAAGGTCAAGCT
TTAATTGATCAACTTCGCGCTAATGGTACTCAAACTTATAAAGCTACTGT
TAAAGTTTACGGAAATAAAGACGGTAAAGCTGACTTGACTAATCTAGTTG
CTACTAAAAATGTAGACATCAACATCAATGGATTAGTTGCTAAAGAAACA
GTTCAAAAAGCCGTTGCAGACAACGTTAAAGACAGTATCGATGTTCCAGC
AGCCTACCTAGAAAAAGCCAAGGGTGAAGGTCCATTCACAGCAGGTGTCA
ACCATGTGATTCCATACGAACTCTTCGCAGGTGATGGCATGTTGACTCGT
CTCTTGCTCAAGGCATCTGACAAGGCACCATGGTCAGATAACGGCGACGC
TAAAAACCCAGCCCTATCTCCACTAGGCGAAAACGTGAAGACCAAAGGTC
AATACTTCTATCAAGTAGCCTTGGACGGAAATGTAGCTGGCAAAGAAAAA
CAAGCGCTCATTGACCAGTTCCGAGCAAATGGTACTCAAACTTACAGCGC
TACAGTCAATGTCTATGGTAACAAAGACGGTAAACCAGACTTGGACAACA
TCGTAGCAACTAAAAAAGTCACTATTAACATAAACGGTTTAATTTCTAAA
GAAACAGTTCAAAAAGCCGTTGCAGACAACGTTAAAGACAGTATCGATGT
TCCAGCAGCCTACCTAGAAAAAGCCAAGGGTGAAGGTCCATTCACAGCAG
GTGTCAACCATGTGATTCCATACGAACTCTTCGCAGGTGATGGTATGTTG
ACTCGTCTCTTGCTCAAGGCATCTGACAAGGCACCATGGTCAGATAACGG
TGACGCTAAAAACCCAGCCCTATCTCCACTAGGTGAAAACGTGAAGACCA
AAGGTCAATACTTCTATCAATTAGCCTTGGACGGAAATGTAGCTGGCAAA
GAAAAACAAGCGCTCATTGACCAGTTCCGAGCAAACGGTACTCAAACTTA
CAGCGCTACAGTCAATGTCTATGGTAACAAAGACGGTAAACCAGACTTGG
ACAACATCGTAGCAACTAAAAAAGTCACTATTAACATAAACGGTTTAATT
TCTAAAGAAACAGTTCAAAAAGCCGTTGCAGACAACGTTAAGACAGTATC
GATGTTCCAGCAGCCTACCTAG 4172.5 (SEQ. ID. NO. 301)
ATGAAACTAAAAAGTTATATTTTGGTTGGATATATTATTTCAACCCTCTT
AACCATTTTGGTTGTTTTTTGGGCTGTTCAAAAAATGCTGATTGCGAAAG
GCGAGATTTACTTTTTGCTTGGGATGACCATCGTTGCCAGCCTTGTCGGT
GCTGGGATTAGTCTCTTTCTCCTATTGCCAGTCTTTACGTCGTTGGGCAA
ACTCAAGGAGCATGCCAAGCGGGTAGCGGCCAAGGATTTTCCTTCAAATT
TGGAGGTTCAAGGTCCTGTAGAATTTCAGCAATTAGGGCAAACTTTTAAT
GAGATGTCCCATGATTTGCAGGTAAGCTTTGATTCCTTGGAAGAAAGCGA
ACGAGAAAAGGGCTTGATGATTGCCCAGTTGTCGCATGATATTAAGACTC
CTATACTTCGATCCAAGCGACGGTAGAAGGGATTTGGATGGGATTATC
AAGGAGTCGGAGCAAGCTCATTATCTAGCAACCATTGGACGCCAGACGGA
GAGGCTCAATAAACTGGTTGAGGAGTTGAATTTTTTGACCCTAAACACAG
CTAGAAATCAGGTGGAAACTACCAGTAAAGACAGTATTTTTCTGGACAAG
CTCTTAATTGAGTGCATGAGTGAATTTCAGTTTTTGATTGAGCAGGAGAG
AAGAGATGTCCACTTGCAGGTAATCCCAGAGTCTGCCCGGATTGAGGGAG
ATTATGCTAAGCTTTCTCGTATCTTGGTGAATCTGGTCGATAACGCTTTT
AAATATTCTGCTCCAGGAACCAAGCTGGAAGTGGTGGCTAAGCTGGAGAA
GGACCAGCTTTCAATCAGTGTGACCGATGAAGGGCAGGGTATTGCCCCAG
AGGATTTGGAAAATATTTTCAAACGCCTTTATCGTGTCGAAACTTCGCGT
AACATGAAGACAGGTGGTCATGGATTAGGACTTGCGATTGCGCGTGAATT
GGCCCATCAATTGGGTGGGAAATCACAGTCAGCAGCCAGTACGGTCTAG
GAAGTACCTTTACCCTCGTTCTCAACCTCTCTGGTAGTGAAAATAAAGCC
TAA 4172.6 (SEQ. ID. NO. 302)
ATGTTTGGTCAAACGGCTCAACATGGTCTTACGAATAGCCTGAAAGACTT
CTGGATTTTTCTGCTGAATATAGGTCCACAATTGGCGTTTTTTGCCAGA
TGCTCCGCTGTTCCAGATCGGTTGAGCAGGGTACTGGAAATCACCGTCGT
GAGTTCAATATGATTCAGCAGATATTCTCGCATTTTGGGATGACTCACTT
GGGACAAATCAAGTTGGTCTATCAAGAGTCGATTGACCTTGAGTTGCTGG
TCAATGCACTTAATCATCACTTGCTCATTGACAGACTGGTCCTCACGCCC
AATCAAATAACGATAGAAATCGACAGGCAGATAGTACATGGTCTTGACCT
GCTGAAGGGGCGTAAAGACAAAGAGATTATCGACATAAAAGTATGTTCA
GGCAGTTAGAACTGGCTAGCACGCAACAAATCTGTCCGATAAATCAGCGA
GTGCATCATGGTATACTGGCCTTTGGAGAAATTTCCGACCTGGTCCCAGC
CAAAAATCTGCCGAACAGGCAAGACTGA 4174.1 (SEQ. ID. NO. 303)
ATGGAACATTTAGCAACTTATTTTTCAACCTATGGAGGAGCTTTCTTCGC
TGCATTGGGAATTGTATTGGCGGTTGGATTAAGCGGTATGGGGTCTGCTT
ATGGAGTTGGTAAGGCTGGGCAATCTGCCGCAGCTTTACTGAAAGAACAG
CCTGAAAAGTTTGCCTCAGCTTTGATATTGCAATTATTGCCCGGAACACA
AGGATTATATGGTTTTGTTATTGGAATTTTAATTTGGTTGCAATTAACTC TABLE 1-continued

CAGAACTTCCTTTAGAAAAAGGCGTTGCTTATTTCTTTGTAGCTCTTCCA

ATTGCTATTGTAGGATACTTTTCAGCTAAGCATCAAGGAAATGTAGCAGT

AGCGGGAATGCAAATCTTGGCTAAAAGACCAAAAGAATTCATGAAGGGAG

CAATTTTAGCTGCCATGGTAGAAACCTATGCAATTCTTGCTTTTGTCGTA

TCATTCATTTTGACCCTTCGTGTATTA 4175.2 (SEQ. ID. NO. 304)
ATGTTAAAATCAGAAAAACAATCACGTTATCAAATGTTAAATGAAGAATT

GTCCTCCTATTGGAAGGCGAAACCAATGTTTTGGCTAATCTTTCCAACGC

CAGTGCTCTCATAAAATCACGTTTTCCTAATACCGTATTTGCAGGCTTTT

ATTTGTTCGATGGAAAGGAATTGGTTTTAGGCCCCTTCCAAGGAGGTGTT

TCCTGCATCCGTATTGCACTAGGCAAGGGTGTTTGTGGTGAGGCAGCTCA

CTTTCAGGAAACTGTTATTGTTGGAGATGTGACGACCTATCTCAACTATA

TTTCTTGTGATAGTCTAGCTAAAAGTGAAATTGTGGTGCCGATGATGAAG

AATGGTCAGTTACTTGGAGTTCTGGATCTGGATTCTTCAGAGATTGAGGA

TTACGATGCTATGGATCGAGATTATTTGGAACAATTTGTCGCTATTTTGC

TTGAAAAGACAGCATGGGACTTTACGATGTTTGAGGAAAATCTTAA 4175.3 (SEQ. ID. NO. 305)
ATGTCAGTATTAGAGATCAAAGATCTTCACGTTGAGATTGAAGGAAAAGA

AATTTTAAAAGGGGTTAACCTGACCCTGAAAACAGGAGAAATTGCCGCTA

TCATGGGACCAAATGGTACAGGTAAATCGACTCTTTCTGCCGCTATCATG

GGAAATCCAAACTATGAAGTAACTAAAGGTGAAGTTTTGTTTGATGGCGT

AAACATCCTTGAGTTGGAAGTGGATGAGCGTGCGCGTATGGGACTTTTCC

TTGCTATGCAATACCCATCAGAAATCCCTGGAATTACCAATGCTGAGTTT

CTTCGTGCCGCTATGAATGCGGGTAAAGAAGATGATGAGAAGATTTCAGT

TCGTGAGTTTATTACTAAGCTAGATGAAAAAATGAATTGCTCAACATGA

AGAAGAAATGGCAGAGCGTTACCTCAACGAAGGCTTCTCTGGTGGTGAG

AAAAAACGCAATGAAATTCTTCAACTTTTGATGTTGGAGCCAACATTTGC

TCTTTTGGACGAGATTGACTCAGGTCTTGATATTGACGCTCTTAAAGTTG

TGTCTAAAGGTGTCAATGCCATGCGTGGTGAAGGTTTTGGTGCTATGATC

ATCACTCACTACCAACGTCTTTTGAACTATATCACACCTGATGTGGTACA

CGTGATGATGGAAGGTCGTGTTGTCCTTTCTGGTGGTCCAGAATTGGCTG

CGCGTTTGGAACGTGAAGGATACGCAAAATTAGCTGAAGAACTTGGCTAC

GACTACAAGGAAGAATTGTAA 4174.4 (SEQ. ID. NO. 306)
ATGCCCTACAAAAGACAAAGGAGTTTTTCAATGGCACTTTCTAAACTAGA

TAGCCTTTATATGGCAGTGGTAGCAGACCATTCGAAAAATCCACATCACC

AAGGGAAGTTAGAAGATGCTGAGCAAATCAGTCTCAACAATCCGACTTGT

GGGGATGTCATCAACCTCTCTGTCAAGTTTGATGCAGAGGACCGTTTGGA

AGATATTGCTTTTCTAAATTCAGGATGCACGATTTCAACTGCTTCTGCTA

GTATGATGACAGATGCCGTTTTAGGAAAAACCAAACAAGAAATTTTAGAA

CTGGCGACTATTTTTTCTGAAATGGTTCAAGGGCAAAAAGATGAGCGTCA

AGACCAACTTGGAGACGCGGCATTCTTGTCAGGTGTTGCCAAATTCCCTC

AAAGAATCAAGTGTGCAACCCTAGCTTGGAATGCCCTTAAGAAAACAATT

GAAAATCAAGAAAAACAGTAA 4175.5 (SEQ. ID. NO. 307)
ATGAAAATTCAAGACCTATTGAGAAAAGATGTCATGTTGCTAGATTTGCA

GGCAACTGAAAAAACAGCTGTCATCGACGAGATGATTAAAAATTTGACAG

ACCACGGTTATGTAACAGATTTTGAAACATTTAAAGAAGGAATTTTGGCG

CGTGAAGCTTTGACTTCTACTGGTTTGGGTGATGGAATCGCAATGCCTCA

CAGCAAAAACGCTGCTGTCAAAGAAGCGACAGTTCTATTTGCTAAGTCAA

ATAAGGGTGTTGACTACGAGAGCTTGGATGGACAAGCAACTGACCTCTTC

TTCATGATTGCAGCTCCAGAAGGTGCCAATGATACTCACTTGGCAGCCTT

GGCAGAATTGTCTCAATACTTGATGAAAGACGGTTTTGCAGACAAACTTC

GTCAAGCAACATCTGCAGACCAAGTTATCGAACTTTTTGACCAAGCTTCA

GAAAAAACTGAGGAACTTGTTCAAGCACCTGCTAATGACTCTGGTGACTT

TATCGTAGCTGTTACAGCTTGTACAACAGGTATTGCCCACACTTACATGG

CCCAAGAAGCCCTCAAAAAGTAGCTGCTGAAATGGGGGTTGGTATCAAG

GTCGAAACCAACGGTGCTAGCGGTGTTGGAAATCAACTAACTGCAGAAGA

TATCCGTAAGGCTAAAGCTATTATCATTGCAGCAGACAAGGCCGTTGAAA

TGGATCGATTTGATGGAAAACCATTGATCCATCGTCCAGTTGCTGACGGT

ATCCGTAAGACAGAAGAGCTAATTAACTTGGCTCTTTCAGGAGATACTGA

AGTCTACCGTGCCGCTAATGGTGCCAAAGCTGCAACAGCCTCTAACGAAA

AACAAAGCCTTGGTGGTGCCTTGTACAAACACTTGATGAGTGGTGTATCT

CAAATGTTACCATTCGTTATCGGTGGTGGTATCATGATTGCCCTTGCCTT

CTTGATTGACGGTGCTTTGGGTGTTCCAAATGAAAACCTTGGCAATCTTG

GTTCTTACCATGAGTTAGCTTCTATGTTCATGAAAATTGGTGGAGCTGCC

TTTGGTTTGATGCTTCCAGTCTTTGCGGGTTATGTTGCCTACTCTATTGC

TGAAAAACCGGGTTTGGTAGCAGGTTTCGTGGCTGGTGCTATTGCCAAAG

AAGGTTTTGCCTTTGGTAAAATTCCTTATGCCGCAGGTGGTGAAGCAACT

TCAACTCTTGCAGGTGTCTCATCTGGTTTCCTAGGTGCCCTTGTTGGTGG

ATTTATCGCAGGTGCCTTGGTTCTTGCCATCAGAAATACGTTAAAGTTCC

TCGTTCACTCGAAGGTGCTAAATCAATCCTTCTATTGCCACTTCTTGGAA

CAATCTTGACAGGATTTGTTATGCTAGCTGTGAATATCCCAATGGCTGCA

ATCAACACTGCTATGAATGACTTCCTAGGCGGTCTTGGAGGAGGTTCAGC

TGTCCTTCTTGGTATCGTCCTTGGTGGAATGATGGCTGTTGACATGGGTG

GACCAGTTAATAAAGCAGCTTATGTCTTTGGTACAGGTACGCTTGCAGCA

ACTGTTTCTTCAGGTGGTTCTGTAGCCATGGCAGCAGTTATGGCTGGAGG

AATGGTGCCACCACTTGCAATCTTTGTCGCAACTCTTCTTTTCAAAGATA

AATTTACTAAGGAAGAACGTAACTCTGGTTTGACAAACATCATCATGGGC

TTGTCATTTATCACTGAGGGAGCGATTCCATTTGGTGCCGCTGACCCAGC

TCGTGCGATTCCAAGCTTCATCCTTGGTTCAGCAGTAGCAGGTGGACTCG

TABLE 1-continued

TTGGTCTTACTGGTATCAAACTCATGGCGCCACACGGAGGAATCTTCGTT

ATCGCCCTTACTTCAAATGCTCTCCTTTACCTCGTTTCTGTCTTGGTAGG

AGCAATCGTAAGTGGTGTGGTTTATGGTTACCTACGCAAACCACAAGCAT

AA 4175.6 (SEQ. ID. NO. 308)
ATGGCAAACAAGAATACAAGTACAACAAGACGGAGACCGTCTAAAGCAGA

ACTGGAAAGAAAAGAAGCGATTCAACGAATGTTGATTTCGTTAGGAATTG

CGATTTTATTGATTTTCGCAGCCTTCAAATTAGGGGCTGCAGGTATAACC

CTTTATAATTTAATTCGCTTGCTAGTGGGTAGCCTAGCTTATCTGGCGAT

ATTCGGCCTATTAATCTATCTCTTCTTTTTCAAGTGGATACGAAAACAGG

AAGGACTCTTATCTGGCTTTTTCACCATATTTGCTGGCTTACTCTTGATT

TTTGAGGCCTACTTGGTTTGGAAATATGGTTTGGACAAGTCCGTTCTAAA

AGGGACCATGGCTCAGGTTGTGACAGATCTGACTGGTTTTCGAACGACTA

GCTTTGCTGGAGGGGGCTTGATCGGGGTCGCTCTTTATATTCCACAGCCT

TTCTCTTTTCAAATATCGGAACTTACTTTATTGGTTCTATCTTGATTTTA

GTGGGTTCTCTCCTAGTCAGCCCTTGGTCTGTTTACGATATTGCTGAATT

TTTCAGTAGAGGCTTTGCCAAATGGTGGGAAGGGCACGAGCGTCGAAAAG

AGGAACGCTTTGTCAAACAAGAAGAAAAAGCTCGCCAAAAGGCTGAGAAA

GAGGCTAGATTAGAACAAGAAGAGACTGAAAAAGCCTTACTCGATTTGCC

TCCTGTTGATATGGAAACGGGTGAAATTCTGACAGAGGAAGCTGTTCAAA

ATCTTCCACCTATTCCAGAAGAAAAGTGGGTGGAACCAGAAATCATCCTG

CCTCAAGCTGAACTTAAATTCCCTGAACAGGAAGATGACTCAGATGACGA

AGATGTTCAGGTCGATTTTTCAGCCAAAGAAGCCCTTGAATACAAACTTC

CAAGCTTACAACTCTTTGCACCAGATAAACCAAAAGATCAGTCTAAAGAG

AAGAAAATTGTCAGAGAAAATATCAAAATCTTAGAAGCAACCTTTGCTAG

CTTTGGTATTAAGGTAACAGTTGAACGGGCCGAAATTGGGCCATCAGTGA

CCAAGTATGAAGTCAAGCCGGCTGTTGGTGTAAGGGTCAACCGCATTTCC

AATCTATCAGATGACCTCGCTCTAGCCTTGGCTGCCAAAGATGTCCGGAT

TGAAGCACCAATCCCTGGGAAATCCCTAATCGGAATTGAAGTGCCCAACT

CCGATATTGCCACTGTATCTTTCCGAGAACTATGGGAACAATCGCAAACG

AAAGCAGAAAATTTCTTGGAAATTCCTTTAGGGAAGGCTGTTAATGGAAC

CGCAAGAGCTTTTGACCTTTCTAAAATGCCCCACTTGCTAGTTGCAGGTT

CAACGGGTTCAGGGAAGTCAGTAGCAGTTAACGGCATTATTGCTAGCATT

CTCATGAAGGCGAGACCAGATCAAGTTAAATTTATGATGGTCGATCCCAA

GATGGTTGAGTTATCTGTTTACAATGATATTCCCACCTCTTGATTCCAG

TCGTGACCAATCCACGCAAAGCCAGCAAGGCTCTGCAAAAGGTTGTGGAT

GAAATGGAAAACCGTTATGAACTCTTTGCCAAGGTGGGAGTTCGGAATAT

TGCAGGTTTTAATGCCAAGGTAGAAGAGTTCAATTCCCAGTCTGAGTACA

AGCAAATTCCGCTACCATTCATTGTCGTGATTGTGGATGAGTTGGCTGAC

CTCATGATGGTGGCCAGCAAGGAAGTGGAAGATGCTATCATCCGTCTTGG

GCAGAAGGCGCGTGCTGCAGGTATCCACATGATTCTTGCAACTCAGCGTC

CATCTGTTGATGTCATCTCTGGTTTGATTAAGGCCAATGTTCCATCTCGT

GTAGCATTTGCGGTTTCATCAGGAACAGACTCCCGTACGATTTTGGATGA

AAATGGAGCAGAAAAACTTCTTGGTCGAGGAGACATGCTCTTTAAACCGA

TTGATGAAAATCATCCAGTTCGTCTCCAAGGCTCCTTTATCTCGGATGAC

GATGTTGAGCGCATTGTGAACTTCATCAAGACTCAGGCAGATGCAGACTA

CGATGAGAGTTTTGATCCAGGTGAGGTTTCTGAAAATGAAGGAGAATTTT

CGGATGGAGATGCTGGTGGTGATCCGCTTTTTGAAGAAGCTAAGTCTTTG

GTTTATCGAAACACAGAAAGCCAGTGCGTCTATGATTCAGCGTCGTTTAT

CAGTTGGATTTAACCGTGCGACCCGTCTCATGGAAGAACTGGAGATAGCA

GGTGTCATCGGTCCAGCTGAAGGTACCAAACCTCGAAAAGTGTTACAACA

ATAA 4176.1 (SEQ. ID. NO. 309)
ATGAGTTATTTTAAAAAATATAAATTCGATAAATCCCAGTTCAAACTTGG

TATGCGAACCTTTAAAACAGGTATTGCTGTTTTTCTAGTTCTCTTGATTT

TTGGCTTTTTTGGCTGGAAAGGTCTTCAAATTGGTGCTTTGACAGCCGTT

TTTAGCCTGAGGGAGAGTTTTGATGAGAGTGTTCATTTTGGGACTTCGCG

TATTCTAGGAAATAGTATCGGTGGACTCTATGCCTTGGTCTTCTTCTTAT

TAAATACCTTTTTCCACGAAGCCTTTTGGGTGACCTTGGTAGTTGTTCCA

ATCTGCACCATGTTAACCATTATGACAAATGTAGCCATGAATAACAAAGC

AGGGGTTATTGGTGGTGTAGCAGCTATGTTAATCATTACCCTATCAATTC

CAAGTGGTGAGACAATTTTGTACGTGTTTGTGCGTGTATTAGAAACGTTT

ATGGGAGTTTTTGTCGCAATTATCGTAAATTACGATATTGATCGTATTCG

TCTCTTTTTAGAGAAAAAAGAAAAATAA 4178.2 (SEQ. ID. NO. 310)
ATGAATAAATCAGAACACCGCCACCAACTTATACGCGCTCTTATCACAAA

AAACAAGATTCATACACAGGCTGAGTTGCAAGCCCTTCTTGCTGAGAACG

ACATTCAAGTAACCCAGGCAACCCTCTCACGCGACATCAAAAATATGAAC

CTATCAAAAGTCCGCGAAGAAGATAGCGCTTATTATGTTCTTAACAATGG

TTCCATCTCAAAATGGGAAAAACGTCTCGAACTCTACATGGAAGACGCCC

TTGTCTGGATGCGCCCAGTTCAACACCAAGTCCTACTAAAAACCCTTCCT

GGACTGGCTCAATCCTTTGGTTCTATCATTGATACTTTGAGCTTCCCTGA

CGCTATCGCTACCCTTTGTGGTAATGATGTCTGTCTTATCATCTGTGAAG

ATGCAGATACTGCTCAAAAGTGCTTTGAAGAACTGAAAAAATTCGCCCCA

CCATTTTCTTTGAAGAATAA 4179.1 (SEQ. ID. NO. 311)
ATGAAAAGTATAAAATTAAATGCTCTATCTTACATGGGAATTCGTGTCTT

GAATATTATTTTTCCCATCCTAACTGGAACCTATGTCGCGCGTGTCTTGG

ACGAACTGACTATGGTTACTTCAACTCAGTCGACACTATTTTGTCATTTT

TCTTGCCCTTTGCAACTTATGGTGTCTATAACTACGGTTTAAGGGCTATC

AGTAATGTCAAGGATAACAAAAAAGATCTTAACAGAACCTTTTCTAGTCT

TABLE 1-continued

TTTTTATTTGTGCATCGCTTGTACGATTTTGACCACTGCTGTCTATATCC
TAGCCTATCCTCTCTTCTTTACTGATAATCCAATCGTCAAAAAGGTCTAC
CTTGTTATGGGGATTCAACTCATTGCCCAGATTTTTTCAATCGAATGGGT
CAATGAAGCTCTGGAAAATTACAGTTTTCTCTTTTACAAAACTGCCTTCA
TCCGTATCCTGATGCTGGTCTCTATTTTCTTATTTGTTAAAAATGAACAC
GATATTGTTGTCTATACACTTGTGATGAGTTTATCGACGCTGATTAACTA
CCTGATTAGTTATTTTTGGATTAAAAGAGACATCAAACTTGTTAAAATTC
ACCTAAGTGATTTTAAACCACTCTTTCTCCCTCTGACAGCCATGTTAGTC
TTTGCCAATGCCAATATGCTCTTCACTTTTTTAGATCGCCTCTTCCTCGT
TAAAACAGGGATTGATGTCAACGTTAGTTACTATACCATAGCTCAGCGAA
TTGTGACCGTTATAGCTGGGGTTGTAACAGGTGCAATTGGAGTGAGTGTG
CCTCGTCTCAGTTACTATCTGGGGAAAGGAGACAAAGAAGCCTATGTTTC
TCTGGTTAATAGAGGTAGTCGAATCTTTAACTTCTTTATCATTCCACTGA
GTTTTGGACTCATGGTTTTAGGACCAAATGCCATCCTACTTTACGGTAGT
GAAAAATATATCGGAGGCGGCATCTTGACCTCTCTCTTCGCTTTTCGTAC
GATTATCCTGGCCTTAGATACCATTCTTGGTTCCCAAATTCTCTTTACCA
ATGGCTATGAAAAACGTATCACAGTCTATACAGTCTTTGCTGGGCTACTC
AATTTGGGCTTGAATAGTCTCCTTTTTTTCAACCATATCGTGGCTCCTGA
ATACTACTTACTGACAACTATGCTATCAGAGACTTCTCTACTTGTTTTCT
ATATCATTTTCATCCATAGAAAACAACTCATCCACTTGGGACATATCTTT
AGCTATACTGTTCGATACTCTCTCTTTTCACTTTCCTTTGTAGCAATTTA
TTTCCTGATTAATTTCGTGTATCCTGTAGATATGGTCATTAATTTGCCAT
TTTTGATTAATACTGGTTTGATTGTCTTGCTATCAGCTATCTCTTATATT
AGTCTACTTGTCTTCACAAAAGATAGCATTTTCTATGAATTTTTAAACCA
TGTCCTAGCCTTAAAAAATAAATTTAAAAAATCATAG 4179.2 (SEQ. ID. NO. 312)
ATGAAACAACTAACCGTTGAAGATGCCAAACAAATTGAATTAGAAATTTT
GGATTATATTGATACTCTCTGTAAAAAGCACAATATCAACTATATTATTA
ACTACGGTACTCTGATTGGGGCGGTTCGACATGAGGGCTTTATCCCTTGG
GACGACGATATTGATCTGTCCATGCCTAGAGAAGACTACCAACGATTTAT
TAACATTTTTCAAAAGGAAAAAAGCAAGTATAAGCTCCTATCCTTAGAAA
CTGATAAGAACTACTTTAACAACTTTATCAAGATAACCGACAGTACGACT
AAAATTATTGATACTCGAAATACAAAAACCTATGAGTCTGGTATCTTTAT
CGATATTTTCCCTATAGATCGCTTTGATGATCCTAAGGTCATTGATACTT
GTTATAAACTGGAAAGCTTCAAACGTCTGTCTTTCAGTAAACATAAAAAT
ATTGTCTATAAGGATAGCCTTTTAAAAGATTGGATACGAACAGCCTTCTG
GTTACTCCTTCGACCGGTTTCTCCTCGTTATTTTGCAAATAAATCGAGA
AAGAAATTCAAAAATATAGTCGTGAAAATGGGCAATATATGGCTTTTATC
CCTTCAAAATTTAAGGAAAAGGAAGTCTTCCCAAGTGGTACCTTTGATAA
AACAATCGATTTACCCTTTGAGAATTTAAGCCTTCCTGCACCTGAAAAAT

TTGATACTATTTTGACACAATTTTATGGAGATTATATGACCCTACCACCA
GAAGAAAAACGCTTCTACAGTCATGAATTTCACGCTTATAAATTGGAGGA
TTTAG 4179.3 (SEQ. ID. NO. 313)
ATGATAAAAATCAATCATCTAACCATCACACAAAACAAAGATTTACGAGA
TCTTGTATCTGACCTAACCATGACCATCCAAGACGGGGAAAAGGTTGCTA
TTATTGGTGAAGAAGGAAATGGCAAATCAACCTTACTTAAAATTTTAATG
GGGGAAGCTTTGTCTGATTTCACTATCAAGGGAAACATCCAATCTGACTA
TCAGTCACTGGCCTACATTCCTCAAAAAGTCCCTGAGGACCTAAAAAAGA
AAACTTTACACGACTACTTCTTTTTAGATTCTATTGATTTAGACTACAGT
ATCCTCTATCGTTTGGCGGAGGAATTGCATTTTGATAGCAATCGTTTCGC
AAGTGACCAAGAGATTGGCAATCTATCAGGGGGCGAAGCTTTGAAAATTC
AGCTTATCCATGAGTTAGCCAAACCCTTTGAGATTCTATTTTTAGATGAA
CCTTCAAATGACCTAGACCTTGAGACAGTTGATTGGCTAAAAGGCCAGAT
TCAAAAGACCAGGCAAACCGTTATTTTCATTTCCCATGATGAAGACTTTC
TTTCTGAAACGGCAGACACTATTGTTCACTTGCGACTGGTCAAACACCGT
AAAGAAGCGGAAACGCTAGTAGAGCATTTAGACTATGATAGCTATAGTGA
GCAGAGAAAGGCTAATTTTGGCAAACAAAGTCAGCAAGCTGCTAACAACC
AAAGAGCCTACGATAAAACCATGGAAAAACATCGGAGAGTTAAGCAAAAT
GTAGAAACTGCGCTTCGAGCTACCAAAGATAGTACTGCCGGTCGCCTATT
GGCTAAAAAGATGAAAACTGTCCTCTCACAAGAAAAACGCTACGAAAAGG
CAGCTCAGTCCATGACTCAAAAGCCACTTGAAGAGGAACAAATCCAACTT
TTCTTTTCAGACATCCAACCATTACCAGCTTCTAAAGTCTTAGTCCAACT
GGAAAAGAAAATTTGTCCATTGACGACCGAGTTTTGGTTCAAAAACTAC
AACTAACTGTCCGTGGCCAAGAAAAAATCGGTATTATCGGGCCAAATGGT
GTTGGGAAATCAACTCTGTTAGCCAAGTTACAGAGACTTCTGAATGATAA
AAGAGAGATTTCACTTGGTTTTATGCCACAAGATTACCACAAAAAACTGC
AATTGGATTTATCCCCAATAGCCTATCTCAGTAAAACTGGGGAAAAAGAG
GAACTACAGAAAATCCAATCTCACCTAGCTAGTCTCAATTTCAGTTATCC
AGAAATGCAGCATCAAATTCGCTCCTTATCTGGCGGACAACAGGGAAAAC
TCCTGCTTTTGGATTTAGTCCTGCGCAAACCAAACTTTCTCCTGCTGGAT
GAACCCACACGAAACTTTTCTCCCACTTCTCAACCCCAAATCAGAAAACT
CTTTGCTACCTATCCAGGCGGTCTCATCACTGTTTCGCATGACCGTCGTT
TCTTAAAAGAAGTCTGCTCGATCAT 4179.4 (SEQ. ID. NO. 314)
ATGAAACCAAAACATTTTACAACTTGCTTGCCGAGCAGAATCTTCCACT
TTCGGACCAGCAAAAAGAACAATTTGAACGTTATTTTGAGCTCTTGGTCG
AGTGGAATGAGAAGATTAATTTGACGGCGATTACGGACAAGGAAGAAGTT
TATCTCAAACATTTTTACGATTCGATTGCACCCATTCTTCAAGGTTTGAT
TCCCAATGAAACTATCAAACTTCTTGATATCGGGGCTGGGGCAGGATTTC

TABLE 1-continued

CTAGTCTACCAATGAAAATTCTCTATCCGGAGTTAGATGTGACCATTATT
GATTCACTCAATAAGCGCATCAACTTCCTACAACTCTTGGCTCAAGAACT
GGATTTGAACGGAGTTCATTTCTACCACGGACGTGCCGAAGATTTTGCCC
AAGACAAGAACTTCCGTGCTCAATATGATTTTGTAACAGCTCGTGCGGTT
GCCCGTATGCAGGTCCTATCTGAATTGACTATTCCCTACCTTAAGGTTGG
TGGCAAACTATTAGCACTCAAGGCTAGCAATGCGCCTGAGGAATTATTAG
AAGCTAAGAATGCCCTCAATCTCCTTTTTAGTAAGGTCGAAGACAATCTC
AGctACGCCCTACCGAATAGAGATCCGCGCTATATCACAGTGGTAGAAAA
GAAAAAAGAAACACCAAATAAATATCCACGTAAGGCTGGTATGCCAAATA
AACGCCCACTTTAA 4179.6 (SEQ. ID. NO. 315)
ATGAGTATTAAACTAATTGCCGTTGATATCGACGGAACCCTTGTCAACAG
CCAAAAGGAAATCACTCCTGAAGTTTTTTCTGCCATCCAAGATGCCAAAG
AAGCTGGTGTCAAAGTCGTGATTGCAACTGGCCGCCCTATCGCAGGCGTT
GCCAAACTTCTAGACGACTTGCAGTTGAGAGACGAGGGGGACTATGTGGT
AACCTTCAACGGTGCCCTTGTCCAAGAAACTGCTACAGGACATGAGATTA
TCAGCGAATCCTTGACTTATGAGGATTATCTAGATATGGAATTCCTCAGT
CGCAAGCTCGGTGTCCACATGCATGCCATTACCAAGGACGGTATCTATAC
TGCAAATCGCAATATCGGAAAATACACTGTACACGAATCAACCCTCGTCA
GCATGCCTATCTTCTACCGTACCCCTGAAGAAATGGCTGGCAAAGAAATT
GTTAAATGTATGTTTATCGATGAACCAGAAATTCTCGATGCTGCGATTGA
AAAAATTCCAGCAGAATTTTACGAGCGCTACTCCATCAACAAATCTGCTC
CTTTCTACCTCGAACTCCTTAAAAAGAATGTAGACAAGGGTTCAGCCATT
ACTCACTTGGCTGAAAAACTCGGATTGACCAAAGATGAAACCATGGCAAT
CGGTGATGAAGAAAATGACCGTGCCATGCTGGAAGTCGTTGGAAACCCCG
TTGTCATGGAAAATGGAAATCCAGAAATCAAAAAAATCGCCAAATACATC
ACCAAAACAAATGACGAATCCGGCGTTGCCCATGCCATCCGAACATGGGT
ACTGTAA 4179.7 (SEQ. ID. NO. 316)
ATGACTTGGATTATTCTTGGAGTTATCGCTCTTATTGTTATTTTTGTGAT
TGTTAGCTATAACGGTTTGGTTAAAAATCGTATGCAAACCAAGGAGGCTT
GGAGTCAGATTGATGTTCAGTTGAAACGTCGCAATGACCTCTTGCCAAAC
TTGATTGAGACTGTAAAAGGTTATGCCAAATATGAAGGTTCTACCCTTGA
AAAGGTGGCAGAACTACGTAACCAAGTGGCGGCAGCGACTTCACCAGCAG
AAGCTATGAAAGCCAGTGATGCCCTCACTCGTCAGGTTTCAGGTATTTTT
GCAGTTGCAGAAAGCTATCCAGATTTGAAAGCTAGTGCTAACTTTGTTAA
ATTGCAAGAGGAGTTGACAAACACAGAAAATAAAATTCTTACTCTCGTC
AACTCTATAACAGTGTTGTCAGCAACTACAATGTAAAATTAGAAACTTTC
CCGAGCAATATTATCGCTGGAATGTTTGGATTTAAAGCGGCAGATTTCCT
TCAAACACCTGAAGAGGAAAAGTCGGTTCCTAAAGTTGATTTTAGCGGTT
TAGGTGACTAA 4179.8 (SEQ. ID. NO. 317)
ATGTTGTTTGATCAAATTGCAAGCAATAAACGAAAAACCTGGATTTTGTT
GCTGGTATTTTTCCTACTCTTAGCTCTTGTTGGTTATGCGGTTGGTTATC
TCTTTATAAGATCTGGACTTGGTGGTTTGGTTATTGCACTGATTATCGGC
TTTATCTACGCTTTGTCTATGATTTTTCAATCGACAGAGATTGTCATGTC
CATGAATGGAGCGCGTGAGGTGGATGAGCAAACGGCACCAGACCTCTACC
ATGTAGTGGAAGATATGGCTCTGGTCGCTCAGATTCCTATGCCCCGTGTT
TTCATCATTGATGATCCAGCCTTAAATGCCTTTGCGACAGGTTCTAATCC
TCAAAATGCGGCTGTTGCTGCGACTTCAGGTCTACTAGCTATCATGAATC
GTGAAGAACTAGAAGCTGTTATGGGACATGAAGTCAGTCATATTCGTAAT
TATGATATCCGTATTTCGACTATTGCAGTTGCCCTTGCTAGTGCTATCAC
CATGCTTTCTAGTATGGCAGGTCGTATGATGTGGTGGGTGGAGCAGGTC
GCAGACGAAGTGATGATGACCGAGATGGAAATGGTCTTGAAATCATTATG
CTAGTGGTTCCCTACTAGCTATTGTACTGGCACCTCTCGCTGCAACCTTG
GTTCAGCTCGCTATTTCTCGTCAGAGGGAATTTCTGGCAGATGCATCTAG
TGTCGAGCTGACTCGCAATCCCCAGGGAATGATTAATGCCCTAGATAAGT
TGGACAATAGCAAACCTATGAGTCGCCACGTCGATGATGCTAGCAGTGCC
CTTTATATCAATGATCCTAAGAAAGGTGGGGGGTTCCAAAAACTCTTTTA
TACCCACCCACCTATCTCAGAACGGATTGAACGTTTAAAACAGATGTAA 4179.9 (SEQ. ID. NO. 318)
ATGAAATTAAATATTCAAGAAATTCGTAAGCAGTCTGAAGGTTTGAACTT
TGAACAAACGTTAGATTTAGTTGATGACCTGCGTGCACGTAATCAAGAAA
TTTTAGATGTAAAAGATATCCTTGCAGTTGGGAAAGTACAATATGAAGAC
CGTATGTATTTCTTAGATTATCAACTATCTTATACCATTGTTCTTGCTTC
GAGTCGCAGTATGGAGCCAGTTGAGTTAGTTGAATCTTATCCAGTCACGG
AAGTTTTCATGGAAGGCGCAACTAACCAGCTAGATCAAGAAGTTTTAGAT
GATGACTTGGTCTTGCCCATCGAAAATGGGGAGCTTGACCTTGCTGAGAG
TGTATCAGACAATATCCTGCTAAACATTCCTATCAAGGTCTTGACGGCTG
AAGAAGAAGCTGGTCAAGGATTTATCTCAGGAAATGACTGGCAAATCATG
ACAGAGGAAGAATACCAAGCTCAAAAAGCAGTAAAGAAAGAAGAAAACAG
TCCTTTTGCTGGCTTACAAGGACTATTTGACGGAGATGAATAA 4179.12 (SEQ. ID. NO. 319)
ATGGAGTTATTTATGAAAATCACAAACTATGAAATCTATAAGTTAAAAAA
ATCAGGTTTGACCAATCAACAGATTTTGAAAGTGCTAGAATACGGTGAAA
ATGTTGATCAGGAGCTTTTGTTGGGTGATATTGCATATATCTCAGGTTGC
CGTAATCCAGCCGTTTTTATGGAACGTTATTTTCAGATAGACGATGCGCA
TTTGTCGAAAGAGTTTCAAAAATTTCCATCTTTCTCTATTTTAGATGACT
GTTATCCTTGGGATTTGAGTGAAATATATGATGCGCCTGTACTTTTATTT
TACAAGGGAAATCTTGACCTCCTGAAATTCCCGAAGGTAGCGGTCGTGGG
CAGTCGTGCTTGTAGCAAACAGGGAGCTAAGTCAGTTGAAAAAGTCATTC
AAGGCTTGGAAAATGAACTGGTTATTGTCAGTGGTCTGGCCAAGGGCATT

TABLE 1-continued

```
GACACAGCAGCTCATATGGCAGCTCTTCAGAATGGCGGAAAAACCATTGC

AGTGATTGGAACAGGACTGGATGTGTTTTATCCTAAAGCCAATAAACGCT

TGCAAGACTACATCGGCAATGACCATCTGGTTCTAAGTGAATATGGACCT

GGTGAACAACCTCTGAAATTTCATTTTCCTGCCCGTAATCGCATCATTGC

TGGACTTTGTCGTGGTGTGATTGTAGCAGAGGCTAAGATGCGTTCAGGTA

GTCTCATTACGTGTGAGCGAGCAATGGAAGAAGGACGCGATGTCTTTGCT

ATTCCTGGTAGCATTTTAGATGGACTATCAGACGGTTGCCATCATTTGAT

TCAAGAAGGAGCAAAATTGGTCACCAGTGGGCAAGATGTTCTTGCGGAAT

TTGAATTTTAA 4181.1 (SEQ. ID. NO. 320)
ATGAAACGTCAATTAGCCTTGGTCGTCTTTAGTGGTGGTCAAGATTCAAC

AACCTGCCTTTTCTGGGTCATGCAACACTATGAAACAGTCGAAGCTGTCA

CCTTTGCCTACGGCCAACGTCATCACCTCGAAATTCAAATTACTAGAGAA

ATCGCTAAGGAACAGGGCATTCGTCACCTATATCCTCGATATGTCTCTGCT

GGGACAAATCACTGCTCAGCCAGACTTTGCGACGATTCATATTTCCTACA

TTCCTGACAAGCTCTGTGTCGAGTCAAAATCCCTCAAACTATATCTATTT

AGCTACCGAAACCACGGAGATTTCCACGAAAACTGTATCAACACCATCGG

GAAAGACTTGGTCAACTTGCTAGACCCTCGCTATTTAGAAGTCTGGGGAA

AATTCACTCCGCGCGGTGGCATTTCAATCGACCCCTACTACAACTACGGT

AAGCAAGGAACTAAGTATGAGGGCTTGGCAGAACAACGCCTCTTCCAACA

CGACCTTTATCCAGAGAAAATTGACAACCGCTAA 4181.2 (SEQ. ID. NO. 321)
ATGACCGAAACGGTAGAAGATAAAGTAAGTCATTCAATTACTGGGCTTGA

TATCCTCAAGGGGATAGTTGCTGCGGGAGCTGTCATAAGTGGAACCGTTG

CAACTCAAACGAAGGTATTTACAAATGAGTCAGCAGTACTTGAAAAAACT

GTAGAGAAAACGGATGCTTTGGCAACAAATGATACAGTAGTTCTAGGTAC

GATATCTACAAGTAATTCAGCGAGTTCAACTAGTTTGTCAGCTTCAGAGT

CGGCAAGTACATCTGCATCTGAGTCAGCCTCAACCAGCGCTTCGACCTCA

GCAAGTACAAGTGCATCAGAATCAGCAAGTACATCGGCTTCGACAAGTAT

TTCTGCATCATCTACTGTGGTAGGTTCACAAACAGCTGCCGCTACAGAAG

CAACTGCTAAGAAGGTCGAAGAAGATCGTAAGAAACCAGCTAGTGATTAT

GTAGCATCAGTTACAAATGTCAATCTCCAATCTTATGCTAAGCGACGCAA

GCGTTCAGTGGATTCCATCGAGCAATTGCTGGCTTCTATAAAAAATGCTG

CTGTTTTTTCTGGCAATACGATTGTAAATGGCGCCCCTGCAATTAATGCA

AGTCTAAACATTTGCTAAAAGTGAGACAAAAGTTTATACAGGTGAAGGTG

TAGATTCGGTATATCGTGTTCCAATTTACTATAAAATTGAAAGTGACAAAT

GATGGTTCAAAATTGACCTTTACCTATACGGTTACGTATGTGAATCCTAA

AACAAATGATCTTGGTAATATATCAAGTATGCGTCCTGGATATTCTATCT

ATAATTCAGGTACTTCAACACAAACAATGTTAACCCTTGGCAGTGATCTT

GGTAAACCTTCAGGTGTAAAGAACTACATTACTGACAAAAATGGTAGACA

GGTTCTATCCTATAATACATCTACAATGACGACGCAGGGTAGTGGGTATA

CTTGGGGAAATGGTGCCCAAATGAATGGTTTCTTTGCTAAGAAAGGATAT

GGATTAACATCATCTTGGACTGTACCAATTACTGGAACGGATACATCCTT

TACATTTACCCCTTACGCTGCTAGAACAGATAGAATTGGAATTAACTACT

TCAATGGTGGAGGAAAGGTAGTTGAATCTAGCACGACCAGTCAGTCACTT

TCACAGTCTAAGTCACTCTCAGTAAGTGCTAGTCAAAGCGCCTCAGCTTC

AGCATCAACAAGTGCGTCGGCTTCAGCATCAACCAGTGCCTCGGCTTCAG

CGTCAACCAGTGCGTCAGCTTCAGCAAGTACCAGTGCTTCAGTCTCAGCA

TCAACAAGTGCTTCAGCCTCAGCATCGACAAGTGCCTCGGCTTCAGCAAG

CACATCAGCATCTGAATCAGCGTCAACCAGTGCTTCGGCTTCAGCAAGTA

CCAGTGCTTCAGCTTCAGCATCAACCAGCGCCTCGGCCTCAGCAAGCACC

TCAGCTTCTGAATCGGCCTCAACCAGCGCCTCGGCCTCAGCAAGCACCTC

AGCTTCTGAATCGGCCTCAACCAGCGCCTCAGCCTCAGCATCAACGAGTG

CTTCGGCTTCAGCAAGCACAAGCGCCTCGGGTTCAGCATCAACGAGTACG

TCAGCTTCAGCGTCAACCAGTGCTTCAGCCTCAGCATCAACAAGTGCGTC

AGCCTCAGCAAGTATCTCAGCGTCTGAATCGGCATCAACGAGTGCGTCTG

AGTCAGCATCAACGAGTACGTCAGCCTCAGCAAGCACCTCAGCTTCTGAA

TCGGCCTCAACCAGTGCGTCAGCCTCAGCATCGACAAGCGCCTCAGCTTC

AGCAAGTACCAGTGCTTCAGCCTCAGCGTCGACAAGTGCGTCGGCCTCAA

CCAGTGCATCTGAATCGGCATCAACCAGTGCGTCAGCCTCAGCAAGTACT

AGTGCATCGGCTTCAGCATCAACCAGTGCCTCGGCTTCAGCGTCAACCAG

TGCGTCAGCTTCAGCAAGTACCAGTGCTTCAGTCTCAGCATCAACAAGTG

CTTCAGCCTCAGCATCGACAAGTGCCTCGGCTTCAGCAAGCACATCAGCA

TCTGAATCAGCGTCGACAAGCGCCTCAGCTTCAGCAAGTCCCAGTGCGTC

AGCTTCAGCATCAACCAGCGCCTCGGCCTCAGCAAGCACCTCAGCTTCTG

AATCGGCCTCAACCAGCGCCTCGGCCTCAGCAAGCACCTCAGCTTCTGAA

TCGGCCTCAACCAGCGCCTCAGCCTCAGCATCAACGAGTGCTTCGGCTTC

AGCAAGCACAAGCGCCTCGGGTTCAGCATCAACGAGTACGTCAGCTTCAG

CGTCAACCAGTGCTTCAGCCTCAGCATCAACAAGTGCGTCAGCCTCAGCA

AGTATCTCAGCGTCTGAATCGGCATCAACGAGTGCGTCTGAGTCAGCATC

AACGAGTACGTCAGCCTCAGCAAGCACCTCAGCTTCTGAATCGGCCTCAA

CCAGTGCGTCAGCCTCAGCATCGACAAGCGCCTCAGCTTCAGCAAGTACC

AGTGCTTCAGCCTCAGCTCGACAAGTGCGTCGGCCTCAACCAGTGCATCT

GAATCGGCATCAACCAGTGCGTCAGCCTCAGCAAGTACTAGTGCATCAGC

TTCAGCATCAACGAGTGCATCGGCTTCAGCATCAACCAGTGCCTCGGCTT

CAGCGTCAACCAGTGCGTCAGCTTCAGCAAGTACCAGTGCTTCAGTCTCA

GCATCAACAAGTGCTTCAGCCTCAGCATCGACAAGTGCcTCGGCTTCAGC

AAGCACATCAGCATCTGAATCAGCGTCGACAAGCGCcTCAGCTTCAGCAA

GTACCAGTGCGTCAGCCTCAGCGTCGACAAGTGCGTCAGCCTCAGCAAGT

ACTAGTGCATCAGCTTCAGCATCAACGAGTGCATCGGCTTCGGCGTCAAC
```

TABLE 1-continued

CAGTGCATCAGAGTCAGCAAGTACCAGTGCGTCAGCTTCCGCATCAACAA
GTGCCTCGGCTTCAGCAAGCACCAGTGCGTCGGCTTCAGCAAGTACTAGC
GCCTCAGCCTCAGCCTCAACCAGTGCGTCAGCCTCAGCAAGTATCTCAGC
GTCTGAATCGGCATCAACGAGTGCGTCCGCTTCAGCAAGTACTAGCGCCT
CAGCCTCAGCGTCAACAAGTGCATCGGCTTCAGCGTCAACGAGTGCGTCT
GAATCGGCATCAACGAGTGCGTCCGCTTCAGCAAGTACTAGCGCCTCAGC
CTCAGCGTCAACAAGTGCATCGGCTTCAGCATCAACGAGTGCGTCCGCTT
CAGCAAGTACTAGCGCCTCAGCCTCAGCGTCAACAAGTGCATCGGCTTCA
GCGTCAACGAGTGCGTCTGAGTCAGCATCAACGAGTGCGTCAGCCTCAGC
AAGCACATCAGCTTCTGAATCTGCATCAACCAGTGCGTCAGCCTCAGCAT
CGACAAGCGCCTCAGCTTCAGCAAGTACCAGTGCGTCAGCCTCAGCGTCG
ACAAGTGCGTCGGCTTCAGCAAGTACCAGTGCGTCAGCCTCAGCAAGTAC
CAGTGCGTCAGCCTCAGCGTCGACAAGTGCGTCGGCCTCAACCAGTGCAT
CTGAATCGGCATCAACCAGTGCGTCAGCCTCAGCAAGTACTAGTGCATCA
GCTTCAGCATCAACGAGTGCATCGGCTTCAGCATCAACCAGTGCATCAGA
GTCAGCAAGTACCAGTGCGTCAGTTCCGCATCAACAAGTGCCTCGGCTTC
AGCAAGTACTAG 4183.1 (SEQ. ID. NO. 322)
ATGGGGGTCGAAACTTGGTTTTATTCTAGCATCTGCTGGCTGGCCATCGG
GCTTGGTTCCGTTTGGAAGTTTCCCTACATGACTGCTGCTAATGGCGGTG
GAGGCTTTTTACTAATCTTTCTCATTTCCACTATTTTAATCGGTTTCCCT
CTCCTGCTGGCTGAGTTTGCCCTTGGCCGTAGTGCTGGCGTTTCCGCTAT
CAAAACCTTTGGAAAACTGGGCAAGAATAACAAGTACAACTTTATCGGTT
GGATTGGCGCCTTTGCCCTCTTTATCCTCTTATCTTTTTACAGTGTTATC
GGAGGATGGATTCTAGTCTATCTAGGTATTGAGTTTGGGAAATTGTTCCA
ACTTGGTGGAACGGGTGATTATGCTCAGTTATTTACTTCAATCATTTCAA
ATCCAGCCATTGCCCTAGGAGCTCAAGCGGCCTTTATCCTATTGAATATC
TTCATTGTATCACGTGGGGTTCAAAAAGGGATTGAAAGAGCTTCGAAAGT
CATGATGCCCCTGCTCTTTATCGTCTTTGTTTTTATCATCGGTCGCTCTC
TCAGTTTGCCAAATGCCATGGAAGGGGTTCTTTACTTCCTCAAACCAGAC
TTTTCAAAACTGACTAGCACTGGTCTCCTCTATGCTCTGGGACAATCTTT
CTTTGCCCTCTCACTAGGGGTTACAGTCATGTTGACCTATGCTTCTTACT
TAGACAAGAAAACCAATCTAGTCCAGTCAGGAATCTCCATCGTAGCCATG
AATATCTCGATATCCATCATGGCAGGTCTAGCCATTTTCCAAGCTCGATC
CCCCTTCAATATCCAGTCTGAAGGGGGACCCAGCCTGCTCTTTATCGTCT
TGCCTCAACTCTTTGACAAGATGCCTTTTGGAACCATTTTCTACGTCCTC
TTCCTCTTGCTCTTCCTTTTTGCGACAGTCACTTTTTCTGTCGTGATGCT
GGAAATCAATGTAGACAATATCACCAACCAGGATAACAGCAAACGTGCCA
AATGGAGTGTTATTTTAGGAATTTTGACCTTTGTCTTTGGCATTCCTTCA
GCCCTATCTTACGGTGTCATGGCGGATGTTCACATTTTTGGTAAGACCTT

CTTTGACGCTATGGACTTCTTGGTTTCCAATCTCCTCATGCCATTTGGAG
CTCTCTACCTTTCACTTTTTACAGGCTATATCTTTAAAAAGGCTCTTGCA
ATGGAGGAACTCCATCTCGATGAAAGAGCATGGAAACAAGGACTGTTCCA
AGTCTGGCTCTTCCTTCTTCGTTTCTTCGTTTCGTCATTCCAATCATCAT
CATTGTGGTCTTCATTGCCCAATTTATGTAATCAAAAAGGACTTGAGTAG 4183.5 (SEQ. ID. NO. 323)
ATGTTGAAAAAATGGCAGTTAAAAGATGTTATCTTGCTTGCTTTCTTGTC
TATCTTTTTTGGTGGGGTTTTCGTTGGTTCAGGATATGTGTATAATATTC
TCAGTCTACTCTTAACACCTCTTGGTTTGCAGGCCTTTGCCAATGAAATC
CTCTTCGGTCTCTGGTGTATGGCTGCGCCCATTGCTGCCATCTTTGTTCC
GAGAGTCGGAAGTGCAACGATTGGAGAAGTGCTAGCTGCGCTTGCTGAAG
TCCTTTATGGTAGCCAATTTGGTCTAGGAGCTCTTTTGTCTGGCTTTGTT
CAAGGTTTGGGAAGTGAATTTGGTTTTATCGTAACTAAGAATCGCTATGA
AAGTTGGCTCTCTCTAACTGCTAATAGTATTGGGATTACGCTTGTTAGCT
TTGTCTATGAATACATTAAGTTAGGTTACTACGCCTTTTCCCTTCCGTTT
GTCCTTTCCTTGCTTGTGGTACGTTTTATTTCTGTTTATTTCTTCTGTAC
CATCTTGGTTCGTGCCATTGTCAAACTCTATCATCAGTTTGCAACTGGAG
GAAAAGCATAG 4183.6 (SEQ. ID. NO. 324)
ATGGTCAAAGTAGCAACCCAGACACCGATTATCAGTCTCTTCTTGCTGAT
TTTATCCTTGGAAACATCTTTCATTCCTTCGATTGCTCTGACTCTTTCGG
TAGTCGCATTTTGTATTCTCTTTATGCTCTATTACCGTCGATTTAAAATG
TTAGCTTGGATGATCATACTTGCCATTTTACCATCTTTTGCCAACTACTG
GGCAGTTCAGTTACACGGAGATGCTTCACAGGCAGTCATGCTTGGAACGA
GGGCCTTTGTGACAGTTTGTATCGGCCTTGTCTTTGTTTCCTCTGTTTCA
CTAAAAGAGCTTCTCTTGTACTTGGCTCAAAAGGGGCTATCACGCTCTTG
GTCCTATGCCTTGATTGTGGTATTCAATTCTTTTCCTCTCATTCAGCAAG
AAATCAAGTCCCTCAAAGAAGCTTGCCTATTACGTGGTCAAGAACTACAT
TTTTGGTCGCCCTTGATTTACAGTAAGGTTCTGATGACAGTCTTTAGGTG
GCGCCATCTTTACCTGAGAGCTCTATCTGCTCACGGATATGACGAACATG
CACAGTTGAAGAATAGCTATCGGACTTTTTATATTCCTAAAAAAACAAAA
TTAATCTACCTGCTTTTCTTTTATTGCTTCAAACCAGTCTATTTTATA
A 4183.7 (SEQ. ID. NO. 325)
ATGAGAAAGCACCAATTACAAGTTCACAAATTAACCATTTTATCTATGAT
GATTGCCCTTGATGTAGTCCTTACACCTATCTTTCGAATTGAGGGAATGG
CACCGATGTCCAGTGTAGTCAATATTCTAGCAGGAATCATGATGGGACCT
GTTTATGCCTTGGCTATGGCTACAGTCACAGCCTTTATCCGTATGACGAC
TCAAGGGATTCCGCCTTTAGCTCTCACAGGAGCGACTTTTGGAGCCCTTC
TAGCAGGTCTCTTTTATAAGTACGGTCGAAAATTTCACTATTCTGCTCTA
GGAGAGATTTGGGAACAGGTATTATTGGTTCCATTGTTTCCTATCCTGT

TABLE 1-continued

TATGGTACTCTTTACAGGATCAGCTGCTAAGCTTAGCTGGTTTATCTACA
CGCCTCGATTTTTCGGAGCAACCTTGATTGGTACAGCGATTTCCTTTATT
GCCTTTCGATTTTTAATCAAGCAGGAATTCTTTAAAAAAGTGCAGGGATA
TTTCTTTAGTGAAAGGATAGACTGA 4183.8 (SEQ. ID. NO. 326)
ATGCAGGAATTTACAAATCCCTTTCCTATAGGCTCTAGTTCCCTCATTCA
CTGCATTACCAATGAGATTTCTTGTGAGATGCTGGCAAATGGGATTTTGG
CTCTGGGATGCAAACCTGTCATGGCAGATGATTCCCGTGAAGTTCTTGAT
TTTACTAAGCAAAGTCAGGCTCTCTTCATCAATTTGGGGCATTTGTCAGC
TGAGAAGGAAAAAGCAATCCGCATGGCAGCTTCGTATGCAAACCAATCTT
CTCTCCCGATGGTAGTAGATGCGGTTGGCGTAACGACTTCATCCATTCGT
AAGAGCTTAGTTAAAGACCTTTTAGACTATAGACCTACGGTCCTTAAAGG
AAACATGTCAGAAATTCGAAGTCTTGTTGGATTAAAGCACCACGGCGTTG
GGGTCGATGCGAGTGCTAAAGATCAAGAAACGGAGGATTTGCTTCAAGTC
TTGAAAGACTGGTGTCAGACCTATCCTGGTATGTCTTTCTTAGTCACAGG
TCCCAAGGACCTCGTCGTTTCGAAAAATCAGGTCGCTGTACTGGGAAATG
GCTGTACTGAATTAGACTGGATAACAGGGACAGGAGACTTGGTTGGAGCC
TTAACAGCTGTTTTTCTCAGCCAAGGAAAGACTGGTTTTGAAGCTTCTTG
CTTAGCAGTCTCTTATCTCAATATCGCTGCTGAGAAAATAGTTGTTCAAG
GAATGGGATTGGAAGAATTTCGTTACCAAGTACTCAATCAGCTTTCGCTC
CTAAGAAGAGATGAAAATTGGCTAGATACCATCAAAGGAGAGGTTTATGA
ATAG 4185.3 (SEQ. ID. NO. 327)
ATGAACCATAAAATCGCAATTTTATCAGATGTTCATGGCAATGCGACGGC
GCTAGAAGCAGTGATTGCAGATGCTAAAAATCAAGGGGCCAGTGAATATT
GGCTTCTGGGAGATATTTTCTTCCTGGTCCAGGCGCAAATGACTTAGTC
GCCCTGCTAAAGGACCTTCCTATCACAGCAAGTGTTCGAGGCAATTGGGA
TGATCGTGTCCTTGAGGCTTTAGATGGGCAATATGGCTTAGAAGACCCAC
AGGAAGTTCAGCTCTTGCGTATGACACAGTATTTGATGGAGCGAATGGAT
CCTGCAACGATTGTCTGGCTACGAAGCTTGCCTTTGCTGGAAAAGAAAGA
AATTGACGGATTGCGCTTTTCTATCTCTCATAATTTACCTGACAAAAACT
ATGGTGGTGACTTGCTAGTTGAGAATGATACAGAGAAATTTGACCAACTG
CTAGATGCGAAACGGACGTGGCAGTTTATGGTCATGTTCACAAGCAGTT
GCTTCGTTATGGAAGTCAAGGGCAACAAATCATCAATCCAGGGTCGATTG
GCATGCCCTATTTTAATTGGGAGGCGTTAAAAAATCACCGTTCCAGTAT
GCCGTGATAGAAGTTGAAGATGGGGAATTACTCAATATCCAATTTCGTAA
AGTTGCTTATGATTACGAAGCTGAGTTAGAATTGGCCAAGTCCAAGGGGC
TTCCCTTTATCGAAATGTATGAAGAACTGCGTCGTGACGATAACTATCAG
GGGCACAATCTGGAATTATTAGCCAGCTTAATAGAAAAGCATGGGTATGT
AGAGGATGTGAAGAATTTTTTTGATTTTTGTAA 4186.1 (SEQ. ID. NO. 328)
ATGAATGTAAATCAGATTGTACGGATTATTCCTACTTTAAAAGCTAATAA
TAGAAAATTAAATGAAACATTTTATATTGAAACCCTTGGAATGAAGGCCT
TGTTAGAAGAATCGGCCTTTCTGTCACTAGGTGACCAAACGGGTCTTGAA
AAGCTGGTTTTAGAAGAAGCTCCCAGTATGCGTACTCGTAAGGTAGAGGG
AAGAAAAAAACTAGCTAGATTGATTGTCAAGGTGGAAAATCCCTTAGAAA
TTGAAGGAATCTTATCTAAAACAGATTCGATTCATCGATTATATAAAGGT
CAAAATGGCTACGCTTTTGAAATTTTCTCACCAGAAGATGATTTGATTTT
GATTCATGCGGAAGATGACATAGCAAGTCTAGTAGAAGTAGGAGAAAAGC
CTGAATTTCAAACAGATTTGGCATCAATTTCTTTAAGTAAATTTGAGATT
TCTATGGAATTACATCTCCCAACTGATATCGAAAGTTTCTTGGAATCATC
TGAAATTGGGGCATCCCTTGATTTTATTCCAGCTCAGGGGCAGGATTTGA
CTGTGGACAATACGGTTACCTGGGACTTATCTATGCTCAAGTTCTTGGTC
AATGAATTAGACATAGCAAGTCTTCGCCAGAAGTTTGAGTCTACTGAATA
TTTTATTCCTAAGTCTGAAAAATTCTTCCTTGGTAAAGATAGAAATAATG
TTGAATTGTGGTTTGAAGAAGTATGA 4186.2 (SEQ. ID. NO. 329)
ATGAAGTGGACCAAGATTATTAAAAAAATAGAAGAACAAATCGAGGCAGG
GATTTATCCCGGAGCCTCTTTTGCGTATTTTAAGGACAATCAATGGACAG
AGTTCTATTTAGGCCAGAGTGACCCAGAGCATGGCTTGCAGACTGAGGCA
GGACTAGTTTATGACCTAGCTAGTGTCAGCAAGGTTGTTGGGGTTGGCAC
AGTTTGTACCTTCTTGTGGGAAATAGGTCAATTAGATATTGATAGACTGG
TAATAGATTTTTTACCTGAGAGTGATTATCCAGACATCACTATTCGCCAG
CTCTTGACTCATGCAACAGACCTTGATCCTTTTCCTAATCGTGATCTTTT
AACAGCCCCTGAATTAAAGGAAGCGATGTTTCATCTCAACAGACGAAGTC
AGCCAGCCTTTCTTTATTCGGATGTCCATTTTTTGCTGTTGGGCTTTATT
TTGGAAAGAATTTTTAATCAAGATTTGGATGTGATTTTAAAGGATCAAGT
CTGGAAACCTTGGGGAATGACGGAAACTAAGTTTGGGCCAGTTGAGCTTG
CTGTTCCAACAGTTAGAGGTGTAGAGGCAGGCATAGTGCATGATCCCAAG
GCTCGTCTCCTGGGTAGACATGCTGGGAGTGCTGGTTTATTTTCGACTAT
AAAGGATTTACAAATCTTTTTAGAACACTATTTAGCAGATGATTTTGCAA
GAGACTTAAATCAAATTTTTCTCCTTTGGATGACAAGGAACGTTCTTTA
GCATGGAATTTGGAAGGAGATTGGCTAGACCATACGGGCTATACAGGTAC
CTTTATCATGTGGAATCGTCAGAAGCAAGAAGCCACTATTTTCCTATCGA
ATCGTACCTATGAAAGGACGAGAGAGCTCAATGGATATTAGACCGCAAT
CAAGTGATGAACTTGATTCGCAAAGAAGAGTAA 4187.2 (SEQ. ID. NO. 330)
ATGATGAAGAAGACTTATAATCATATTTTGGTCTGGGGAGTCATTTTCTA
TAGCATTTGCATTGTCTGTTTTTGCTTTACTCCTCAAGAACAATCTACCG
TGGGAGTGGGAACTCCAGGTATTCAGCATCTTGGACGCCTGGTTTTTCTT
TTGACTCCTTTCAATTCTCTCTGGAAACTGGGCGAAGTGAGTGACATTGG

TABLE 1-continued

ACAATTATGTTGGATTTTTTACAAAATATCCTCAATGTCTTCTTGTTTT
TTCCTCTGATTTTCCAACTCCTTTATCTATTTCCAAATTTGCGGAAAACA
AAAAAGGTCCTTCTTTTTAGTTTTCTTGTGAGTCTTGGAATCGAGTGATC
GCAATTAATCTTGGACTTTTTCTTTGATTTCAATCGCGTCTTTGAGATTG
ATGATTTGTGGACCAACACTTTGGGTGGCTATCTGGCTTGGCTCCTTTAT
AAACGATTACATAAAAACAAGGTAAGGAATTAA 4188.1 (SEQ. ID. NO. 331)
ATGAAGATTCCTCTCTTAACTTTTGCAAGGCATAAATTTGTTTATGTCTT
GCTTACTTTGCTTTTTCTTGCTTTGGTTTATCGTGATGTTTTGATGACTT
ATTTCTTTTTTGATATTCATGCGCCCGATCTAGCTAAATTCGATGGACAA
GCAATAAAAATGACTTATTAAAATCAGCATTAGATTTTCGTATTCTCCAG
TTCAATCTAGGTTTTTATCAATCATTTATTATTCCAATCATCATTGTTTT
GCTAGGTTTTCAATATATTGAGCTGAAAAATAAAGTTTTACGATTGAGTA
TTGGAAGAGAAGTGAGTTATCAAGGGTTAAAAAGAAAGTTGACTTTGCAA
GTTGCAAGTATCCCTTGTTTGATATATTTAGTGACTGTGCTGATAATTGC
AATTATAACCTATTTCTTTGGGACTTTTTCTCCTCTTGGATGGAATTCTC
TATTTTCTGATGGAAGTGGTTTACAAAGACTCCTAGATGGAGAGATAAAA
AGCTATTTGTTCTTTACTTGTGTCCTACTAATCGGTATTTTCATCAATGC
AATCTATTTTTTACAAATAGTTGATTATGTGGGGAATGTGACTCGTTCGG
CAATCACCTATTTGATGTTTCTTTGGCTTGGTTCTATGCTGCTTTATAGT
GCCTTGCCTTACTATATGGTTCCTATGACGAGTTTGATGCAAGCTAGCTA
TGGGGATGTAAGTTTGATGAAACTCTTTACTCCTTATATCCTTTATATTG
TCCCTTACATGGTGCTTGAAAAATATGAAGATAATGTTTAA 4188.2 (SEQ. ID. NO. 332)
ATGAAGATAATGTTTAAGAATTTTAACAATATTTTGCTAAATATAGAAGAT
TGTTTTACTACTTCGTATAGTTCTGATGATGATTTTGATAAACCATCTAT
TGTCAACAGCGGTTCAAAGCAGGATGCTGTTATCTTTTTCAAGAGAGAAT
TGATTTCAATTTTTTCCTATAATGACTATTCTGAAGCGAATTTAGAAATC
CCCAAACTATTGTTAAACCTTTCGCTTTTCATGGTAGGATGGCTCTCTGT
CATTTTACTTGAAAGTGATTTGGCAGACCATTACCATCACTTGATTCGCT
ATCAATCAAGCTCCTTTTTCGATTATACAAGGAAACGATTGGTTGTCATT
TCTAAATTTTTTACTCAAGATTTGTTTGTCTGGTTTCTTGGTTTACTTCC
TCTAGGAATTCATTTCAAAACAGTCGCACTTTTCTTTTTACTTGCTCAGT
TAATGATGYTTGTACTTACTACTGTCTTATCTGATAGCACTGATTAGTGC
GGGCGCTGGTTTTTCCTTTTTTCTCTATTTTTTAGCATTTGTGGGACAAG
AATGGATGATGGATCATATTGTAACAGTGTATTTAGTACTCTTAAGTTTA
TTAGTTATGTTGATTGTTAGTCGCTTGGAAGAGAAATTTAAGAAAGGATA
A 4188.5 (SEQ. ID. NO. 333)
ATGGGCAAAGGAGAGATGGGCAAAGGAGTTATTGGCTTGGAGTTCGACTC
AGAAGTATTGGTCAACAAGGCTCCAACCCTTCAATTGGCAAATGGTAAAA

CAGCGACTTTCCTAACCCAGTATGATAGCAAGACCTTGTTGTTTGCAGTA
GATAAGGAAGATATCGGACAGGAAATTATTGGTATAGCTAAAGGAAGCAT
CGAAAGTATGCATAATCTTCCTGTAAATCTAGCAGGTGCCAGAGTTCCTG
GCGGAGTAAATGGTAGCAAAGCAGCGGTGCATGAAGTTCCAGAATTTACA
GGGGGAGTTAATGGTACAGAGCCAGCTGTTCATGAAATCGCAGAGTATAA
GGGATCTGATTCGCTTGTAACTCTTACTACAAAAAAAGATTATACTTACA
AAGCTCCTCTTGCTCAGCAGGCACTTCCTGAAACAGGAAACAAGGAGAGT
GACCTCCTAGCTTCACTAGGACTAACAGCTTTCTTCCTTGGTCTGTTTAC
GCTAGGGAAAAAGAGAGAACAATAA 4188.10 (SEQ. ID. NO. 334)
ATGTTTAAAGTTTTACAAAAAGTTGGAAAAGCTTTTATGTTACCTATAGC
TATACTTCCTGCAGCAGGTCTACTTTTGGGGATTGGTGGTGCACTTTCAA
ACCCAACCACGATAGCAACTTATCCAATACTAGACAATAGTATTTTTCAA
TCAATATTCCAAGTAATGAGCTCTGCAGGAGAGGTTGTATTCAGTAATTT
GTCACTACTTCTCTGTGTGGGATTATGTATTGGCTTAGCGAAACGAGATA
AAGGAACCGCTGCGTTAGCAGGAGTAACTGGTTACTTAGTTATGACTGCA
ACGATCAAAGCTTTGGTAAAACTTTTTATGGCAGAAGGATCTGCAATTGA
TACTGGAGTTATTGGAGCATTAGTTGTCGGAATAGTTGCCGTATATTTGC
ACAACCGATATAACAATATTCAATTACCTTCCGCTTTAGGATTCTTTGGA
GGTTCACGCTTCGTTCCTATTGTTACATCGTTCTCTTCTATCTTGATTGG
CTTTGTCTTCTTTGTTATTTGGCCACCTTTCCAACAACTTCTTGTTTCTA
CAGGTGGATATATTTCTCAGGCGGGTCCAATTGGAACTTTTCTATATGGA
TTTTTAATGAGACTTTCTGGAGCAGTAGGCTTACATCATATAATTTACCC
TATGTTTTGGTATACTGAACTTGGTGGTGTTGAAACTGTTGCAGGACAAA
CAGTGGTTGGAGCTCAAAAATATTTTTTGCTCAATTAGCCGATTTGGCC
CATTCTGGATTATTTACAGAAGGAACAAGGTTTTTTGCAGGTCGTTTCTC
AACAATGATGTTCGGTTTACCGGCTGCCTGTTTAGCGATGTACCATAGTG
TTCCTAAAAATCGTCGTAAAAAATACGCGGGTTTGTTTTTTGGAGTTGCT
TTAACATCTTTTATTACCGGTATTACAGAACCAATTGAATTTATGTTTCT
ATTCGTCAGTCCGGTTCTATATGTTGTTCACGCATTCCTTGATGGTGTTA
GCTTCTTTATTGCAGACGTCTTAAATATTTCAATAGGAAACACATTTTCA
GGAGGTGTAATCGATTTCACTTTATTTGGAATTTTGCAGGGGAACGCTAA
GACGAATTGGGTTCTTCAGATTCCATTTGGACTTATTTGGAGTGTTTTGT
ATTATATTATTTTTAGATGGTTCATTACTCAATTCAACGTTCTAACGCCA
GGGCGAGGAGAAGAAGTAGATTCTAAAGAAATTTCTGAATCCGCAGATTC
AACTTCAAATACTGCAGATTATTTAAAACAGGATAGCCTACAAATTATCA
GAGCCTTGGGTGGATCAAATAATATAGAAGATGTAGATGCTTGTGTGACA
CGTTTACGTGTAGCTGTAAAAGAAGTAATCAAGTTGATAAAGCACTTTTA
AAACAAATTGGTGCAGTTGATGTCTTAGAAGTGAAGGGTGGCATTCAAGC
AATCTATGGAGCAAAAGCAATCTTATATAAAAATAGTATTAATGAAATTT

TABLE 1-continued

TAGGTGTAGATGATTAA 4188.11 (SEQ. ID. NO. 335)
ATGAAATTTAGAAAATTAGCTTGTACAGTACTTGCGGGTGCTGCGGTTCT
TGGTCTTGCTGCTTGTGGCAATTCTGGCGGAAGTAAAGATGCTGCCAAAT
CAGGTGGTGACGGTGCCAAAACAGAAATCACTTGGTGGGCATTCCCAGTA
TTTACCCAAGAAAAAACTGGTGACGGTGTTGGAACTTATGAAAAATCAAT
CATCGAAGCGTTTGAAAAAGCAAACCCAGATATAAAAGTGAAATTGGAAA
CCATCGACTTCAAGTCAGGTCCTGAAAAAATCACAACAGCCATCGAAGCA
GGAACAGCTCCAGACGTACTCTTTGATGCACCAGGACGTATCATCCAATA
CGGTAAAAACGGTAAATTGGCTGAGTTGAATGACCTCTTCACAGATGAAT
TTGTTAAAGATGTCAACAATGAAAACATCGTACAAGCAAGTAAAGCTGGA
GACAAGGCTTATATGTATCCGATTAGTTCTGCCCCATTCTACATGGCAAT
GAACAAGAAAATGTTAGAAGATGCTGGAGTAGCAAACCTTGTAAAGAAG
GTTGGACAACTGATGATTTTGAAAAAGTATTGAAAGCACTTAAAGACAAG
GGTTACACACCAGGTTCATTGTTCAGTTCTGGTCAAGGGGGAGACCAAGG
AACACGTGCCTTTATCTCTAACCTTTATAGCGGTTCTGTAACAGATGAAA
AAGTTAGCAAATATACAACTGATGATCCTAAATTCGTCAAAGGTCTTGAA
AAAGCAACTAGCTGGATTAAAGACAATTTGATCAATAATGGTTCACAATT
TGACGGTGGGGCAGATATCCAAAACTTTGCCAACGGTCAAACATCTTACA
CAATCCTTTGGGCACCAGCTCAAAATGGTATCCAAGCTAAACTTTTAGAA
GCAAGTAAGGTAGAAGTGGTAGAAGTACCATTCCCATCAGACGAAGGTAA
GCCAGCTCTTGAGTACCTTGTAAACGGGTTTGCAGTATTCAACAATAAAG
ACGACAAGAAAGTCGCTGCATCTAAGAAATTCATCCAGTTTATCGCAGAT
GACAAGGAGTGGGGACCTAAAGACGTAGTTCGTACAGGTGCTTTCCCAGT
CCGTACTTCATTTGGAAAACTTTATGAAGACAAACGCATGGAAACAATCA
GCGGCTGGACTCAATACTACTCACCATACTACAACACTATTGATGGATTT
GCTGAAATGAGAACACTTTGGTTCCCAATGTTGCAATCTGTATCAAATGG
TGACGAAAAACCAGCAGATGCTTTGAAAGCCTTCACTGAAAAAGCGAACG
AAACAATCAAAAAAGCTATGAAACAATAG 4188.12 (SEQ. ID. NO. 336)
ATGCAATCTACAGAAAAAAAACCATTAACAGCCTTTACTGTTATTTCAAC
AATCATTTTGCTCTTGTTGACTGTGCTGTTCATCTTTCCATTCTACTGGA
TTTTGACAGGGGCATTCAAATCACAACCTGATACAATTGTTATTCCTCCT
CAGTGGTTCCCTAAAATGCCAACCATGGAAAACTTCCAACAACTCATGGT
GCAGAACCCTGCCTTGCAATGGATGTGGAACTCAGTATTTATCTCATTGG
TAACCATGTTCTTAGTTTGTGCAACCTCATCTCTAGCAGGTTATGTATTG
GCTAAAAAACGTTTCTATGGTCAACGCATTCTATTTGCTATCTTTATCGC
TGCTATGGCGCTTCAAAACAAGTTGTCCTTGTACCATTGGTACGTATCG
TCAACTTCATGGGAATCCATGATACTCTCTGGGCAGTTATCTTGCCTTTG
ATTGGATGGCCATTCGGTGTCTTCCTCATGAAACAGTTCAGTGAAAATAT
CCCTACAGAGTTGCTTGAATCAGCTAAAATCGACGGTTGTGGTGAGATTC

GTACCTTCTGGAGTGTAGCCTTCCCGATTGTGAAACCAGGGTTTGCAGCC
CTTGCAATCTTTACCTTCATCAATACTTGGAATGACTACTTCATGCAATT
GGTAATGTTGACTTCACGTAACAATTTGACCATCTCACTTGGGGTTGCGA
CCATGCAGGCTGAAATGGCAACCAACTATGGTTTGATTATGGCAGGAGCT
GCCCTTGCTGCTGTTCCAATCGTCACAGTCTTCCTAGTCTTCCAAAAATC
CTTCACACAGGGTATTACTATGGGAGCGGTCAAAGGATAA 4191.1 (SEQ. ID. NO. 337)
ATGAAAAAAACTTTTTCTTACTGGTGTTAGGCTTGTTTTGCCTTCTTCC
ACTCTCTGTTTTTGCCATTGATTTCAAGATAAACTCTTATCAAGGGGATT
TGTATATTCATGCAGACAATACGGCAGAGTTTAGACAGAAGATAGTTTAC
CAGTTTGAGGAGGACTTTAAGGGCCAAATCGTGGGACTTGGACGTGCTGG
TAAGATGCCTAGCGGGTTTGACATTGACCCTCATCCAAAGATTCAGGCCG
CGAAAAACGGTGCAGAACTAGCAGATGTGACTAGCGAAGTAACAGAAGAA
GCGGATGGTTATACTGTGAGAGTCTATAATCCAGGTCAGGAGGGCGACAT
AGTTGAAGTTGACCTCGTCTGGAACTTAAAAAATTTACTTTTCCTTTATG
ATGATATCGCTGAATTAAATTGGCAACCTCTGACAGATAGTTCAGAGTCT
ATTGAAAAGTTTGAATTTCATGTAAGGGGAGACAAGGGGGCTGAAAAACT
CTTTTTCCATACAGGGAAACTTTTTAGAGAGGGAACGATTGAAAAGAGTA
ACCTTGATTATACTATCCGTTTAGACAATCTTCCGGCTAAGCGTGGAGTT
GAGTTGCATGCCTATTGGCCTCGGACCGATTTTGCTAGCGCTAGGGATCA
GGGATTGAAAGGGAATCGTTTAGAAGAGTTTAATAAGATAGAAGACTCGA
TTGTTAGAGAAAAAGATCAGAGTAAACAACTCGTTACTTGGGTCCTCCCT
TCGATCCTTTCCATCTCCTTGTTATTGAGTGTCTGCTTCTATTTTATTTA
TAGAAGAAAGACCACTCCTTCAGTCAAATATGCCAAAAATCATCGTCTCT
ATGAACCACCAATGGAATTAGAGCCTATGGTTTTATCAGAAGCAGTCTAC
TCGACCTCCTTGGAGGAAGTGAGTCCCTTGGTCAAGGGAGCTGGAAAATT
CACCTTTGATCAACTTATTCAAGCTACCTTGCTAGATGTGATAGACCGTG
GGAATGTCTCTATCATTTCAGAAGGAGATGCAGTTGGTTTGAGGCTAGTA
AAAGAAGATGGTTTGTCAAGCTTTGAGAAAGACTGCCTAAATCTAGCTTT
TTCAGGTAAAAAAGAAGAAACTCTTTCCAATTTGTTTGCGGATTACAAGG
TATCTGATAGTCTTTATCGTAGAGCCAAAGTTTCTGATGAAAAACGGATT
CAAGCAAGAGGGCTTCAACTCAAATCTTCTTTTGAAGAGGTATTGAACCA
GATGCAAGAAGGAGTGAGAAAACGAGTTTCCTTCTGGGGCTCCCAGATT
ATTATCGTCCTTTAACTGGTGGGAAAAGGCCTTGCAAGTGGGTATGGGT
GCCTTGACTATCCTGCCCCTATTTATCGGATTGGTTTGTTCTTGTACAG
TTTAGACGTTCATGGCTATCTTTACCTCCCTTTGCCAATACTTGGTTTTC
TAGGGTTAGTTTTGTCTGTTTTCTATTATTGGAAGCTTCGACTAGATAAT
CGTGATGGTGTTCTAAATGAAGCGGGAGCTGAGGTCTACTATCTCTGGAC
CAGTTTTGAAAATATGTTGCGTGAGATTGCACGATTGGATCAGGCTGAAC
TGGAAAGTATTGTGGTCTGGAATCGCCTCTTGGTCTATGCGACCTTATTT

TABLE 1-continued

GGCTATGCGGACAAGGTTAGTCATTTGATGAAGGTTCATCAGATTCAAGT

GGAAAATCCAGATATCAATCTCTATGTAGCTTATGGCTGGCACAGTACGT

TTTATCATTCAACAGCACAAATGAGCCATTATGCTAGTGTCGCAAATACA

GCAAGCACCTACTCTGTATCTTCTGGAAGTGGAAGTTCTGGTGGTGGCTT

CTCTGGAGGCGGAGGTGGCGGCAGTATCGGTGCCTTTTAA 4191.2 (SEQ. ID. NO. 338)
ATGAAAAAAGTAAGAAAGATATTTCAGAAGGCAGTTGCAGGACTGTGCTG

TATATCTCAGTTGACAGCTTTTTCTTCGATAGTTGCTTTAGCAGAAACGC

CTGAAACCAGTCCAGCGATAGGAAAAGTAGTGATTAAGGAGACAGGCGAA

GGAGGAGCGCTTCTAGGAGATGCCGTCTTTGAGTTGAAAAACAATACGGA

TGGCACAACTGTTTCGCAAAGGACAGAGGCGCAAACAGGAGAAGCGATAT

TTCAAACATAAAACCTGGGACATACACCTTGACAGAAGCCCAACCTCCAG

TTGGTTATAAACCCTCTACTAAACAATGGACTGTTGAAGTTGAGAAGAAT

GGTCGGACGACTGTCCAAGGTGAACAGGTAGAAAATCGAGAAGAGGCTCT

ATCTGACCAGTATCCACAAACAGGGACTTATCCAGATGTTCAAACACCTT

ATCAGATTATTAAGGTAGATGGTTCGGAAAAAACGGACAGCACAAGGCG

TTGAATCCGAATCCATATGAACGTGTGATTCCAGAAGGTACACTTTCAAA

GAGAAATTTATCAAGTGAATAATTTGGATGATAACCAATATGGAATCGAAT

TGACGGTTAGTGGGAAAACAGTGTATGAACAAAAAGATAAGTCTGTGCCG

CTGGATGTCGTTATCTTGCTCGATAACTCAAATAGTATGAGTAACATTCG

AAACAAGAATGCTCGACGTGCGGAAAGAGCTGGTGAGGCGACACGTTCTC

TTATTGATAAAATTACATCTGATTCAGAAAATAGGGTAGCGCTTGTGACT

TATGCTTCCACTATCTTTGATGGGACCGAGTTTACAGTAGAAAAGGGGT

AGCAGATAAAAACGGAAAGCGATTGAATGATTCTCTTTTTTGGAATTATG

ATCAGACGAGTTTTACAACCAATACCAAAGATTATAGTTATTTAAAGCTG

ACTAATGATAAGAATGACATTGTAGAATTAAAAAATAAGGTACCTACCGA

GGCAGAAGACCATGATGGAAATAGATTGATGTACCAATTCGGTGCCACTT

TTACTCAGAAAGCTTGATGAAGGCAGATGAGATTTTGACACAACAAGCGA

GACAAAATAGTCAAAAAGTCATTTTCCATATTACGGATGGTGTCCCAACT

ATGTCGTATCCGATTAATTTTAATCATGCTACGTTTGCTCCATCATATCA

AAATCAACTAAATGCATTTTTTAGTAAATCTCCTAATAAAGATGGAATAC

TATTAAGTGATTTTATTACGCAAGCAACTAGTGGAGAACATACAATTGTA

CGCGGAGATGGGCAAAGTTACCAGATGTTTACAGATAAGACAGTTTATGA

AAAAGGTGCTCCTGCAGCTTTCCCAGTTAAACCTGAAAAATATTCTGAAA

TGAAGGCGGCTGGTTATGCAGTTATAGGCGATCCAATTAATGGTGGATAT

ATTTGGCTTAATTGGAGAGAGTATTCTGGCTTATCCGTTTAATTCTAA

TACTGCTAAAATTACCAATCATGGTGACCCTACAAGATGGTACTATAACG

GGAATATTGCTCCTGATGGGTATGATGTCTTTACGGTAGGTATTGGTATT

AACGGAGATCCTGGTACGGATGAAGCAACGGCTACTAGTTTTATGCAAAG

TATTTCTAGTAAACCTGAAAACTATACCAATGTTACTGACACGACAAAAA

TATTGGAACAGTTGAATCGTTATTTCCACACCATCGTAACTGAAAAGAAA

TCAATTGAGAATGGTACGATTACAGATCCGATGGGTGAGTTAATTGATTT

GCAATTGGGCACAGATGGAAGATTTGATCCAGCAGATTACACTTTAACTG

CAAACGATGGTAGTCGCTTGGAGAATGGACAAGCTGTAGGTGGTCCACAA

AATGATGGTGGTTTGTTAAAAAATGCAAAAGTGCTCTATGATACGACTGA

GAAAAGGATTCGTGTAACAGGTCTGTACCTTGGAACGGATGAAAAAGTTA

CGTTGACCTACAATGTTCGTTTGAATGATGAGTTTGTAAGCAATAAATTT

TATGATACCAATGGTCGAACAACCTTACATCCTAAGGAAGTAGAACAGAA

CACAGTGCGCGACTTCCCGATTCCTAAGATTCGTGATGTGCGGAAGTATC

CAGAAATCACAATTTCAAAAGAGAAAAAACTTGGTGACATTGAGTTTATT

AAGGTCAATAAAAATGATAAAAAACCACTGAGAGGTGCGGTCTTTAGTCT

TCAAAAACAACATCCGGATTATCCAGATATTTATGGAGCTATTGATCAAA

ATGGCACTTATCAAAATGTGAGAACAGGTGAAGATGGTAAGTTGACCTTT

AAAAATCTGTCAGATGGGAAATATCGATTATTGAAAATTCTGAACCAGCT

GGTTATAAACCCGTTCAAAATAAGCCTATCGTTGCCTTCCAAATAGTAAA

TGGAGAAGTCAGAGATGTGACTTCAATCGTTCCACAAGATATACCAGCGG

GTTACGAGTTTACGAATGATAAGCACTATATTACCAATGAACCTATTCCT

CCAAAGAGAGAATATCCTCGAACTGGTGGTATCGGAATGTTGCCATTCTA

TCTGATAGGTTGCATGATGATGGGAGGAGTTCTATTATACACACGGAAAC

ATCCGTAA 4191.3 (SEQ. ID. NO. 339)
ATGAAATCAATCAACAAATTTTTTAACAATGCTTGCTGCCTTATTACTGAC

AGCGAGTAGCCTGTTTTCAGCTGCAACAGTTTTTGCGGCTGGGACGACAA

CAACATCTGTTACCGTTCATAAACTATTGGCAACAGATGGGGATATGGAT

AAAATTGCAAATGAGTTAGAAACAGGTAACTATGCTGGTAATAAAGTGGG

TGTTCTACCTGCAAATGCAAAAGAAATTGCCGGTGTTATGTTCGTTTGGA

CAAATACTAATAATGAAATTATTGATGAAAATGGCCAAACTCTAGGAGTG

AATATTGATCCACAAACATTTAAACTCTCAGGGCAATGCCGGCAACTGC

AATGAAAAAATTAACAGAAGCTGAAGGAGCTAAATTTAACACGGCAAATT

TACCAGCTGCTAAGTATAAAATTTATGAAATTCACAGTTTATCAACTTAT

GTCGGTGAAGATGGAGCAACCTTAACAGGTTCTAAAGCAGTTCCAATTGA

AATTGAATTACCATTGAACGATGTTGTGGATGCGCATGTGTATCCAAAAA

ATACAGAAGCAAAGCCAAAAATTGATAAAGATTTCAAAGGTAAAGCAAAT

CCAGATACACCACGTGTAGATAAAGATACACCTGTGAACCACCAAGTTGG

AGATGTTGTAGAGTACGAAATTGTTACAAAAATTCCAGCACTTGCTAATT

ATGCAACAGCAAACTGGAGCGATAGAATGACTGAAGGTTTGGCATTCAAC

AAAGGTACAGTGAAAGTAACTGTTGATGATGTTGCACTTGAAGCAGGTGA

TTATGCTCTAACAGAAGTAGCAACTGGTTTTGATTTGAAATTAACAGATG

CTGGTTTAGCTAAAGTGAATGACCAAAACGCTGAAAAAACTGTGAAAATC

ACTTATTCGGCAACATTCAATGACAAAGCAATTGTAGAAGTACCAGAATC

TABLE 1-continued

TAATGATGTAACATTTAACTATGGTAATAATCCAGATCACGGGAATACTC
CAAAGCCGAATAAGCCAAATGAAAACGGCGATTTGACATTGACCAAGACA
TGGGTTGATGCTACAGGTGCACCAATTCCGGCTGGAGCTGAAGCAACGTT
CGATTTGGTTAATGCTCAGACTGGTAAAGTTGTACAAACTGTAACTTTGA
CAACAGACAAAAATACAGTTACTGTTAACGGATTGGATAAAAATACAGAA
TATAAATTCGTTGAACGTAGTATAAAAGGGTATTCAGCAGATTATCAAGA
AATCACTACAGCTGGAGAAATTGCTGTCAAGAACTGGAAAGACGAAAATC
CAAAACCACTTGATCCAACAGAGCCAAAAGTTGTTACATATGGTAAAAAG
TTTGTCAAAGTTAATGATAAAGATAATCGTTTAGCTGGGGCAGAATTTGT
AATTTGCAAATGCTGATAATGCTGGTCAATATTTAGCACGTAAAGCAGAT
AAAGTGAGTCAAGAAGAGAAGCAGTTGGTTGTTACAACAAAGGATGCTTT
AGATAGAGCAGTTGCTGCTTATAACGCTCTTACTGCACAACAACAAACTC
AGCAAGAAAAAGAGAAAGTTGACAAAGCTCAAGCTGCTTATAATGCTGCT
GTGATTGCTGCCAACAATGCATTTGAATGGGTGGCAGATAAGGACAATGA
AAATGTTGTGAAATTAGTTTCTGATGCACAAGGTCGCTTTGAAATTACAG
GCCTTCTTGCAGGTACATATTACTTAGAAGAAACAAAACAGCCTGCTGGT
TATGCATTACTAACTAGCCGTCAGAAATTTGAAGTCACTGCAACTTCTTA
TTCAGCGACTGGACAAGGCATTGAGTATACTGCTGGTTCAGGTAAAGATG
ACGCTACAAAAGTAGTCAACAAAAAAATCACTATCCCACAAACGGGTGGT
ATTGGTACAATTATCTTTGCTGTAGCGGGGGCTGCGATTATGGGTATTGC
AGTGTACGCATATGTTAAAAACAACAAAGATGAGGATCAACTTGCTTAA 4191.4 (SEQ. ID. NO. 340)
ATGACAATGCAGAAAATGCAGAAAATGATTAGTCGTATCTTCTTTGTTAT
GGCTCTGTGTTTTTCTCTTGTATGGGGTGCACATGCAGTCCAAGCGCAAG
AAGATCACACGTTGGTCTTGCAATTGGAGAACTATCAGGAGGTGGTTAGT
CAATGCCATCTCGTGATGGTCATCGGTTGCAAGTATGGAAGTTGGATGAT
TCGTATTCCTATGATGATCGGGTGCAAATTGTAAGAGACTTGCATTCGTG
GGATGAGAATAAACTTTCTTCTTTCAAAAAGACTTCGTTTGAGATGACCT
TCCTTGAGAATCAGATTGAAGTATCTCATATTCCAAATGGTCTTTACTAT
GTTCGCTCTATTATCCAGACGGATGCGGTTTCTTATCCAGCTGAATTTCT
TTTTGAAATGACAGATCAAACGGTAGAGCCTTTGGTCATTGTAGCGAAAA
AAACAGATACAATGACAACAAAGGTGAAGCTGATAAAGGTGGATCAAGAC
CACAATCGCTTGGAGGGTGTCGGCTTTAAATTGGTATCAGTAGCAAGAGA
TGTTTCTGAAAAGAGGTTCCCTTGATTGGAGAATACCGTTACAGTTCTT
CTGGTCAAGTAGGGAGAACTCTCTATACTGATAAAAATGGAGAGATTTTT
GTGACAAATCTTCCTCTTGGGAACTATCGTTTCAAGGAGGTGGAGCCACT
GGCAGGCTATGCTGTTACGACGCTGGATACGGATGTCCAGCTGGTAGATC
ATCAGCTGGTGACGATTACGGTTGTCAATCAGAAATTACCACGTGGCAAT
GTTGACTTTATGAAGGTGGATGGTCGGACCAATACCTCTCTTCAAGGGGC
AATGTTCAAAGTCATGAAGAAGAAAGCGGACACTATACTCCTGTTCTTC

AAAATGGTAAGGAAGTAGTTGTAACATCAGGGAAAGATGGTCGTTTCCGA
GTGGAAGGTCTAGAGTATGGGACATACTATTTATGGGAGCTCCAAGCTCC
AACTGGTTATGTTCAATTAACATCGCCTGTTTCCTTTACAATCGGGAAAG
ATACTCGTAAGGAACTGGTAACAGTGGTTAAAAATAACAAGCGACCACGG
ATTGATGTGCCAGATACAGGGGAAGAAACCCTTGTATATCTTGATGCTTG
TTGCCATTTTGTTGTTTGGTAG 4191.5 (SEQ. ID. NO. 341)
ATGAGCCACATATACTTATCTATTTTCACAAGTCTCTTGCTGATGCTAGG
ACTTGTCAATGTTGCTCAAGCCGATGAATATTTACGCATCGGTATGGAAG
CAGCATATGCTCCCTTTAACTGGACCCAGGATGATGATAGCAACGGAGCT
GTCAAAATCGATGGGACCAATCAGTATGCCAACGGATACGATGTTCAAAT
CGCCAAGAAAATCGCTAAGGACTTAGGTAAAGAACCTTTGGTTGTTAAAA
CCAAGTGGGAAGGTCTAGTCCCTGCCCTTACTTCTGGTAAGATTGACATG
ATTATCGCAGGTATGAGTCCAACTGCAGAACGCAAACAAGAAATTGCCTT
TTCGAGCAGTTACTATACTAGCGAACCAGTTTTGCTTGTCAAAAAAGATT
CTGCCTACGCAAGTGCTAAATCTTTGGATGACTTTAACGGTGCAAAAATC
ACTTCTCAACAAGGGGTCTACCTTTATAACTTGATTGCACAAATCCCAGG
TGCTAAAAAAGAAACAGCCATGGGAGACTTCACTCAAATGCGACAAGCTC
TTGAGGCTGGTGTCATTGATGCTTATGTTTCTGAACGTCCAGAAGCACTG
ACTGCTGAAGCTGCGAACTCTAAGTTCAAGATGATTCAAGTAGAACCTGG
TTTCAAAACTGGGGAAGAAGATACAGCTATCGCTATCGGGCTTCGTAAAA
ATGACAATCGTATTAGCCAAATCAATGCCAGCATTGAAACCATTTCAAAA
GATGACCAAGTTGCCTTGATGGATCGTATGATCAAGGAACAACCTGCCGA
AGCTACAACAACTGAAGAGACTAGCAGTAGTTTCTTTAGCCAAGTTGCTA
AAATTCTTTCTGAAAACTGGCAACAACTCTTGCGTGGTGCTGGTATCACT
CTTTTTAATCTCTATCGTCGGAACCATCATAGGTCTCATTATTGGACTTGC
CATTGGTGTCTTCCGTACTGCTCCTCTCTCTGAAAACAAAGTCATTTACG
GCCTACAAAAACTAGTCGGCTGGGTTCTCAATGTCTACATTGAAATTTTC
CGTGGTACGCCAATGATTGTTCAATCGATGGTTATCTACTATGGAACTGC
CCAAGCTTTCGGGATCAACCTTGACCGTACACTGGCTGCTATCTTCATCG
TTTCAATCAATACCGGTGCCTACATGACTGAAATCGTCCGTGGTGGTATC
CTAGCAGTTGACAAGGGACAATTTGAAGCTGCGACTGCTCTTGGTATGAC
CCATAACCAGACCATGCGTAAGATTGTCCTACCTCAGGTAGTCCGTAACA
TCCTACCTGCAACTGGTAATGAATTTGTCATCAATATCAAAGATACATCT
GTATTGAACGTTATCTCTGTTGTCGAACTTTATTCTCAGGAAATACCGT
GGCAACACAAACCTATCAATACTTCCAGACATTTACAATCATCGCCGTGA
TTTACTTTGTCCTCACCTTCACCGTAACACGTATCCTACGCTTTATCGAG
CGCAGAATGGACATGGATACCTACACTACAGGTGCTAACCAAATGCAAAC
GGAGGATTTGAAATAA

TABLE 1-continued 4191.6 (SEQ. ID. NO. 342)
ATGACACAAGCAATCCTTGAAATTAAACACCTCAAAAAATCCTATGGACA
AAACGAAGTGCTAAAAGACATTTCACTCACTGTCCACAAGGGAGAGGTCA
TCTCTATCATCGGAAGCTCTGGAAGCGGAAAATCGACCTTCCTACGCTCC
ATTAACCTACTTGAAACACCAACTGATGGACAAATCCTTTATCATGGACA
AAACGTCCTCGAAAAAGGCTATGACCTCACGCAATACCGTGAAAAGTTGG
GGATGGTTTTCCAATCCTTTAACCTCTTTGAAAATCTCAATGTTCTTGAA
AACACAATCGTCGCTCAGACAACTGTCCTAAAACGCGAACGCACAGAAGC
TGAAAAGATTGCCAAAGAAAACCTGGAAAAGGTCGGCATGGGAGAACGCT
ACTGGCAAGCCAAACCAAAACAACTCTCAGGTGGTCAAAAACAACGTGTG
GCCATCGCTCGTGCCCTCTCCATGAATCCGGACGCTATTCTCTTTGATGA
ACCAACATCAGCTCTCGATCCAGAAATGGTTGGAGAAGTCCTCAAAATCA
TGCAGGACCTGGCTCAGGAAGGCTTGACCATGATTGTCGTAACCCATGAA
ATGGAATTTGCCCGTGATGTCTCTCACCGTGTTATCTTTATGGATAAGGG
CGTGATCGCTGAAGAAGGTAAACCAGAAGACCTCTTCACCAATCCTAAAG
AAGACCGAACAAAAGAGTTCCTTCAACGCTATCTCAAATAA 4192.3 (SEQ. ID. NO. 343)
ATGAAAAAGTATCAACTTCTATTCAAAATAAGTGCAGTCTTCTCTTACTT
ATTTTTCGTATTTAGTCTTTCTCAGCTGACGCTTATCGTCCAAAACTATT
GGCAATTTTCTTCTCAGATAGGCAATTTATTCTGGATTCAAAATATCTTG
AGTTTACTTTTTATTGGAGTCATGATTGTGGTTCTTGTTAAGACAGGCCA
TGGTTATCTCTCCGCATTCCAAGAAAAAATGGCTTTGGTATTCGATTTT
GACAGTATTAGTGCTAGTGTTCCAGATCTCTTTTAACGTTCAGACAGCTA
AACATGTTCAGTCAACTGCGGAAGGTTGGGCTGTATTGATTGGTTATAGT
GGGACTAACTTTGCAGAGCTAGGTATTTATATAGCCCTGTTCTTTCTGGT
TCCACTGATGGAAGAATTGATTTATAGAGGATTACTGCAACATGCTTTCT
TTAAGCATTCGCGATTTGGTCTTGATTTGCTTCTTCCTTCTATTTTATTT
GCTCTCCCTCATTTTCAAGCCTGCCTAGTCTGTTAGATATCTTCGTCTTT
GCAACAGTTGGAATCATCTTTGCTGGTTTGACCCGCTATACCAAGAGCAT
TTATCCATCCTATGCGGTGCATGTGATCAATAATATTGTAGCGACCTTCC
CGTTTTTGCTCACTTTTCTACATAGGGTCTTGGGGTAA 4193.1 (SEQ. ID. NO. 344)
ATGAACAAGAAACAATGGCTAGGTCTTGGCCTAGTTGCAGTGGCAGCAGT
TGGACTTGCTGCATGTGGTAACCGCTCTTCTCGTAACGCAGCTTCATCTT
CTGATGTGAAGACAAAAGCAGCAATCGTCACTGATACTGGTGGTGTTGAT
GACAAATCATTCAACCAATCAGCTTGGGAAGGTTTGCAGGCTTGGGGTAA
AGAACACAATCTTTCAAAAGATAACGGTTTCACTTACTTCCAATCAACAA
GTGAAGCTGACTACGCTAACAACTTGCAACAAGCGGCTGGAAGTTACAAC
CTAATCTTCGGTGTTGGTTTTGCCCTTAATAATGCAGTTAAAGATGCAGC
AAAAGAACACACTGACTTGAACTATGTCTTGATTGATGATGTGATTAAAG
ACCAAAAGAATGTTGCGAGCGTAACTTTCGCTGATAATGAGTCAGGTTAC cTTGCAGGTGTGGCTGCAGCAAAAACAACTAAGACAAAACAAGTTGGTTT
TGTAGGTGGTATCGAATCTGAAGTTATCTCTCGTTTTGAAGCAGGATTCA
AGGCTGGTGTTGCGTCAGTAGACCCATCTATCAAAGTCCAAGTTGACTAC
GCTGGTTCATTTGGTGATGCGGCTAAAGGTAAAACAATTGCAGCCGCACA
ATACGCAGCCGGTGCAGATATTGTTTACCAAGTAGCTGGTGGTACAGGTG
CAGGTGTCTTTGCAGAGGCAAAATCTCTCAACGAAAGCCGTCCTGAAAAT
GAAAAAGTTTGGGTTATCGGTGTTGATCGTGACCAAGAAGCAGAAGGTAA
ATACACTTCTAAAGATGGCAAAGAATCAAACTTTGTTCTTGTATCTACTT
TGAAACAAGTTGGTACAACTGTAAAAGATATTTCTAACAAGGCAGAAAGA
GGAGAATTCCCTGGCGGTCAAGTGATCGTTTACTCATTGAAGGATAAAGG
GGTTGACTTGGCAGTAACAAACCTTTCAGAAGAAGGTAAAAAAGCTGTCG
AAGATGCAAAAGCTAAAATCCTTGATGGAAGCGTAAAAGTTCCTGAAAAA
TAA 4193.3 (SEQ. ID. NO. 345)
ATGTCTAAAAAATTACAACAAATTTCGGTTCCCTTGATTTCTGTATTCCT
AGGAATTTTACTCGGAGCCATTGTCATGTGGATCTTCGGTTATGATGCTA
TTTGGGGCTACGAAGAATTGTTCTATACAGCCTTTGGCAGTCTGCGTGGG
ATTGGAGAAATCTTCCGTGCTATGGGTCCTCTGGTCTTGATTGGTCTTGG
TTTTTGCCGTTGCCAGTCGAGCTGGTTTCTTTAACGTCGGACTTCCTGGTC
AGGCTTTGGCAGGTTGGATTCTCAGTGGTTGGTTTGCCCTGTCGCATCCA
GATATGCCCCGTCCCTTGATGATTCTAGCAACCATCGTGATTGCCTTGAT
TGCTGGTGGGATTGTCGGAGCGATTCCAGGTATTCTTAGGGCCTATCTAG
GGACGTCAGAGGTTATTGTAACCATCATGATGAACTACATTGTCTTGTAT
GTAGGGAATGCCTTTATCCATGCTTTCCCTAAAGACTTCATGCAAAGTAC
AGATTCGACCATTCGTGTTGGGGCTAATGCAACCTATCAGACACCTTGGT
TGGCTGAGTTGACTGGTAACTCACGGATGAATATTGGTATTTTCTTTGCC
ATCTTGCCGTTGCAGTTATTTGGTTCATGCTCAAGAAAACAACTCTTGGT
TTTGAAATCCGTGCAGTTGGTCTTAATCCACATGCTTCAGAATATGCTGG
TATTTCTGCCAAGCGGACTATTATCCTATCTATGATTATTTCAGGTGCCT
TTGGCAGGTCTTGGTGGAGCTGTTGAAGGTTTGGGAACCTTCCAGAACGT
CTATGTTCAAGGTTCGTCATTAGCTATCGGATTTAACGGAATGGCGGTTA
GTTTGCTTGCGGCCAACTCACCAATTGGTATACTCTTTGCAGCCTTCCTA
TTTGGCGTTCTCCAAGTTGGGGCTCCTGGTATGAATGCGGCGCAGGTACC
ATCTGAGCTTGTCAGCATTGTAACAGCGTCTATTATCTTCTTTGTCAGTG
TTCATTACCTTATCGAACGCTTTGTCAAACCGAAAAAACAAGTTAAAGGA
GGTAAGTAA 4194.1 (SEQ. ID. NO. 346)
ATGGGAGTGAAAAAGAAACTAAAGTTGACTAGTTTGCTAGGACTGTCTCT
GTTAATCATGACAGCCTGTGCGACTAATGGGGTAACTAGCGATATTACAG
CCGAATCGGCTGATTTTTGGAGTAAATTGGTTTACTTCTTTGCGGAAATC TABLE 1-continued ATTCGCTTTTTATCGTTTGATATTAGTATCGGAGTGGGGATTATCTCTTT
ACGGTCTTGATTCGTACAGTCCTCTTGCCAGTCTTTCAGGTGCAAATGGT
GGCTTCTAGGAAAATGCAGGAAGCTCAGCCACGCATTAAGGCGCTTCGAG
AACAATATCCAGGTCGAGATATGGAAAGCAGAACCAAACTAGAGCAGGAA
ATGCGTAAAGTATTTAAAGAAATGGGTGTCAGACAGTCAGACTCTCTTTG
GCCGATTTTGATTCAGATGCCGGTTATTTTGGCCCTGTTCCAAGCCCTAT
CAAGAGTTGACTTTTTAAAGACAGGTCATTTCTTATGGATTAACCTTGGT
AGTGTGGATACAACCCTTGTTCTTCCGATTTTAGCAGCAGTATTCACCTT
TTTAAGTACTTGGTTGTCCAACAAAGCTTTGTCTGAGCGAAATGGCGCTA
CGACTGCGATGATGTATGGGATTCCAGTCTTGATTTTTATCTTTGCAGTT
TATGCGCCAGGTGGAGTCGCCCTATACTGGACAGTGTCTAATGCTTATCA
AGTCTTGCAAACCTATTTCTTGAATAATCCATTCAAGATTATCGCAGAGC
GCGAGGCCGTAGTACAGGCACAAAAAGATTTGGAAAATAGAAAAAGAAAA
GCCAAGAAAAAGGCTCAGAAAACGAAATAA 4194.4 (SEQ. ID. NO. 347)
ATGGTTATCGATCCATTTGCTATCAACGAACTAGACTATTACTTAGTTTC
ACACTTCCACAGTGATCATATCGACCCATACACAGCTGCAGCAATTCTCA
ATAATCCTAAGTTAGAGCATGTTAAGTTTATCGGTCCTTACCACTGTGGA
CGAATCTGGGAAGGATGGGGTGTTCCAAAAGAACGTATCATCGTTGTTAA
ACCAGGTGACACTATCGAATTAAAAGATATGAAGATTCATGCAGTAGAAT
CATTTGACCGTACTTGCTTGGTAACTCTCCCAGTGAACGGTGCTGATGAG
ACAGGCGGTGAACTTGCTGGCTTGGCTGTTACAGATGAAGAAATGGCTCA
AAAGGCTGTTAACTATATCTTTGAAACACCAGGTGGAACCATCTATCATG
GTGCAGATTCTCACTTCTCAAACTATTTTGCAAAACATGGTAAAGACTTT
AAAATTGATGTTGCTTTGAATAACTATGGTGAAAATCCGGTAGGTATCCA
AGACAAAATGACATCTATCGACCTTCTTCGTATGGCAGAAAATCTGCGTA
CCAAAGTCATTATCCCAGTTCACTATGATATCTGGTCTAACTTCATGGCT
TCTACTAATGAGATTCTAGAACTTTGGAAAATGCGAAAAGATCGCTTGCA
ATACGATTTCCATCCATTTATCTGGGAAGTTGGCGGTAAGTACACTTATC
CTCAAGATCAACACTTAGTAGAATACCATCATCCACGTGGTTTTGATGAT
TGTTTTGAACAAGACTCTAACATTCAATTTAAAGCTTTGCTATAA 4196.2 (SEQ. ID. NO. 348)
ATGTTCCTTTCAGGCTGGTTGTCTAGTTTTGCTAATACTTATATCCATGA
TTTACTGGGGGTTCTTTTCCCAGATAGTCCATTTTTAAATGCCTTTGAAA
GTGCTATTGCGGCTCCTTTGGTAGAAGAACCCTTGAAATTATTGTCACTT
GTTTTTGTTTTGGCTTTGATTCCTGTGCGAAAATTAAAATCTTTGTTTTT
ACTTGGAATTGCTTCCGGTTTGGGATTCCAAATGATTAAGGATATTGGTT
ATATTCGTACGGATTTGCCAGAGGGCTTTGACTTTACTATTTCGCGAATT
TTAGAGCGTATCATCTCAGGAATTGCCTCTCACTGGACTTTTTCAGGTCT
AGCTGTAGTAGGTGTTTACTTGCTTTACAGAGCCTATAAAGGACAGAAGG
TTGGCAAGAAACAGGGCCTTATTTTTCTAGGTTTAGCCTTGGGAACTCAC TTCTTGTTTAACTCTCCTTTTGTGGAGTTGGAAACAGAGTTGCCTTTAGC
GATTCCAGTGGTTACGGCTATTGCTCTCTATGGTTTTTATCATGCTTATT
GCTTTGTTGAGAAACACAATGAGTTGATGACCTAG 4197.1 (SEQ. ID. NO. 349)
ATGAAGGTGGAACCACGTTGCGACGTCCTTTCGAGGATGTCGCATTTTTT
TATTAGGATACTAATTATGGAGTTGCAAGAATTAGTGGAGCGCAGTTGGG
CAATCCGACAAGCTTATCACGAACTGGAAGTTAAGCATCATGATTCCAAG
TGGACGGTAGAAGAAGACCTCTTGGCTTTATCTAATGATATTGGAAATTT
CCAACGACTGGTGATGACAAAGCAAGGACGCTACTATGATGAAACACCCT
ACACACTGGAACAAAAACTTTCAGAAAATATCTGGTGGCTATTAGAACTT
TCTCAACGTTTGGATATAGACATTCTGACGGAAATGGAAAACTTCCTCTC
TGATAAAGAAAAGCAATTGAACGTTAGGACTTGGAAGTAG 4197.4 (SEQ. ID. NO. 350)
ATGCTTGATTGGAAACAATTTTTTCTAGCCTATCTGCGCTCCCGTAGTCG
TCTTTTTATCTATCTGCTTTCTTTGGCATTTCTTGTCTTACTCTTTCAGT
TTTTATTTGCCAGTCTAGGAATTTACTTCCTCTACTTTTTCTTCTTGTGT
TGCTTTGTAACCATATTATTTTTCACTTGGGACATATTGGTGGAAACGCA
GGTCTATCGCCAGGAACTTCTCTATGGAGAGAGGGAAGCCAAGTCTCCTT
TGGAAATAGCTTTAGCAGAAAAATTAGAAGCGCGTGAGATGGAACTCTAT
CAGCAGAGGTCAAAAGCAGAAAGAAAACTGACGGATTTGCTGGATTACTA
TACCTTGTGGGTCCATCAGATAAAGACCCCCATTGCAGCCAGTCAACTCT
TAGTTGCAGAAGTGGTCGACCGCCAACTGAAGCAGCAGCTAGAACAGGAA
ATTTTCAAAATCGACTCCTATACCAACCTAGTTTTACAGTACCTGCGTTT
AGAAAGTTTCCATGATGATTTGGTCTTAAAGCAGGTTCAAATTGAGGACT
TGGTCAAGGAAATAATTCGTAAATATGCTCTTTTCTTTATTCAAAAGGC
TTAAATGTCAATCTACATGACCTTGATAAAGAAATCGTGACGGATAAAAA
GTGGCTGCTAGTGGTTATTGAGCAAATCATCTCAAACAGTCTCAAGTACA
CCAAGGAAGGTGGTCTGGAGATTTATATGGATGACCAAGAGCTTTGTATC
AAAGATACGGGAATCGGGATAAAAAACAGTGATGTCCTCCGAGTATTTGA
ACGTGGCTTTTCAGGATACAATGGCCGTTTGACCCAGCAGTCCTCTGGAC
TTGGCCTTTATCTATCTAAGAAAATTTCTGAAGAACTGGGGCACCAGATT
CGTATCGAGTCTGAGGTCGGAAAAGGAACGACAGTGCGGATTCAGTTTGC
TCAAGTGAACTTAGTCCTTGAGTAA 4211.2 (SEQ. ID. NO. 351)
ATGGAACTTAATACACACAATGCTGAAATCTTGCTCAGTGCAGCTAATAA
GTCCCACTATCCGCAGGATGAACTGCCAGAGATTGCCCTAGCAGGGCGTT
CAAATGTTGGTAAATCCAGCTTTATCAACACTATGTTGAACCGTAAGAAT
CTCGCCCGTACATCAGGAAAACCTGGTAAAACCCAGCTCCTGAACTTTTT
TAACATTGATGACAAGATGCGCTTTGTGGATGTGCCTGGTTATGGCTATG
CTCGTGTTTCTAAAAAGGAACGTGAAAGTGGGGGTGCATGATTGAGGAG
TACTTAACGACTCGGGAAAATCTCCGTGCGGTTGTCAGTCTAGTTGACCT TABLE 1-continued

TCGTCATGACCCGTCAGCAGATGATGTGCAGATGTACGAATTTCTCAAGT

ATTATGAGATTCCAGTCATCATTGTGGCGACCAAGGCGGACAAGATTCCT

CGTGGTAAATGGAACAAGCATGAATCAGCAATCAAAAAGAAATTAAACTT

TGACCCGAGTGACGATTTCATCCTCTTTTCATCTGTCAGTAAGGCAGGGA

TGGATGAGGCTTGGGATGCAATCTTAGAAAAATTGTGA 4211.3 (SEQ. ID. NO. 352)
ATGACAAAGAAACAACTTCACTTGGTGATTGTGACAGGGATGAGTGGCGC

AGGGAAAACTGTAGCCATTCAGTCCTTCGAGGATCTAGGTTATTTCACCA

TTGATAATATGCCGCCAGCTCTCTTGCCTAAGTTTTTGCAGCTGGTTGAA

ATTAAGGAAAGACATCCTAAGTTGGCCTTGGTAGTGGATATGCGTAGCCG

TTCTTTCTTTTCAGAGATTCAAGCTGTTTTGGATGAGTTGGAAAATCAAG

ATGGTTTGGATTTCAAAATCCTCTTTTTGGATGCGGCTGATAAGGAATTC

CTCGCTCGTTACAAGGAAACCAGACGGAGTCACCCACTAGCAGCAGACGG

TCGTATTTTAGATGAATCAAGTTGGAACGTGAACTCTTGGCACCTTTGA

AAAATATGAGCCAAAATGTGGTGGATACGACTGAACTCACTCCACGTGAG cTGCGCAAAACCCTTGCAGAGCAGTTTTCAGACCAAGAACAAGCCCAGTC

TTTCCGTATCGAAGTCATGTCTTTCGGATTTAAGTATGGAATCCCGATTG

ATGCGGACTTGGTCTTGATGTCCGTTCTTGCCAAATCCCTATTATTTAC

CAGAACTGAGAAACCAAACGGGTGTGGATGAACCTGTTTATGATTATGTC

ATGAACCATCCTGAGTCAGAAGACTTTTATCAACATTTATTGGCCTTGAT

TGAGCCGATTCTGCCAAGTTACCAAAAGGAAGGTAAGTCCGTTTTGACCA

TTGCCATGGGATGTACGGGTGGACAACACCGTAGTGTGGCATTTGCTAAA

CGCTTGGCGCAGGACTTATCCAAGAATTGGTCTGTTAATGAAGGGCATCG

CGACAAAGACCGCAGAAAGGAAACGGTAAACCGTTCATGA 4211.4 (SEQ. ID. NO. 353)
ATGAGAAAACCAAAGATAACGGTGATTGGTGGAGGGACTGGAAGTCCCGT

CATTCTAAAAAGTCTGCGGGAAAAAGATGTGGAAATCGCAGCTATCGTGA

CGGTGGCAGATGATGGTGGTTCTTCAGGTGAACTCCGAAAAAATATGCAA

CAGTTGACACCGCCAGGTGATCTTCGTAATGTCCTTGTGGCCATGTCGGA

TATGCCTAAGTTTTATGAGAAGGTCTTTCAGTATCGGTTCTCTGAGGATG

CCCGGAGCCTTTGCTGGCCATCCATTGGGAAATCTCATCATTGCTGGCTTG

TCAGAAATGCAGGGTTCAACCTATAATGCCATGCAGTTATTGAGCAAATT

TTTCCATACAACAGGGAAAATTTATCCTTCCAGTGACCATCCTTTGACCC

TTCATGCAGTCTTTCAGGATGGGACAGAAGTGGCTGGAGAGAGTCATATT

GTAGACCATCGAGGCATAATTGACAATGTCTATGTGACCAATGCCCTAAA

CGATGATACGCCTCTGGCCAGCCGTCGAGTAGTGCAGACCATCCTTGAAA

GTGACATGATTGTCCTAGGGCCAGGTTCCCTCTTTACCTCTATTTTGCCC

AATATCGTGATTAAGGAAATTGGGCGGGCTCTTTTGGAAACCAAGGCAGA

AATTGCCTATGTCTGCAATATCATGACCCAACGTGGGGAGACGGAACACT

TTACAGATAGCGACCACGTGGAAGTCTTGCATCGTCACCTTGGTCGCCCT

TTTATCGACACTGTCTTGGTGAATATTGAAAAAGTGCCTCAGGAATACAT

GAATTCCAACCGTTTTGATGAATACTTAGTGCAAGTGGAACACGATTTTG

TAGGTCTTTGTAAGCAAGTTTCGCGCGTGATTTCATCTAACTTCCTTCGT

CTGGAAAATGGCGGTGCCTTCCACGATGGAGATTTGATTGTGGACGAGTT

GATGCGCATTATACAGGTGAAAAAATGA 4213.1 (SEQ. ID. NO. 354)
ATGAAAAATTTGATAAAGTTGCTAATAATTAGATTGATTGTTAACTTAGC

AGACAGTGTATTTTATATAGTAGCATTGTGGCACGTTAGCAATAATTATT

CTTCGAGCATGTTCTTAGGAATATTTATTGCAGTAAATTATCTACCGGAT

TTGTTACTAATCTTTTTTGGACCAGTTATTGACAGAGTAAATCCGCAAAA

AATTCTTATAATATCAATTTTGGTTCAATTAGCAGTGGCTGTAATATTTT

TATTATTATTAAACCAAATATCATTTTGGGTGATAATGAGTCTAGTGTTT

ATTTCAGTAATGGCTAGCTCCATAAGTTACGTGATAGAAGATGTGTTGAT

TCCTCAAGTGGTAGAATATGATAAGATTGTATTTGCAAATTCTCTTTTTA

GTATTTCGTATAAAGTATTAGATTCTATTTTTAATTCATTCGCATCATTT

TTACAGGTGGCAGTAGGATTTATTTTATTGGTTAAGATAGATATAGGCAT

ATTTTTACTTGCTCTATTTATATTGTTGTTGTTAAAATTTAGAACTAGCA

ATGCGAATATAGAAAACTTCTCTTTCAAATATTACAAGAGAGAAGTGTTG

CAAGGTACAAAGTTTATTTTAAATAATAAATTATTATTTAAAACCAGTAT

TTCTTTAACGCTTATAAACTTTTTTATTCATTCAGACAGTAGTTGTACCG

ATTTTTTCTATTCGATATTTTGATGGTCCGATTTTTTATGGTATTTTTTT

AACTATTGCTGGTTTGGGTGGTATATGGGAAATATGCTAGCGCCAATCG

TAATAAAATATTTAAAATCGAATCAAATTGTTGGTGTATTTCTTTTTTG

AACGGCTCAAGTTGGTTAGTAGCAATTCTTATAAAAGACTATACTTTATC

ACTTATTTTATTTTCGTTTGTTTTATGTCTAAAGGAGTCTTCAATATTA

TTTTTAATTCGTTGTACCAACAAATACCTCCACATCAACTTCTTGGTAGG

GTAAATACTACCATTGATTCTATTATTTCTTTTGGAATGCCAATTGGTAG

TTTAGTTGCAGGAACGCTTATTGATTTGAATATTGAATTAGTGTTAATTG

CTATTAGCATACCTTATTTTTGTTTTCTTATATTTTTATCGGATAATG

GATTGAAAGAATTTAGTATATATTAG 4213.2 (SEQ. ID. NO. 355)
ATGATGTCTAACAAAAATAAGGAAATTCTGATTTTTGCGATTCTCTATAC

AGTCCTCTTTATGTTTGATGGCGTTAAATTGCTGGCTTCTTTAATGCCAT

CTGCCATTGCAAATTATCTTGTTTATGTAGTTTTAGCTCTATATGGCTCC

TTCTTGTTCAAGGATAGATTGATCCAACAATGGAAGGAGATTAGAAAGAC

TAAAAGAAAATTCTTCTTTGGAGTCTTAACAGGATGGCTCTTTCTCATTC

TGATGACTGTTGTCTTTGAATTTGTATCAGAGATGTTGAAGCAGTTTGTG

GGACTAGATGGACAAGGTCTAAATCAGTCTAATATTCAAAGTACCTTTCA

AGAACAACCACTACTGATAGCTGTTTTTGCTTGTGTCATTGGACCTCTGG

TAGAAGAATTATTTTTCCGTCAGGTCTTATTGCATTACTTGCAGGAACGG

TTGTCAGGTTTACTAAGCATTATTCTGGTAGGACTTGTTTTTGCTCTGAC

TABLE 1-continued

TCATATGCACAGTTTGGCTCTATCAGAGTGGATTGGTGCAGTTGGTTACT

TAGGTGGAGGCCTTGCCTTTTCTATTATTTATGTGAAAGAAAAAGAGAAT

ATCTACTATCCCTACTTGTTCACATGTTAAGCAACAGCCTCTCCTTAAT

CATTTTAGCTATCAGTATAGTAAAATGA 4224.1 (SEQ. ID. NO. 356)
TTGAAAAAGCCAATTATCGAATTCAAAAACGTCTCTAAAGTTTTTGAAGA

CAGCAACACCAAGGTTCTCAAAGACATCAACTTTGAGTTGGAAGAAGGGA

AATTCTACACCCTTCTAGGTGCATCTGGTTCGGGGAAATCAACTATCCTA

AACATTATTGCAGGTTTACTGGATGCGACGACAGGAGATATCATGCTAGA

CGGTGTTCGTATCAATGATATTCCAACCAACAAGCGCGACGTACATACCG

TCTTCCAATCCTATGCCTTGTTCCCACATATGAATGTGTTTGAAATGTT

GCCTTTCCACTTCGCTTGCGTAAAATTGATAAGAAAGAAATCGAGCAGCG

TGTAGCGGAAGTTCTCAAGATGGTTCAGTTGGAAGGTTATGAAAAACGTT

CCATCCGCAAACTTTCTGGAGGACAACGTCAGCGTGTGGCCATCGCCCGT

GCTATCATCAACCAACCCCGTGTGGTCTTGTTGGACGAGCCTTTATCAGC

GCTGGACTTGAAATTGAGAACAGACATGCAGTACGAATTGCGTGAATTAC

AACAACGATTGGGCATTACCTTTGTCTTTGTCACTCACGATCAGGAAGAA

GCTCTTGCCATGAGTGACTGGATTTTCGTTATGAATGATGGCGAGATTGT

CCAGTCTGGAACCCCTGTGGACATCTACGATGAGCCAATCAACCACTTTG

TTGCCACCTTTATCGGGGAGTCAAACATCTTGCCAGGTACCATGATTGAG

GACTACTTGGTCGAATTTAACGGCAAACGCTTTGAAGCGGTTGATGGTGG

GATGAAGCCAAATGAACCTGTTGAGGTCGTTATTCGTCCAGAGGACTTGC

GCATTACCCTTCCTGAAGAAGGCAAGCTCCAAGTTAAGGTCGATACCCAG

CTTTTCCGTGGAGTTCATTATGAAATTATCGCCTATGACGAACTTGGAAA

TGAATGGATGATCCACTCAACCCGTAAGGCTATCGTGGGTGAGGAAATCG

GTCTGGACTTTGAACCAGAAGACATCCACATCATGCGTCTCAATGAAACC

GAAGAAGAGTTCGATGCTCGTATTGAGGAGTACGTAGAAATCGAAGAGCA

AGAAGCAGGTTTGATCAATGCAATCGAGGAGGAAAGAGATGAAGAAAACA

AGCTCTAA 4252.1 (SEQ. ID. NO. 357)
ATGAAATCAATGAGAATCTTATTTTTGTTAGCTTTAATTCAAATCATTTG

AGTAGCTGTTTCCTATGGAAGGAATGCATCTTGTCCTTTAAACAAAGTAC

AGCTTTTTTCATCGGAAGCATGGTTTTCGTTTCAGGAATCTGTGCTGGAG

TAAATTATCTTTATACCCGTAAGCAAGAAGTCCATAGTGTCCTAGCCAGT

AAGAAGTCGGTGAAGCTTTTTTACAGTATGTTACTCTTAATTAATTTGTT

AGGAGCTGTTCTTGTTTTGTCAGATAACTTGTTCATCAAAAATACGCTGC

AGCAAGAATTAGTTGACTTTTTATTGCCATCCTTCTTTTTCCTATTTGGG

CTAGATTTGCTGATTTTTTTACCCTTGAAAAAATACGTGCGCGATTTTCT

TGCTATGCTGGACAGAAAAAGACAGTGTTGGTGACTATTTTAGCAACAC

TTCTTTTCTTAAGAAATCCAATGACCATTGTCTCACTTCTGATTTATATT

GGACTGGGCTTGTTTTTTGCAGCCTATCTTGTCCCAAATTCGGTTAAGAA

GGAAGTTTCCTTTTTATGGTCATATTTTCCGAGATCTTGTATTGGTCATT

GTTACGCTCATTTTCTTTTAG 4252.2 (SEQ. ID. NO. 358)
ATGGTTAAAAAAATTATTGGAATGGTGCTACGTTTACTTTCTGTAACTGT

AGTAGGAGTAGGTGTTTTTGCTTATACTATTTATCAACAAGGGACAGAAA

CCTTAGCTAAAACCTATAAAAAAATCGGTGAAGAAACCAAGGTTATTGAA

GCGACTGAACCTCTAACCATTCTGTTAATGGGAGTGGACACCGGAAATGT

TGAACGAACTGAAACTTGGGTCGGTAGAAGTGATAGCATGATCTTGATGA

CAGTGAATCCTAAAACGAAAAAAACAACAATGATGAGTTTAGAGCGGGAT

ATTCGACGCGCATTGAATCAGGGAATGGTCAGGCTCATGAAGCGAAACTG

AACTCAGCATATGCAGATGGTGGAGCAGAGCTTGCTATAGAAACCATTCA

AAAAATGATGAATATCCATATTGATCGCTATGTGATGGTCAATATGAGAG

GATTGCAAAAACTAGTGGATGCAGTAGGAGGTATTACAGTCAATAATATC

CTAGGTTTCCCAATTTCTATCAGTGACCAAGAAGAATTTAATACTATTTC

TATCGGTGTTGGGGAGCAACATATTGGGGGAGAAGAAGCCCTAGTCTATG

CACGAATGCGTTACCAAGATCCTGAGGGGGATTATGGTCGTCAAAAACGT

CAACGTGAAGTTATTCAAAAAGTCATGGAAAAAGCTCTCAGTTTAAATAG

CATTGGTCATTATCAAGAGATTCTAAAAGCTTTGAGTGACAATATGCAGA

CCAATATTGATTTGTCTGCAAAAAGTATCCCTAACTTGCTAGGCTATAAA

GATTCATTTAAAACCATTGAAACTCAGCAGTTGCAGGGTGAAGGAGAGAT

ACTTCAAGGTGTTTCTTACCAGATTGTTTCGAGAGCACATATGTTGGAAA

TGCAAAATCTACTCCGACGTTCTTTGGGACAAGAAGAAGTTACTCAGCTT

GAAACCAATGCGGTTTTATTTGAAGATTTATTTGGCAGAGCACCTGTTGG

TGATGAAGATAATTAA 4256.2 (SEQ. ID. NO. 359)
ATGAAAAAACAAGCCTATGTCATTATTGCTCTCACCTCCTTCCTATTTGT

CTTTTTTTTCTCCCACAGCTTGCTGGAAATACTTGATTTTGACTGGTCTA

TCTTTTTGCACGATGTCGAAAAAACAGAAAAATTTGTCTTTTTATTGTTG

GTTTTCAGCATGTCCATGACCTGTCTCTTAGCCCTGTTTGGCGAGGGAT

CGAAGAGCTTTCTCTAAGAAAAATGCAGGCTAATCTCAAGCGTTTATTAG

CAGGGCAAGAAGTGGTTCAGGTTGCAGATCCAGATTTGGATGCCAGTTTC

AAGTCCTTATCAGGTAAACTTAACCTTTTGACAGAGGCTCTTCAAAAAGC

TGAAAATCAGAGCCTTGCTCAGGAAGAGGAAATCATCGAGAAGGAACGGA

AGCGAATTGCTCGGGATTTGCACGATACAGTCAGTCAGGAGTTGTTTGCG

GCCCACATGATTTTATCGGGTATCAGTCAGCAGGCTTTGAAATTGGATAG

AGAAAAGATGCAGACCCAGTTGCAGAGTGTCACAGCTATTTTAGAAACAG

CCCAGAAGGATTTGCGGGTTTGCTCTTGCATTTGCGACCAGTTGAACTG

GAGCAGAAGAGCTTGATAGAAGGGATTCAAATTCTTTTAAAAGAGCTTGA

GGACAAGAGTGATCTTAGGGTTAGTCTCAAGCAGAATATGACGAAATTGC

CTAAGAAAATCGAGGAGCATATCTTCCGTATCCTGCAAGAGTTGATTAGC

AATACCCTCCGCCATGCCCAGGCATCTTGCCTAGATGTCTACCTCTATCA

GACAGATGTTGAATTGCAACTGAAGGTGGTGGACAATGGGATTGGTTTCC

AGTTAGGGAGCTTAGACGACTTGAGTTATGGACTGCGAAATATCAAGGAG

CGGGTTGAAGATATGGCTGGAACAGTTCAACTCTTGACAGCTCCCAAGCA

AGGGCTGGCGGTTGATATCCGTATTCCCCTGTTAGATAAGGAATGA 4263.1 (SEQ. ID. NO. 360)
ATGATTGTTTCCATTATTTCTCAAGGATTTGTCTGGGCTATTCTAGGTCT

GGGAATCTTTATGACATTTAGGATTTTAAACTTTCCAGATATGACGACAG

AAGGTTCCTTCCCTCTTGGGGGAGCTGTTGCTGTCACTTTGATAACCAAA

GGCGTGAACCCATTTTTAGCGACACTTGTTGCTGTAGGAGCAGGTTGTTT

GGCTGGAATGGCAGCAGGCCTTCTTTATACAAAAGGGAAGATCCCAACCT

TGCTCTCAGGGATTTTGGTGATGACTTCTTGTCACTCAATCATGCTCTTG

ATTATGGGACGTGCGAATTTAGGCCTGCTTGGAACCAAGCAAATTCAGGA

TGTTTTGCCTTTTGATTCGGATTTGAATCAACTCTTGACAGGTCTCATCT

TTGTGAGTATTGTTATTGCTCTCATGCTCTTTTTCTTGGACACTAAACTC

GGACAAGCCTATATTGCTACAGGGGATAATCCTGATATGGCTAGAAGTTT

CGGGATTCATACTGGACGCATGGAGCTCATGGGCTTGGTCTTATCAAATG

GTGTGATTGCCCTTGCAGGTGCCCTCATTGCTCAGCAAGAAGGTTATGCC

GATGTGTCTCGAGGGATCGGGGTTATCGTTGTGGGGCTTGCAAGTTTGAT

TATTGGAGAAGTTATTTTCAAGAGTTTGAGCTTGGCAGAGCGTTTGGTTA

CTATCGTTGTAGGTTCTATCGCTTATCAATTTTTAGTGTGGGCAGTTATC

GCACTTGGCTTTAATCAAGTTACCTTCGTTTATACAGTGCCTTGATTTT

AGCAGTCTGCCTCATGATTCCAACATTTAAGCAAACAATCTTGAAAGGAG

CCAAGTTAAGCAAATGA 4346.1 (SEQ. ID. NO. 361)
ATGAAAAAAATGAAAGTTTGGTCTACTGTACTTGCAACGGGAGTTGCTCT

TACTACACTTGCTGCTTGCTCTGGAGGTTCAAATTCTACGACTGCTTCTT

CATCTGAAGAAAAGCTGATAAAAGTCAAGAATTAGTTATCTATTCGAAC

TCAGTCTCAAATGGTCGTGGTGATTGGTTAACTGCTAAAGCAAAAGAAGC

TGGTTTTAATATAAAAATGGTTGATATCGCTGGCGCTCAATTAGCAGACC

GTGTTATTGCTGAGAAGAATAATGCAGTTGCAGATATGGTATTTGGAATT

GGTGCTGTTGATTCAAATAAAATTAGAGATCAAAAATTACTAGTACAGTA

CAAGCCTAAATGGTTAGATAAAATTGATCAATCTTTATCAGATAAAGATA

ATTATTATAATCCTGTGATTGTTCAACCATTAGTTTTAATTGGGGCGCCT

GATGTAAAAGAAATGCCTAAAGATTGGACTGAATTAGGTAGTAAGTATAA

AGGTAAATATTCAATTTCTGGTCTTCAAGGAGGTACAGGACGGGCAATTC

TAGCAAGTATCTTAGTTCGATACCTTGATGATAAAGGTGAATTAGGTGTT

TCCGAAAAAGGTTGGGAAGTAGCAAAAGAATATTTGAAAAATGCATACAC

TCTTCAAAAGGGAGAAAGTTCAATTGTTAAGATGTTAGACAAAGAAGATC

CAATACAATATGGAATGATGTGGGGTTCTGGTGCATTAGTTGGACAAAAA

GAACAAAATGTTGTTTTCAAAGTTATGACTCCTGAGATTGGTGTACCATT

TGTAACTGAACAAACTATGGTTTTAAGCACTAGTAAAAAACAAGCGTTAG

CTAAAGAATTTATTGATTGGTTTGGTCAATCAGAAATTCAAGTAGAATAT

AGTAAGAACTTTGGATCTATTCCTGCAAATAAAGATGCCCTCAAAGATCT

ACCTGAAGATACGAAGAAATTTGTTGATCAAGTGAAACCACAAAATATTG

ACTGGGAAGCTGTTGGAAAGCATTTGGATGAATGGGTAGAAAAAGCTGAA

TTAGAATACGTACAATAA 4346.2 (SEQ. ID. NO. 362)
ATGATTAAATTTGATAATATTCAAATTAAATATGGTGATTTTGTTGCAAT

TGATAATCTGAATTTAGATATACATGAAGGGGAATTTTTTACATTTCTTG

GGCCTTCAGGATGTGGTAAATCAACTACTTTGAGAGCATTGGTAGGTTTT

CTAGATCCATCATCAGGAAGTATTGAAGTTAATGGAACAGATGTCACTCA

TTTGGAACCTGAAAAGCGTGGAATTGGTATTGTATTTCAATCTTATGCGC

TATTTCCAACTATGACTGTTTTTGATAATATTGCATTTGGTTTAAAGTTA

AGAAGGTAGCTCCAGATGTTATTAAAGCTAAAGTATCAGCAGTGGCAGCA

AAAATTAAGATCTCTGATCAACAGTTACAGCGTAATGTATCAGAATTATC

TGGGGGTCAACAACAAAGGGTAGCATTGGCTCGTGCTCTGGTTCTTGAAC

CTAAAATTCTTTGTCTAGATGAACCATTGTCAAACCTTGACGCAAAATTC

GTGTAGATTTGAGAAAAGAGTTGAAAAGACTTCAAAAAGAGTTAGGTATT

ACTACTTTATATGTTACTCATGATCAAGAGGAAGCCTTGACTTTATCTGA

TAGAATTGCAGTCTTTAACAATGGATACATCGAACAGGTCGGTACACCAG

TAGAGATTTATCATAATTCTCAAACTGAATTTGTATGTGATTTTATTGGA

GATATTAATGTTTTGACCGATGAAACAGTCCACGAAGTATTATTGAAAAA

TACAAGCGTTTTCTTAGAGGATAAAAAAGGATACATTCGATTAGAGAAAG

TTCGATTCAATCGTGAAACTGAACAAGATTTTATTCTAAAAGGGACAATT

ATTGATGTTGAGTTTTCTGGAGTTACAATTCACTATACAATAAAAGTTTC

TGAAAGTCAGATTCTTAATGTAACAAGTATTGATAGTCAGGCTGCTATTA

GATCTGTCGGAGAAAGTGTGGAATTATTTATCACACCATCAGACGTTCTG

CAATTTTAA 4346.3 (SEQ. ID. NO. 363)
ATGCGTCATAAATTAAATTTAAAAGATTGGCTTATTCGTTTAGGGTTAAT

CTGGTTCTTAGTAACATTTATTTATTTATCCAAACTTTGATCTAGTAGTG

AATGTATTTGTAAAAGGAGGAGAATTTTCCCTTGATGCTGTACATCGTGT

TCTAAAATCTCAGAGGGCACTTCAGAGTATTATGAACAGTTTTAAGTTAG

CATTTTCACTCATTATTACAGTTAATGTCGTAGGTATTCTTTGTGTTCTA

TTTACAGAGTACTTTGATATTAAAGGTGCTAAATTTTAAAATTAGGTTA

TATGACCTCTTTAATTTATGGAGGAGTGGTTTTAGCGACTGGATATAAAT

TTGTCTATGGTCCTTATGGATTGATTACAAAATTTTTACAAAATGTTATC

CCTTCTTTAGACCCTAACTGGTTTATTGGGTATGGTGCAGTCTTATTCAT

TATGACATTTCAGGAACTGCTAATCATACATTGTTTTTAACAAATACAAT

TCGAAGCGTTGACTATCACACTATTGAGGCTGCTCGAAATATGGGAGCAA

TABLE 1-continued

```
AACCATTTACTGTTTTCCGAAAAGTAGTGTTACCAACCTTAATTCCAACT
CTATTTGCACTTACTATTATGGTTTTTCTTAGTGGTTTATCTGCAGTAGC
AGCACCCATGATTTTTGGTGGTAAAGAATTTCAAACTATAAATCCAATGA
TTATTACATTTGCAGGGATGGGGAATTCTCGTGATTTAGCTGCCCTACTT
GCAATTATTTTAGGTATTGCAACTACAATTTTGCTTACTATCATGAATAA
GATAGAAAAGGTGGAAATTATATTTCTATCTCTAAGACTAAAGCGCCTC
TTAAAAAACAAAAAATTGCGTCTAAGCCTTGGAATATCATTGCTCACATT
GTAGCATATGGATTGTTCACAGTTTTCATGCTTCCACTAATTTTTATAGT
ATTATACTCATTTACAGATCCAGTTGCAATTCAAACAGGTAACTTAACAT
TATCAAACTTTACTTTAGAAAATTATCGCTTATTCTTTAGTAATAGTGCG
GCATTCTCTCCATTCTTGGTCAGCTTTATTTATTCTATTATTGCTGCGAC
AACAGCAACAATTCTCGCAGTTGTATTTGCTCGTGTTGTCAGAAAACATA
AATCTCGTTTTGATTTCTTATTTGAATATGGTGCTCTACTTCCTTGGTTA
CTACCAAGTACACTTTTAGCAGTAAGTTTATTATTACTTTTAATCAGCC
ACAATTTCTTGTCTTGAATCAGATTTTGGTAGGTAGTTTGGTAATTCTAC
TTATTGCATATATAGTTGTAAAAATCCCATTTTCTTATAGAATGGTACGT
GCTATTTTATTTAGTGTTGATGATGAGATGGAAGATGCAGCAAGAAGTAT
GGGTGCTTCACCTTTTTATACTATGATGAAGGTTATCATTCCATTTATTT
TACCGGTTGTTCTCTCTGTTATTGCTTTAAACTTTAACTCTTTATTAACT
GACTTCGACTTATCTGTATTCCTTTACCATCCCCTAGCTCAACCATTAGG
TATTACGATTCGATCTGCAGGTGATGAAACAGCAACATCTAATGCACAAG
CTCTGGTATTTGTTTATACAATTGTTCTGATGATTATTTCTGGAACGGTA
TTATACTTCACACAAAGACCGGGCGTAAAGTAAGGAAATAA
```

TABLE 2

(SEQ ID. NO. 1)
MEELVTLDCLFIDRTKIEANANKYSFVWKKTTEKFSAKLQEQIQVYFQEE
ITPLLIKYAMFDKKQKRGYKESAKNLANWHYNDKEDSYTHPDGWYYRFHH
TKYQKTQTDFQQEIKVYYADEPESAPQKGLYMNERYQNLKAKECQALLSP
QGRQIFAQRKIDVEPVFGQIKASLGYKRCNLRGKRQVRIDMGLVLMANNL
LKYSKMKZ (SEQ ID. NO. 2)
MGKGHWNRKRVYSIRKFAVGACSVMIGTCAVLLGGNIAGESVVYADETLI
THTAEKPKEEKMIVEEKADKALETKNIVERTEQSEPSSTEAIASEKKEDS
AVTPKEEKVSAKPEEKAPRIESQASNQEKPLKEDAKAVTNEEVNQMIEDR
KVDFNQNWYFKLNANSKEAKPDADVSTWKKLDLPYDWSIFNDFDHESPAQ
NEGGQLNGGEAWYRKTFKLDEICDLKKNVRLTFDGVYMDSQVYVNGQLVG
HYPNGYNQFSYDITKYLQKDGRENVIAVHAVNKQPSSRWYSGSGIYRDVT
LQVTDKVHVEKNGTTILTPKLEEQQHGKVETHVTSKIVNTDDKDHELVAE
YQIVERGGHAVTGLVRTASRTLKAHESTSLDAILEVERPKLWTVLNDKPA

TABLE 2-continued

LYELITRVYRDGQLVDAKKDLFGYRYYHWTPNEGFSLNGERIKFHGVSLH
HDHGALGAEENYKAEYRRLKQMKEMGVNSIRTTHNPASEQTLQIAAELGL
LVQEEAFDTWYGGKKPYDYGRFFEKDATHPEARKGEKWSDFDLRTMVERG
KNNPAIFMWSIGNEIGEANGDAHSLATVKRLVKVIKDVDKTRYVTMGADK
RRFGNGSGGHEKIADELDAVGFNYSEDNYKALRAKHPKWLIYGSETSSAT
RTRGSYYRPERELKHSNGPERNYEQSDYGNDRVGWGKTATASWTFDRDNA
GYAGQRWTGTDYIGEPTPWHNQNQTPVKSSYFGIVDTAGIPKHDFYLYQS
QWVSVKKKPMVHLLPHWNWENKELASKVADSEGKIPVRAYSNASSVELFL
NGKSLGLKTFNKKQTSDORTYQEGANANELYLEWKVAYQPGTLEAIARDE
SGKEIARDKITTAGKPAAVRLIKEDHAIAADGKDLTYIYYEIVDSQGNVV
PTANNLVRPQLHGQGQLVQVDNGEQASRERYKAQADGSWIRKAFNGKGVA
IVKSTEQAGKFTLTAHSDLLKSNQVTVFTGKKEGQEKTVLGTEVPKVQTI
IGEAPEMPTTVPFVYSDGSRAERPVTWSSVDVSKPGIVTVKGMADGREVE
ARVEVIALKSELPVVKRIAPNTDLNSVDKSVSYVLIDGSVEEYEVDKWEI
AEEDKAKLAIPGSRIQATGYLEGQPIHATLVVEEGNPAAPAVPTVTVGGE
AVTGLTSQKPMQYPXLAYGAKLPEVTASAKNAAVTVLQASAANGMRASII
IQPKDGGPLQTYAIQFLEEAPKIAHLSLQVEKADSLKEDQTVKLSVRAHY
QDGTQAVLPADKVTFSTSGEGEVAIRKGMLELHKPGAVTLNAEYEGAKDQ
VELTIQANTEKKIAQSIRPVNVVTDLHQEPSLPATVTVEYDKGFPKTHKV
TWQAIPKEKLDSYQTFEVLGKVEGIDLEARAKVSVEGIVSVEEVSVTTPI
AEAPQLPESVRTYDSNGHVSSAKVAWDAIRPEQYAKEGVVVNGRLEGTQL
TTKLHVRVSAQTEQGANISDQWTGSELPLAFASDSNPSDPVSNVNDKLIS
YNNQPANRWTNWNRTNPEASVGVLFGDSGILSKRSVDNLSVGFHEDHGVG
VPKSYVIEYYVGKTVPTAPKNPSFVGNEDHVFNDSANWKPVTNLKAPAQL
KAGEMNHFSFDKVETYAVRIRMVKADNKRGTSITEVQIFAKQVAAAKQGQ
TRIQVDGKDLANFNPDLTDYYLESVDGKVPAVTASVSNNGLATVVPSVRE
GEPVRVLAKAENGDILGEYRLHFTKDKSLLSHKPVAAVKQARLLQVGQAL
ELPTKVPVYFTGKDGYETKDLTVEWEEVPAENLTKAGQFTVRGRVLGSNL
VAEITVRVTDKLGETLSDNPNYDENSNQAFASATNDIDKNSHDRVDYLND
GDHSENRRWTNWSPTPSSNPEVSAGVIFRENGKIVERTVTQGKVQFFADS
GTDAPSKLVLERYVGPEFEVPTYYSNYQAYDADHPFNNPENWEAVPYRAD
KDIAAGDEINVTFKAIKAKAMRWRMERKADKSGVAMIEMTFLAPSELPQE
STQSKILVDGKELADFAENRQDYQITYKGQRPKVSVEENNQVASTVVOSG
EDSFPVLVRLVSESGKQVKEYRIHLTKEKPVSEKTVAAVQEDLPKIEFVE
KDLAYKTVEKKDSTLYLGETRVEQEGKVGKERIEFAINPDGSKEEKLREV
VEVPTDRIVLVGTKPVAQEAKKPQVSEKADTKPIDSSEASQTNKAQLPST
GSAASQAAVAAGLTLLGLSAGLVVTKGKKEDZ (SEQ ID. NO. 3)
MKIMKXKYWTLAILFFCLFNNSVTAQEIPKNLDGNITHTQTSESFSESDE
KQVDYSNKNQEEVDQNKFRIQIDKTELPVTTDKHLEKNCCKLELEPQINN

TABLE 2-continued

DIVNSESNNLLGEDNLDNKIKENVSHLDNRGGNIEHDKDNLESSIVRXYE
WDIDKVTGGGESYKLYSKSNSKVSIAILDSGVDLQNTGLLKNLSNMSKNY
VPNKGYLGKEEGEEGIISDIQDRLGHGTAVVAQIVGDDNINGVNPHVNIN
VYRIFGKSSASPDWIVKAWDAVDDGNDHNLSTGQYLMIDGEYEDGTNDFE
TFLKYKKAIDYANQKGVIIVAALGNDSLNVSNQSDLLKLISSRIZKVRKP
GLVVDVPSYFSSTISVGGIDRIGNLSDFSNKGDSDAIYAPAGSTLSLSEL
GLNNFINAEKYKEDWIFSATLGGYTYLYGNSFAAPKVSGAIAMIIDKYKL
KDQPYNYMFVKKFWKKHYQZ (SEQ ID. NO. 4)
MKKTWKVFLTLVTALVAVVLVACGQGTASKDNKEAELKXVDFILDWTPNT
NHTGLYVAKEKGYFKEAGVDVDLKLPPEESSSDLVINGKAPFAVYFQDYM
AKKLEKGAGITAVAAIVEHNTSGILSRKSDNVSSPKDLVGKKYGTWNDPT
ELAMLKTLVESQGGDFEKVEKVPNNDSNSITPIANGVFDTAWWIYGWDGI
LAKSQGVDANFMYLKDYVKEFDYYSPVIIANNDYLKDNKEEARKVIQAIK
KGYQYAMEHPEEAADILIKNAPELKEKRDFVIESQKYLSKEYASDKEKWG
QFDAARWNAFYKWDKENGILKEDLTDKGFTNEFVKZ (SEQ. ID. NO. 5)
MKRTWRNSFVTNLNTPFMIGNIEJPNRTVLAPMAOVTNSAFRTIAKELGA
GLVVMEMVSDKGIQYNNEKTLHMLHIDEGENPVSIQLFGSDEDSLARAAE
FIQENTKTDIVDINMGCPVNKIVKNEAGAMWLKDPDKIYSIINIVQSVLD
IPLTVKMRTGWADPSLAVENALAAEAAGVSALAMHGRTREQMYTGHADLE
TLYKVAQALTICIPFIANGDIRTVQEAKQRIEEVGADAVMIGRAAMGNPY
LFNQINHYFETGEILPDLTFEDKMKIAYEHLKRLINLKGENVAVRERGLA
PHYLRGTSGTSGAAKLRGAISQASTLAEIETLLQLEKAZ (SEQ. ID. NO. 6)
MIKNPKLLTKSFLRSFAILGGVGLVIHIAIYLTFPFYYIQLEGEKFNESA
RVFTEYLKTKTSDELPSLLQSYSKSLTISAHLKRDIVDKRLPLVHDLDIK
DGKLSNYIVMLDMSVSTADGKQVTVQFVHGVDVYKEAKNILLLYLPYTFL
VTIAPSFVFSYFYTKRLLNPLFYISEVTSKMQDLDDNIRFDERJCDEVGE
VGKQINGMYEELLKVIYELESRNEQIVKLQNQKVSFVRGASHELKTPLAS
LRMLENMQHNIGDYKDHPKYIAKSINKIDQMSHLLEEVLESSKFQEWTEC
RETTVKPVLVDILSRYQELAHSIGVTIENQLTDATRVVMSLRALDKVLTN
LISNAIKYSDKNGRVHSEQDGYLSIKNTCAPLSDQELEHLFDFYHSQIVT
DKDESSGLGLY1VNNILESYQMDYSFLPYEHGMEFKISLZ (SEQ. ID. NO. 7)
MYLGDLMEKAECGQFSILLQESQTTVKAVMEETGFSKATLTKYVTLLNDK
ALDSGLELAIHSEDENLRLSIGAATKGRDIRSLFLESAVKYQILVYLLYH
QQFLAHQLAQELVISEATLGRHLAGLNQILSEFDLSIQNGRWRGPEHQIH
YFYFCLFKVWSSQEWEGHMQKPERKQEIANLEEICGASLSAGQKLDLVLW
AHISQQRLRVNACQFQVIEEKMRCYPDNIFYLRLLRKVPSFFAGQHIPLG
VEDGEMMIFFSFLLSHRILPLHTMEYILGFGGQLADLLTQLIQEMKKEEL

LGDYTEDHVTYELSQLCAQVYLYKGYILQDRYKYQLENRHPYLLMEHDFK
ETAEEIFHALPAFQQGTDLDKKILWEWLQLIEYMAEGGQHMRIGLDLTSG
FLVFSRMAAILKRYLEYNRFITTIEAYDPSRHYDLLVTNNPIHKKEQTPV
YYLKNDLDMEDLVAIRQLLFTZ (SEQ. ID. NO. 8)
MEFSKKTRELSIKKMQERTLDLLHGGGITGAGVALQAAASGLETGLIEMQ
DFAEGTSSRSTKLVHGGLRYLKQFDVEVVSDTVSERAVVQQIAPHIPKSD
PMLLPVYDEDGATFSLFRLKVAMDLYDLLAGVSNTPAANKVLSKDQVLER
QPNLKKEGLVGGGVYLDFRNNDARLVIENIKRANQDGALANHKAEGFLFD
ESGKITGVVARDLLTDQVFEIKARLVINTTGPWSDKVRNLSNKGTQPSQM
RKGVHLVVDSSKIKVSQPVYFDTGLGDGRMVFVLPRENKTYEGTTDTDYT
GDLEHPKVTQEDVDYLLGIVNNRFPESNITIDDIESSWAGLRPLIAGNSA
SDYNGGNNGTISDESFDNLIATVESYLSKEKTREDVESAVSKLESSTSEK
HLDPSAVSRGSSLDRDDNGLLTLAGGKITDYRKMAEGAMERVVDIICAEF
DRSFKLINSKTYPVSGGELNPANVDSEIEAFAQLGVSRGLDSKEAHYLAN
LYGSNAPKVFALAHSLEQAPLSLADTLSHYAMRNELLTLSPVDFLLRRTN
HMLFMRDSLDSIVEPILDEMGRFYDWTEEEKATYRADVEAALANNDLAEL
KNZ (SEQ. ID. NO. 9)
MMNELFGEFLGTLIILLGNGVVAGVVLPKTKSNSSGWIVITMGWGIAVAV
AVFVSGKLSPAYLNPAVTIGVALKGGLPWASVLPYIIALQFAGAMLGQILV
WLQFKPHYEAEENAGNILATFSTGPAIKDTVSNLISEILGTFVLVLTIPA
LGLYDFQAGIGTFAVGTLIVGIGLSLGGTTGYALNPARDLGPRIMHSILP
IPNKGDGDWSYAWIPVVGPVIGAALAVLVFSLFZ (SEQ. ID. NO. 10)
MTKKKERISVIHREKILWLKWYFMRDKEQPKYSVLERKMFDAAKNQDMLA
YQKYATIKQTSEADIRVQTSEADILEAVKEVVYNHMNVIGACQRILFIS
QSPAYDKLNKWPNIYSDLYFSVVPLPKMGVYHEMVGIZ (SEQ. ID. NO. 11)
MKNSNEAEMKLLYTDIRTSLTEILTREAEELVAAGKRVFYIAPNSLSFEK
ERAVLEYLSQQASFSITVTRFAQMARYLVLNDLPAKTTLDDIGLGLAFYK
CLAELDPKDLRVYGAIKQDPQLIQQLIELYHEMTKSQMSFLDLENLTDED
KRADLLLIFEKVTAYLNQGQLAQESQLSHLIEAIENDKVSSDFNQIALVI
DGFTRFSAEEERVVDLLHGKGVEWIGAYASKKAYTSPFSEGNLYQAVKFL
HHLASKYQTPAQDCSQTHEKMDSFDKASRLLESSYDFSELALDVDEKDRE
NLQIWSCLTQKEELELVARSIRQKLHENSDLSYKHFRJLLGDVASYQLSL
KTIFDQYQIPFYLGRSEAMAHHPLTQFVESILALKRYRPRQEDLINLLRT
DLYTDLSQSDIDAFEQYIRYLGINGLPAFQQTFTKSHHGKFNLERLNVLR
LRILAPLETLFASRKQKAEKLLQKWSVFLKEGAVTKQLQDLTITLEAVEQ
ERQAEVWKAFCNVLEQFATVFAGSQVSLEDFLALLHSGMSLSQYRTIPAT
VDTVLVQSYDLIAPLTADFVYAIGLTQDNLPKISQNTSLLTDEERQNLNQ
ATEEGVQLLIASSENLKKNRYTMLSLVNSARKQLFLSAPSLFNESESKES

TABLE 2-continued

AYLQELIHFGFRRREKRMNHKGLSKEDMGSYHSLLSSLVAYHQQGEMSDT
EQDLTFVKVLSRVIGKKLDQQGLENPAIPTSPSSKTLAKDTLQALYPAKQ
EFYLSTSGLTEFYRNEYSYFLRYVLGLQEELRLHPDARSHGNFLHRFEAL
QLPNEDSFDQRLEQAIQETSQERBFSAIYQESLEAQITKEVLLDVARTTG
HILRHNPAIETIKEEANFGGKDQAFIQLDNGRSVFVRGKVDRIDRLKANG
AIGVVDYKSSLTQFQFPHFFNGLNSQLPTYLAALKREGEQNFFGAMYLEM
AEPVQSLMAVKSLAGAVVEASKSMKYQGLFLEKESSYLGEFYNKNKANQL
TDEEFQLLLDYNAYLYKKAAEKILAGRFAINPYTENGRSIAPYVQQHQAI
TGFEANYHLGQARFLEKLDLADGKRLVGEKLKQAWLEKIREELNRZ (SEQ. ID. NO. 12)
MKLIPPFLSEEEIQKLQEAEANSSKEQKKTAEQIEAIYTSAQNILVSASAG
SGKTFVMAERLDQLARGVEISQLFISTFTVKAATELKERLEKJCISKKIQ
ETDDVDLKQHLGRQLADLPNAAIGTMDSFTQKFLGKHGYLLDIAPNFRIL
QNQSEQULENEVFHEVFEAHYQGKQKETFSHLLKNFAGRGKDERGLRQQV
YKIYDFLQSTSNPQKWLSESFLKGFEKADFTSEKEKLTEQIKQALWDLES
FFRYHLDNDAKEIIAKAAYLENVQLILDEEGSLNQESDSQAYQAVLARVV
AISKEKNGRALTNASRKADLKPLADAYNEERKTQFAKLGQISDQIAILDY
QERYHGDTWKLAKTFQSFMSDFVEAYRQRKRQENAPEFADISHYTIEILE
NFPQVRESYQERFHEVMVDEYQDTNHIQERMLELLSNGHNRFMVGDIKQS
IYRFRQADPQCFNEKFQRYAQNPQEGRLIILKENFRSSSEVLSATNDVFE
RLMDQEVGEINYDNKHQLVFANTKLTPNPDNKAAFLLYDKDDTGEEEESQ
RETKLTGEMRLVIKEILKLHQEKGVAFKRIALLTSSRSRNOQILLALSEY
GEPVKTDGEQNNYLQSLEVQVMLDTLRVIHNPLQDYALVALMKSPMFGFD
EDELARLSLQKAEDGVHENLYEKLVNAQKMASSQKGLIHTALAEKLKQFM
DILASWRLYAKTHSLYDLIWKIYNDRFYYDYVGALPNGPARQANLYALAL
RADQFEKSNFEKGLSRFIRMIDQVLEAQHDLASVAVAPPKDAVELMTIHK
SKGLEFPYVFILNMDQDINKQDSMSEVILSRQNGLGVKYIAKMETGAVED
HYPKTIKLSIPSLTYRQNEEELQLASYSEQMRLLYVAMTRAEKKLYLVGK
GSREKLESKEYPAAKNGKLNSNTRLQARNFQDWLWAISKVFTKDKLNFSY
RFIGEDQLTREAIGELETKSPLQDSSQADNRQSDTIKEALEMLKEVEVYN
TLHRAAIELPSVQTPSQUCKPYEPVMDMEGVEIAGQGQSVGKKISFDLPD
FSTKEKVTGAEIGSATHELMQRIDLSQQLTLASLTETLKQVQTSQAVRDK
INLDKILAFFDTVLGQEILANTDHLYREQPFSMLKRDQKSQEDFVVRGIL
DGYLLYENKIVLFDYKTDRYDEPSQLVDRYRGQLALYEEALSRAYSIENI
EKYLILLGKDEVQVVKVZ (SEQ. ID. NO. 13)
MELARHAESLGVDALATIPPIYFRLPEYSVAKYWNDISSAAPNTDYVCYN
IPQLAGVALTPSLYTEMLKNPRVIGVKNSSMPVQDIQTFVSLGGEDMIVF
NGPDEQFLGGRLMGARAGIGGTYGAMPELFLKLNQLIADKDLETARELQY
AINAHGKLTSAHGNMYGVIKEVLKINBGLNIGSVRSPLTPVTEEDRPVVE
AAAALIRETKERFLZ (SEQ. ID. NO. 14)
MYKTKCLREKLVLFLKIFFPIUYQFANYSASFVDTAMTGQYNTMDLAGVS
MATSTWNPPFTPLTGIVSALVPIIGHHLGRGKKEEVASDFYQFIYLALGL
SVVLLGMVLPLAPIILNHIGLEAAVAAVAVRYLWFLSIGIIPLLLFSVIR
SLLDSLGLTKLSMYLMLLLLPLNSGFNYLLIYGAFGVPELGGAGAGLGTS
LAYWVLLGISVLVLFKQEKLKALHLEKRIPLNMDKIKEGVRLGLPIGGTV
FAEVAIFSVVGLIMAKFSPLIIASHQSAMNFSSLMYAFPMSISSAMAIVV
SYEVGAKRFDDAKTYIGLGRWTALIFAAVFTLTFLYIFRGNVASLYGNDP
KFIDLTVRFLTYSLFFQLADTFAAPLQGILRGYKDTVIPFYLGLLGYWGV
AIPVYAIZ (SEQ. ID. NO. 15)
MSTLAKIEALLFVAGEDGIRVRQLAELLSLPPTGIQQSLGKLAQKYEKDP
DSSLALIETSGAYRLVTKPQFAEILKEYSKAPINQSLSRALETLIIAYKQ
PITRIEIDAIRGVNSSGALAKLQAFDLIKEDGKKEVLGRPNLYWITDYFL
DYMGINHLEELPVIDELEIQAQESQLFGERIEEDENQZ (SEQ. ID. NO. 16)
MDTMISRFFRHLPEALKSLKRNGWMTVAAVSSVMITLTLVAIFASVIFNT
AKLATDIENNVRVVVYIRKDVEDNSQTIEKEGQTVTNNDYHKVYDSLKNM
STVKSVTFSSKEEQYEKLTEIMGDNWKIFEGDANPLYDAYIVEANTPNDV
KTIAEDAKKIEGVSEVQDGGANTERLFKLASFIRVWGLGIAALLIFIAVF
LISNTIRITIISRSREIQIMRLVGAKNSYIRGPFLLEGAFIGLLGAIAPS
VLVFIVYQIVYQSVNKSLVGQNLSMISPDLFSPLMIALLFVIGVFIGSLG
SQGISMRRFLKIZ (SEQ. ID. NO. 17)
MKKVRFIFLALLFFLASPEGAMASDGTWQGGQYLKEDGSQAANEWVFDTH
YQSWFYIKADANYAENEWLKQGDDYFYLKSGGYMAKSEWVEDKGAFYYLD
QDGKMKRNAWVGTSYVGATGAKVIEDWVYDSQYOAWFYIKADGQHAEKEW
LQIKGKDYYFKSGGYLLTSQWINQAYVNASGAKVQQGWLFDKQYQSWFYI
KBNGNYADKEWIFENGFHYYYLKSGGYMAANEWEWDKESWFYLKFDGKMA
EKEWVYDSHSQAWYYFKSGGYMTANEWIWDKESWFYLKSDGKIAEKEWVY
DSHSQAWYYFKSGGYMTANEWIWDKESWFYLKSDGKIAEKEWVYDSHSQA
WYYFKSGGYMAKNETVDGYQLGSDGKWLGGKTTNENAAYYQVVPVTANVY
DSDGEKLSYISQGSVVWLDKDRKSDDKRLAITISGLSGYMKTEDLQALDA
SKDFIPYYESDGHRFYHYVAQNASIPVASHLSDMEVGKKYYSADGLHFDG
FKLENPFLFICDLTEATNYSAEELDKVFSLLNINNSLLENKGATFKEAEE
HYHINALYLLAHSALESNWGRSKIAKDKNNFFGITAYDITPYLSAKTFDD
VDKGILGATKWIKENYIDRGRTFLGNKASGMNVEYASDPYWGEKIASVMM
KINEKLGGKDZ

TABLE 2-continued (SEQ. ID. NO. 18)
MKKVLQKYWAWAFVVIPLLLQAIPFYVPMFQGAFYSFTNWTGLTYNYKFV
GLNNFKLLFMDPKFMNAIGFTAIIAIAMVVEIALCIARVLNSKIKGQTFF
RAWFFFPAVLSGLTVALIFKQVFNYGLPAIGNALHIEFFQTSLLGTKWGA
IFAAVFVLLWQOVAMPEIIFLAGLQSIPTEITEAARIDGATSKQVFWNIE
LPYLLPSVSMVFELALKGGLTAFDQVFAMTGGGPNNATTSLGLLVYNYAF
KNNQFGYANAIAVILFFLIVVISHQLRVSKKFEIZ (SEQ. ID. NO. 19)
MMKQDERKALIGKYILLILGSVLILVPLLATLFSSFKPTKDIVDNFFGFF
TNFTWDNFSRLLADGIGGYYWNSVVITVLSLLAVMIFIPMAAYSIARNMS
KRKAVFTIMYTLLILGIFVPFQVIMIPITVMMSKLGLANTPGLILLYLTY
AIPQTLFLYVGYIKISIPESLDEAAEIDGANQFTTYFRIIFPMMKPMHAT
TMIIALWFWNDFMLPLLVLNRDSKMWTLPLFQNYAGQYFNDYGPSFASY
VVGIISITIVYLFFQRHIHSGMSNGAVKZ (SEQ. ID. NO. 20)
MKSILQKMGEHPMLLLFLSYSTVISILAQNWMGLVASVGMFLFTIFFLHY
QSILSHKFFRLILQFVLFGSVLSAAFASLEHPQIVKKPNYAPLSPNMQVW
HQNRAEVTFFNPNYYGIICCFCIMIAPYLFTTTKLNWLKVFCVIAGPVNL
FGLNFTQNRTAFPAIIAGAIIYLFTTTKNWKAFWLSIGVFAIGLSFLFSS
DLGVRMGTLDSSMEERISIWDAGMALFKQNPFWGEGPLTYMNSYPRIHAP
YHEHAHSLYIDTILSYGIVGTILLVLSSVAPVRLMMDMSQESGKRPIIGL
YLSFLTVVAVHGIFDLALFWIQSGFIFLLVMCSIPLEHRMLVSDMTDZ (SEQ. ID. NO. 21)
MSKMDVQKIIAPMMKFVNMRGIIALIKDGMLAILPLTVVGSLFLIMGQLP
FEGLNKSIASVFGANWTEPPMQVYSGTFAIMGLISCFSIAYSYAKNSGVE
ALPAGVLSVSAFFILLRSSYIPKQGEAIGDAISKVWFGGQGHGAHIGLVV
GSIYTFFIKRKIVIKMPEQVPQAIAKQFEAMIPAVIFLSSMIVYILAKSL
TNGGTFIEMIYSAIQVPLQGLTGSLYGAIGIAFFISFLWWFGVHGQSVVN
GVTALLLSNLDANKAMLASANLSLENGAHIVTQQFLDSFLILSGSGITFG
LVVAMLFAAKSKQYQALGKVAAFPAIFNVNEPVVFGFPEVMNPVMFVPFI
LVPVLAAVIVYGAIATGFMQPFSGVTLPWSTPAILSGFLVGGWQGVETQL
VILAMSTLVYFPPFFKVQDRLAYQNEIKQSZ (SEQ. ID. NO. 22)
MKKKDLVDQLVSEIETGKVRTLGIYHGASGKSTFAQELYQALDSTTVNL
LETDPYITSGRHLVVPKDAPNQKVTASLPVAHELESLQRDILACRRVW
MSZ (SEQ. ID. NO. 23)
MKKRYLVLTALLALSLAACSQEKTKNEDGETKTEQTAKADGTVGSKSQGA
AQKKAEVVNKGDYYSIQGKKYDEIIVANKHYPLSKDYNPGENPTAKAELVK
LIKAMQEAGPPISDHYSGFRSYETQTKLYQDYVNQDGKAAADRYSARPGY
SEHQTGLAFDVIGTDGDLVTEEKAAQWLLDHAADYGFVVRYLKGKEKETG
YMAEEWHLRYVGKEAIKEIAASGLSLEEYYGFEGGDYVDZ (SEQ. ID. NO. 24)
MREPDFLNHFLKKGYFKKHAKAVLALSGGLDSMFLFKVLSTYQKELEEEL
ILAHVNHKQRIESDWEEKELRKLAAEAELPIYISNFSGEFSEARARINFR
YDFFQEVMKKTGATALVTAHHADDQVETIFMRLIRGTRLRYLSGIKEKQV
VGEIEIIRPFLHFQKKDFPSIFHFEDTSNQENHYFRNRIRNSYLPELEKE
NPRFRDAILGIGNEILDYDLAIAELSNNINVEDLQQLPSYSESTQRVLLQ
TYLNRFPDLNLTKAQFAEVQQILKSKSQYRHPIKNGYELEKEYQQFQICK
ISPQADEKBDELVLHYQNQVAYQGYLFSFGLPLEGELIQQIPVSRETSIH
IRHRKTGDVLIKNGHRKKLRRLFIDLKIPMEKRNSALIIEQFGEIVSILG
IATNNLSKKTKNDIMNTVLYIEKIDRZ (SEQ. ID. NO. 25)
MRKPLIILLLPSFLTISKVVSTEKEVVYTSKEIYYLSQSDFGIYFRBKLS
SPMVYGEVPVYANEDLVVESGKLTPKTSFQITEWRLNKQGIPVPKLSNHQ
FIAADKRFLYDQSEVTPTIICKVWLESDFKLYNSPYDLKEVKSSLSAYSQ
VSIDKTMFVEGREFLHIDQAGWVAKESTSEEDNRMSKVQEMLSEKYQKDS
FSIYVKQLTTGKSAGINQDEKMYAASVLKLSYLYYTQEKINEGLYQLDTT
VKYVSAVNDFPGSYKPEGSGSLPKKEDNKEYSLKDUTKVSKESDNVAHNL
LGYYISNQSDATFKSKMSAIMGDDWDPKEKLISSKMAGKFMEAIYNQNGF
VLESLTKTDFDSQRIAKGVSVKVAHKIGDADEFKHDTGVVYADSPFILSI
FTKNSDYDTISKIAKDVYEVLKZ (SEQ. ID. NO. 26)
MKKQNNGLIKNPFLWLLFIFFLVTGFQYFYSGNNSGGSQQINYTELVQEI
TDGNVKELTYQPNGSVIEWSGVYKNPKSTKEETGIQFFTPSVTKVEKFTS
TILPADITVSELQKLATDHKAEVTVKHBSSSGIWINLLVSWPFGILFFFL
FSNIMGNMGGGNGRNPMSFGRSKAXANKBDIKVRFSDVAGAEEEKQELVE
VVEFLKDPKRFKLGARIPAGVLLEGPPGTGKLLLAKAVAGEAGVPFFSDS
GSDLVEMFVGVGASRVRSLFEDAKKAAPAIIFIDEIDAVGRQRGVGLGGG
NFRTRQTLNQLLIEMDGFEGNEGIIVIAATNSDVLDPALLRPGRFDRKVL
VGRPDVKGEAILKVHAKNKPLAEDVDLKLVAQQTPGFGFVGADLENVLNE
AALVAARRNSIIDASDIDEAEDRVIAGPSKKKDKTVSQKERELVAYHEAG
HIVGLVLSNARVVHKVTIVPRGRAGGYMIALPKEDQMLEDMKEQLAGLMG
GRVAEEIIFNVQITGASNDFEQATQMARAMVTEYGMSEKLGPVQYEGNHA
MLGAQSPQSEQTAYEIDEEVRSLLNEARNKAAEHQSNRETHKLLEALLKY
ETLDSTQIKALYETGKMPEAVEEESHALSYDEVKSKMNDEKZ (SEQ. ID. NO. 27)
MKRSSLLVRMVISIFLVFLILLALVGTFYYQSSSSAIEATIEGNSQSQTS
HFIQSYIKKLETTSGLTQQTDVLAYAENPSQDKVEGIRDLFLTILKSDK
DLKTVVLVTKSGQVISTDDSVQMKTSSDMMAEDWYQKAIHQGAMPVLTPA
RKSDSQWVISVTQELVDAKGANLGVLRLDSYETLEAYLNQLQLGQQGFAF
IINENHEFVYHPQHTVYSSSSKMEAMKPYDTGQGYTPGHKSYVSQEKIAG
TDWTVLGVSSLEKLDQVRSQLLWTLLGASVTSLLVCLCLVWFSLKRWIAP
LKDLRETMLEIASGAQNLRAKEVGAYELREVTRQFNAMLDQIDQLMVAIR TABLE 2-continued

SQEETTRQYQLQALSSQINPHFLYNTLDTIIWMAEFHDSQRVVQVTKSLA

TYFRLALNQGKDLICLSDEINHVRQYLFIQKQRYGDKLEYEINENVAFDN

LVLPKLVLQPLVENALYHGIKEKEGQGHIKLSVQKQDSGLVIREDDGVGF

QDAGDSSQSQLKRGGVGLQNVDQRLKLHPGANYHMKIDSRPQKGTKVEIY

INRIETSZ (SEQ. ID. NO. 28)
MKRSSLLVRMVISIFLVFLILLALVGTIYYQSSSSAIEATIEGNSQTTIS

QTSHFIQSYIKKLETTSTGLTQQTDVLAYAENPSQDKVEGIRDLFLTILK

SDKDLKTVVLVTKSGQVISTDDSVQMKTSSDMMAEDWYQKAIHQGAMPVL

TPARKSDSQWVISVTQELVDAKGANLGVLRLDISYETLEAYLNQLQLGQQ

GFAFIINENHEFVYHPQHTVYSSSSKMEAMKPYIDTGQGYTPGHKSYVSQ

EKIAGTDWTVLGVSSLEKLDQVRSQLLWTLLGASVTSLLVCLCLVWFSLK

RWIAPLKDLRETMLEIASGAQNLRKEVGAYELREVTRQFNAMLDQIDQLM

VA1RSQEET1RQYQLQALSSQINPHFLYNTLDTUWMAEFHDSQRVVQVTK

SLATYFRLALNQGKDLICLSDENHVRQYLPIQKQRYGDKLEYEINENVAF

DNLVLPKLVLQPLVENALYHGIKEKEGQGHIKLSVQKQDSGLVIRIEDDG

VGFQDAGDSSQSQLKRGGVGLQNVDQRLKLHFGANYHMKIDSRPQKGTKV

EIYINRIETSZ (SEQ. ID. NO. 29)
MFFKLLREALKVKQVRSKILETIFWLVFRIGTSITVPGVNANSLNALSGL

SFLNMLSLVSGNALKNFSIFALGVSPYITASIVVQLLQMDILPKFVEWGK

QGEVGRRKLNQATRYIALVLAFVQSIGITAGFNTLAGAQLIKTALTPQVF

LTIGIILTAGSMIVTWLGEQETDKGYGNGVSMHFAGWSSIPEMIQGIYVD

YFVNVPSSRITSSIIFVHLIITVLLIIYFTTYVQQAEYKIPIQYTKVAQG

APSSSYLPLKVNPAGVIPVIFASSITAAPAAILQFLSATGHDWAWVRVAQ

EMLATTSPTGIAMYALLIILFTFFYTFVQINPEKAAERYKRVVPISMEFV

LVKVQKNILCLNFFVVLQLLVPSSLVZ (SEQ. ID. NO. 30)
MDIRQVTETIAMIEEQNFDIRTITMGISLLDCIDPDENRAAEKIYQKITT

KAANLVAVGDEIAAELGIPIVNKRVSVTPISLIGAATDATDYVVLAKALD

KAAKE1GVDFIGGFSALVQKGYQICGDEILINSIPRALAETDKVCSSVNI

GSTKSGINMTAVADMGRIIKETANLSDMGVAKLVVFANAVEDNPFMAGAF

HGVGEADVIINVGVSGPGVVKRALEKVRGQSPDVVAETVKKTAFKITRIG

QLVGQMASERLGVEFGIVDLSLAPTPAVGDSVARVLEEMGLETVGTHGTT

AALALLNDQVKKGGVMACNQVGGLSGAFIPVSEDEGMEAAVQNGSLNLEK

LEAMTAICSVGLDMIAIPEDTPAETIAAMIADEAAIGVINMKTTAVRIIP

KGKEGDMIEIGGLLGTAPVMKVNGASSVDFISRGGQIPAPIHSFKNZ (SEQ. ID. NO. 31)
MTQIIDGKALAAKLQGQLAEKTAKLKEETGLVPGLVVILVGDNPASQVYV

RNKERSALAAGFRSEVVRVPETITQEELLDLIAKYNQDPAWHGILVQLPL

PKHIDEEAVLLAIDPEKDVDGFHPLNMGRLWSGHPVMIPSTPAGIMEMFH

EYGIDLEGKNAVVIGRSNIVGKPMAQLLLAKNATVTLTHSRTHNLSKVAA

XADILVVAIGRAKFVTADFVKPGAVVIDVGMNRDENGKLCGDVDYEAVAP

LASHITPVPGGVGPMTITMLMEQTYQAALRTLDRKZ (SEQ. ID. NO. 32)
MSKFNRIHLVVLDSVGIGAAPDANNFVNAGVPDGASDTLGHISKTVGLNV

PNMAKIGLGNIPRETPLKTVAAESNPTGYATKLEEVSLGKDTTGHWEIMG

LNITEPFDTFWNGFPEE1LTKLEEFSGRKVIREANKPYSGTAVIYDFGPR

QMSTGELHYTSADPVLQIAAHEDIIPLDELYRICEYARSITLERPALLGR

IIARPYVGEPGNFTRTANRRDLAVSPFFPTVLDKLNEAGIDTYAVGKIND

IFNGAGINHDMGHNKSNSHGIDTLLKTMGLAEFEKGFSFTNLVDFDALYG

HRRNAHGYRDCLHEPDERLPEHAAMRENDLLLITADHGNDPTYAGTDHTR

EYIPLLAYSPAFKGNGLIPVGHFADISATVADNFGVETAMIGESFLD

KLVZ (SEQ. ID. NO. 33)
MFISISAGLVTFLLTLVEPAFIQFYRKAQITGQQMNEDVKQHQAKAGTPT

MGGLVPLITSVLVAFFFALFSSQFSNNVGMILFILVLYGLVGFLDDFLKV

FRKINEGLNPKQKLALQLLGGVIFYLFYERGGDILSVPGYPVHLGFFYIP

FALFWLVGFSNAVNLTDGVDGLASISVVISLSAYGVIAYVQGQMDLLLVI

LAMIGGLLGFFIPNHKPAKVFMGDVGSLALGGMLAAISMALHQEWTLLUG

IVYVFEFTSVMMQVSYFKLTGGKPIFRMTPVHHHFELGGLSGKGNPWSEW

KVDFFFWGVGLLASLLTLAILYLMZ (SEQ. ID. NO. 34)
LFKKNKDELNIALPAMGENFLQMLMGMVDSYLVAHLGLIAISGVSVAGNI

MYQAIRALGAAISSVLSKSIGQKDQSKLAYNVTEALKITLLLSILLGFLS

IFAGKSMIGLLGTERDVAESGGLYLSLVGGSIVLLGLMTSLGALIRATHN

PRLPLYVSFLSNALNILFSSLAIFVLDMGIAGVAWGTIVSRLVGLVILWS

QLKLPYGKPTFGLDKELLTLALPAAGERLMMRAGDVVHALVVSFGTEAVA

GNAIGEVLTQFNYMPAFGVATATVMLLARAVGEDDWKRVASLSKQTLFLS

LFMLPLSFSIYVLGVPLTHLYTDSLAVEASVLVTLFSLLGTPMTTGTVIY

TAVWQGLGNARLPFYATSIGMWCIRIGTGYLMGIVLGWGLPGIWAGSLLD

NGFRWLFLRYRYQRYMSLKGZ (SEQ. ID. NO. 35)
MQTQEKRSQAAVLGLQHLAMYSGSILVPIMIATALGYSAEQLTYLISTDI

FMCGVATFLQLQLNKYFGIGLPVVLGVAFQSVAPLIMIGQSHGSGAMFGA

LIASGIYVVLVSGIFSKVANLFPSIVTGSVITTIGLTLIPVAIGNMGNNV

PEPTGQSLLAAITVLIILINIFTKGFIKSISILIGLVVGTAIAATMGLVD

FSPVAVAPLVHPTPLYFG, PTFEISSIVMMCIIATVSMVESTGVYLALSD

ITKDPIDSTRLRNGYREGLAVLLGGIFNTFPYTGFSQNVGLVKLSGIKKR

LPIYYAAGFLVLLGLLPKFGALAQIIPSSVLGGAMLVMFGFVSIQGMQIL

ARVDFANNEHNFLIAAVSIAGVGLNNSNLFVSMPTAFQMFFSNGIVVASL

LAIVLNAVLNHKKKZ

TABLE 2-continued (SEQ. ID. NO. 36)
MKDRKEYLQDKGKVTVNDLAQALGKDSSKDFRELIKTLLMERKHQIRFEE
DGSLTLEIKKKHEITLKGIFHAHKNGFGFVSLEGEEDDLFVGKNDVNYAI
DGDTVEVVHCKVADRNKGTAAEAKIIDILEHSLTTVVGQIVLDQEKPKYA
GYISKNQK1SQPIYVKKPALKLEGTEVLKVPEDKYPSKKHDFFVASVLDV
VGHSTDVGIDVLEVLESMDIVSEFPEAVVKEAESVPDAPSQKDMEGRLDL
RDEDGADAKDLDOAVHIKALKNGNLEPGVHADVSYYEGSALDKEALNRTS
VYYTDRVVPMLPERSNGICSLNPQVDRLTQSAIMEIDKHGRVVNTQTVIK
TSFRMTYSDVNDILAGDEEKEYHKIVSSIELMAKLHETLENMRVKRGALN
FDTNEAKILVDKQGKPVDIVLRQRGIAERMIESFMLMANETVAEHFSKLD
LPRYIHEBPKAEKVQKFIDYASSFGLRIYGTASELSQEALQDIMRAVEGB
PYADVLSMMLRSMQQARYSEHNHGHYGLAADYYTHFTSPIRRYPDLLVHR
MIRDYGRSKEIAEHFEQVIPEIATQSSNRERRAIEAEREVEAMKKAEYME
EYVGEEYDAVVSSIVKFGLFVELPNTVEGLINTNLPEFYHFNERDLTLRG
EKSGITFRVGQQIRIRVERADKMTGEIDFSFVPSEDFDVIEKGLKQSSRS
GRGRDSNRRSDKKEDKRKSGRSNDKRKHSQKDKKKKGKKPFYKEVAKKGA
KHGKGRGKGRRTKZ (SEQ. ID. NO. 37)
MGTTGFTIIDLIILIVYLLAVLVAGIYFSKKEMKGKEFFKGDGSVPWYVT
SVSIFATMLSPISFLGLAGSSYAGSWLWFAQLGMVVAIPLTHIILPIFAR
DIDTAYDYLDKRFNSKALRISALLFIIYQLGRMSUMYLPSAGLSVLTGID
INILIILMGVVAIVYSYTGGLKSVLWTDFIQGVILJSGVVLALFVLIANI
KGGFGAVAETLANGKFLAANEKLFDPNLLSNSIFLIVMGSGPILSSYASS
QDLVQRFTTTQNIKKLNKMLFTNGVLSLATAVFYLIGTGLYVFYQVQNAD
SAASNIPQDQIFMYFIAYQLPVGITGLILAAIYAASQSTISTGLNSVATS
WTLDIQDVISKNMSDNRRTKIAQFVSLAVGLPSIGVSIVMAHSDIKSAYE
WFNSFMGLVLGLLGGVRLGVSKKANKQGAYAALPIVMVFICYFLPPTAVS
YWAYSLISISVSVVSGYIVSVLTGNKVSAPKYTTIEDITEIKADSSWEVR
MZ (SEQ. ID. NO. 38)
MKFSKKYAGSAVIVSLSLCAYALNQHRSQENKDNNRVSYVDGSQSSQKSE
NLTPDQVSQKEGIQAEQAEQIVIKITDQGYVTSHGDHYHYYNGKVPYDAL
FSEELLMKDPNYQLKDADIVNEVKGGYUKVDGKYYVLKDAAHADNVRTK
DEINRQKQEHVKDNEKVNSNVAVARSQGRYTNDGYVPNPADIIEDTGNAY
IVPHGGHYHYIPKSDLSASELAAAKAHLGKNMQPSQLSYSSTASDNNTQS
VAKGSTSKPANKSENLQSLLKELYDSPSAQRYSESDGLVIDPAKIISRTP
NGVAIPHGDHYHPIPYSKLSALEEKTARVPISGTGSTVSTNAKPNEVVSS
LGSLSNPSSLTTSKELSSASDGYIFNPKDIVEETATAYWRHGDHFHYIPK
SNQIGQPTLPNNSLATPSPSLPINPGTSHEKHEEDGYGFDANRIIAEDES
GFVMSHGDHNHYFFKKDLTEEQIKVRKNIZ (SEQ. ID. NO. 39)
MKKRAIVAVIVLLLIGLDQLVKSYIVQQIPLGEVRSWIPNFVSLTYLQNR
GAAPSILQDQQLLFAVITLVVVIGAIWYLHKHMEDSFWMVLGLTLUAGGL
GNFIDRVSQGPVVDMFHLDFINFAIFNVADSYLTVGVIILLIAMLKEEIN
GNZ (SEQ. ID. NO. 40)
MNTNLASFIVGLHDENDRFYFVQKDGQTYALAKEEGQHTVGDTVKGFAYT
DMKQKLRLTTLEVTATQDQFGWGRVTEVRKDLGVFVDTGLPDKEIVVSLD
ILPELKELWPKXGDQLYIRLEVDKKDRIWGLLAYQEDFQRLARPAYNNMQ
NQNWPAIVYRKLSGTFVYLPENNNMLGFIHPSERYAEPRLGQVLDARVIG
FREVDRTLNLSLKPRSFEMLENDAQMILTYLSSNGGFMTLNDKSSPDDIK
ATFGISKGQFKKALGGLMKAGKIKQDQFGTELIZ (SEQ. ID. NO. 41)
MKDVSLFLLKKVFKSRLNWIVLALFVSVLGVTFYLNSQTANSHSLESRLE
SR1AANERAINENEEKLSQMSDTSSEEYQFAXNNLDVQKNLLTRKTEILT
LLKEGRWKEAYYLQWQDEBKNYEFVSNDPTASPGLKMGVDRERKIYQALY
PLNIKAHTLEFPTHGIDQIVWILEVIIPSLFVVAIIFMLTQLFAERYQNH
LDTAHLYPVSKVTFAISSLGVGVGYVTVLFIGICGFSPLVGSLISGFGQL
DYPYNYSLVNQEVTIGKIQDVLFPGLLLAFLAFIVIVEVVVYLIAYPFKQK
MPVLFLSLIGIVGLLFGIQTIQPLQRIAHLIPFTYLRSVEILSGRLPKQI
DNVDLNWSMGMVLLPCLIIFLLLGILFISRWGSSQKICEFFNRFZ (SEQ. ID. NO. 42)
MMKFILDIVSTPAILVALIAILGLVLQKKKLPDIIKGGIKTFVGFLVVSG
GAGIVQNSLNPFGTMPEHAPHLSOVVPNNEAIVAVAUITYGSATAMIMFA
GMVFNILIARFTRFKYIFLTGHHTLYMACMIAVILSVAGFTSLPLILLGG
LALGUMSISPAFVQKYMVQLTGNDKVALGHFSSLGYWLSGFTGSLIGDKS
KSTEDIICPPKSLAPLRDSTVSITLSMAVIYUVAIFAGSEYIEKEISSGT
SGLVYALQLAGQFAAGVFVLAGVRLILGEIVPAPKGISERLVPNSKPALD
CPIVYTYAPNAVLIGFTSSFVGGLVSMVIMIASGTVVILPGVVPHFFCGA
TAGVTGNASGGVRGATIGAPLQGILISFLPVFLMPVLGGLGFQGSTFSDA
DFGLSGIILGMLNQFGSQAGIVIGLVLILAVMFGVSPIKKPSATEEZ (SEQ. ID. NO. 43)
MIKTFLSALSVILFSIPIITYSFPPSSNLNZWLSTQPILAQIYATPLATA
TMAAILSLFLFFFLSFYKKNKQIRFYSGILLLLSLILLLFGTDKTLSSASN
KTKTLKLVTWNVANQIEAQHIERIFSKFDADMAIFPELATNIRGEQENQR
IKLLFHQVGLSMANYDIFTSPPTNSGIAPVTVIVKXSYGFYTEAKTFHTT
RFGTIVLHSRKQNIPDIIALHTAPPLPGLMEIWKQDLNIIHNQLASKYPK
AIIAGDFNATMRHGALAKISSHRDALNALPPFERGTWNSQSPKLFNATID
HILLPKNHYYVKDLDIVSFQNSDHRCIFTEITFZ (SEQ. ID. NO. 44)
MNPIQRSWAYVSRKRLRSFLILLVLLAGISACLTLMKSNKTVESNLYKSL
NTSPSIKKIENGQTFKLSDLASVSKIKGLENVSPELEVAKLKDKEAVTGE TABLE 2-continued QSVERDDLSAADNNLVSLTALEDSSKDVTFTSSAFNLKEGRLHLQKGDSK
KILHEELAKKNGSLHDKIGLDAGQSESGKGQTVEFEIIGWSGKKQEKFTG
LSSDFSENQVFTDYESSQTLLGNSEAQVSAARFYVENPKEMDGLMKQVEN
IALENQGYQVEKENKAFEQIKDSVATFQTPLTIFLYGMLIAGAGALILVL
SLWLRERVYEVGILLALGKGKSS1FLQFCLEVVLVSLGALLPAFVAGNAI
TTYLLQTLLASGDQASLQDTLAKASSLTSILSFAESYVFLVLLSCLSVAL
CFLFLFRKSPKEILSSISZ (SEQ. ID. NO. 45)
MLHNAFAYVTRKFFKSIVTFLIILLMASLSLVGLSIKGATAKASQETFKN
ITNSFSMQINRRVNQGTPRGAGNEKGEDIKKITENKAIESYVKRINAIGD
LTGYDLIETPETKKNLTADRAKRFGSSLMITGVNDSSKEDKFVSGSYKLV
EGEHLTNDDKDKILLHKDLAAKHGWKVGDKVKLDSNIYDADNEKGAKETV
EVTIKGLFDGHNKSAVTYSQELYENTAITDIHTAAKLYGYTEDTAIYGDA
TFFVTADKNLDDVMKELNGISGINWKSYTLVKSSSNYPALEQSISGMYXM
ANLLFWGSLSPSVLLLALLLSLWINARRKEVGILLSIGLKQASILGQFIT
ESILIAIPALVSAYFLANYTARAIGNTVLANVTSGVAKQASKAAQASNLG
GGAEVDGFSKTLSSLD1SIQTSDFIIIFVLALVLVVLVMALASSNLLRKQ
PKELLLDGEZ (SEQ. ID. NO. 46)
MSQDKQMKAVSPLLQRVNISSIVGGVGSLIFCIWAYQAGILQSKETLSAF
IQQAGIWGPPLFIFLQILQTVVPIIPGALTSVAGVFIYGHIIGTIYNYIG
IVIGCAIIFYLVRLYGAAFVQSVVSKRTYDKYIDWLDKGNRFDRFFIIFM
MIWPISPADFLCMLAALTKMSFKRYMTIIILTKPFTLVVYTYGLTYIIDF
EWQMLZ (SEQ. ID. NO. 47)
MRNMWVIKETYLRHVESWSFFFMVISPFLFLGISVGIGHLQGSSMAKNNK
VAVVTTVPSVAEGLKNVNGVNFDYKDEASAKEAIKEEKLKGYLTIDQEDS
VLKAVYHGETSLENGIKFEVTGTLNELQNQLNRSTASLSQEQEKRLAQTI
QFTEKIDEAKENXKFIQTIAAGALGFFLYMILITYAGVTAQEVASEKGTK
IMEVVFSSIRASHYFYARMMALFLVILTHIGIYVVGGLAAVLLFKDLPFL
AQSGILDHLGDAISLNTLLFILISLFMYVVLAAFLGSMVSRPEDSGKALS
PLMILIMGGFFGVTALGAAGDNLLLKIGSYIPFISTFFMPFRTINDYAGG
AEAWISLALTVWAVVATGFIGRMYASLVLQTDDLGIWKTFKRALSYKZ (SEQ. ID. NO. 48)
MTETIKLMIKAHTSVRRFKEQEIPQVDLNEILTAAQMASSWKNFQSYSVI
VVRSQEKKDALYELVPQEAIRQSAVFLLFVGDLNRAEKGARLHTDTFQPQ
GVEGLLISSVDAALAGQNALLAAESLGYGGVHGLVRYKSEEVAELFNLPD
YYTYSVFGMALGVPNQHHDMKPRLPLENVVFEEEYQEQSTEAIQAYDRVQ
ADYAGARATTSWSQRLAEQFGQAEPSSTRKNLEQKKLLZMLKLIAIVGTN
SKRSTNRQLLQYMQKHFTDKAEIELVEIKAIPVFNKPADKQVPAEILEIA
AKIEEADGVHGTPEYDHSIPAVLMSALAWLSYGIYPLLNKPIMITGASYG TLGSSRAQLQLRQILNAPEIKANVLPDEFLLSHSLQAFNPSGDLVDLDVI
KKLDAIFDDPRIFVKITEKLRNAQELLRKDAEDFDWENLZ (SEQ. ID. NO. 49)
MNTYQLNNGVEIPVLGFGTFICAKDGEEAYRAVLEALKAGYRHIDTAAIY
QNEESVGQAIKDSGVPREEMFVTTKLWNSQQTYSQTRQALEKSIEKLGLD
YLDLYLIHWPNPKPLRENDAWFTRNAEVWRAMEDLYQEGKIRAIGVSNFL
PHHLDALLETATIVPAVNQVRLAPGVYQDQVVAYCREKGILLEAWGPPGQ
GELFDSKQVQEIAANHGKSVAQLALAWSLAEGFLPLPKSVTTSRIQANLD
CFGIELSHEERETLKTIAVQSGAPRVDDVDFZ (SEQ. ID. NO. 50)
MRCKMLDPIAIQLGPLAIRWYALCIVTGLILAVYLTMKEAPRKKIIPDDL
DPILVAFPLAILGARLYYVIFRFDYYSQNLGEIFAIWNGGLAIYGGLITG
ALVLYIFADRKLINTWDFLDIAAPSVMIAQSLGRWGNFFNQEAYGATVDN
LDYLPGRRDQMYIEGSYRQPTFLYESLWNLLGFALILIFRRKWKSLRRGH
ITAFYLIWYGFGRMVIEGMRTDSLMFFGFRVSQWLSVVLIGLGIMIVIYQ
NRKKAPYYITEEENZ (SEQ. ID. NO. 51)
MGKLSSILLGTVSGAALALFLTSDKGKQVCSQAQDPLDDLREDPEYAKEQ
VCEKLTEVKEQATDFVLKTKEQVESGEITVDSILAQTKSYAFQATEASKN
QLNNLKEQWQEKAEALDDSEEIVIDITEEZ (SEQ. ID. NO. 52)
MKTKLIFWGSMLFLLSLSILLTIYLAWIFYPMEIQWLNLTNRVYLKPETI
QYNFHILMNYLTNPFSQVLQMPDFRSSAAGLNHFAVVKNLFHLVQLVALV
TLPSFYVFVNRIVKKDFLSLYRKSLLALVVLPVMIGLGGVLIGFDQFFTL
FHQILFVGDDTWLFDPAKDPVIMILPETFFLHAFLLFFALYENFFGYLYL
KSRRKZ (SEQ. ID. NO. 53)
MTYHFTEEYDHVIGAGHAGVEASLAASRMGCKVLLATINIEMLAFMPCNP
SIGGSAKGIVVREVDALGGEMAKTIDKTYIQMKMLNTGKGPAVRALRAQA
DKELYSKEMRKTVENQENLTLRQTMIDEILVEDGKVVGVRTATHQEYAAK
AVNTTGTALRGEIIIGDLKYSSGPNHSLASINLADNLKELGLEIGRFKTG
TPPRVKASSINYDVTEIQPGDEVPNHFSYTSRDEDYVKDQVPCWLTYTNG
TSHEUQNNLHRAPMFTGVVKGVGPRYCPSIEDKIVRFADKERHQLFLEPE
GRNTEEVYVQGLSTSLPEDVQRDLVHSIKGLENAEMMRTGYAIEYDMVLP
HQLRATLETKKISGLFTAGQTNGTSGYEEAAGQGUAGINAALKIQGKPEL
ILKRSDGYIGVMIDDLVTKGTIEPYRLLTSRAEYRLILRHDNADMRLTEM
GREIGLVDDERWARIFEIKICNQFDNEMKRLDSIKLKPVKETNAKVEEMG
FKPLTDAVTAKEFLRRPEVSYQDVVAFIGPAAEDLDDKIIELIETEIKYE
GYISKAMDQVAKMKRMEEKRIPANIDWDDIDSIATEARQKFKUNPETIGQ
ASRISGVNPADISILMVYLEGKNRSISKTLQKSKZ TABLE 2-continued (SEQ. ID. NO. 54)
MTKQVLLVDDEEHILKLLDYHLSKEGFSTQLVTNGRKALALAETEPFDFI
LLDIMLPQLDGMEVCKRLRAKGVKTPIMMVSAKSDEFDKVLALELGADDY
LTKPFSPRELLARVKAVLRRTKGEQEGDDSDNIADDSWLFGTLKVYPERH
EVYKANKLLSLTPKEFESDKNPFFEVFPKVSKVTAQZ (SEQ. ID. NO. 55)
MTTFKDGFLWGGAVAAHQLEGGWQEGGKGISVADVMTAGRHGVAREITLG
VLEGKYYPNHEAIDFYHRYKEDIALFAEMGFKCPRTSIAWTRFPKGDELE
PNEEGLQFYDNLPDECLKNGIEPVITLSHFEMPYHLVTEYGGWKNRKLID
FPAREAEVVFKRYKDKVKYWMTFNEINNQANYQEDFAPFTNSGIVYEEGD
NREAIMYQAAHYELVASARAVKIGHEINPDFQIYYMSFAIDSHRENNPYD
YLETEDLVKNNYVKASEWEWQIDPEGLRYALNWFTDHYHLPLFNENGFGM
DQVAADGMVHDDYREYLGAHIREMKKAVVEDGVDLMGYTPWGCIDLVSAG
TGEMRKRYGFIYVDKDDNGKGSYNRSPKKFGWYKEVISSNGESVEZ (SEQ. ID. NO. 56)
MDQQNGLFGFLENHVMGPMGKLAQPKVVLTAAGMAAVPFWGSMFLVFSIL
PQAPSPPWADIFSASFDKFTSLYMVANYATMGSLSLYFVLSLAYELTKIY
AEEEELNMNPLNGALLALMAFVMTVPQUFDGGMMKTSLKEGAVIADGWMA
GNVVARFGTTGIFTAHMAIVTVLIYRMCVKHNWVIKMPEAVPEGVSRGPT
ALVPGFVVAFVVIFINGLLVAMGTDIKVLMPFGFVSNLTNSWIGLMUYLL
TQLLWWGIHGANIVFAFVSPIALANMAENAAGGHFAVAGEFSNMFLVIAG
GSGATLGLCLYIAFASKSEQLKIGRSVVPALFNINEPLILGLPIIYNPAL
AIPFILAPMVTATIYYVANSLNFIKPIIAQVPWPTPVGIGAFLGTADLRA
VLVALVCAFAAPLVYLPFTRVYDQKLVKEEQGIZ (SEQ. ID. NO. 57)
MKKFYVSPIFPILVGLIAFGVLSTFIIFVNNNLLTVLILPLFVGGYVFLF
KKLRVHYTRSDVEQIQYVNHQAEESLTALLEQMPVGVMKLNLSSGEVEWF
NPYAELILTKEGDFDLEAVQTIIKASVGNPSTYAKLGEKRYAVHMDASSG
VLYFVDVSREQAITDELVTSRPVIGVSVDNYDDLEDETSESDISQENSFV
ANFISEFSEKHMMFSRRVSMDRFYLFTDYTVLEGLMNDKFSVIDAFREES
KQRQLPLTLSMGFSYGDGNHDEIGKVALLNLNLAEVRGGDQVVVKENDST
KNPVYFGGGSAASTIKRTRTRTRAMMTASDKIRSVDQVFVVGHKNLDMDA
LGSAVGMQLFASNVIENSYALYDEEQMSPDIERAVSFIEKEGVTKLLSVK
DAMGMVTNRSLLILVDHSKTALTLSKEFYDLFTQTIVIDHHRRPQDFPDN
AVITYIESGASSASELVTELIQPQNSKKNRLSRMQASVLMAOMMLDTKNF
TSRVTSRTFDVASYLRTRGSDSIAIQEIAATDFEEYREVNEULQGRKLGS
DVLIAEAKDMKCYDTVVISKAADAMLAMSGIEASFVLAKNTQOFISLSAR
SRSKLNVQR1MEELGGGGHFNLAAAQIKDVTLSEAGEKLTEIVLNEMKEK
EKEEZ (SEQ. ID. NO. 58)
MKEKNMWKELLNRAGWILVFLLAVLLYQVPLVVTSILTLKEVALLQSGLI
VAGLSIVVLALFIMGARKTKLASFNFSFFRAKDLARLGLSYLVIVGSNIL
GSILLQLSNETTTANQSQINDMVQNSSIISSFFLLALLAPICEEILCRGI
VPKKIFRGKENLGFVVGTIVFALLHQPSNLPSLLIYGGMSTVLSVIAYKT
QRLEMSLLLHMIVNGIAFCLLALVVIMSRTLGISVZ (SEQ. ID. NO. 59)
MKEKNMWKELLNRAGWILVFLLAVLLYQVPLVVTSILTLKEVALLQSGLI
VAGLSIVVLALFIMGARKTKLASFNFSFFRAKDLARLGLSYLVIVGSNLG
SILLQLSNETITANQSQINDMVQNSSLISSPFLLALLAPICEEILCRGIV
PKKIPRGKENILGFVVGTWFALLHQPSNLPSLLIYGGMSTVLSWAYKTQR
LEMSILLHMIVNGIAFCLLALVVIMSRTLGISVZ (SEQ. ID. NO. 60)
MDTQKIEAAVKMUEAVGEDANREGLQETPARVARMYQEIFSGLGQTAEEH
LSKSFEIIDDNMVVEKDIFFHTMCEHHFLPFYGRAHIAYIPDGRVAGLSK
LARTVEVYSKKPQIQERLNIEVADALMDYLGAKGAFVVIEAEHMCMSMRG
VRKPGTATUTVARGLFETDKDLRDQAYRLMGLZMKDLFLKRKQAFRKECL
GYLRYVLNDHFVLFLLVLLGFLAYQYSQLLQHFPENHWPILLFVGITSVL
LLLWGGTATYMEAPDKLFLLVGEEEIKLHLKRQTGISLVFWLFVQTLFLL
LFAPLFLAMGYGLPVFLLYVLLLGVGKYFHFCQKASKFFTETGLDWDYVI
SQESKRKQVLLRFFALFTQVKGISNSVKRRAYLDFILKAVQKVPGKIWQN
LYLRSYLRNGDLFALSLRLLLLSLLAQVFIEQAWIATAVVVLFNYLLLPQ
LLALYHAFDYQYLTQLFPLDKGQKEKGLQEVVRGLTSFVLLVELVVGLIT
FQEKLALLALLGAGLVLLVLYLPYQVKRQMQDZ (SEQ. ID. NO. 61)
MRKSIVLAADNAYLIPLETTIKSVLYHNRDVDFYILNSDIAPEWFKLLGR
KMEVVNSTIRSVHIDKELFESYKTGPHINYASYFRFFATEVVESDRVLYL
DSDIIVTGELATLFEIDLKGYSIGAVDDVYAYEGRKSGFNTGMLLMDVAK
WKEHSIVNSLLELAAEQNQVVNLGDQSILNIYFEDNWLALDKTYNYMVGI
DEYHLAQECERLDDNPPTIVHYASHDKPWNTYSISRLRELWWVYRDLDWS
EIAFQRSDLNYFERSNQSKKQVMLVTWSADIKHLEYLVQRLPDWHPHLAA
PCDCSEELTSLSQYTNVTVYQNVLHSRIDWLLDDSEVYLDINTGGEVFNV
VTRAQESGKICIFAFDITRKSMDDGLYDGIFSVERPDDLVDRMKNIEIEZ (SEQ. ID. NO. 62)
MTKIYSSIAVKKGLFTSFLLFIYVLGSRIILPFVDLNTKDFLGGSTAYLA
FSAALTOGNLRSLSIFSVGLSPWMSAMILWQMFSFSKRLGLTSTSIEIQD
RkKMYLTLLIAVIQSLAVSLRLPVQSSYSAILVVLMNTILLIAGTFFLVW
LSDLNASMGIGGSIVLLLSSMVLNIPODVLETFQTVHIPTGHVLLALLTL
VFSYLLALMYRARYLVPVNKIGLHNRFKRYSYLEIMLNPAGGMPYMYVMS
FLSVPAYLFILLGFIFPNHSGLAALSKEIMVGKPLWVYVYISVLFLFSII
FAFVTMNGEEIADRMKKSGEYIYGIYPGADTSRFINRLVLRFSVIGGLFN
VIMAGGPMLFVLFDEKLLRLAMIPGLFMMFGGMIFTIRDEVKALRLNETY
RPLIZ TABLE 2-continued (SEQ. ID. NO. 63)
MSSLSDQELVAKTVEFRQRLSEGESLDDWVEAFAVVREADKRILGMFPYD
VQVMGAIVMHYGNVAEMNTGEGKTLTATMPVYLNAPSGEGVMVVTPNEYL
SKRDAEEMGQVYRFLGLTXGVPFTEDPKKEMKASEKKLIYASDWYTTINS
NLGPDYLNDNLASNEEGKFLRPFNYVUDEIDDILLDSAQTPLIIAGSPRV
QSNYYAIIDTLVTTLVEGWYIPKEEKEEVWLTTKGAKSAENELGIDNLYK
EEHASFARHLVYAIRAHKLFTKDKDYHRGNEMVLVDKGTGRLMEMTKLQG
GLHQAIEAKEHVKLSPETRAMASITYQSLPKMFNKISGMTGTGKVAEKEF
IETYNMSVVRIPTNRPRQRIDYPDNLYITLPEKVYASLEYIKQYHAKGNP
LLVFVGSVEMSQLYSSLLFREGIAHNVLNANNAAREAQIISESGQMGAVT
VATSMAGRGTDCKLGKGVAELGGUVIGTERMESQRIDLQIRGRSGRQGDP
GMSKFFVSLEDDVIKKEGPSWVHKKYKDYQVQDMTQPEVLKGRKYRKLVE
KAQHASDSAGRSARRQTLEYAESMNIQRDIVYKERNRLIDGSRDLEDVVV
DIIERYTEEVAADHYASRELLFWPIVTNISFHVKEVPDYIDVTDKTAVRS
FMKQVIDKELSEKKELLNQHDLYEQPLRLSLLKAIDDNWVEQVDYLQQLS
MAIGGQSASQKNPEVEYYQEAYAGFEAMKEQIHADMVRNLLMGLVEVTPK
GEIVTHFPZ (SEQ. ID. NO. 64)
MIGTFAAALVAVLANRVPIEITPNSANTEIAPPDGIGQVLSNLLLKLVDN
PVNALLTANYIRILSWAVIFGIAMREASKNSQELLKTIADVTSKIVEWII
NLAPFGILGLVFKISDKGVGSLANYGILLVLLVTTMLPVAPVVNPLIAPF
FMRRNPYPLVWNCLRVSGVTAPFTRSSATNTPVNMKLCMDLGLNPDTYSV
SIPLOSTINMAGVAITINLLTLAAVNTLGTPVDFATAFVLSVVAAISSCD
ASGIAGGSLLUPVACSLFGISNDIAIQIVGVGPVIGVQDSCETALNSSTD
VLFTAVAEYAATRKKZ (SEQ. ID. NO. 65)
MSISQRTTKLILATCLACLLAYFLNLSSAVSAGIIALLSLSDTRRSTLKL
ARNRLFSMLLALAIGVLAFHLSGFHIWSLGLYLAVPLAYKMGWEIGITPS
TVLVSHLLVQESTSPDLLVNEFLLFAIGTGFALLVNLYMPSREEEIQHYH
TLVEEKDILQRFKYYLSRGDGRNRAQLVAELDTLLKEALRLVYLDHSDHL
FHQTDYHIHYFEMRQRQSRILRNMAQQINTCHLAASESLILAQLFSKAGQ
LSQTNPASDLLDEIERYLEVFRNRSLPKTREEPETRATLLQLLREAKTFI
QVKVDFYQKYRQZ (SEQ. ID. NO. 66)
MEIMSLAIAVFAVIIGLVIGYVSISAKM1SSQEAAELMLLNAEQEATNLR
GQAEREADLLVNEAKRESKSLKKEALLEAKEEARKYREEVDAEFKSERQE
LKQIESRLTERATSLDRXDDNLTSKEQTLEQKEQSISDRAKNLDAREEQL
EEVERQKEAELERIGALSQAEARDIILAQTSENLTREIASRIREAEQEVK
ERSDKMAKDILVQAMQRIAGEYVAESTNSTVHLPDDTMKGRIIGREGRNI
RTFESLTGVDVIIDDTPEVVTLSGFDPIRREIARMTMEMLLKDGRIHPAR
IEELVEKNRQEIDNKIREYGEAAAYEIGAPNLHPDLMKIMGRLQPRTSYG QNVLRHSIIEVAKLAGIMASELGENAALARRAGFLHDIGKAIDHEVEGSH
VEIGMELARKYKEPPVVVNTLASHHGDVEAESVIAVIVAAADALSAARPG
ARSESLESYIKRLHDLEEIANGFEGVQTSFALQAGREIRIMVNPGKIKDD
KVTILAHKVRKKIENNLDYPGNIKVTVIRELRAVDYAKZ (SEQ. ID. NO. 67)
MMLKPSIDTLLDKVPSKYSLVILBAKRAHELEAGAPATQGFKSEKSTLRA
LEEIESGNVTIHPDPEGKREAVRRRIEEEKRRKEEEEKKIKEQIAKEKED
GEKIZ (SEQ. ID. NO. 68)
MSAYQLPTVWQDEASNQGAFTGLNRPTAGARFEQNLPKGEQAFQLYSLGT
PNGVKVTILLEELLEAGFKEAAYDLYKIAIMDGDQFGSDPFKLNPNSKIP
ALLDQSGTENVRVFESAHILLYLAEKEGAFLPSNPVEKVEVLNWLFWQAG
AAPFLGGGFGHFFNYAPEKLEYPINRFTMEVKRQLDLLDKELAQKPYIAG
NDYTIADIAIWSWYGQLVQGNLYQGSAKFLDASSYQNLVKWAEKANRPAV
KRGLEVTYTEIKZ (SEQ. ID. NO. 69)
LASLITSIIMFYVGFDVLRDTIQKILSREETVIDPLGATLGIISAAIMFV
VYLYNTRLSKKSNSNALKAAAKDNLSDAVTSLGTAIAILASSFNYPIVDK
LVAIIITFFILKTAYDIFIESSFSLSDGFDDRLLEDYQKAIMEIPKISKV
KSQRGRTYGSNIYLDITLEMNPDLSVFESHEIADQVESMLEERPGVFDTD
VHIEPAPIPEDEILDNVYKKLLMREQLIDQGNQLEELLTDDFVYIRQDGE
QMDKEAYKTKKELNSAIKDIQITSISQKTKLICYELDGIIHTSIWRRMET
WQNIFHQETKKEZ (SEQ. ID. NO. 70)
MTIKLVATDMDGTFLDGNGRFDMDRLKSLLVSYKEKGIYFAVASGRGFLS
LEKLFAGVRDDIIFIAENGSLVEYQGQDLYEATMSRDFYLATFEKLKTSP
YVDINKLLLTGKKGSYVLDTVDETYLKVSQHYNENIQKVASLEDITDDIF
KFTTNFTEETLEDGEAWVNENVPGVKAMTTGFESIDIVLDYVDKGVAIVE
LVKKLGITMDQVMAFGDNLNDLHMMQVVGHPVAPENARPEILELAKTVIG
HHKERSVIAYMHGLZ (SEQ. ID. NO. 71)
MADIKLIALDLDGTLLITTDKRLTDRTKETLQAARDRGIKVVLTTGRPLK
AMDFFLHELGTDGQEDEYTITFNGGLVQKNTGEILDKTVFSYDDVARLYE
ETEKLSLPLDAISEGTVYQIQSDQELYAKFNPALTFVPVDFEDLSSQMTY
NKCVTAFAQEPLDAAEQKISPELFDQYEIFKSREMLLEWSPKNVHKATGL
AKLISHLGIDQSQVMACGDEANDLSMIEWAGLGVAMQNAVPEVKAAANVV
TPMTNDEEAVAWAIEEYVLKENZ (SEQ. ID. NO. 72)
MESLLILLLIANLAGLFLIWQRQDRQEKHLSKSLEDQADHLSDQLDYRFD
QARQASQLDQKDLEVVVSDRLQEVRKELHQGLTQVRQEMTDNLLQTRDKT
DQRLQALQESNEQRLEQMRQTVEEKLEKTLQTRLQASFETVSKQLESVNR
GLDEMQTVARDVGALNKVLSGTKTRGALGELQLGQHEDIMTPAQYEREYA
TVENSSERVEYAIKLPGQGDQEYVYLPIDSKFPLADYYRLEEAYETGKDD

TABLE 2-continued

EIERCRKSLLASVKRFARDIRNKYIAPPRTTNFGVLFVPTEGLYSEIVRN
PVFFDDLRREEQIWAGPSTLSALLNSLSVGFKTLNIQKSADHISKTLASV
KTEFGKFGGILVKAQKHLQHASGNIDELLNRRTIAIERTLRHIELSEGEP
ALDLLHFQENEEEYEDZ (SEQ. D. NO. 73)
MKISHMKKDELFEGFYLIKSADLRQTRAGKNYLAFTFQDDSGEIDGKLWD
AQPHNIEAFTAGKVVHMKGRREVYNNTPQVNQLTLRLPQAGEPNDPADFK
VKSPVDVIKEIRDYMSQMLFKIENPVWQRIVRNLYTKYDKEFYSYPAAIC
TNHHAFETGLAYHTATMVRLADALSEVYQLNKSLLYAGIMLHDLAKVIEL
TGPDQTEYTVRGNLLGHIALIDSEITKTVMELGIDDTKEEVVLLRHVILS
HHGLLEYGSPVRPRIMEAEIIHMIDNLDASMMMMSTALALVDKGEMTNKI
FAMDNRSFYKPDLDZ (SEQ. 1ID. NO. 74)
MSEKAKKGFKMPSSKTVLLIIIAIMAVLTFIPAGAPIEGIYETQPQNPQG
IWDVLMAPIRAMLGTHPEEGSLIKBTSAAIDVAPRLMVGGFLGIVNKTGA
LDVGIASIVKKYKGREKMLILVLMPLFALGGTTYGMGEETMAFYPLLVPV
MMAVGFDSLTGVAIILLGSQIGCLASTLNPFATGIASATAGVGTGDGVLR
LIFWVTLTALSTWFVYRYADKIQKDPTKSLVYSTRKEDLKHFNVEESSSV
ESTLSSKQKSVLFLPVLTFILMVLSRPWTDLGVTIPDDFNTWLTGLPVIG
NIVGSSTSALGTWYFPEGAMLFAFMGILIGVIYGLKEDKUSSFMNGAADL
LSVALIVAIARGIQVIMNDGMITDTILNWGKEGLSGISSQVFIVVTYIFY
LPMSFLIPSSSGLASATMGIMAPLGEFVNVRPSLIITAYQSASGVLNLIA
PTSGIVMGALALGRINIGTWWKFMGKLVVAIIVVTIALLLLGTPLPFLZ (SEQ. ID. NO. 75)
MSNSFVKLLVSQLFANLADIFFRVTIIANIYUSKSVIATSLVPILIGISS
FVASLLVPLVTKRLALNRVLSLSQFGKTILLAILVGMPTVMQSVAPLVTY
LFVVAISILDGFAAPVSYAIVPRYATDLGKANSALSMTGEAVQLIGWGLG
GLLFATIGLLPTTCINLVLYIISSFLMLFLPNAEVEVLESETNLEILLKG
WKLVARNPRLRLIWSANLLEFSNTIWVSSHLVFVTELLNKTESYWGYSNT
AYSIGIIISGLLRISEKFLAAKWEPQLFTPNLIVFIQNPCLSLDPGWFLF
SPNGCFLLDKKEFPLYGISVEKNTKRKETHMNSLPNHHIQNKSFYQLSFD
GGHLTQYGGLIFFQELFSQLKLKERISKYLVTNDQRRYCRYSDSDILVQP
LPQLLTGYGTDYACKELSADAYFPKLLEGGQLASQPRFSRTDEETVHSLR
CLNLELVEFFLQPHQLNQLIVDEDSTHFTTYGKQEGVAYNAHYRAHGYHP
LYAFEGKTGYCFNAQLRPGNRYCSEEADSFTTPVLERFNQLLFRMDSGFA
TPKLYDLIEKTGQYYUKLKKNTVLSRLGDLSLPCQDEDLTILPHSAYSET
LYQAGSWSHKRRVCQFSERKEONLPYDVISLVTNMTSGTSQDQFQLYRGR
GQAENFIKEMKBGFFGDKTDSSTLIKNEVRMMMSCIAYNLYLFLKHLAGG
DFQTLTIKRFRMLHVVGKCVRTGRKQLLKLSSLYAYSELFSALYSRIRKV
NLNLPVPYEPPRRKASLMMHZ (SEQ. ID. NO. 76)
MMEFFQQLPHLEPYGNPQYFVYVIAATLPIFIGLFFKKRFAWYEVLVSLF
FIVTMLVGGKTNQLAALGIYLCWEILLLLFYKHYRKDGKWVFYLVSFLSL
LPIIFVKVQPAINGTQSLLGFLGISYLTPRSVGIVIELRDGVIKDPTLWE
FLRFLLFMPTFSSGPIDRFKRFNENYQAIPERDELMDMLDESVRYIMWGF
LYKFILAHVLGETLLPPLKNLALQSGGFFNLYALAVMYTFGLELFFDFAG
YSMPALAISNLMGIRSPINFNKPFLSRDLKEFWNRWHMSLSFWFRDFVPM
RMVMVLTRKKVFKNRNVTSSMAYIVNMLMGFWHGVTWYYIAYGLFHGLGL
VINDAWVRKKKTLNKERKKAGKAALPENRWIQLLGMVVTFHVVMLSFLIF
SGFLNNLWFKKZ (SEQ. ID. NO. 77)
MLKRLWMIFGPVLIAGLLVFLLIFFYPTEMHHNLGAEKRSAVATTIDSFK
ERSQKVRALSDPNVRFVPFFGSSEWLRFDGAHPAVLAEKYNRSYRYLLGQ
GGAASLNQYFGMQQMLPQLENKQVVYVISPQWFSKNGYDPAAPQQYPNGD
QLTSFLKHQSGDQASQYAATRLLQQPPNVAMKDLVQKLASKEELSTADNE
MIELLARFNERQASFFGQFSVRGYVNYDKHVAKYLKILPDQPSYQAIEDV
VKADAEKTSNNEMGMENYPYNEQIKKDLKKLKDSQKSPTYLKSPEYNDLQ
LVLTQFSKSKVNPIFIIPPVNKKWMNYAGLREDMYQQTVQKIRYQLESQG
FTNIADFSKDGGEPPFFMKDTIHLGWLGWLAFDKAVDPFLSNPTPAPTYHL
NERFFSKDWATYDGDVKEFQZ (SEQ. ID. NO. 78)
MEKNLKALKQTTDQEGPAIEPEKAEDTKTVQNGYFEDAAVKDRTLSDYAG
NWQSVYPFLEDGTFDQVFDYKAKLTGKIMTQAEYKAYYTKGYHTDVTKJN
ITDNTMEFVQGGQSKKYTYKYVGKKILTYKKGNRGVRFLFEATDADAGQF
KYVQFSDHNVAPVKAEHFHIFFGGTSQEALFEEMDNWPTYYPDNLSGQEI
AQEMLAHZ (SEQ. ID. NO. 79)
MKDGHLLAHHIRLLNGRIFQKLLSQDPEALYRGEQGKILAVLWNSETGCA
TATDIALATGLANNTLTTMIKKLEEQKLVIVSPCGKDKRKKYLVLTELGK
SQKEVGHRVSQKLDTIFYKGFSEEEIHQFEGFQERILANLKEKGNEVZ (SEQ. ID. NO. 80)
MTNLIATFQDRFSDWLTALSQHLQLSLLTLLLAILLAIPLAVFLRYHEKL
ADWVLQIAGIFQTIPSLALLGLFIPLMGIGTLPALTALVLYAIFPILQNT
GLKGIDPNLQEAGIAFGMTRWERLKIFEIPLAMPVIMSGIRTAAVLIGTA
TLAALIGAGGLGSPILLGLDRNNASLILIGALSSAVLAIAFNFLLKVMEK
KLRTSGFALVALLLGLSYSPALLVQKEKENLVIAGKIGPEPEILANMYKL
LIEENTSMTATVKPNPGKTSFLYEALKKGDIDIYPEETGTVTESLLQPSP
KVSHEPEQVYQVARDGIAKQDHLAYLICPMSYQNTYAVAVPKKIAQEYGL
KTISDLKKVEGQLKAGFTLEFNDREDGNKGLQSMYGLNLNVATIEPALRY
QAIQSGDIQITDAYSTDAELERYDLQVLEDDKQLFPPYQGAPLMKEALLK
KHPELERVLNTLAGKITESQMSQLNYQVGVEGKSAKQVAKEFLQEQGLL
KKZ

TABLE 2-continued (SEQ. ID. NO. 81)
MMHTYLQKKIENIKTTLGEMSGGYRRMVAAMADLGFSGTMKAIWDDLPAH
RSFAQWIYLLVLGSFPLWLELVYEHRIVDWIGMICSLTGIICVIFVSEGR
SNYLFGLINSVIYLILALQKGFYGEVLTTLYFTVMQPIGLLVIYQAQFKK
EKQEFVARKLDGKGWTKYLSISVLWWLAFGFIYQSIGANRPYRDSITDAT
NGVGQILMTAVYREQWIFWAATNVFSIYLWWGESLQIQGKYLIYLINSLV
GWYQWSKAAKQNTDLLNZ (SEQ. ID. NO. 82)
MRNMKAKYAVWVAPFLNLTYAIVEFLAGGVFGSSAVLADSVHDLGDAIAI
GISAFLETISNREEDNQYTLGYKRFSLLGALVTAVILVTGSVLVILENVT
KILHPQPVNDEGILWLGILTLNLLSLVVGKGKTKNESILSLHFLEDTLGW
VAVILMAIVLRFTDWYILDPLLSLVISFFILSKALPRFWSTLKIFLDAVP
EGLDIKQVKSGLERDNVASLNQLNLWTMDALEKNAIVHVCLKEMEHMETC
KESIRIFLKDCGFQNITIEIDADLETHQTHKRKVCDLERSYEHQHZ (SEQ. ID. NO. 83)
MIEYKNVALRYTEKDVLRDVNLQIEDGEFMVLVGPSGSGKTTMLKMINPL
LEPTDGNIYMDGKRIKDYDERELRLSTGYVLQAIALIPNLTVAENIALIP
EMKGWSKEEITKKTEELLAKVGLPVAEYGHRLPSELSGGEQQRVGIVLRA
MIGQPICIFLMDEPFSALDAISRKQLQVLTKELIEFGMTTIFVTHDTDEA
LKLADRJAVLQDGEIRQVANPETILKAPATDFVADLPGGSVHDZ (SEQ. ID. NO. 84)
MSAVAISAMTKVMQETHGNPSSIHGHGRQAGKLLREARQELAQLLRTKPQ
HIFFTSGGTEGNNTTIIGYCLRHQEQGKHIITTAIEHHAVLETIDYLVQH
FGFEATIIQPENQEITAQQIQKALRDDTILVSTMFVNNETGNLLPIAEIG
QILKQHPAAYHVDAVQAIGKIPHSEELGDFLTASAHKFHGPKGIGFLYAS
SMDFDSYLHGGDQEQKRAGTENLPAIVGMVAALKEDLEKQEEHFQHVQNL
ETAFLAELEGIQYYLNRGKHHLPYVLNIGFPGQKNDLLLLRLDLAGISTG
SACTAGVVQSSHVLEAMYGANSERLKESLRISLSPQNTVEDLQTLAKTLK
EUGGZ (SEQ. ID. NO. 85)
MLFKLSKEKIELGLSRLSPARRIFLSFALVILLGSLLLSLOFVQVESSRA
TYFDHLFTAVSAVCVTGLSTLPVAHTYNIWGQIICLLLIQIGGLGLMTFI
GVFYIQSKQKLSLRATIQDSFSYGSLRFVYSIFLTTFLVESLGAILLSFR
LIPQLGWGRGLFSSIFLAISAFCNAGPDNLGSTSLFAFQTDLLVNLVIAG
LIITGGLGPMVWFDLAGHVGRKKKGRLHFHTKLVLLLTIGLLLFGTATTL
FLEWNNAGTIGNLPVADKVLVSFFQTVTMRTAGFSTIDYTQAHPVTLLIY
ILQMFLGGAPGGTAGGLKITTFFVLLVFARSELLGLPHANVARRTIAPRT
VQKSFSFIIFLMSFLIGILLGITAKGNPPFIHLVFETISALSTVGVTANL
TPDLGKLALSVIMPLMFMGRIGPLTLFVSLADYXPEKKDMLHYMKADIS
IGZ (SEQ. ID. NO. 86)
MSDRTIGILGLGIFGSSVLAALAKQDMNIIAIDDHAERINQFEPVLARGV
IGDITDEELLRSAGIDTCDTVVVATGENLESSVLAVMHCKSLGVPTVIAK
VKSQTAKKVLEKLIGADSVISPEYEMGQSLAQTILFHNSVDVFQLDKNVS
IVEMKIPQSWAGQSLSKLDLRGKYNLNILGFREQENSPLDVEFGPDDLLK
ADTYILAVINNQYLDTLVALNSZ (SEQ. ID. NO. 87)
MKLLSIAISSYNAAAYLHYCVESLVIGGEQVGILIINDGSQDQTQEIAEC
LASKYPNIVRAIYQENKCHGGAVNRGLVEASGRYFKVVDSDDWVDPRAYL
KILETLQELESKGQEVDVFVTNFVYEKEGQSRKKSMSYDSVLPVRQIFGW
DQVGNFSKGQYTMMHSLIYRTDLLRASQFZ (SEQ. ID. NO. 88)
MKFNPNQRYTRWSRRLSVGVASVVVASGFFVLVGQPSSVRADGLNPTPGQ
VLPEETSGTKEGDLSEKPGDTVLTQAKPEGVTGNTNSLPTPTERTEVSEE
TSPSSLDTLPBKDEEAQKNPELTDVLXETVDTADvDGTQASPAERRPEQV
KGGVKENTKDSIDVPAAYLEKAEGKGPFTAGVNQVIPYELFAGDGMLTRL
LLKASDNAPWSDNGTAKJSIPALPPLEGLTICGKYFYEVDLNGNTVGKQG
QAUDQLRANGTQTYKATVKVYGNKDGKADLTNLVATKNVDININGLVAKE
TVQKAVADNVKDSIIDVPAAYLEKGEGPTAGVNHVIPYELFAGDGMLTRL
LLLSDKAPWSDNGDAKNPALSPLGENVKTKGQYFYQVALDGNVAGKEKQA
LIDQFRANGTQTYSATVNVYGNKDGKPDLDNIVATKKVTLNNGLSKETVQ
KAVADNVKDSIDVPAAYLEKAKGEGPFTAGVNHVIPYELFAGDGMLTRLL
LKASDKAPWSDNGDAKNPALSPLGENVKTKGQYFYQVALDGNVAGKEKQA
LIDQFRANGTQTYSATVNVYGNKDGKPDLDNIVATKXVTININGLISKET
VQKAVADNVKTVSMFQQPTZ (SEQ. ID. NO. 89)
MKLKSYILVGYIISTLLTILVVFWAVQKMLIAKGEIYFLLGMTIVASLVG
AGISLFLLLPVFTSLGKLKEHAKRVAAKDFPSNLEVQGPVEFQQLGQTFN
EMSHDLQVSFDSLEESEREGLMIAQLSHDIKTPITSIQATVEGILDGIIK
ESEQAHYLATIGRQTERLNKLVEELNFLTLNTARNQVETTSKDSIFLDKL
LIECMSEFQFLIEQERRDVHLQVIPESARIEGDYAKLSRJLVNEITVSSQ
YGLGSTETLVLNLSGSENKAZ (SEQ. ID. NO. 90)
MFGQTAQHGLTNSLKDFWIFLLNIGPQLAFFCQMLRCSRSVEQGTGNHRR
EFNMIQQIFSHFGMTHLGQIKLVYQESIDLELLVNALNHHLLIDRLVLTP
NQITIEIDRQIVHGLDLLKGRXDKEIIDIKSMFRQLELASTQQICPNQRV
HHGILAFGEISDLVPAKNLPNRQDZ (SEQ. ID. NO. 91)
MEHLATYPSTYGGAPAALGWLAVGLSGMGSAYGVGKAGQSAAALLKEQPE
KFASALILQLLPGTQOLYGFVIGLIWLQLTPSLPLEKGVAYFVALPIA1V
GYFSAKHQGNVAVAGMQILAKRPKEFMKGAILAAMVETYAILAIWVSFIL
TLRVZ TABLE 2-continued (SEQ. ID. NO. 92)
MLKSEKQSRYQMLNEELSFLLEGETNVLANLSNASALIKSRFPNTVFAGF
YLFDGKELVLGPFQGGVSCIIRIALGKGVCGEAAGHFQETVIVGDVTTYL
NYISCDSLAKSEIVVPMMKNGQLLGVLDLDSSEIEDYDAMDRDYLEQFVA
ILLEKTAWDFTMFEEKSZ (SEQ. ID. NO. 93)
MSVLEKDLHVEIEGKEILKGVNLTLTGEAAIMGPNGTGKSAAIMGNPNYE
VTKGEVLFDGVNILELEVDERARMGLFLAMQYPSEIPGITNAEFLRAAMN
AGKEDDEKISVREFITKLDEKMELLNMKEEMAERYLNEGFSGGEKKRNEI
LQLLMLEPTFALLDEIDSGLDIDALKVVSKGVNAMRGEGFGAMIITHYQR
LLNYITPDVVHVMMEGRVVLSGGPELAARLEREGYAKLAEELGYDYKE
ELZ (SEQ. ID. NO. 94)
MPYKRQRSFSMALSKLDSLYMAVVADHSKNPHHQGKLEDAEQISLNNPTC
GDVINLSVKFDAEDRLEDIAFLNGCTISTASASMMTDAVLGKKQEILELA
T1FSEMVQGQKDERQDQLGDAAGVAKFPQPJKCATWNALKIENQEKQZ (SEQ. ID. NO. 95)
MKIQDLLRKDVMLLDLQATEKTAVIDEMIKNLTDHGYVTDEFETFKEGIL
AREALTSTGLGIAMPHSKNAAVKEATVLFAKSNKGVDYESLDGQATDLFF
MIAAPEGANDTHLAALAELSQYLMKDGFADKLRQATSADQVIELFDQASE
KTEELVQAPANDSGDFIVAVTACTTGIAHTYMAQEALQKVAAEMGVGIKV
ETNGASGVGNQLTAEDIRKAKAIIIAADKAVEMDRFDGKPLINRPVADGI
RKTEELINLALSGDTEVYRANGAJ(AATASNEKQSLGGALYLMSGVSQML
PFVIGGGIMIALAFLIDGALGVPNENLGNLGSYHELASMFMKIGGAAFGL
MLPVFAGYVAYSIAEKPGLVAGFVAGALAKEGFAFGKIPNDFLGGLGGGS
AVLLGIVLGGMMAVDMGGPVNKAAYVFGTGTLAATVSSGGSVAMAAVMAG
GMVPPLAIFVATLLFVLVGAIVSGVVYGYLRKPQAZ (SEQ. ID. NO. 96)
MANKNTSTTRRRPSKAELERKEAIQRMLISLGIAILLIFAAFKLGAAGIT
LYNLIRLLVGSLAYLAIFGLLIYLFFFKWIRKQEGLLSGFFTIFAGLLLI
FEAYLVWKYGLDKSVLKGTMAQVVTDLTGFRTTSFAGGGLIGVALYPTAF
LFSNIGTYFIGSLILVGSLLVSPWSVYDIAEFSRGFAKWWEGHERRXEER
FVKQEEKARQKAEKEARLEQEETEKALLDLPPVDMETGEILTEEAVQNLP
PIPEEKWVEPEIILPQAELKFPEQEDDSDDEDVQVDFSAKEALEYKLPSL
QLFAPDKPKDQSKEKKWRENIKILEATFASFGIKVTVERAEIGPSVTKYE
VKPAVGVRVNRISNLSDDLALALAAKDVRIEAPIPGKSUGTEVPNSDIAT
VSFELWEQSQTKAENFLEIPLGKAVNGTARAFDLSKMPHLLVAGSTGSGK
SVAVNGIIASILMKARPDQVKFMMVDPKMVELSVYNDIPILLJPVVTNPR
KASKALQKVVDEMENRYELFAKVGVRNIAGFNAKVEEFNSQSEYKQIPLP
FIVVIVDELADLMMVASKBVEDAIIRLGQKARAAGIHMILATQRPSVDVI
SGUKANVPSRVAFAVSSGTDSRTLDNGAEKLLGRGDMLFKPIDENHPVRL
QGSFISDDDVERIVNPIKTQADADYDESFDPGEVSENBGEFSDGDAGGDP (SEQ. ID. NO. 96 cont.)
LFEEAXSLVIETQKASASMIQRRLSVGFNRATRLMEELEIAGVIGPAEGT
KPPJCVLQQZ (SEQ. ID. NO. 97)
MSYFKKYKFDKSQFKLGMRTKTGIAVFLVLLIFGFGWKGLQIGALTAVFS
LRESFDESVHFGTSRILGNSIGGLYALVFLLNTFFWEAWVTLVVVPICTM
LTIMTNVAMNNCAGVIGGVAAMLHTLSPSGETILYVFVRVLETFMGVFVA
UVNYDIDRIRLFLEKKEKZ (SEQ. ID. NO. 98)
MNKSEHRHQLIRAUTKNKIHTQAELQALLAENDIQVTQATLSRDIKNMNL
SKVREEDSAYYVLNNGSISKWEKRLELYMEDALVWMRPVQHQVLLKTLPG
LAQSFGSHDTLSFPDAATLCGNDVCLIICEDADTAQKCFEELKKFAPPFF
FEEZ (SEQ. ID. NO. 99)
MCSIKLNALSYMGRVLNIFPItTGTYVARVLDRTDYGYFNSVDTILSFFL
PFATYGVYNYGLRAISNVKDNKKDLNRTFSSLFYLCIACTILTRAVYILA
YPLFFTDNPIVKKVYLVMGIQLIAQFSIEWVNBALENYSILFYKTAFRIL
MLVSIFLPVKNEHDEVVYTLVMSLTLINYLSYFWKRDIKLVKIHLSDFKP
LFLPLTAMLVANANMLFTTLDRLFLVICTGIDVNVSYAQRJVTVIAGVVT
GAIGVSVPRLSYYLGKGDKEAYVSLVNRCSRIFNPFHPLSFGLMVLGNAI
LLYGSEKYIGGGILTSLFAFRTULALDTILGSQILFTNGYHKRTVYTVFA
GLLNLGLNSLLFFNHVAPEYYLLTRMLSETSLLVFYIIFEHRKQLIHLGH
IFSYTVRYSLFSLSWAIYFUNFVYPVDMVINLPFLINTGLIVLLSAISYI
SLLVFRKDStFYEFLNHVLALKNKFKKSZ (SEQ. ID. NO. 100)
MELFMKITNYEIYXLKKSGLTNQQILICVLEYGENVDQELLLGDIADISG
CRNPAVFMERYPQIDDAHLSKEFQKFPSPSILDDCYPWDLSEIYDAPVLL
FYKGNLDLLKFPKVAVVGSRACSKQGAKSVEKVIQGLENELVIVSGLAXG
DTAAHMAALQNGGKTAVIGTGLDVFPKANKRLQDYIGNDHLVLSEYGPGE
QPLKHFPARNRIAGLCRGVIVAEAKMRSGSLTCERAMEEGRDVFAIPGSI
LDGLSDGCIIMLIQEGAKLVTSGQDVLAEFEPZ (SEQ. ID. NO. 101)
MKQLTVEDAKQIELEILDYIDTLCKKIININYGTLIGAVRHEGFIPWDDD
IDLSMPRBDYQRFINIFQKEKSKYKLLSLERDKNYNNFIKTDSTRKIIDT
RNTKTYESGIIDIFPDRFDDPKVDTCYKESKLLSFSKHKNWYKDSLLKDW
IRTAFWLLLRPVSPRYFANKIEKEIQKYSRENGQYMAFIPSKFKEKEVFP
SGTFDKTIDLPPENLSLPAPEKPDTWTQFYGDYMTLPPEEKRFYSHEFHA
YKLEDZ (SEQ. ID. NO. 102)
MIKINHLTITQNKDLRDLVSDLTMTIQDGEKVAIIGEEGNGKSTLLKIMG
EALSDFTIKGNIQSDYQSLAYPQKVPEDLKKKTLHDYFFLDSLDLDYSIL
YRLAEELHFDSNRFASDQEIGNLSGGEALKEQLIHELAICPFEILFLDEP
SNDLDLETVDWLKGQIQKTRQTVTFISHDEDPLSETADTIVLRLVKHRKE
AETHVEHLDYDSYSEQRKANFAKQSQQAANNQRAYDKTMEKIRRVKQNVE TALRATKDSTAGRLLAKKMDTVLSQEKRYEKAAQSMTQKPLEEEQIQLFF
SDIQPLPASKVLQLEKENLSIDDRVLVQKLQLTVVRGQEKIGIIGPNGVG
KSTLLAKLQRLLNDKREISLGIMPQDYHXJCLQLDLSPIAYLSKTGEKEE
LQKQSHLASLNFSYPMQHQRSLSGGQQGKLLLLDLVLRKPNFLLLDEPTR
NPSPTSQPQIRKLFATYPGGLITVSHDRRFLKEVCSIIYRMTEHGLKLVN
LEDLZ (SEQ. ID. NO. 103)
MKPKTFYNLLAEQNLPLSDQQKEQFERYFELLVEWNEKINLTAITDKEEV
YLKNFYDSIAPILQGLIPNETIKLLDIGAGAGFPSLEPMKILYPELDVTI
IDSLNKRINGLQLLAQELDLNGVHFYHGRAEDGAQDKNFRAQYDFVTARA
VARMQVLSELTIPYLKVGGKLLALKASNAPEELLEAKNALNLLFSKVEDN
LSYALPNRDPRYTIVVEKKKETPNKYPRKAGMPNKRPLZ (SEQ. ID. NO. 104)
MSIKUAVDIDGTLVNSQKEITPEVFSAIQDAKEAGVKVVIATGRPIAGVA
ICLLDDLQLRDEGDYVVTFNGALVQETATGHEIISSLTYEDYLDMEFLSR
KLGVHMHAITKDGIYTANRNIGKYTVHESTLVSMPYRTPEEMAGKJVKCM
FIDEPIPEIKKIAKYITKTNDESGVAHAITRWVLZ (SEQ. ID. NO. 105)
MTWIILGIVALIVIIVSYNGLVKNRMQTKEAWSQIDVQLKRRNDLLPNLI
ETVKGYAYEGLEKVAELRNQVTSPAEAMKASDALTRQVSGIFAVAESYPD
LKADANPVICLQEELTNTENKSYSRQLYNSVVSNYNVKLETFSNIIAGMF
GFKAADFLQTPEEEKSVPKVDPSGLGDZ (SEQ. ID. NO. 106)
MLFDQIASNKRKTWILLLVFFLLLALVGYAVGYLIRSGLGGLVIALIIGF
IYALSMIFQSTEVMSMNGAREVDEQTAPDLYHVVEDMALVAQIPMPRVFI
IDDPALNAFATGSNPQNAAVAATSGLLAIMNREELEAVMGHEVSHIRNYD
IRISIAVALASITMLSSMAGRMMWWGGAGRRRSDDDRDGNGLEIIMLVVS
LLAIVLAPLAATLVQLAISRQREFLADASSVELTRNPQGMINALDLKDNS
KPMSRHVDDASSALYINDPKKGGGFQKLFYTHPPtSERIERLKQMZ (SEQ. ID. NO. 107)
MKLNIQEIRKQSEGLNFEQTLDLVDDLRARNQEILDVKDILAVGKVQYED
RMYFLDYQLSYTIVLASSRSMEPVELVESYPVTEFMEGATNQLDQEVLDD
DLVLPIENGELDLAESVSDNLLNIPIKVLTAEEBAGQCPISGNDWQIMTE
EEYQAQKAVKKEENSPFAGLQGLFDGDEZ (SEQ. ID. NO. 108)
MKRQLALVVPSGGQDSRTCLWVMQHYETVEAVTFAYGQRMHLEQRRREIA
KEQGRHHIIDMSLLGQITAQPDFATIHSYIPDKLCVESKSLKLYLFSYRN
HGDFHENCNTIGKDLVNLLDPRYLEVWGKFTPRGGISDPYYNYGKQGTKY
EGLAEQRLFQHDLYPEKIDNRZ (SEQ. ID. NO. 109)
MTETVEDKVSHSn*GLDILKGIVAAGAVISGTVATQTKVFTNESAVLEKT
VEKTDALATNDTVVLGTISTSNSASSTSLSASESASTSASESASTSASTS
ASTSASESASTSASTSISASSTVVGSQTAAATEATAKXVEEDRKKPASDY
VASVTNVNLQSYAgRRKRSVDSIEQLLASIKNAAVSGNTVNGAPAINASL
NLAKSETKVYTGEGVDSVYRVPIYYKLKVTNDGSKLTFTYTVTYVNPKTN
DLGNISSMRPGYSYNSGTSTQTMLTGSDLGKPSGVKNYITDKNGRQVLS
YNTSTMTRQGSGYTWGNGAQMNGFFAKXGYGLTSSWTVPITGTDTSFTFT
PYAARTDRIGINYFNGGGKVVESSITSQSLSQSKSLSVSASQSASASAST
SASASASTSASASASTSASASASTSASVSASTSASASASTSASASASTSA
SESASTSASASASTSASASASTSASASASTSASESASTSASASASTSASE
SASTSASASASTSASASTSASGSASTSTSASASTSASASASTSASASA
SISASESASTSASESASTSTSASASTSASESASTSASASASTSASASAST
SASASASTSASESASASTSASASTSASTSASASTSASASSASASTSASA
SASTSASVSASTSASASASTSASASASTSASESASTSASASASTSASASA
STSASASASTSASASASTSASASTSASESASTSASASASTSASASAST
SASGSASTSTSASASTSASASTSASASASISASESASTSASESASTST
SASASTSASESASTSASASASTSASASASTSASASARQVRRPQPVHLNRM
QPVRQPQQVLVHQLQHQRVHRLQHQPVPRLQRQPVRQLQQVPVLQSQHQQ
VLQPQHRQVPRLQQAHQHLNQRRQAPQLQQVPVRQPQRRQVRQPQQVLVH
QLQHQRVHRLRRQPVHQSQQVPVRQLPHQQVPRLQQAPVRRLQQVLAPQP
QPQPVRQPQQVSQRLNRIIQRVRPLQQVLAPQPQRQQVHRLQRQRVRLNR
HQRVRPLQQVLAPQPQRQQVHRLQHQRVRPLQQVLAPQPQRQQVHRLQRQ
RVRLSQHQRVRQPQQAHQLLNLHQPVRQPQHRQAPQLQQVPVRQPQRRQV
RRLQQVPVRQPQQVPVRQPQRRQVRRPQPVHLNRNQPVRQPQQVLVHQLQ
MQRVHRLQHQPVHQSQQVPVRQPRINKCLGFSKYZ (SEQ. ID. NO. 110)
MGVETWFYSSICWLALGLGSVWKFPYMTAANGGGGFLLIFLLSTILIGPL
LLAEALGRSAGVSAIKTFGKLGKNNKYNIGWIGAFLFLLSFYSVIGGWTL
VYLGIEFGKLFQLGGTGDYAQLFTSfLSNPAIALGAQAAPILLNIFIVSR
GVQKGIERASKVMMPLLFIVFVFIIGRSLSLPNAMEFVLYPDSKLTSTGL
LYALGQSFALSLGVTVMLTYASYLDKXTNLVQSGISIVAMNISISIMAGL
AFFQARSPFNQSEGGPSLLVLPQLIDKMPFGTUYVLFLLLFLFATVTFSV
VMLEINVDNITNQDNSKRAXWSVILGLTFVFGTPSALSYGVMADVHIFGK
TFFDAMDFLVSNLLMPFGALYLSLTGYTFKKALAMEELHLDERAWKQGLF
QVWLFLLRFFVSSFQSSSLWSSLPNLCNQKGLEZ (SEQ. ID. NO. 111)
MLKKWQLKDVILLAFLSIFFC3GVFVGSGYVYNELSLLLTPLGLQAFANE
ILFGLWCMAAPIAAIFVPRVGSATIGEVLAALAEVLYGSQFGLFALLSGF
VQGLGSEFGFIVTKNRYESWLSLTANSIGITLVSFVYEYIKLGYYAFSLP
FVLSLLVVRFISBYFFCTILVRAIVKLYHQFATGGKAZ (SEQ. ID. NO. 112)
MVKVATQTPHSLLLILSLETSFIPSIALTLSVVAPCILFMLYYRRFKMLA
WMLLLAILPSFANYWAVQLHGDASQAVMLGTRAFVTVCIGLVFVSSVSLK
ELLLYLAQKGLSRSWSYALIVVFNSFPLQQEIKSLKEACLLRGQELHFWS

PLIYSKVLMTVFRWRHLYLRALSAHGYDEHAQLKNSYRTFYPKKTKLIYL
LFFLLLQTSLLZ (SEQ. ID. NO. 113)
MRKHQLQVHKLTLSMMALDVVLTPRIEGMAPMSSVVNLAGIMMGPVYALA
MATVRAFXRNfFRQGIPPLALTGATFGALLAGLFYKYGRKFHYSALGEIL
GTGUGSIVSYPVMVLFTGSAAKLSWFEYTPREFGATLIGTALSFIAFRFL
KQEFFKKVQGYFFSERIDZ (SEQ. ID. NO. 114)
MQETNPFPIGSSSLIHCFLNEISCEMLANGILALGCKPVMADDSREVLDF
IKQSQALNLGHLSAEKEKJJRMAASYANQSSLPMVVDAVGVRSSIRKSLV
KDLLDYRPRVLKGNMSEIRSLVGLKHHGVGVDASAJCDQETEDLLQVLKD
WCQTYPGMSFLVTGPKDLVVSKNQVAVLGNGCTELDWITGTGDLVGALTA
VFLSQGKTGPEASCLAVSYLNIAAEKIVVOOMGLEEFRYQVLNQLSLLRR
DENWLDTIKGEVYEZ (SEQ. ID. NO. 115)
MNHKAILSDVMGNATALEAVL&DAXNQGASEYWLLGDIFLPGPGANDLVA
LLKDLPPASVRGNWDDRVLEALDGQYGLEDPQEVQLLRMTQYLMERMDPA
TIVWLRSLPLLEKKEIDGLRFSISHNLPDKNYGGDLLVENDTEKFDQLLD
AETDVAVYGHVHKQLLRYGSQGQQIINPGSIGMPYFNWEALKNHRSQYAV
IEVEDGELLNIQFRKVAYDYEAELELAKSKGLPFIEMYEELRRDDNYQGH
NLELLASLIEKHGYVEDVKNFFDFLZ (SEQ. ID. NO. 116)
MNVQIVRIIPTLKANNRKLNETFYIETLGMKALLEESAFLSLGDQTGLEK
LVLEEAPSMRTRKVEGRKKLARLIVKVENPLEIEGTTDSIHRLYKGQNGY
AFEIPSPEDDLILIHAEDDIASLVEVGEKPEQTDLASKEISMELHLDIFL
ESSEIGASLDFIPAQGQDLTVDNTVTWDLSMLKFLVNELDLSLRQKFEST
EYFIPKSEKGKDNVELWEVZ (SEQ. ID. NO. 117)
MKWTKHIIKKIEEQIIEAGIYPGASFAYFKDNQWTEFYLGQSDPEHGLQT
EAGLVYDLASVSKVVGVGTVCTFLWEIGQLDIDRLVIDFLPESDYPDTIR
QLLTRATDLDPPIPNRDLLTAPELKEAMFHLNRSQPAFLYSDVHPLLLGF
LEFNQDLDVILKDQVWKPWGMTETKFGPVELAVPTVRGVEAGIVHDPKAR
LLGREAGSAGLFSTIKDLQIFLEHYLADDFALNQNFSPLDDKERSLAWNL
EGDWLDHTGYTGTFIMWNRQKQEATFLSNRTYEKDERAQWILDRNQVMNL
IEEZ (SEQ. ID. NO. 118)
MKKTYNHILVWGVIGYSICIVCFCFTPQEQSTVGVGTPGIQHLGRLVFLL
TPFNSLWKLGEVSDIGQLCWIFLQNILNVVFLFFPLIFQLLYLFPNLRKT
KKVLLFSFLVSLGIECTQLILDFFFDFNRVFEIFFLWTNTLFFYLAWLLY
KRLHKVRNZ (SEQ. ID. NO. 119)
MKIPLLTFLARHKFVYVLLTLLFLALVYRDVLMYFFDIHAPDLAKFDGQA
IKNDLLKSALDFRILQNLGQSFIIPIIIVLLGFQYIELKNXVLRLSRBVS
YQGLKRKLTLQVASIPCLIYLVTVLUAHTYFFGTFSPLGWNSLSDGSGLQ
RLLDGEIKSYLFFTCVLLIGIFINAIYFLQIVDYVGNVTRSAITYLMFLW
LGSMLLYSALPYYMVPMTSLMQASYGDVSLMKLPYILYIVPYMVLEICYE
DNVZ (SEQ. ID. NO. 120)
MFKVLQKVGKAFMLPIAILPAAGLLLGLGGALSNPRTIATYPILDNSIFQ
SIFQVMSSAGEVVFSNLSLLLCVGLCIGLAKRDKGTAALAGVTGYLVMTA
TUALVKLFMAEGSAIDTGVIGALVVGIVAVYLHNRYNNIQLPSALGGGSP
PISFSSILIGFVFFVWPPFQQLLVSTGGYSQAGPIGTLYGFLMRLSGAVG
LHHIIYPMTYTELGGVETVAGQTVGAQKIPAQLADLAHSGLFREGTREAG
RFSTMMFGLPAACLAMYHSVPKNRRKKYAGLFGVALTSFITGITEPLEFM
FLPVSPVLYVHAFLDGVSPFIADVLNISIGNTFSGGVIDFRLFGILQGNA
KTNWVLQIPGLIWSVLYYIIFRWFTQNVLTRGEEVDSKEISESADSTSNT
ADYLKQDSLQIIRALGGSNNIEDVDACVTRLRVAVEVNQVDKALLKQIGA
VDVIEVKGGIQAIYGAKAILYKNSINEILGVDDZ (SEQ. ID. NO. 121)
MKFRKLACVLAGAAVLGLAACGNSGGSKDAAKSGGDGAKTEITWWAFPVF
TQEKTGDGVGTYEKSUEAFEKANPDIKVKLETDFKSGPEKNTAIEAGTAP
DVLFDAPGRIIQYGKNGKLAELNDLFTDEFVKDVNNENRVQASKAGDKAY
MYPISSAPFYMAMNKKMLEDAGVANLVKEGWITDDFEKVLKALKDKGYTP
GSLFSSGQGGDQGTRAFISNLYSGSVTDEKVSKYTRDDPKFVKGLEKATS
WIKDNLINNGSQFDGGADIQNFANGQTSYTILWAPAQNGIQAKLLEASKV
EVVEVPFPSDEGKPALEYLVNGFAVNNKDDKKVAASKKIQFIADDKEWGP
KDVVRTGAFPVRTSFGKLYEDKRMETSGWTQSPYYNTIDGFAEMRTLWPM
LQSVSNGDEKPADALKAFTEKANETIKKAMKQZ (SEQ. ID. NO. 122)
MQSTEKKPLTAFTVISTIILLLLTVLFIPPFYWILTGAFKSQPDTIVIPP
QWFPKMPTMENFQQLMVQNPALQWMWNSVFISLVTMFLVCATSSLAGYVL
AKKRFYGQRILFAIFIAAMALPKQVVLVPLVRIVNFMGHDTLWAVILPLI
GWPFGVFLMKQFSENIPTELLESAKIDGCGEIRTFWSVAPPVKPGFAALA
IPTFINTWNDYFMQLVMLTSRNNLTISLGVATMQAEMATNYGLMAGAALA
AVPIVTVFLVFQKSTQGITMGAVKGZ (SEQ. ID. NO. 123)
MKIMFKNFNNILLNRCIVLLLRIVLMMILINHLLSTAVQKDAVLFFKRE
LSFSYNDYSEANLEIPICLLLNLSIFMVGWLSVLLLESDLADHYHHLIRY
QSSSFFDYTRKRLVVISKFFTQDLFVWFLGLLPLGIHFKTVALFFLLAQL
MMLYLLLSYUALISAGAGFSFFLYPLAFVGQEWMMDHIVTVYLVLLSLLV
MLVSRLESKFKKGZ (SEQ. ID. NO. 124)
MGKGEMGKGVIGLEFDSEVLVNKAPTLQLANGKTATFLTQYDSICTLLPA
VDKEDIGQEIIGIAKGSIESMHNLPVNLAGARVPGVNGSKAAVHEVPEFT

TABLE 2-continued

GGVNGTEPAVHEIAEYKGSDSLVTLTTGKDYTYKAPLAQQALPETGNKES
DLLASLGLTAFLGLFTLGKXREQZ (SEQ. ID. NO. 125)
MKKTFFLLVLGLFCLLPLSVIAIDFKINSYQGDLYIHADNTAEFRQKIVY
QFEEDFKGQIVGLGRAGKMPSGFDIDPHPKIQAAKNGAELADVTSEVTEA
DGYTVRVYNPGQEGDIVEVDLVWNL,KNLLPLYDDIAELNWQPLTDSSES
IEKFEFHVRGDKGAEKLFFTGKLBGTIEKSNLDYTIRLDNLPAKRGVELH
AYWPRTDFASARDQGLKGNRLEENKIEDSIVREKDQSKQLVTWVLPSILS
ISLLLSVCYFIYRRKTRPSVKYAKNHRLYEPPMELEPMVLSEAVY5TSLE
EVSPLVKGAGKFTFDQLIQATLLDVIDRGNVSIISEGDAVGLRLVKEDGL
SSFEKDCLNLAFSGKICEETLSNLFADYKVSDSLYRRAKVSDEKRIQARG
LQLKSSPEEVLNQMQEGVRKRVSFWGLPDYYRPLTGGEKALQVGMGALTL
PLFIGFGLFLYSLDVNGYLYLPLPILGFLGLVLSVFYYWKLRLDNRDGVL
NBAGAEVYYLWTSFENMLRIARLDQAELESVVWNRLLVYATLFGYADKVS
HLMKVNQIQVENPDINLYVAYGWHSTYHSTAQMSHYASVANTASTYSVSS
GSGSSGGGFSGGGGGGSIGAFZ (SEQ. ID. NO. 126)
MKKVRKIFQKAVAGLCCISQLTASSIVALAETPETSPAIGKVVIKBTOEG
GALLGDAVFELKNNTDGTTVSQRTEAQTGEAIFSNIKPGTYTLTEAQPPV
GYKPSTKQWTVEVEKNGRTTVQGEQVENREEALSDQYPQTGTYPDVQTPY
QUCVDGSEKNGQHKALNPNPYERVPEGTLSKRIYQVNNLDDNQYGIELTV
SGKTVYEQKDKSVPLDVVILLDNSNSMSNIRNKNARRAERAGEATRSLID
KTSDSENRVALVTYASTIFDGTEFTVBKGVADKNGKRLNDSLFwNYDQTS
VITNTKDYSYLKLTNDKNDIVELKNKVPTEAEDHDGNRLMYQFGATFTQK
ALMKADEIILTQQARQNSQKVIFHITDGVPTMSYPINFNHATFAPSYQNQ
LNAFFSKSPNKDGLLSDRTQATSGEITIVRGDGQSYQMFTDKTVYEKGAP
AAFPVKPEKYSEMKAAGYAVGDPNGGYWLNWRESILAYPFNSNTAKITNH
GDPTRWYYNGNIAPDGYDVFTVGIGINGDPGTDEATATSFMQSISSKPEN
YTNVTDTRKILEQLNRYFHTIVTEKKSENGTITDPMGELIDLQLGTDGRF
DPADYTLTANDGSRLENGQAVGGPQNDGGLLKNAKVLYDRREKRIRVTGL
YLGTDEKVTLTYNVRLNDEFVSNKFYDTNGIfLRLHPKEVEQNTVRDFPI
PKIRDVRKYPEITSKEKKLGDIBFIKVNKNDKKPLRGAVFSLQKQHPDYP
DIYGAIDQNGTYQNVRTGEDGKLTFKNLSDGKYRLFENSEPAGYKPVQNK
PIVAFQIVNGEVRDVTSVPQDIPAGYEFTNDKHYRRNEPIPPKREYPRTG
GIGMLPFYLIGCMMMGGVLLYRRKHPZ (SEQ. ID. NO. 127)
MKSINKFLTMLAALLLTASSLFSAATVFAAGTTTTSVTVHKLLATDGDMD
KIANELETGNYAGNKVGVLPANAKEIAGTLTGSKAVPIEIELPLNDVVDA
HVYPKNTEAKPKIDKDFKGKANPDTPRVDKDTPVNHQVGDVVEYEIVTKI
PALANYATANWSDRMTEGLAFNKGTVVTVDDVALEAGDYALTEVATGFDL
KLTDAGLAKVNDQNAEKTVKITYSATLNDKAIVEVPESNDVTINYGNNPD
HGNTPKPNKPNENGDLTLTKTWVDATGAPIPAGAEATFDLVNAQTGKVVQ
TVTLDKNTVTVNGLDKNTEYKFVERSIKGYSADYQEITAGEIAVKNWKDE
NPKPLDTEPKVVTYGKKFVKVNDKDNRIAGAEFEWVADKDNENVVKLVSD
AQGRFEITGLLAGTYYLEETKQPAGYALLTSRQKFEVTATSYSATGQGIE
YTAGSGKDDATKVVNKKITIPQTGGIGTIIFAVAGAAIMGIAVYAYVKNN
KDEDQLAZ (SEQ. ID. NO. 128)
MTMQKMQKMSRJFFVMALCPSLVWGAHAVQAQEDHTLVLQLENYQEVVSQ
LPSRDGHRLQVWKLDDSYSYDDRVQIVRDLHSWDENKLSSFKKTSFEMTF
LENQIEVSHIPNGLYYVRSUQTDAVSYPAEPLFEMTDQTVEPLVIVAKJC
TDTMVKLIKVDQDHNRLEGVGFKLVSVARDVSEKEVPLIGEYRYSSSGQV
GRTLYTDKGEIPVRNLPLGNYRYKEVELAGYAVTTLDTDVQLVDHQLVTI
TVVNQKLPRGNVDFMKVDORTNTSLQGAMFKVMKEESGHYTPVLQNGKEV
VVTSGKDGRFRVEGLEYGTYYLWELQAPTGYVQLTSPVSFTIGKDTRKEL
VTVVKNNKRRJDVPDTGEETLVYLDACCHVVWZ (SEQ. ID. NO. 129)
MSHIYLSIFTSLLLMLGLVNVAQADEYLRIGMEAAYAPFNWTQDDDSNGA
VKIDGTNQYANGYDVQIAKKAKDLGKEPLVVKTKWEGLVPALTSGKIDMI
IAGMSAERICQEIAFSSSYYTSEPVLLVKKDSAYAS&YLDDPNGAKITSQ
QGVYLYNLL4QIPGAKICITAMGDFAQMRQALEAGVDAYVSERPEALTAE
AANSKFKMIQVEPGFKGEEDTAIAIGLRKNDNRISQINASIETSKDDQVA
LMDRMIKEQPAEATITEETSSSFFSQVAKILSENWQQLLRGAGITLLISV
GTIIGLIIGLAIGVFRTAPLSENKVIYGLQKLVGWVLNVYIEIRGTPMVQ
SMVIYYGTAQAFGINLDRTLAAIFIVSINTGAYMTEVRGGILAVDKGQFE
AATALGMTHNQTMRKWLPQVVRNILPATGNEFVINIKDTSVLNVISVVEL
YFSGNTVATQTYQYFQTFRIIAVIYFVLTFTVTRILRFIERRMDMDTYTR
OANQMQTEDLKZ (SEQ. ID. NO. 130)
MTQAILEIKHLKKSYGQNEVLKDSLTHKGEVISIIGSSGSGKSTFLRINL
LETPTDGQYHGQNVLEKGYDLTQYREKLGMVFQSFNLFENLNVLENTIVA
QTRVLKRERTEAEKIAKENLEKVGMGERYWQAKPKQLSGGQKQRVALARA
LSMNPDAILFDETSALDPEMVGEVLKIMQDLAQEGLTMIVVTHEMEFARD
VSHRVFMDKGVLAEEGKPEDLFTNPKEDRTKEFLQRYLKZ (SEQ. ID. NO. 131)
MKKYQLLFSAVFSYLFFVFSLSQLTLIVQNYWQFSSQGNLPWIQNILSLL
FIGVMIVVLVQGHGYLFPJPPJCKWLWYSLTVLVLVQISFNVQTAKHVQS
TAEGWAVLIGYSGTNFAELGIYALFFLVPLMEELYRGLLQHAFFKRFGLD
LLLPSILFALPHFSSLPSLLDIFVFATVGIIFAGLTRYTKSIYPSYAVHV
INNIVATFPFLLTFLHRVLGZ (SEQ. ID. NO. 132)
MNKKQWLGLGLVAVAAVGLAACGNRSSRNAASSSDVKTKIVTDTGGVDDK
SFNQSAWEGLQAWGKEHNKDNGFTYFQSTSEADYANNLQQAAGSYNLIFG

TABLE 2-continued

```
VGFALNNAVKDAAKEHTDLNYYLIDDVIKDQKNVASVTFADNESGYLAGV
AAAKTTKTKQVGFVGGIESEVISRFEAGFKAGVASVDPISKVQVDYAGSF
GDAAKGKTIAAQYAAGADIVYQVAGGTGAGVFAEAKSLNESRPENEKVWI
GVDRDQEAEGKYTSKDGKESNFVLVSTLKQVGTTVKDISNKAERGEFPGG
QVIVYSLKDKGVDLAVTNLEEGKKAVEDAKAKILDGSVKPEKZ (SEQ. ID. NO. 133)
MSKKLQQISVPLISVFLGILLGAIVMWIFGYDAIWGYEELPYTAFGSLRG
IGEIFRAMGPLVLIGLGFAVASRAGFPNVGLPGQALAGWILSGWFALSHP
DMPRPLMILATIVIALIAGGIVGAIPGILRAYLGTS2VIVTIMMNYWLYV
GNAPIHAPPKDFMQSTDSTIRVGANATYQTPWLAELTGNSRMNIGIFFAI
IAVAVIWFMLKKTRLGFEIRAVGLNPMASEYAGISAKRTHLSMIISGALA
GLGGAVEGLGTFQNVYVQGSSLAIGFNGMAVSLLAANSPIGILPAAFLFG
VLQVGAPGMNAAQVPSELVSIVTASIIFFVSVEYLIERPVKPKKQVKG
GKZ (SEQ. ID. NO. 134)
MGVKKLKLTSLLGSLLITACATNGVTSDITAESADWSKLVYFFAEIIRFL
SFDISIGVGuLFRVLIRTVLLPVQVQMVASRKMQEAQPRIKALREQYPGR
DMESRTKLEQEMRKVFKEMGVRQSDSLWPILIQMPVILALFQALSRVDFL
KTGHFLWINLGSVDTRLVLPILAAVFTFLSTWLSNKALSERNGATTAMMY
GIPVLIRPAVYAPGGVALYWTVSNAYQVLQTYFLNNPFKIIAEREAVVQA
QKDLENRKRKAKKKAQKTKZ (SEQ. ID. NO. 135)
MVIDPFANELDYYLVSHFHSDHIDPYTAAAILNNPKLEHVKIGPYHCGRI
WEGWGVKERFLVVKPGDTIELKDMKIHAVESFDRTCLVTLPVNGADETGG
ELAGLAVTDEEMAQKAVNYIPETPGGTIYHGADSHFSNYFAJCHGKDFKI
DVALNNYGENPVGIQDKMTSIDLLRMAENLRTKVIIPVHYDJWSNFMAST
NEILELwKMRKDRLQYDFHPFIwEVGGKYTYPQDQHLVEYHHPRGFDDCF
EQDSNIQFKALLZ (SEQ. ID. NO. 136)
MFLSGWLSFANYIHDLLVLFPDSPFLNAFESAIAAPLVEELSCVFVTM4P
VRXKSTLTGIASOLCFQMIKNGYIRTDLPEGFDFTISRILERJISGIASH
WTFSGLAVVGVYLLYRAYKC3QKVGKKQGLIFLGLALGTHFLFNSPFVEL
ETEIPLAIPVVTAIALYGFYMAYCFVEKHNELMTZ (SEQ. ID. NO. 137)
MKVEPRCDVLSRMSHFFIRILIMLQELVERSWAIRQAYHELEVKHHDSKV
RRVEEDLLALSNDIGNPQRLVMTKQGRYYDETPYTLEQKLSENIWWLLEL
SQRLDIDILTEMENFLSDKEKQLNVRTWKZ (SEQ. ID. NO. 138)
MLDWKQFFLAYLRSRSRLFIYLLSLAFLVLLFQFLASLGIYFLYFPPLCC
FVTILFRWDILVETQVYRQELLYGEREAKSPLEIALAEKLEAREMELYQQ
RSKAERKLTDLLDYYTLWVHQIKTPIAASQLLVAEVVDRQLKQQLEQEIF
ICIDSYTNLVLQYLRLESPHDDLVLKQVQIEDLVKEIIRKYALFRQKGLN
VNLHDLDKEIVTDKJCwLLVVIEQIISNSLKYTKEGGLEIYMDDQELCIK
DTGIGIKNSDVLRVFERGFSGYNGRLTQQSSGLGLYLSKKISEELGHQIR
IESEVGKGTRVRIQFAQVNLVLEZ (SEQ. ID. NO. 139)
MELNTHNAEILLSAANKSHYPQDELPEIALAGRSNVGKSSFINTMLNRIX
NLARTSGKPGQLLNFFNIDDKMRFVDVPGYGYARVSKKEREKWGCMIEEY
LTRRENLAVVSLVDLRHDPSADDVQMYEFLKYYEIPVIRVATKADKIPRG
KWNKHESAIKKKLNFDPSDDFILFSSVSKAGMDEAWDAILEKLZ (SEQ. ID. NO. 140)
MTKKQLHLVVTGMSGAGKTVAIQSFBDLGYFEDNMPPALLPKFLQLVEIK
EDNPKLALVVDMRSRSFFSEIQAVLDELENQDGLDPKILLDAADKELVAR
YKETRRSHPLAADGRLDGIgLRELLAPLKNMSQNVVDRRELTPRELRITL
AEQFSDQEQAQSFPJEVMSFGIKYGIPIDADLVFDVRFLPNPYYLPELRN
QTGVDEPVYDYVMNHPESEDFYQHLLALIEPILPSYQKEGKSVLTIAMGC
TGGQMRSVAFAKRLAQDLSKNWSVNEGHPDKDRRKETVNRSZ (SEQ. ID. NO. 141)
MRKPKITVIGGGTGSPVTLKSLREKDVEAAIVTVADDGGSSGELRKNMQQ
LTPPGDLRNVLVAMSDMPKFYEKVFQYRFSEDAGAFAGHPLGNLUAGLEM
QGSTYNAMQLLSKFPHRGKYPSSDHPLTLVFQTEVAGHIVDMRGIIDNEV
LHRLRPFIDTVLVNEKVPEYMNSNRPDEYLVQVEHDFVGLCKQVSRVISS
NPLPENGGAIDLIVDELMRIQVKKZ (SEQ. ID. NO. 142)
MKNLIKLLIUVNLADSVFYIVALWHVSNNYSSSMFLGFIAVNYLPDLLLI
GPVDRVNPQKILIILVQLAVAVIFTLLLNQISFWVIMSLVFSVMASSISY
VIEDVLIQVVEYDKIVFANSLFSISYKVLDSFNSFFLQVAVGILLVKIDI
GIPLLALFILLLLKRTSNANIENFSFKYYKREVLQGTHFILNNGLLFTSI
SLTLINFFYSFQTVVVPFSIRYGPIJYGIPLTGLGGILGNMLAPIVIKYL
KSNQVGVFLFLNGSSWLVAIVIKDYTLSLILFFVCFMSKGVNIIINSLYQQ
IPPHQLLGRVNTTIDSIISFGMPIGSLVAGTLIDLNIELVLIAISIIPYF
LFSYLFYTDNGLKEFSIYZ (SEQ. ID. NO. 143)
MMSNKNKEILIFAILYTVLFMFDGVKLLASLMPSAIANYLVYVVLALYGS
FLFKDRLIQQWKEIRKTKRKFFFGVLTGWLFLILMTVVFEFVSEMLKQFV
GLDGQGLNQSNIQSTFQEQPLLIAVFACVIGPLVEELFFRQVLLHYLQER
LSGLLSIILVGLVFALTHMHSLALSEWIGAVGYLGGGLAFSIIYVKEKEN
IYYPLLVHMLSNSLSLIILAISIVKZ (SEQ. ID. NO. 144)
LKKPIIEFKNVSKVFEDSNTCVLKDNFELEEGICYTLLGASGSGKSTILN
HAGLLDATRGDIMLDGVRINDPTIKRDVHTVFQSYALFPHMNVFENVAFP
LRLRKIDKKEIEQRVAEVLKMVQLEGYEKRSLRKLSGGRQRVAIARAII
NQPRVVLLDEPLSALDLKLRTDMQYELRELQQRLGITFVFVTHDQEALAM
SDWTVMNDGETVQSGTPVDIYDEPINHFVATFGBSNILPGTMIEDYLVEF
NGKREAVDGGMKPNEPVEVVIRPEDLRTLPEEGKLQVKVDTQLFRGVHYE
```

TABLE 2-continued

UAYDELGNEWMIHSTRKAVGEEGLDFBPEDIHIMRLNETEEEFDAPJEEY
VEIEEQEAGLINAIEEERDEENKLZ (SEQ. ID. NO. 145)
MKSMRILFLLALIQISLSSCFLWKECILSFKQSTAFFIGSMVFVSGICAG
VNYLYTRKQEVHSVLASKKSVKLFYSMLLLNLLGAVLVLSDNLFKNLQQE
LVDFLLPSFFLFGLDLLIFLPLKXYVRDFLAMLDRXTVLVTILATLLFLR
NPMTVSLLIYIGLGLFFAAYLVPNSVKKEVSFYGHIRDLVLVIVTLIFFZ (SEQ. ID. NO. 146)
MVKKIIGMVLALLSVTVVGVGVFAYTIYQQGTETLAIZTYKKIGEETKVI
EATEPLTILLMGVURGNVERTETWVGRSDSMILMTVNPKTKRITMMSLER
DILTRIESGNGQAHEAKLNSAYADGGAELAIETIQKMMNIHIDRYVMVNM
RGLQKLVDAVGGRRVNNLGFPISSDQEENTSIGVGEQHIGGEEALVYARM
RYQDPEGDYGRQKRQREVIQKVMEKALSLNSIGHYQEILKALSDNMQTNI
DLSAKSPNLLGYPZDSFKTIETQQLQGEGEILQGVSYQIVSRAHMLEMQN
LLRRSLGQEEVTQLETNAVLFEDLFGRAPVGDEDNZ (SEQ. ID. NO. 147)
MKKQAYVUALTSFLFVFFFSHSLLEILDFDWSIFLHDVEKTEKFVFLLLV
FSMSMTCLLALFwRGIEELSLRKMQANLKRLLAGQEVVQVADPDLDASFK
SLSGKLNLLTEALQKAENQSLAQEEEIIEKERKRIARDLHDTVSQELFAA
HMILSGISQQALKLDREKMQTQLQSVTAILETAQKDLRVLLLHLRPVELE
QKSLIEGIQILLKELEDKSDLRVSLKQNMTKLPKKLEEHIFRJLQELSNT
LRHAQASCLDVYLYQTDVELQLKVVDR4GIGFQLGSLDDLSYGLRNIKER
VEDMAGTVQLLTAPKQGLAVDIRIPLLDKEZ (SEQ. ID. NO. 148)
MIVSIISQGFVWAILGLGIFMTFRILNFPDMTTEGSIPLGGAVAVTLITK
GVNPFLATLVAVGAGCLAGMAAGLLYTKGKIPTLLSGILVMTSCHSIMLL
IMGRANLGLLGTKQIQDVLPFDSDLNQLLTGLRFVSRVXALMLPLLDTKL
GQAYIATGDNPDMARSFGHTGRMELMGLVLSNGVIALAOALAQQEGYADV
SRGGVIVVGLASLIIGEVISLAEPVTIVVGSIAYQFLVWAVIAIOFNTSY
LRLYSALILAVCLMUTFKQTILKGAJCLSKZ (SEQ. ID. NO. 149)
MKKMKVWSTVLATGVALTRLAACSGGSNSTTASSSEEKADKSQELVIYSN
SVSNGRGDWLTAXAEAGFNIKMVDIAGAQLADRVLAEKNNAVADMVFGIG
AVDSNKIRDQKLLVQYKPKWLDKIDQSLSDKDNYYNPVIVQPLVLIGAPD
VKEMPKDWTELGSKYKGKYSISGLQGGTGRALASILVRYLDDKGELGVSE
KGWEVAICEYLKNAYTLQKOESSIVKMLDKEDPIQYGMMWGSGALVGQKE
QNVVPKVMTPEIGVPFVTEQTMVLSTSKKQALAKEFIDWFGQSEIQVEYS
KNFGSIPANKDALKDLPEDTKKFVDQVKPQNIDWEAVGKHLDEWVEKAEL
EYVQZ (SEQ. ID. NO. 150)
MIKFDNIQIKYGDFVAIDNLNLDHEGEFTFLGPSGCGKSTLRALVGFLDP
SSGSIEVNGTDVTHLEPEKRGIGVFQSYALFPTMTVDNIAFGLKVKKVAP
DVIKAKVSAVAAKIKISDQQLQRNVSELSGGQQQRVALARLVLEPKILCL
DEPLSNLDAKLRVDLRKELKRLQKELGRITLYVTHDQEEALTLSDRIAVF
NNGYIEQVGTPVEIYHNSQTEVCDPIGDNVLTDETVHEVLLKNTSVFLED
KKGYIRLEKVRFNRETEQDFLKGTUDVEFSGVTEHYTIKVSESQILNVTS
IDSQAARSVGESVELFITPSDVLQFZ (SEQ. ID. NO. 151)
MRHKLNLKDWLRLGLRWFLVTRIYPNFDLVVNVFVKGGESLDAVHRVLKQ
PALQSMNSPSLIVNVVGILCVLFTEYFDIKGAKZLKLGYMTSLIYGGVVL
ATGYKFVYGPYGLITKFLQNVIPSLDPNWPIGYGAVLFIMTFSGTANHTL
FLTNTHSVDYTIEARNMGKPVFRICVVLPTLITLFALTIMVFLSGLSAVA
APMIVGGKEFQTINPMIITFAGMGNSRDLAALLAIILGIATTILLTIMNK
IEKGGNYISISKTKAPLKKQKIASKPWNIIAHIVAYGLFTVFMLPLIFIV
LYSPTDPVVIALNFNSLLTDFDLSVFLYHPLAQPLGITIPSAGDETATSN
AQALVF®YTIVLMIISGTVLYPTQPJGPJVPJCZ

TABLE 3

ID201-4106.4

(SEQ. ID. NO. 168)
ATGATAAAAAATCCTAAATTATTAACCAAGTCTTTTTTAAGAAGTTTTGC
AATTCTAGGTGGTTGGTCTAGTCATTCATATAGCTATTTATTTGACCTTT
CCTTTTTATTATATTCAACTGGAGGGGGGAAAAGTTTATGAGAGCGCAAG
AGTGTTTACGGAGTATTTAAAGACTAAGACATCTGATGAAATTCCAAGCT
TACTCCAGTCTTATTCAAAGTCCTTGACCATATCTGCTCACCTTAAAAGA
GATATTGTAGATTAGCGGCTCCCTCTTGTGCATGACTTGGATATTAAAGA
TGGAAAGCTATCAAATTATATCGTGATGTTAGATATGTCTGTTAGTACAG
CAGATGGTAAACAOGTAACCGTGCAATTTGTTCACGGGGTGGATGTCTAC
AAAGAAGCAAAGAATATTTTGCTTTTGTATCTCCCATATACATTTTTGGT
TACAATTGCTTTTTCCTTTGTTTTTTCTTATTTTTATACTAAACGCTTGC
TCAATCCTCTTTTTTACATTTTCAGAAGTGACTAGTAAAATGCAAGATTTG
GATGACAATATTCGTTTTGATGAAAGTAGGAAAGATGAAGTTGGTGAAGT
TGGAAAACAGATTAATGGTATGTATGAGCACTTGTTGAAGGTTATTTATG
AGTTGGAAAGTCGTAATGAGCAAATTGTAAAATTGCAAAATCAAAAGGTT
TCCTTTGTCCGCGCGGAGCATCACATGAGTTGAAAACCCTTTAGCCAGTC
TTAGAATTATCCTAGAGAATATGCAGCATAATATTGGAGATTACAAAGAT
CATCCAAAATATTGCAAAGAGTATAAATAAGATTGACCAGATGAGCCACT
TATTAGAAGAAGTACTGGAGTCTTCTAAATTCCAAGAGTGGACAGAGTGT
CGTGAGACCTTGACTGTTAAGCCAGTTTTAGTAGATATTTTATCACGTTA
TCAAGAATTAGCTCATTCAATAGGTGTTACAATTGAAATCAATTGACAG
ATGCTACCAGGGTCGTCATGAGTCTTAGGGCATTGGATAAGGTTTTGACA
AACCTGATTAGTAATGCAATTAAATATTCAGATAAAAATGGGCGTGTAAT

TABLE 3-continued

CATATCCCAGCAAGATGGCTATCTCTCTATCAAAATACATGTGCGCCTC
TAAGTGACCAAGAACTAGAACATTTATTTGATATATTCTATCATTCTCAA
ATCGTGACAGATAAGGATGAAAGTTCGGTTTGGGTCTTTACATTGTGAAT
AATATTTTAGAAAGCTATCAAATGGATTATAGTTTTCTCCCTTATGAACA
CGGTATCGAATTTAAGATTACCTTATAG (SEQ. ID. NO. 152)
MIKNPKLLTKSFLRSFAILGGVGLVIHIAIYLTFPFYYIQLEGEKFENSA
RVFTEYLKTKTSDEIPSLLQSYSKSLTISAHLKRDIVDKRLPLVHDLDIK
DGKISNYIVMLDMSVSTADGKQVTVQFVHGVDVYKEAKNILLLYLPYTFL
VTIAFSFVFSYFYTKRLLNPLFYISEVTSKMQDLDDNIRFDESRKDEVGE
VGKQINGMYEHLLKVIYELESRNEQIVKLQNQKVSFVRGASHELKTPLAS
LRIILENMQHNIGDYKDHPKYIAKSINKIDQMSHLLEEVLESSKFQEWTE
CRETLTVKPVLVDILSRYQELAHSTGVTTENGLTDATRVVMSLRALDKVL
TNLTSNATTCYSDJGRVIISEQDGYLSIKNTCAPLSDQELEHLFDIFYHS
QIVTDKDESSGLGLYIVNNILESYQMDYSFLPYEHGMEFKISLZ

ID202-41069

(SEQ. ID. NO. 169)
ATGGATAAAATTATTAAAACTATATCAGAAAGCGGAGCCTTTCGTGCTTT
TGTCCTTGATAGCACTGAAACCGTCCGCACTGCTCAAGAAAAACATCAAA
CCCAAGCTAGCTCAACTGTAGCGCTTGGTCGAACTCTTATCGCTAGCCAG
ATTCTCGCAGCCAATGAAAAAGGAAATACCAAACTTACAGTTAAGGTGTT
GGGATCTAGCTCTCTAGGTGCTATTATCACCGTCGCTGATACCAAGGGGA
ACGTCAAAGGCTATGTTCAAAATCCTGGTGTTGACATCAAAAAGACTGCG
ACTGGTGAAGTCCTAGTCGGACCTTTTGTTGGAAATGGTCAATTCCTCGT
TATCACAGACTACGGTACTGGAAATCCTTACAACTCTATAACTCCCCTCA
TCTCTGGAGAAATCGGTGAAGACCTTGCCTTTTACCTTACTGAAAGCCAA
CAAACGCCTTCAGCGGTCGGCCTCAATGTCCTTTTGGACGAGGAAGACAA
GGTCAAGGTTGCAGGTGGTTTCCTAGTTCAAGTCTTGCCAGGAGCCAAGA
AAGAAGAGATTGCTCGCTTTGAAAAACGCATCCAAGAAATGCCAGCTATC
TCTACTCTTCTCGAAACGTTTCCAATGTGACTGTAGCCATGAACGCTTTA
TGAACGCTCTTGCCAGCCTTCCAAGCTCAGACTTACAGGAAATGAAAGAG
GAAGACCACGGGGCAGAAATCACTTGTCAATTCTGCCAAACTACTTACAA
CTTTGATGAAAGGACCTGGAGGACTCATTCGTGACAAATCTTAA (SEQ. ID. NO. 153)
MDKIIKTISESGAFRAFVLDSTETVRTAQEKHQTQASSTVALGRTLIASQ
TLAANEKGNTKLTVKVLGSSSLGAIITVADTKCNV1CGYVQPCVDTKKTA
TGEVLVGPFVGNGQFLVTTDYGTG&PYNSTTPLTSGETGEDLAFYLTESQ
QTPSAVGLNLLDEEDKVKVAGGFLVQVLPGAKKEETARFETCRTQEMPAT
STLLESDDHIEALLKATYGDEAYKRLSEEEIRFQCDCSHERFMNALASLP
SSDLQEMKEEDHGAEITCQFCQTTYNFDEKDLEELTRDKSZ

ID203-4115

(SEQ. ID. NO. 170)
ATGAAATCAATAACTAAAAAGATTAAAGCAACTCTTGCAGGAGTAGCTGC
CTTGTTTGCAGTATTTGCTCCATCATTTGTATCTGCTCAAGAATCATCAA
CTTACACTGTTAAAGAAGGTGATACACTTTCAGAAATCGCTGAAACTCAC
AACACAACAGTTGAAAAATTGGCAGAAAACAACCACATTGATAACATTCA
TTTGATTTATGTTGATCAAGAGTTGGTTATCGATGGCCCTGTAGCGCCTG
TTGCAACACCAGCGCCAGCTACTTATGCGGCACCAGCCGCTCAAGATGAA
ACTGTTTCAGCTCCAGTAGCAGAAACTCCAGTAGTAAGTGAAACAGTTGT
TTCAACTGTAAGCGGATCTGAAGCAGAAGCCAAAGAATGGATCGCTCAAA
AAGAATCAGGTGGTAGTATACAGCTACAAATGGACGTTATATCGGACGTT
ACCAATTAA (SEQ. ID. NO. 154)
MKSITKKIKATLAGVAALFAVFAPSFVSAQESSTYTVKEGDTLSEIAETH
NTTVEKLAENNHTDNTHLTYVDQELVIDGPVAPVATPAPATYAAPAAQDE
TVSAPVAETPVVSETVVSTVSGSEAEAKEWIAQKESGGSIQLQMDVISDV
TNZ

ID204-4111.7

(SEQ. ID. NO. 171)
ATGAATTTAGGAGAATTTTGGTACAATAAAATAAATAAGAACAGAGGAAG
AAGGTTAATGAAGAAAGTAAGATTTATTTTTTTAGCTCTGCTATTTTTCT
TAGCTAATCCAGAGGGTGCAATGGCTAGTGATGGTACTTGGCAAGGAAAA
CAGTATCTGAAAGAAGATGGCAGTCAAGCAGCAAATGAGTGGGTTTTTGA
TACTCATTATCAATCTTGGTTCTATATAAAAGCAGATGCTAACTATGCTG
AAAATGAATGGCTAAAGCAAGGTGACGACTATTTTTACCTCAAATCTGGT
GGCTATATGGCCAAATCAGAATGGGTAGAAGACAAGGGAGCCTTTTATTA
TCTTGACCAAGATGGAAAGATGAAAAGAAATGCTTGGGTAGGAACTTCCT
ATGTTGGTGCAACAGGTGCCAAAGTAATAGAAGACTGGGTCTATGATTCT
CAATACGATGCTTGGTTTATATCAAAGCAGATGGACAGCACGCAGAGAA
AGAATGGCTCCAAATTAAAGGGAAGGACTATTATTTCAAATCCGGTGGTT
ATCTACTGACAAGTCAGTGGATTAATCAAGCTTATGTGAATGCTAGTGGT
GCCAAAGTACAGCAAGGTTGGCTTTTTGACAAACAATACCAATCTTGGTT
TTACATCAAAGAAAATGGAAACTATGCTGATAAAGAATGGATTTTCGACA
ATGGTCACTATTATTATCTAAAATCCGGTGGCTACATGGCAGCCAATGAA
TGGATTTGGGATAAGGAATCTTGGTTTTATCTCAAATTTGATGGGAAATG
GCTGAAAAAGAATGGGTCTACGATTCTCATAGTCAAGCTTGGTACTACTT
CAAATCCGGTGGTTACATGACAGCCAATGAATGGATTTGGGATAAGGAAT
CTTGGTTTTATCTCAAATCTGATGGGAAATAGCTGAAAAGAATGGGTC
TACGATTCTCATAGTCAAGCTTGGTACTACTTCAAATCCGGTGGTTACAT
GACAGCCAATGAATGGATTTGGGATAAGGAATCTTGGTTTTACCTCAAAT
CTGATGGGAAATAGCTGAAAAGAATGGGTCTACGATTCTCATAGTCAA

TABLE 3-continued

```
GCTTGGTACTACTTCAAATCTGGTGGCTACATGGCGAAAAATGAGACAGT
AGATGGTTATCAGCTTGGAAGCGATGGTAAATGGCTTGGAGGAAAAACTA
CAAATGAAAATGCTGCTTACTATCAAGTAGTGCCTGTTACAGCCAATGTT
TATGATTCAGATGGTGAAAAGCTTTCCTATATATCGCAAGGTAGTGTCGT
ATGGCTAGATAAGGATAGAAAAGTGATGACAAGCGCTTGGCTATTACTA
TTTCTGGTTTGTCAGGCTATATGAAAACAGAAGATTTACAAGCGCTAGAT
GCTAGTAAGGACTTTATCCCTTATTATGAGAGTGATGGCCACCGTTTTTA
TCACTATGTGGCTCAGAATGCTAGTATCCCAGTAGCTTCTCATCTTTCTG
ATATGGAAGTAGGCAAGAAATATTATTCGGCAGATGGCCTGCATTTTGAT
GGTTTTAAGCZTGAGAATCCCTTCCTTTTCAAAGATTTAACAGAGGCTAC
AAACTACAGTGCTGAAGAATTGGATAAGGTATTTAGTTTGCTAAACATTA
ACAATAGCCTTTTGGAGAACAAGGGCGCTACTTTTAAGGAAGCCGAAGAA
CATTACCATATCAATGCTCTTTATCTCCTTGCCCATAGTGCCCTAGAAAG
TAACTGGGGAAGAAGTAAAATGCCAAAGATAAGAATAATTTCTTTGGCAT
TACAGCCTATGATACGACCCCTTACCTTTCTGCTAAGACATTTGATGTGG
ATAAGGGAATTTTAGGTGCAACCAAGTGGATTAAGGAAAATTATATCGAT
AGGGGAAGAACTTTCCTTGGAAACAAGGCTTCTGGTATGAATGTGGAATA
TGCTTCAGACCCTTATTGGGGCGAAAAAATTGCTAGTGTGATGATGAAAA
TCAATGAAAGCTAGGTGGCAAAGATTAG
```

(SEQ. ID. NO. 155)
MNLGEFWYNKINKNRGRRLMKKVRFIFLALLFFLASPEGAMASDGTWQGK
QYLKEDGSQAANEWVFDTHYQSWFYIKADANYAENEWLKQGDDYFYLKSG
GYMAKSEWVEDKGAFYYLDQDGKMKRNAWVGTSYVGATGAKVIEDWVYDS
QYDAWFYIKADGQHAEKEWLQIKGKDYYFKSGGYLLTSQWINQAYVNASG
AKVQQGWLFDKQYQSWFYTKENGNYADKEWIFENGHYYYLKSGGYMAANE
WIWDKESWFYLKFDGKMAEKEWVYDSHSQAWYYFKSGGYMTANEWTWDKE
SWFYLKSDGKIAEKEWVYDSHSQAWYYFKSGGYMTANEWIWDKESWFYLK
SDGKIAEKEWVYDSHSQAWYYFKSGGYMAKNETVDGYQLGSDGKWLGGKT
TNENAAYYQVVPVTANVYDSDGEKLSYISQGSVVWLDKDRKSDDKRLAIT
ISGLSGYMKTEDLQALDASKDFIPYYESDGHRFYHYVAQNASIPVASHLS
DMEVGKKYYSADGLHFDGFKLENPFLFKDLTEATNYSAEELDKVFSLLNI
NNSLLENKGATFKEAEEHYHINALYLLAHSALESNWGRSKIAKDKNNFFG
ITAYDTTPYLSAKTFDDVDKGILGATKWIKENYWRGRTFLGNKASGMNVE
YASDPYWGEKIASVMMKINEKLGGKDZ

ID205-41181.1

(SEQ. ID. NO. 172)
ATGAAAAAATTAGGTACATTACTCGTTCTCTTTCTTTCTGCAATCATTCT
TGTAGCATGTCCTAGCGGAAAAAAAGATACAACTTCTGGTCAAAAACTAA
AACTTGTTGCTACAAACTCAATCATCGCTGATATTACTAAAAATATTGCT
GGTGCAAAATTGACCTTCATAGTATCGTTCCGATTGGGCAAGACCCCACAC

GAATACGAACCACTTCCTGAAGACGTTAAGAAAACTTCTGAGGCTAAATT
TGATTTTCTATAACGGTATCAACCTTGAAACAGGTGGCAATGCTTGGTTT
ACAAAATTGGTAGAAAATGCCAAGAAAACTGAAAACAAAGACTACTTCGC
AGTCAGCGACGGCGTTGATGTTATCTACCTTGAAGGTCAAAATGAAAAAG
GAAAAGAAGACCCACACGCTTGGCTTAACCTTGAAAACGGTATTATTTTT
GCTAAAAATATCGCCAAACAATTGAGCGCCAAAGACCCTAACAATAAAGA
ATTCTCATGAAAAAAATCTCAAAGAATATACTGATAAGTTAGACAAACTT
GATAAAGAAAGTAAGGATAAATTTAATAAGATCCCTGCTGAAAAGAAACT
CCATTGTAACCAGCGAAAGGAGCATTCAAATACTTCTCTAAAGCCTATGG
TGTCCCAAGTGCTTTACATCTGGGAAATCAATACTGAAGAAGAAGGAACT
CCTGAACAAATCAAGACCTTGGTTGAAAAACTTCGCCAAACAAAACTTCC
ATCACTCTTTGTAGAATCAAGTGTGGATGACCGTCCAATGAAAACTGTTT
CTCAAGACACAAACATCCCAATCTACGCTCAAATCTTTACTGACTCTATC
GCAGAACAAGGTCCCGAAGGCGACAGCTACTACAGCATGATGAAATACAA
CCTTGACAAGATTGCTGAAGGATTGGCAAAATAA (SEQ. ID. NO. 156)
MKKLGTLLVLFLSAIILVACASGKKDTTSGQKLKVVATNSIIADITKNIA
GDKIDLHSIVPIGQDPHEYEPLPEDVKKTSEANLIFYNGINLETGGNAWF
TKLVENAKKTENKDYFAVSDGVDVIYLEGQNEKGKEDPHAWLNLENGIIF
AKNIAKQLSAKDPNNKEFYEKNLKEYTDKLDKLDKESKDKFNKIPAEKKL
IVTSEGAFKYFSKAYGVPSAYIWEINTEEEGTPEQIKTLVEKLRQTKVPS
LFVESSVDDRPMKTVSQDTNIPIYAQIFTDSIAEQGKEGDSYYSMMKYNL
DKIAEGLAKZ

ID206-41191.1

(SEQ. ID. NO. 173)
ATGGAATGGTATAAAAAAATGGACTTCTTGCAACTACAGGTTTAGCTTTG
TTTGGGCTCGGCGCTTGCTCCAACTATGGTAAATCTGCGGATGGCACGTG
ACCATCGAGTATTTCAACCAGAAAAAAGAAATGACCAAAACCTTGGAAGA
AATCACTCGTGATTTTGAGAAGGAAAACCCTAAGATCAAGGTCAAAGTCG
TCAATGTACCAAATGCTGGTGAAGTATTGAAGACACGCGTTCTCGCAGGA
GATGTGCCTGATGTGGTCAATATTTACCCACAGTCCATCGAACTGCAAGA
ATGGGCAAAAGCAGGTGTTTTTGAAGATTGACCAACAAAGACTACCTGAA
ACGCGTGAAAATGGCTACGCTGAAAAATATGCTGTAAACGAAAAAGTTTA
CAACGTTCCTTTTACAGCTAATGCTTATGGAATTTACTACAACAAAGATA
AATTCGAAGAACTGGGCTTGAAGGTTCCTGAAACCTGGGATGAATTTGAA
CAGTTAGTCAAAGATATCGTTGCTAAAGGACAAACACCATTTGGAATTGC
AGGTGCAGATGCTTGGACACTCAATGGTTACAATCAATTAGCCTTTGCGA
CAGCACAGGTGGAGGAAAGAAGCAAATCAATACCTTCGTTATTCTCAAC
CAAATGCCATTAAATTGTCGGATCCGATTATGAAAGATGATATCAAGGTC
ATGGACATCCTTCGCATCAATGGATCTAAGCAAAAGAACTGGGAAGGTGC
TGGCTATACCGATGTTATCGGAGCCTTCGCACGTGGGGATGTCCTCATGA
```

TABLE 3-continued

```
CACCAATGGGTCTTGGGCGATCACAGCGATTAATGAACAAAAACCGAACT
TTAAGATTGGGACCTTCATGATTCCAGGAAAAGAAAAAGGACAAAGCTTA
ACCGTTGGTGCGGGAGACTTGGCATGGTCTATCTCAGCCACCACCAAACA
TCCAAAAGAAGCCAATGCCTTTGTGGAATATATGACCCGTCCAGAAGTCA
TGCAAAAATACTACGATGTGGACGATCTCCAACAGCGATCGAAGGGGTC
AAACAAGCAGGAGAAGATTCACCGCCTTGCTGGTATGACCGAATATGCCT
TTACGGATCGTCACTTGGTCTGGTTGCAACAATACTGGACCAGTGAAGCA
GACTTCCATACCTTGACCATGAACTATGTCTTGACCGGTGATAAACAAGG
CATGGTCAATGATTTGAATGCCTTCTTTAACCCGATGAAAGCGGATGTGG
ATTAG
```

(SEQ. ID. NO. 157)
MEWYKKIGLLATTGLALFGLGACSNYGKSADGTVTIEYFNQKKEMTKTLE
EITRDFEKENPKIKVKVVNVPNAGEVLKTRVLAGDVPDVVNIYPQSIELQ
EWAKAGVFEDLSNKDYLKRVKNGYAEKYAVNEKVYNVPFTANAYGIYYNK
DKFEELGLKVPETWDEFEQLVKDIVAKGQTPFGIAGADAWTLNGYNQLAF
ATATGGGKEANQYLRYSQPNAIKLSDPIMKDDIKVMDILRTNGSKQKNWE
GAGYTDVIGAFARGDVLMTPNGSWAITATNEQKPNFKIGTFMIPGKEKGQ
SLTVGAGDLAWSISATTKHPKEANAFVEYMTRPEVMQKYYDVDGSPTAIE
GVKQAGEDSPLAGMTEYAFTDRHLVWLQOYWTSEADFHTLTMNYVLTGDK
QGMVNDLNAFFNPMKADVDZ

ID207-4123.1

(SEQ. ID. NO. 174)
```
ATGAAGAAAATCAAACCGCATGGACCGTTACCAAGTCAGACTCAGCTAGC
TTATCTGGGAGATGAACTAGCAGCTTTTATCCACTTCGGTCCTAATACCT
TTTATGACCAAGAATGGGGGACTGGACAGGAGGATCCTGAGCGCTTTAAC
CCGAGTCAGTTGGATGCGCGTGAGTGGGTTCGTGTGCTCAAGGAAACGGG
CTTCAAAAAGTTGATTTTGGTGGTCAAGCACCACGATGGCTTTGTCCTTT
ATCCGACAGCTCACACAGATTATTCGGTTAAGGTCAGTCCTTGGAGGAGA
GGAAAGGGCGAGTTGCTCCTTGAAGTATCCCAAGCTGCCACAGAGTTTGA
TATGGATATGGGGGTCTACCTGTCACCGTGGGATGCCCATAGTCCCCTCT
ATCATGTGGACCGAGAAGCGGACTACAATGCCTATTATCTGGCTCAGTTG
GAAGGAAATCTTATCAAATCCTAACTATGGGAATGCTGGTAAGTTCGCTG
AGGTTTGGATGGATGGTGCCAGAGGAGAGGGCGCGCAAAAGGTTAATTAT
GAATTTGAAAATGGTTTGAAACCATTCGTGACCTGCAGGGCGATTGCTT
GATTTTTTCAACAGAAGGCACCAGTATCCGCTGGATTGGCAATGAACGAG
GGTATGCAGGTGATCCACTGTGGCAAAAGGTGAATCCTGATAAACTAGGA
ACAGAAGCAGAGCTGAACTATCTTCAGCACGGGGATCCCTCGGGCACGAT
TTTTTCAATCGGAGAGGCAGATGTTTCCATCCGTCCAGGCTGGTTCTACC
ATGAGGATCAGGATCCTAAGTCTCTCGAGGAGTTGGTCGAAATCTACTTT
CACTCAGTAGGGCGAGGAACTCCACTCTTGCTTAATATTCCGCCGAATCA
```

AGCTGGGCTCTTTGATGCAAAGGATATTGAACGACTTTATGAATTTGCGA
CCTATCGCAATGAGCTCTATAAAGAAGATTTGGCCTCTGGGAGCTGAGGT
ATCTGGTCCAGCTCTTTCCGCAGACTTTGCTTGTCGCCATTTGACAGACG
GCCTTGAGACCAGCTCTTGGGCAAGCGATGCAGACTTGCCCATCCAGTTA
GAACTCGACTTAGGTTCTCCTAAAACTTTTGATGTAATTGAGTTAAGAGA
AGATTTGAAGCTAGGGCCCGAATCGCTGCTTTTCATGTGCAAGTAGAGGT
GGATGGTGTCTGGCAGGAGTTTGGTTCGGGTCATACTGTTGGTTACAAAC
GTCTCTTACGAGGAGCAGTTGTTGAGGCACAGAAGATACGTGTAGTCATT
ACAGAATCACAGGCCTTTGCCTTTGTTGACCAAGATTTCCCTTTATAAAA
CTCCTGGATTATCAAAAAAGAAGTTGTTCAGGAACTAGCATTTGCAGAA
AAAAGCCTAGCTGTGGCAAAGGGAGAAAATGCCTATTTTACAGTTAAGCG
CAGAGAATGTAGTGGTCCTTTAGAAGCTAAGATTTCGATTCAACCGGGA
CAGGTGTCCATGGTGTCGCCTATCAGGATGAGATTCAAGTCCTTGCGTTT
CAAACTGGTGAGACTGAAAAAAGTCTGACGCTACCAACCTTGTATTTCGC
AGGAGATAAAACCTTGGATTTCTATCTGAACCTAACGGTGGATGGTCAGC
TTGTGGATCAACTTCAAGTCCAAGTTTCATAA (SEQ. ID. NO. 158)
MKKIKPHGPLPSQTQLAYLGDELAAFIHFGPNTFYDQEWGTGQEDPERFN
PSQLDAREWVRVLKETGFKKLLILVVKHHDGFVLYPTAHTDYSVKVSPWR
RGKGDLLLEVSQAATEFDMDGVYLSPWDAHSPLYHVDREADYNAYYLAQ
LKEILSNPNYGNAGKFAEVWMDGARGEGAQKVNYEFEKWFETIRDLQGDC
LIFSTEGTSIRWIGNERGYAGDPLWQKVNPDKLGTEAELNYLQHGDPSGT
IFSIGEADVSIRPGWFYHEDQDPKSLEELVEIYFHSVGRGTPLLLNIPPN
QAGLFDAKDIERLYEFATYRNELYKEDLALGAEVSGPALSADFACRHLTD
GLETSSWASDADLPIQLELDLGSPKTFDVIELREDLKLGQRIAAFHVQVE
VDGVWQEFGSGHTVGYKRLLRGAVVEAQKTRVVTTESQALPLLTKTSLYK
TPGLSKKEVVQELAFAEKSLAVAKGENAYFTVKRRECSGPLEAKISIQPG
TGVHGVAYQDEIQVLAFQTGETEKSLTLPTLYFAGDKTLDFYLNLTVDGQ
LVDQLQVQVSZ

ID208-4125.12

(SEQ. ID. NO. 175)
```
ATGCTTGAAAGACTGAAAAGAATACATTATATGTTTTGGATCAGTTTAAT
TTTTATGATTTTCCCCATCCTGTCTGTAGTGACTGGGTGGCTTTCTGCCT
GGCATTATTGATTGATATTCTATTTGTAGTGGCATATTTGGGTGTTTTA
ACAACTAAGAGCCAGCGCCTATCTTGGCTATATTGGGGCCTCATGCTGAC
TTATGTAGTTGGGAATACTGCCTTTGTTGCTGTTAATTATATCTGGTTTT
TCTTTTTCCTATCCAATCTCTTAAGTTATCATTTCAGCGTACGTAGTTTA
AAGTCTTTACATGTCTGGACTTTTCTTCTTGCTCAAGTCCTTGTTGTGGG
GCAACTGTTGATTTTCAGAGAATCGAAGTTGAGTTTCTATTCTATCTAC
TTGGTAATTCTTACTTTTGTCGATTTATGACTTTTGGATTGGTTCGGATT
CGTATTGTCGAGGATTTGAAAGAAGCTCAGGTCAAGCAAAATGCTCAGAT
```

TABLE 3-continued

```
AAATCTATTGCTTGCTGAAAATGAACGTAGTCGTATCGGTCAGGATTTGC
ATGATAGTCTGGGACATACCTTTGCTATGCTGAGTGTCAAGACAGATTTA
GCCTTGCAGTTATTTCAGATGGAGCTTATCCACAGGTGGAAAGGAATTAA
AGAAATTCACCAGATAGCAGGATCCATGA
```

(SEQ. ID. NO. 159)
MLERLKRTHYMFWTSLTFMTFPTLSVVTGWLSAWHLLTDTLFVVAYLGVL
TTKSQRLSWLYWGLMLTYVVGNTAFVAVNYIWFFFFLSNLLSYHFSVRSL
KSLHVWTFLLAQVLVVGQLLIFQRIEVEFLFYLLVILTFVQLMTFGLVRI
RIVEDLKEAQVKQNAQINLLLAENERSRIGQDLHDSLGHTFAMLSVKTDL
ALQLFQMEAYPQVEKELKEIHQISKDPZ

ID209-4126.3

(SEQ. ID. NO. 176)
ATGAATGATAAGTTAAAAATCTTCTTGTTGCTAGGAGTATTTTTTCTAGC
CATAACCGGTTTCTATGTTCTATTGATACGAAATGCAGGGCAGACAGATG
CCTCGCAAATTGAAAAGGCGGCAGTTAGCCAAGGAGGAAAAGCAGTGAAA
AAAACAGAAATTAGTAAAGACGCAGACTTGCACGAAATTTATCTAGCTGG
AGGTTGTTTCTGGGGAGTGGAGGAATATTTCTCACGTGTTCCCGGGGTGA
CGGATGCCGTTTCAGGCTATGCAAATGGTAGAGGAGAAACAACCAAGTAC
GAATTGATTAACCAAACAGGTCATGCAGAAACCGTCCATGTCACCTATGA
TGCCAAGCAAATTTCTCTCAAGGAAATCCTGCTTCACTATTTCCGCATTA
TCAATCCAACCAGCAAA)*ATAAACAAGGAAATGATGTGGGGACCCAGTA
CCGTACTGGTGTTTATTACACAGATGACAAGGATTTGGAAGTGATTAACC
AAGTCTTTGATGAGGTGGCTAAGAAATACGATCAACCTCTAGCAGTTGAA
AAGGAAAACTTGAAGAATTTTGTGGTGGCTGAGGATTACCATCAAGACTA
TCTAAAGAAAAATCCAAATGGCTACTGCCATATCAATGTTAATCAGGCGG
CCTATCCTGTCATTGATGCCAGCAAATATCCAAAACCAAGTGATGAGGAA
TTGAAAAAGACCCTGTCACCTGAGGAGTATGCAGTTACCCAGGAAAATCA
AACAGAACGAGCTTTCTCAAACCGTTACTGGGATAAATTTGAATCCGGTA
TCTATGTGGATATAGCAACTGGGGAACCTCTCTTTTCATCAAAGACAAAT
TTGAGTCTGGTTGTGGCTGGCCTAGTTTTACCCAACCCATCAGTCCAGAT
GTTGTCACCTACAAGGAAGATAAGTCCTACAATATGACGCGTATGGAAGT
GCGGAGCCGAGTAGGAGATTCTCACCTTGGGCATGTCTTTACGGATGGTC
CACAGGACAAGGGCGGCTTACGTTAACTGTATCAATAGCCTCTCTATCCG
CTTTATTCCCAAAGACCAAATGGAAGAAAAAGgcTACGCTTATTTACTAG
ATTATGTTGATTAA (SEQ. ID. NO. 160)
MNDKLKIFLLLGVFFLAITGFYVLLIRNAGQTDASQIEKAAVSQGGKAVK
KTEISKDADLHETYTAGGCFWGVEEYFSRVPGVTDAVSGYANGRGETTKY
ELINQTGHAETVHVTYDAKQISLKEILLHYFRIINPTSKNKQGNDVGTQY
RTGVYYTDDKDLEVNQVFDEVAKKYDQPLAVEKENLKNFVVAEDYHQDYL
KKNPNGYCHINVNQAAYPVIDASKYPKPSDEELKKTLSPEEYAVTQENQT

ERAFSNRYWDKFESGIYVDIATGEPLFSSKDKFESGCGWPSFTQPISPDV
VTYKEDKSYNMTRMEVRSRVGDSHLGMVFTDGPQDKGGLRYCINSLSIRF
IPKDQMEEKGYAYLLDYVDZ

ID210-4127.1

(SEQ. ID. NO. 177)
ATGAAAAAGAAATGGATGTATTATGCTGCTTGTTCTTCTAATGAATCTGC
CGATGACAGTTCATCTGATAAAGGAGACGGCGGTTCGCTAGTCGTTTATT
CACCAAACTCAGAGGGCTTAATTGGAGCAACTATTCCTGCCTTTGAAGAA
AAATATGGTATCAAAGTAGAACTGATTCAAGCTGGTACTGGAGAACTTTT
CAAAA)ACTAGAGTCAGAAAAAGAAGTTCCTGTAGCTGATGTTATCTTTG
GTGGTTCTTATACACAATATACTACCCACGGAGAACTCTTTGAAAACTAT
ACTTCAAAAGAAAATGATAATGTTATCAAAGAATATCAAAACACAACTCG
CTACTCTACTCCTTATACACTAGATGGTAGTGTTTTAATCGTCAACCCTG
ATTTAACTAAAGGCATGAACATCGAAGGATATAACGATCTTTTCAAACCT
GAACTAAAAGGAAAAATCGCAACTGCTGACCCAGCAAACTCTTCTAGCGC
CTTTGCTCAATTAACAAATATGCTACAAGCTCAAGGTGGTTAACAAAGAT
GATAAGGCTTGGTCTTATGTAAAAGATCTTTTCACACTTATTGATGGTAA
AATCGGTTCAGTTCATCTAGTGTCTATAAAGTAGTCGCTGATGGAGAAAT
GGCTGTTGGTCTCTCTTATGAAGATCCAGCAGTTAAACTCTTAAATGACG
GAGCTAACATTAAGGTAGTCTATCCAAAAGAAGGAACCGTCTTCCTACCT
GCTAGTGCTGCTATCGTTAAAAAATCTAAAAATATGGAAAATGCCAAGAA
ATTTATCGATTTTATTATCTCTCAAGAAGTACAAGATACACTTGGTACAA
CCACTACTAACCGTCCTGTTCGTAAAAATGCTAAAACAAGCGAAAACATG
AAACCAATTGACAAAATCAAAACACTCACTGAAGATTATGATTATGTCAT
CAAGAATAAATCAGATATCGTTAAGAAATACAACGAAGTCTTTACAGATA
TCCAATCTAAACAGTAA (SEQ. ID. NO. 161)
MKKKWMYYAACSSNESADDSSSDKGDGGSLVVYSPNSEGLIGATIPAFEE
KYGIKVELIQAGTGELFKKLESEKEVPVADVIFGGSYTQYTHGELFENYT
SKENDNVIKEYQNTTGYSTPYTLDGSVLIVNPDLTKGMNIEGYNDLFKPE
LKGKIATADPANSSSAFAQLTNMLQAQGGYKDDKAWSYVKDLFTLIDGKI
GSSSSSVYKVVADGEMAVGLSYEDPAVKLLNDGANIKVVYPKEGTVFLPA
SAAIVKKSKNMENAKKFIDFIISQEVQDTLGTTTTNRPVRKNAKTSENMK
PIDKIKTLTEDYDYVIKNKSDIVKKYNEVFTDIQSKQZ

ID211-4127.2

(SEQ. ID. NO. 178)
ATGGTGAGATCAAAATTATTAACGCCAAAAAAATCTACCACGATGTCCCT
GTTATTGAGAATTTGAACATTACAATTCCAAAAGGAAGTCTCTTTACCTT
CTTGGAGCTTCAGGATGTGGGAAAACGACCCTTCTTCGTATGATTGCAGG
TTTCAACAGTATCGAAGGTGGAGAATTTTACTTCGATGATACAAAAATCA
ATAATATGGAACCCAGCAAACGCAATATCGGGATGGTTTTCCAAAACTAC
```

TABLE 3-continued

```
GCTATTTTCCCACATTTGACTGTCCGAGACAACGTTCGTTTTGGTCTTAT
GCAAAAGAAGGTTCCAAAAGAAGAATTGATTCAACAGACCAACAAGTATC
TTGAACTCATGCAAATTGCTCAATATGCGGATCGAAAGCCCGATAAACTC
AGTGGTGGACAACAACAACGTGTCACTTGGCATGCGCCTTAGCGGTTAAT
CCAAGTGTTCTCCTCATGGACGAGCCACTTAGTAATCTGGAGGCCAAACT
TCGCTTGGATATGCGTCAAGCCATCCGAGAAATCCAACACGAAGTGGGAA
TTACAACTGTTTATGTAACCCACGACCAAGAAGAAGCCATGGCTATTTCA
GACCCAAATTGCTGTTATGAAAGATGGGGTGATCCAACAAATCGGCCGACC
AAAAGAATCTATCATAAACCAGCTAATGAGTTTGTGGCAACCTTTATCGG
ACGCACAAATATTATCCCTGCCAATCTTGAAAAACGGAGCGACGGCGCTT
ATATCGTCTTTTCAGATGGCTATGCCCTTCGAATGCCAGCTCTTGATCAG
GTTGAGGAGCAAGCTATTCATGTAAGCATTCGTCCCGAAGAGTTTATCAA
AGATGAATCTGGAGATATTGAAGGAACTATTAGAGATAGCGTCTATCTTG
GACTAAATACGGATTATTTCATTGAGACAGGTTTTGCCTCAAAAATTCAA
GTTAGTGAAGAATCAACTTTTGAAGAAGATCTACAAAAAGGCAATCGTAT
TCGTCTACGAATCAATACGCAAAAATTAAACATCTTTTCTGCAGATGGTT
CCCAAAACCTGATAAAAGGAGTCAACCATGGAACGTAA
```

(SEQ. ID. NO. 162)
```
MSEIKIINAKKIYHDVPVIENLNITIPKGSLFTLLGASGCGKTTLLRMIA
GFNSIEGGEFYFDDTKINNMEPSKRNIGMVFQNYAIFPHLTVRDNVAFGL
MQKKVPKEELIQQTNKYLELMQIAQYADRKPDKLSGGQQQRVTLACALAV
NPSVLLMDEPLSNLEAKLRLDMRQAIREIQHEVGITTVYVTHDQEEAMAI
SDQIAVMKDGVIQQIGRPKELYHKPANEFVATFIGRTNIIPANLEKRSDG
AYIVFSDGYALRMPALDQVEEQAIHVSIRPEEFIKDESGDIEGTIRDSVY
LGLNTDYFIETGFASKIQVSEESTFEEDLQKGNRIRLRINTQKLNIFSAD
GSQNLIKGVNHGTZ
```

ID212-4136.1

(SEQ. ID. NO. 179)
```
ATGAAGAAAAAATTATTGGCAGGTGCCATCACACTATTATCAGTAGCAAC
TTTAGCACGTTGTTCGAAAGGGTCAGAAGGTGCAGACCTTATCAGCATGA
AGGGGATGTCATTACAGAACATCAATTTTATGAGCAAGTGAAAACGAAC
CCTTCAGCCCAACAAGTCTTGTTAAATATGACCATCCAAAAAGTTTTTGA
AAAACAATATGGCTCAGAGCTTGATGATAAAGAGGTTGATGATACTATTG
CCGAAGAAAAAAAACAATATGGCGAAAACTACCAACGTGTCTTGTCACAA
GCAGGTATGACTCTTGAAACACGTAAAGCTCAAATTCGTACAAGTAAATT
AGTTGAGTTGGCAGTTAAGAAGGTAGCAGAAGCTGAATTGACAGATGAAG
CCTATAAGAAAGCCTTTGATGAGTACACTCCAGATGTAACGGCTCAAATC
ATCCGTCTTAATAATGAAGATAAGGCCAAAGAAGTTCTCGAAAAAGCCAA
GGCAGAAGGTGCTGATTTTGCTCAATTAGCCAAAGATAATTCAACTGATG
AAAAAACAAAAGAAAATGGTGGAGAAATTACCTTTGATTCTGCTTCAACA
GAAGTACCTGAGCAAGTCAAAAAAGCCGCTTTCGCTTTAGATGTGGATGG
TGTTTGTGATGTGATTACAGCAACTGGCACACAAGCCTACAGTAGCCAAT
ATTACATTGTAAAACTCACTAAGAAAACAGAAAAATCATCTAATATTGAT
GACTACAAAGAAAAATTAAAAACTGTTATCTTGACTCAAAAACAAAATGA
TTCAACATTTGTTCAAAGCATTATCGGAAAAGAATTGCAAGCAGCCAATA
TCAAGGTTAAGGACCAAGCCTTCCAAAATATCTTTACCCAATATATCGGT
GGTGGAGATTCAAGCTCAAGCAGTAGTACATCAAACGAATAG
```

(SEQ. ID. NO. 163)
```
MKKKLLAGAITLLSVATLAACSKGSEGADLISMKGDVITEHQFYEQVKSN
PSAQQVLLNMTIQKVFEKQYGSELDDKEVDDTIAEEKKQYGENYQRVLSQ
AGMTLETRKAQIRTSKLVELAVKKVAEAELTDEAYKKAFDEYTPDVTAQI
IRLNNEDKAKEVLEKAKAEGADGAQLAKDNATDEKTKENGGEITFDSAST
EVPEQVKKAAFALDVDGVSDVITATGTQAYSSQYYIVKLTKKTEKSSNID
DYKEKLKTVILTQKQNDSTFVQSIIGKELQAANIKVKDQAFQNIFTQYIG
GGDSSSSSSTSNEZ
```

ID213-4137.3

(SEQ. ID. NO. 180)
```
ATGAAAAAAAATATTAAACAATATGTAACCTTAGGTACTGTAGTGGTATT
ATCAGCATTTGTTGCTAACTCAGTTGCAGCTCAGGAGACTGAAACTTCTG
AAGTATCAACACCAAAGTTGGTGCAACCTGTTGCACCAACGACTCCGATT
TCGGAAGTACAACCTACATCGGATAACTCTTCGGAAGTTACTGTACAACC
TCGAACAGTTGAAACTACTGTTAAGGATCCATCTTCTACAGCGGAAGAAA
CTCCTGTCTTAGAAAAAAATAATGTTACTTTAACAGGGGGCGGAGAAAAT
GTTACTAAAGAGTTAAAGGATAAATTTACTAGCGGTGACTTTACTGTAGT
GATTAAGTACAATCAGTCAAGTGAGAAAGGCTTACAAGCTCTGTTTGGAA
TATCTAATTCCAAACCCGGTCAACAAAATAGTTATGTAGATGTGTTCCTT
AGAGACAATGGTGAGTGGGGATGGAAGCGCGTGATACTTCTTCCAATAAA
AATAACCTAGTATCCAGACCTGCTTCAGTTTGGGGTAAGTACAAACAAGA
GGCTCTGACTAACACTGTTGCAGTAGTAGCAGATTCAGTCAAAAAAACAT
ATTCTTTATACGCAAATGGTACAAAAGTAGTAGAAAAGAAAGTGGATAAT
TTCCTAAACATCAAGGATATTAAAGGTATTGATTACTATATGCTTGGGGG
AGTGAAACGTGCAGGAAAAACGGCGTTTGGTTTAACGGAACACTAGAAA
ATATCAAATTCTTTAATAGTGCATTGGATGAAGAAACTGTTAAAAGATG
ACAACAAACGCTGTTACTGGACATTTAATTTATACGGCTAATGATACAAC
AGGTTCTAACTATTTCCGTATTCCAGTTCTGTATACTTTTAGCAATGGTC
GGGTATTTTCAACGATTGACGCTCGTTACGGTGGAACTCATGATTTCTTG
AATAAAATTAATATTGCTACAAGTTATAGTGATGATAATGGTAAGACATG
GACTAAACCAAAATTAACATTGGCATTCGATGATTTGCGCCAGTACCAT
TAGAATGGCCTCGTGAAGTTGGTGGACGTGACTTACAAATCAGCGGTGGT
GCAACCTATATTGACTCTGTTATTGTTGAAAAAAAGAACAAACAAGTACT
CATGTTTGCTGATGTGATGCCTGCTGGAGTAAGTTTTAGAGAAGCAACTA
```

TABLE 3-continued

```
GAAAAGATTCAGGTTATAAACAAATTGATGGTAATTATTACCTTAAATTA
AGGAAACAAGGTGATACTGATTACAATTATACTATTCGTGAGAATGGTAC
TGTATACGACGATCGTACCAACAGACCAACTGAATTTTCAGTAGATAAAA
ATTTCGGTATTAAACAAAATGGTAATTATTTGACGGTAGAGCGG
```

(SEQ. ID. NO. 164)
```
MKKNIKQYVTLGTVVVLSAFVANSVAAQETETSEVSTPKLVQPVAPTTPI
SEVQPTSDNSSEVTVQPRTVETTVKDPSSTAEETPVLEKNNVTLTGGGEN
VTKELKDKFTSGDFTVVIKYNQSSEKGLQALFGISNSKPGQQNSYVDVFL
RDNGELGMEARDTSSNKNNLVSRPASVWGKYKQEAVTNTVAVVADSVKKT
YSLYANGTKVVEKKVDNFLNIKDIKGIDYYMLGGVKRAGKTAFGFNGTLE
NIKFFNSALDEETVKKMTTNAVTGHLIYTANDTTGSNYFRIPVLYTFSNG
RVFSSIDARYGGTHDFLNKINIATSYSDDNGKTWTKPKLTLAFDDFAPVP
LEWPREVGGRDLQISGGATYIDSVIVEKKNKQVLMFADVMPAGVSFREAT
RKDSGYKQIDGNYYLKLRKQGDTDYNYTIRENGTVYDDRTNRPTEFSVDK
NFGIKQNGNYLTVER
```

ID214-4185

(SEQ. ID. NO. 181)
```
ATGAAAAAATTTAGCCTATTACTAGCTATCCTACCATTTTTGGTTGCCTG
TGAGAATCAAGCTACACCCAAAGAGACTAGCGCTCAAAAGACAATCGTCC
TTGCTACAGCTGGCGACGTGCCACCATTTGACTACGAAGACAAGGGCAAT
CTGACAGGCTTTGATATCGAAGTTTTAAAGGCAGTAGATGAAAAACTCAG
CGACTACGAGATTCAATTCCAAAGAACCGCCTGGGAGAGCATCTTCCCAG
GACTTGATTCTGGTCACTATCAGGCTGCGGCCAATAACTTGAGTTACACA
AAAGAGCGTGCTGAAAAATACCTTTACTCGCTTCCAATTTCCAACAATCC
CCTCGTCCTTGTCAGCAACAAGAAAAATCCTTTGACTTCTCTTGACCAGA
TCGCTGGTAAAACAACACAAGAGGATACCGGAACTTCTAACGCTCAATTC
ATCAATAACTGGAATCAGAAACACACTGATAATCCCGCTACAATTAATTT
TTCTGGTGAGGATATTGGTAAACGAATCCTAGACCTTGCTAACGGAGAGT
TTGATTTCCTAGTTTTTGACAAGGTATCCGTTCAAAAGATTATCAAGGAC
CGTGGTTTAGACCTCTCAGTCGTTGATTTACCTTCTGCAGATACGGGGAG
CAATTATATCATTTTCTCAAGCGACCAAAAAGAGTTTAAAGAGCAATTTG
ATAAAGCGCTCAAAGAACTCTATCAAGACGGAACCCTTGAAAAACTCAGC
AATACCTATCTAGGTGGTTCTTACCTCCCAGATCAATCTCAGTTACAA
TAA
```

(SEQ. ID. NO. 165)
```
MKKFSLLLAILPFLVACENQATPKETSAQKTIVLATAGDVPPFDYEDKGN
LTGFDIEVLKAVDEKLSDYEIQFQRTAWESIFPGLDSGHYQAAANNLSYT
KERAEKYLYSLPISNNPLVLVSNKKNPLTSLDQIAGKTTQEDTGTSNAQF
INNWNQKHTDNPATINFSGEDIGKRILDLANGEFDFLVFDKVSVQKIIKD
RGLDLSVVDLPSADSPSNYIIFSSDQKEFKEQFDKALKELYQDGTLEKLS
NTYLGGSYLPDQSQLQZ
```

ID215-4211.1

(SEQ. ID. NO. 182)
```
ATGAAAAAAATAGTTTATATATCATATCCTCACTCTTTTTTGCTTGTGT
CTTATTTGTCTATGCTACGGCGACGAATTTTCAAAACAGTACCAGTGCTA
GGCAGGTAAAAACGGAAACCTATACTAATACAGTAACAAATGTCCCTATT
GACATAGCGTATAATAGTGATAAGTATTTTATTAGCGGTTTTGCTTCAGA
AGTATCAGTGGTCTTGACTGGTGCAAATCGCCTATCGCTAGCTAGTGAAA
TGCAAGAAAGTACACGTAAATTCAAGGTTACTGCTGACCTAACAGATGCC
GGTGTTGGAACGATTGAAGTTCCTTTGAGCATTGAAGATTTACCCAATGG
GCTGACCGCTGTGGCGACTCCGCAAAAAATTACAGTCAAGATTGGTAAGA
AGGCTCAGAAGGATAAGGTAAAGATTGTACCAGAGATTGACCCTAGTCAA
ATTGATAGTCGGGTACAAATTGAAAATGTCATGGTGTCAGATAAGAAGT
GTCTATTACGAGTGACCAAGAGACATTGGATAGAATTGATAAGATTATCG
CTGTTTTGCCAACTAGCGAACGTATAACAGGTAATTACAGTGGTTCAGTA
CCTTTGCAGGCAATCGACCGCAATGGTGTTGTCTTACCGGCAGTTATCAC
TCCGTTTGATACAATAATGAAGGTGACTACAAAACCAGTAGCACCAAGTT
CAAGCACATCAAATTCAAGTACAAGCAGTTCATCGGAGACATCTTCGTCA
ACGAACTAGTTCAAAAACGAATTAA
```

(SEQ. ID. NO. 166)
```
MKKNSLYIISSLFFACVLFVYATATNFQNSTSARQVKTETYTNTVTNVPI
DIRYNSDKYFISGFASEVSVVLTGANRLSLASEMQESTRKFKVTADLTDA
GVGTIEVPLSIEDLPNGLTAVATPQKITVKIGKKAQKDKVKIVPEIDPSQ
IDSRVQIENVMVSDKEVSITSDQETLDRIDKIIAVLPTSERITGNYSGSV
PLQAIDRNGVVLPAVITPFDTIMKVTTKPVAPSSSTSNSSTSSSSETSSS
TKATSSKTNZ
```

ID216-4127.3

(SEQ. ID. NO. 183)
```
ATGTTGATTGGCGAAGGGTATCGGACTTTCCCTGTCCTGATTTATACCCA
ATTTATTAGCGAGGTTGGAGGAAATTCTGCTTTTGCAATTATGGCGATTA
TCATTGCCTTGGCAATTTTCCTTATCCAAAAACACATTGCAAACCGCTAC
AGTTTCAGCATGAATCTGCTCCATCCAATTGAGCCTAAAAAAASTACAAA
AGGAAAAATGGCTGCCATTTATGCAACAGTCTACGGAATTATCTTTATCT
CTGTTTTACCTCAAATCTACTTAATTTATACCTCTTTCCTAAAAACATCA
GGTATGGTATCTGTTAAAGGTTATTCTCCAAACAGTTACAAGGTAGCTTT
CCATCGTATGGGATCTGCTATTTTCAATACCATTCGTATCCCTTTGATTG
CCTTAGTTCTAGTTGTTCTATTTGCGACATTTATCTCCTACCTAGCCGTT
AGAAAACGGAATTTGTTTACAAACTTAATTGACAGCCTCAGTATGGTACC
TTATATTGTACCAGGAACCGTTCTAGGGATTGCCTTCATTTCTTCCTTCA
ATACTGGTCTATTTGGAAGTGGATTTCTTATGATTACAGGGACTGCTTTC
ATCTTGATTATGTCTCTATCTGCCAGAAGATTACCTTATACTATTCGCTC
ATCTGTGCTAGCTTACAACAAATAGCACCAAGTATTGAAGAAGCTGCTGA
```

TABLE 3-continued

```
AAGCTTAGGAAGTAGTCGTCTCAATACCTTTGCTAAGATTACAACTCCAA
TGATGCTATCTGGTATCATTTCTGGAGCCATCTTATCTTGA
```

(SEQ. ID. NO. 167)
```
MLIGEGYRTFPVLIYTQFISEVGGNSAFAIMAIIALAIFLIQKHIANRY
SFSMNLLHPIEPKKTTKGKMAAIYATVYGIIFISVLPQIYLIYTSFLKTS
GMVSVKGYSPNSYKVAFHRMGSAIFNTIRIPLIALVLVVLFATFISYLAV
RKRNLFTNLIDSLSMVPYIVPGTVLGIAFISSFNTGLFGSGFLMITGTAF
ILIMSLSARRLPYTIRSSVASLQQIAPSIEEAAESLGSSRLNTFAKITTP
MMLSGIISGAILSZ
```

TABLE 4

ID301

(SEQ. ID. NO. 196)
```
ATGAATAAGAAAAAAATGATTTTAACAAGTCTAGCCAGCGTCGATATCTT
AGGGGCTGGTTTTGTTACGTCTCAGCCTACTTTTGTAAGAGCAGAAGAAT
CTCCACAAGTTGTCGAAAAATCTTCATTAGAGAAGAAATATGAGGAAGCA
AAAGCAAAAGCTGATACTGCCAAGAAAGATTACGAAACGGCTAAAAAGAA
AGCAGAAGACGCTCAGAAAAAGTATGAAGATGATCAGAAGAGAACTGAGG
AGAAAGCTCGAAAAGAAGCAGAAGCATCTCAAAAATTGAATGATGTGGCG
CTTGTTGTTCAAAATGCATATAAAGAGTACCGAGAAGTTCAAAATCAACG
TAGTAAATATAAATCTGACGCTGAATATCAGAAAAAATTAACAGAGGTCG
ACTCTAAAATAGAGAAGGCTAGGAAAGAGCAACAGGACTTGCAAAATAAA
TTTAATGAAGTAAGAGCAGTTGTAGTTCCTGAACCAAATGCGTTGGCTGA
GACTAAGAAAAAAGCAGAAGAAGCTAAAGCAGAAGAAAAAGTAGCTAAGA
GAAAATATGATTATGCAACTCTAAAGGTAGCACTAGCGAAGAAAGAAGTA
GAGGCTAAGGAACTTGAAATTGAAAAACTTCAATATGAAATTTCTACTTT
GGAACAAGAAGTTGCTACTGCTCAACATCAAGTAGATAATTTGAAAAAAC
TTCTTGCTGGTGCGGATCCTGATGATGGCACAGAAGTTATAGAAGCTAAA
TTAAAAAAAGGAGAAGCTGAGCTAAACGCTAAACAAGCTGAGTTAGCAAA
AAAACAAACAGAACTTGAAAAACTTCTTGACAGCCTTGATCCTGAAGGTA
AGACTCAGGATGAATTAGATAAAGAAGCAGAAGAAGCTGAGTTGGATAAA
AAAGCTGATGAACTTCAAAATAAAGTTGCTGATTTAGAAAAAGAAATTAG
TAACCTTGAAATATTACTTGGAGGGGCTGATCCTGAAGATGATACTGCTG
CTCTTCAAAATAAATTAGCTGCTAAAAAAGCTGAGTTAGCAAAAAAACAA
ACAGAACTTGAAAAACTTCTTGACAGCCTTGATCCTGAAGGTAAGACTCA
GGATGAATTAGATAAAGAAGCAGAAGAAGCTGAGTTGGATAAAAAAGCTG
ATGAACTTCAAAATAAAGTTGCTGATTTAGAAAAAGAAATTAGTAACCTG
GAAATATTACTTGGAGGGGCTGATTCTGAAGATGATACTGCTGCTCTTCA
AAATAAATTAGCTACTAAAAAAGCTGAATTGGAAAAAACTCAAAAAGAAT
TAGATGCAGCTCTTAATGAGTTAGGCCCTGATGGAGATGAAGAAGAAACT
```

TABLE 4-continued

```
CCAGCGCCGGCTCCTCAACCAGAGCAACCAGCTCCTGCACCAAAACCAGA
GCAACCAGCTCCAGCTCCAAAACCAGAGCAACCAGCTCCTGCACCAAAAC
CAGAGCAACCAGCTCCAGCTCCAAAACCAGAGCAACCAGCTCCAGCTCCA
AAACCAGAGCAACCAGCTAAGCCGGAGAAACCAGCTGAAGAGCCTACTCA
ACCAGAAAAACCAGCCACTCCAAAAACAGGCTGGAAACAAGAAAACGGTA
TGTGGTATTTCTACAATACTGATGGTTCAATGGCAATAGGTTGGCTCCAA
AACAACGGTTCATGGTACTACCTAAACGCTAACGGCGCTATGGCAACAGG
TTGGGTGAAAGATGGAGATACCTGGTACTATCTTGAAGCATCAGGTGCTA
TGAAAGCAAGCCAATGGTTCAAAGTATCAGATAAATGGTACTATGTCAAC
AGCAATGGCGCTATGGCGACAGGCTGGCTCCAATACAATGGCTCATGGTA
CTACCTCAACGCTAATGGTGATATGGCGACAGGATGGCTCCAATACAACG
GTTCATGGTATTACCTCAACGCTAATGGTGATATGGCGACAGGATGGGCT
AAAGTCAACGGTTCATGGTACTACCTAAACGCTAACGGTGCTATGGCTAC
AGGTTGGGCTAAAGTCAACGGTTCATGGTACTACCTAAACGCTAACGGTT
CAATGGCAACAGGTTGGGTGAAAGATGGAGATACCTGGTACTATCTTGAA
GCATCAGGTGCTATGAAAGCAAGCCAATGGTTCAAAGTATCAGATAAATG
GTACTATGTCAATGGCTTAGGTGCCTTGCAGTCAACACAACTGTAGATGG
CTATAAAGTCAATGCCAATGGTGAATGGGTTTAA
```

(SEQ. ID. NO. 184)
```
MNKKKMILTSLASVAILGAGFVTSQPTFVRAEESPQVVEKSSLEKKYEEA
KAKADTAKKDYETAKKKAEDAQKKYEDDQKRTEEKARKEAEASQKLNDVA
LVVQNAYKEYREVQNQRSKYKSDAEYQKKLTEVDSKIEKARKEQQDLQNK
FNEVRAVVVPEPNALAETKKKAEEEAKAEEKVAKRKYDYATLKVALAKKEV
EAKELEIEKLQYEISTLEQEVATAQHQVDNLKKLLAGADPDDGTEVIEAK
LKKGEAELNAKQAELAKKQTELEKLLDSLDPEGKTQDELDKEAEEAELDK
KADELQNKVADLEKEISNLEILLGGADPEDDTAALQNKLAAKKAELAKKQ
TELEKLLDSLDPEGKTQDELDKEAEEAELDKKADELQNKVADLEKEISNL
EILLGGADSEDDTAALQNKLATKKAELEKTQKELDAALNELGPDGDEEET
PAPAPQPEQPAPAPKPEQPAPAPKPEQPAPAPKPEQPAPAP
KPEQPAPKPEKPAEEPTQPEKPATPKTGWKQENGMWYFYNTDGSMAIGWLQ
NNGSWYYLNANGAMATGWVKDGDTWYYLEASGAMKASQWFKVSDKWYYVN
SNGAMATGWLQYNGSWYYLNANGDMATGWLQYNGSWYYLNANGDMATGWA
KVNGSWYYLNANGAMATGWAKVNGSWYYLNANGSMATGWVKDGDTWYYLE
ASGAMKASQWFKVSDKWYYVNGLGALAVNTTVDGYKVNANGEWVZ
```

ID302

(SEQ. ID. NO. 197)
```
ATGTTTGCATCAAAAAGCGAAAGAAAAGTACATTATTCAATTCGTAAATT
TAGTGTTGGAGTAGCTAGTGTAGTTGTTGCCAGTCTTGTTATGGGAAGTG
TGGTTCATGCGACAGAGAACGAGGGAGCTACCCAAGTACCCACTTCTTCT
AATAGGGCAAATGAAAGTCAGGCAGAACAAGGAGAACAACCTAAAAAACT
```

TABLE 4-continued

```
CGATTCAGAACGAGATAAGGCAAGGAAAGAGGTCCAGGAATATGTAAAAA
AAATAGTGGGTGAGAGCTATGCAAAATCAACTAAAAAGCGACATACAATT
ACTGTAGCTGCCAGTCTTGTTATGGGAAGTGTGGTTCATGCGACAGAGAA
CGAGGGAGCTACCCAAGTACCCACTTCTTCTAATAAGATACTGATGATGG
AGAGTCGATCAAAAGTAGATGAAGCTGTGTCTAAGTTTGAAAAGGACTCA
TCTTCTTCGTCAAGTTCAGACTCTTCCACTAAACCGGAAGCTTCAGATAC
AGCGAAGCCAAACAAGCCGACAGAACCAGGAGAAAAGGTAGCAGAAGCTA
AGAAGAAGGTTGAAGAAGCTGAGAAAAAAGCCAAGGATCAAAAGAAGAA
GATCGTCGTAACTACCCAACCATTACTTACAAAACGCTTGAACTTGAAAT
TGCTGAGTCCGATGTGGAAGTTAAAAAAGCGGAGCTTGAACTAGTAAAAG
TGAAAGCTAACGAACCTCGAGACGAGCAAAAAATTAAGCAAGCAGAAGCG
GAAGTTGAGAGTAAACAAGCTGAGGCTACAAGGTTAAAAAAAATCAAGAC
AGATCGTGAAGAAGCAGAAGAAGAAGCTAAACGAAGAGCAGATGCTAGAT
GCGAAGTCTTCAGATTCTAGCGTAGGTGAAGAAACTCTTCCAAGCCCATC
CCTGAAACCAGAAAAAAAGGTAGCAGAAGCTGAGAAGAAGGTTGAAGAAG
CTAAGAAAAAGCCGAGGATCAAAAGAAGAAGATCGCCGTAACTACCCA
ACCAATACTTAGAAAACGCTTGAACTTGAAATTGCTGAGTCCGATGTGGA
AGTTAAAAAAGCGGAGCTTGAACTAGTAAAAGAGGAAGCTAAGGAACCTC
GAAACGAGGAAAAAGTTAAGCAAGCAAAAGCGGAAGTTGAGAGTAAAAAA
GCTGAGGCTACAAGGTTAGAAAAAATCAAGACAGATCGTAAAAAAGCAGA
AGAAGAAGCTAAACGAAAAGCAGCAGAAGAAGATAAAGTTAAGAAAAAC
CAGCTGAACAACCACAACCAGCGCCGGCTCCAAAAGCAGAAAAACCAGCT
CCAGCTCCAAAACCAGAGAATCCAGCTGAACAACCAAAAGCAGAAAAACC
AGCTGATCAACAAGCTGAAGAAGACTATGCTCGTAGATCAGAAGAAGAAT
ATAATCGCTTGACTCAACAGCAACCGCCAAAAACTGAAAAACCAGCACAA
CCATCTACTCCAAAAACAGGCTGGAAACAAGAAAACGGTATGTGGTACTT
CTACAATACTGATGGTTCAATGGCGACAGGATGGCTCCAAAACAATGGCT
CATGGTACTACCTCAACAGCAATGGCGCTATGGCGACAGGATGGCTCCAA
AACAATGGTTCATGGTACTATCTAAACGCTAATGGTTCAATGGCAACAGG
TTGGCTCCAAAACAATGGTTCATGGTACTACCTAAACGCTAATGGTTCAA
TGGCGACAGGATGGCTCCAATACAATGGCTCATGGTACTACCTAAACGCT
AATGGTTCAATGGCGACAGGATGGCTCCAATACAATGGCTCATGGTACTA
CCTAAACGCTAATGGTGATATGGCGACAGGTTGGGTGAAAGATGGAGATA
CCTGGTACTATCTTGAAGCATCAGGTGCTATGAAAGCAAGCCAATGGTTC
AAAGTATCAGATAAATGGTACTATGTCAATGGCTCAGGTGCCCTTGCAGT
CAACACAACTGTAGATGGCTATGGACTCAATGCCAATGGTGAATGGGTAA
ACTAA
                                (SEQ. ID. NO. 185)
MFASKSERKVHYSIRKFSVGVASVVVASLVMGSVVHATENEGATQVPTSS
NRANESQAEQGEQPKKLDSERDKARKEVEEYVKKIVGESYAKSTKKRHTI
TVALVENELNNIKNEYLNKIVESTSESQLQILMMESRSKVDEAVSGEKDS
SSSSSSSDSSTKPEASDTAKPNKPTEPGEKVAEAKKKVEEAEKKAKDQKEE
DRRNYPTITYKTLELEIAESDVEVKKAELELVKVKANEPRDEQKIKQAEA
EVESKQAEATRLKKIKTDREEAEEEAKRRADAKEQGKPKGRAKRGVPGEL
ATPDKKENDAKSSDSSVGEETLPSPSLKPEKKVAEAEKKVEEAKKKAEDQ
KEEDRRNYPTNTYKTLELEIAESDVEVKKAELELVKEEAKEPRNEEKVKQ
AKAEVESKKAEATRLEKIKTDRKKAEEEAKRKAAEEDKVKEKPAEQPQPA
PAPKAEKPAPAPKPENPAEQPKAEKPADQQAEEDYARRSEEEYNRLTQQQ
PPKTEKPAQPSTPKTGWKQENGMWYFYNTDGSMATGWLQNNGSWYYLNSN
GAMATGWLQNNGSWYYLNANGSMATGWLQNNGSWYYLNANGSMATGWLQY
NGSWYYLNANGSMATGWLQYNGSWYYLNANGDMATGWVKDGDTWYYLEAS
GAMKASQWFKVSDKWYYVNGSGALAVNTTVDGYGVNANGEWVNZ
```

ID303

```
                                (SEQ. ID. NO. 198)
ATGGTAAAAAGACGTATAAGGAGAGGGACGAGAGAACCTGAAAAAGTTGT
TGTTCCTGAGCAATCATCTATTCCTTCGTATCCTGTATCTGTTACATCTA
ACCAAGGAACAGATGTAGCAGTAGAACCAGCTAAAGCAGTTGCTCCAACA
ACAGACTGGAAACAAGAAAATGGTATGTGGTATTTTTATAATACTGATGG
TTCCATGGCAACAGGTGGGTACAAGTTAATAGTTCATGGTACTACCTCAA
CAGCAACGGTTCTATGAAAGTCAATCAATGGTTCCAAGTTGGTGGTAAAT
GGTATTATGTAAATACATCGGGTGAGTTAGCGGTCAATACAAGTATAGAt
GGCTATAGAGTCAATGATAATGGTGAATGGGTGCGTTAA
                                (SEQ. ID. NO. 186)
MVKRRIRRGTREPEKVVVPEQSSIPSYPVSVTSNQGTDVAVEPAKAVAPT
TDWKQENGMWYFYNTDGSMATGWVQVNSSWYYLNSNGSMKVNQWFQVGGK
WYYVNTSGELAVNTSIDGYRVNDNGEWVRZ
```

ID304

```
                                (SEQ. ID. NO. 199)
CTGAATACAAGTTTTGTTCATGCTGCTGATGGGATTCAATATGTCAFAGA
TGATACTAGAGATAAAGAAGAGGGAATAGAGTATGATGACGCTGACAATG
GGGATATTATTGTAAAAGTAGCGACTAAACCTAAGGTAGTAACCAAGAAA
ATTTCAAGTACGCGAATTCGTTATGAAAAAGATGAAACAAAAGACCGTAG
TGAAAATCCTGTTACAATTGATGGAGAGGATGGCTATGTAACTACGACAA
GGACCTACGATGTTAATCCAGAGACTGGTTATGTTACCGAACAGGTTACT
GTTGATAGAAAAGAAGCCACGGATACAGTTATCAAAGTTCCAGCTAAAAG
CAAGGTTGAAGAAGTTCTTGTTCCATTTGCTACTAAATATGAAGCAGACA
ATGACCTTCTGCAGGACAGGAGCAAGAGATTACTCTAGGAAAGAATGGG
AAAACAGTTACAACGATAACTTATAATGTAGATGGAAAGAGTGGACAAGT
AACTGAGAGTACTTTAAGTCAAAAAAAAGACTCTCAAACAAGAGTTGTTA
AAAAAAGAACCAAGCCCCAAGTTCTTGTCCAAGAAATTCCAATCGAAACA
```

TABLE 4-continued

GAATATCTCGATGGCCCAACTCTTGATAAAAGTCAAGAAGTAGAAGAAGT

AGGAGAAATTGGTAAATTACTCTTACTACAATCTATACTGTAG (SEQ. ID. NO. 187)
LNTSFVHAADGIQYVRDDTRDKEEGIEYDDADNGDIIVKVATKPKVVTKK

ISSTRIRYEKDETKDRSENPVTIDGEDGYVTTTRTYDVNPETGYVTEQVT

VDRKEATDTVIKVPAKSKVEEVLVPFATKYEADNDLSAGQEQEITLGKNG

KTVTTITYNVDGKSGQVTESTLSQKKDSQTRVVKKRTKPQVLVQEIPIET

EYLDGPTLDKSQEVEEVGEIGKLLLLQSILZ

ID305

(SEQ. ID. NO. 200)
ATGAAGCTTTTGAAAAAAATGATGCAAATCGCACTAGCCACATTTTTCTT

CGGTTTGTTAGCGACAAATACAGTATTTGCAGATGATTCTGAAGGATGGC

AGTTTGTCCAAGAAAATGGTAGAACCTACTACAAAAAGGGGGATCTAAAA

GAAACCTACTGGAGAGTGATAGATGGAAGTACTATTATTTTGATCCTTT

ATCCGGAGAGATGGTTTGTCGGCTGGCAATATATACCTGCTCCACACAAG

GGGGTTACGATTGGTCCTTCTCCAAGAATAGAGATTGCTCTTAGACCAGA

TTGGTTTTATTTTGGTCAAGATGGTGTATTACAAGAATTTGTTGGCAAGC

AAGTTTTAGAAGCAAAAACTGCTACGAATACCAACAAACATCATGGGGAA

GAATATGATAGCCAAGCAGAGAAACGAGTCTATTATTTTGAAGATCAGCG

TAGTTATCACTTTAAAAACTGGTTGGATTTATGAAGAGGGTCATTGGT

ATTATTTACAGAAGGATGGTGGCTTTGATTCGCGCATCAACAGATTCACG

GTTGGAGAGCTAGCACGTGGTTGGGTTAAGGATTACCCTCTTACGTATGA

TGAAGAGAAGCTAAAAGCAGCTCCATGGTACTATCTAAATCCAGCAACTG

GCATTATGCAAACAGGTTGGCAATATCTAGGTAATAGATGGTACTACCTC

CATTCGTCAGGAGCTATGGCAACTGGCTGGTATAAGGAAGGCTCAACTTG

GTACTATCTAGATGCTGAAAATGGTGATATGAGAACTGGCTGGCAAAACC

TTGGGAACAAATGGTACTATCTCCGTTCATCAGGAGCTATGGCAACTGGT

TGGTATCAGGAAAGTTCGACTTGGTACTATCTAAATGCAAGTAATGGAGA

TATGAAAACAGGCTGGTTCCAAGTCAATGGTAACTGGTACTATGCCTATG

ATTCAGGTGCTTTAGCTGTTAATACCACAGTAGGTGGTTACTACTTAAAC

TATAATGGTGAATGGGTTAAGTAA (SEQ. ID. NO. 188)
MKLLKKMMQIALATFFFGLLATNTVFADDSEGWQFVQENGRTYYKKGDLK

ETYWRVIDGKYYFDPLSGEMVVGWQYIPAPHKGVTIGPSPRIEIALRPD

WFYFGQDGVLQEFVGKQVLEAKTATNTNKHHGEEYDSQAEKRVYYFEDQR

SYHTYLHSSGAMATGWYKEGSTWYYLDAENGDMRTGWQNLGNKWYYLRSS

GAMATGWYQESSTWYYLNASNGDMKTGWFQVNGNWYYAYDSGALAVNTTV

GGYYLNYNGEWVKZ

ID306

(SEQ. ID. NO. 201)
TTGGCTGGTAGATATGGTTCTGCTGTTCAGTGTACAGAAGTGACTGCCTC

AAACCTTTCAACAGTTAAAACTAAAGCTACGGTTGTAGAAAAACCACTGA

AAGATTTTAGAGCGTCTACGTCTGATCAGTCTGGTTGGGTGGAATCTAAT

GGTAAATGGTATTTCTATGAGTCTGGTGATGTGAAGACAGGTTGGGTGAA

AACAGATGGTAAATGGTACTATTTGAATGACTTAGGTGTCATGCAGACTG

GATTTGTAAAATTTTCTGGTAGCTGGTATTACTTGAGCAATTCAGGTGCT

ATGTTTACAGGCTGGGGAACAGATGGTAGCAGATGGTTCTACTTTGACGG

CTCAGGAGCTATGAAGACAGGCTGGTACAAGGAAAATGGCACTTGGTATT

ACCTTGACGAAGCAGGTATCATGAAGACAGGTTGGTTTAAAGTCGGACCA

CACTGGTACTATGCCTACGGTTCAGGAGCTTTGGCTGTGAGCACAACAAC

ACCAGATGGTTACCGTGTAAATGGTAATGGTGAATGGGTAAACTAG (SEQ. ID. NO. 189)
LAGRYGSAVQCTEVTASNLSTVKTKATVVEKPLKDFRASTSDQSGWVESN

GKWYFYESGDVKTGWVKTDGKWYYLNDLGVMQTGFVKFSGSWYYLSNSGA

MFTGWGTDGSRWFYFDGSGAMKTGWYKENGTWYYLDEAGIMKTGWFKVGP

HWYYAYGSGALAVSTTTPDGYRVNGNGEWVNZ

ID307

(SEQ. ID. NO. 200)
ATGAAAATTTTGAAAAAAACTATGCAAGTTGGACTGACAGTATTTTTCTT

TGGTTTGCTAGGGACCAGTACAGTATTTGCAGATGATTCTGAAGGATGGC

AGTTTGTCCAAGAAAACGGAAGAACCTACTACAAAAAGGGGGACCTCAAA

GAAACCTACTGGCGAGTGATTGATGGTAAGTACTATTATTTTGATTCTCT

ATCTGGAGAGATGGTTGTCGGCTGGCAATATATCCCGTTTCCATCTAAAG

GTAGTACAATTGGTCCTTACCCAAATGGTATCAGATTAGAAGGTTTTCCA

AAGTCAGAGTGGTACTACTTCGATAAAAATGGAGTGCTACAAGAGTTTGT

TGGTTGGAAAACATTAGAGATTAAAACTAAAGACAGTGTTGGAAGAAAGT

ACGGGGAAAAACGTGAAGATTCAGAAGATAAAGAAGAGAAGCGTTATTAT

ACGAACTATTACTTTAATCAAAATCATTCTTTAGACACACGTTCGCTTTA

TGATCAGTCTAACTCGTATTATCTAGCTAAGACGGAAATTAATGGAGAAA

ACTACCTTGGTGGTGAAAGACGTGCGGGGTGGATAAACGATGATTCGACT

TGGTACTACCTAGATCCAACAACTGGTATTATGCAAACAGGTTGGCAATA

TCTAGGTAATAAGTGGTACTACCTCCGTTCCTCAGGAGCAATGGCCACTG

GCTGGTATCAGGAAGGTACCACTTGGTATTATTTAGACCACCCAAATGGC

GATATGAAACAGGTTGGCAAAACCTTGGGAACAAATGGTACTATCTCCG

TTCATCAGGAGCTATGGCAACTGGTTGGTATCAAGATGGTTCAACTTGGT

ACTACCTAAATGCAGGTAATGGAGACATGAAGACAGGTTGGTTCCAGGTC

AATGGCAACTGGTACTATGCTTAT

TABLE 4-continued (SEQ. ID. NO. 190)
MKILKKTMQVGLTVFFFGLLGTSTVFADDSEGWQFVQENGRTYYKKGDLK
ETYWRVIDGKYYYFDSLSGEMVVGWQYIPFPSKGSTIGPYPRGIRLEGFP
KSEWYYFDIQGVLQEFVGWKTLEILKTISVGRKYGEKREDSEDKEEKRYY
TNYYFNQNHSLETGWLYDQSNWYYLAKTIENGENYLGGERRAGWINDDST
WYYLDPTTGIMQTGWQYLGNKWYYLRSSGAMATGWYQEGTTWYYLDHPNG
DMKTGWQNLGNKWYYLRSSGAMATGWYQDGSTWYYLNAGNGDMKTGWFQV
NGNWYYAYSSGALAVNTTVDGYSVNYNGEWVRZ

ID308

(SEQ. ID. NO. 203)
ATGAAAAAGAAATTAACTAGTTTAGCACTTGTAGGCGCTTTTTTAGGTTT
GTCATGGTATGGGAATGTTCAGGCTGAAGAAAGTTCAGGAAATAAAATCC
ACTTTATCAATGTTCAAGAAGGTGGCAGTGATGCGATTATTCTTGAAAGC
AATGGACATTTTGCCATGTGGATACAGGAGAAGATTATGATTTCCCAGA
TGGAAGTGATTCTCGCTATCCATGGAGAGAAGGAATTGAAACGTCTTATA
AGCATGTTCTAACAGACCGTGTCTTTCGTCGTTTGAAGGAATTGGGTGTC
CAAAAACTTGATTTTATTTTGGTGACCCATACCCACAGTGATCATATTGG
AAATGTTGATGAATTACTGTCTACCTATCCAGTTGACCGAGTCTATCTTA
AGAAATATAGTGATAGTCGTATTACTAATTCTGAACGTCTATGGGATAAT
CTGTATGGCTATGATAAGGTTTTACGACTGCTGCAGAAAAAGGTGTTTC
AGTTATTCAAAATATCACACAAGGGGATGCTCATTTTCAGTTTGGGGACA
TGGATATTCAGCTCTATAATTATGAAAATGAAACTGATTCATCGGGTGAA
TTAAAGAAAATTTGGGATGACAATTCCAATTCCTTGATThGCGTGGTGAA
AGTCAATGGCAAGAAAATTTACCTTGGGGGCGATTTAGATAATGTTCATG
GAGCAGAAGACAAGTATGGTCCTCTCATTGGAAAAGTTGATTTGATGAAG
TTTAATCATCACCATGATACCAACAAATCAAATACCAAGGATTTCATTAA
AAATTTGAGTCCAGTTTGATTGTTCAAACTTCGGATAGTCTACCTTGGA
AAAATGGTGTTTGATAGTGAGTATGTTAATTGGCTCAAAGAACGAGGAAT
TGAGAGAATCACGCAGCCAGCAAAGACTATGATGCAACAGTTTTTGATAT
TCGAAAAGACGGTTTTGTCAATATTTCAACATCCTACAAGCCGATTCCAA
GTTTTCAAGCTGGTTGGCATAAGAGTGCATATGGGAACTGGTGGTATCAA
GCGCCTGATTCTACAGGAGAGTATGCTGTCGGTTGGAATGAAATCGAAGG
TGAATGGTATTACTTTAACCAAACGGGTATCTTGTTACAGAATCAATGGA
AAAAATGGAACAATCATTGGTTCTATTGACAGACTCTGGTGCTTCTGCT
AAAAAATTGGAAGAAAATCGCTGGAATCTGGTATTATTTTAACAAAGAAAA
CCAGATGGAAATTGGTTGGATTCAAGATA)*AGAGCAGTGGTATTATTTG
GATGTTGATGGTTCTATGAAGACAGGATGGCTTCAATATATGGGGCAATG
GTATTACTTTGCTCCATCAGGGGAAATGAAAATGGGCTGGGTAAAAGATA
AAGAAACCTGGTACTATATGGATTCTACTGGTGTCATGAAGACAGGTGAG
ATAGAAGTTGCTGGTCAACATTATTATCTGGAAGATTCAGGAGCTATGAA
GCAAGGCTGGCATAAAAAGGCAAATGATTGGTATTTCTACAAGACAGACG
GTTCACGAGCTGTGGGTTGGATCAAGGACAAGGATAAATGGTACTTCTTG
AAAGAAAATGGTCAATTACTTGTGAACGGTAAGACACCAGAAGGTTATAC
TGTGGATTCAAGTGGTGCCTGGTTAGTGGATGTTTCGATCGAGAAATCTG
CTACAATTAAAACTACAAGTCATTCAGAAATAAAAGAATCCAAAGAAGTA
GTGAAAAAGGATCTTGAAAATAAAGAAACGAGTCAACATGAAAGTGTTAC
AAATTTTTCAACTAGTCAAGKTTTGACATCCTCAACTTCACAAAGCTCTG
AAACGAGTGTAAACAAATCGGAATCAGAACAGTAG (SEQ. ID. NO. 191)
MKKKLTSLALVGAFLGLSWYGNVQAQESSGNKIHFINVQEGGSDAIILES
NGHFAMVDTGEDYDFPDGSDSRYPWREGIETSYKHVLTDRVFRRLKELGV
QKLDFILVTHTHSDHIGNVDELLSTYPVDRVYLKKYSDSRITNSERLWDN
LYGYDKVLQTAAEKGVSVIQNITQGDAHFQFGDMDIQLYNYENETDSSGE
LKKIWDDNSNSLISVVKVNGKKIYLGGDLDNVHGAEDKYGPLIGKVDLMK
FNHHHDTNKSNTKDFIKNLSPSLIVQTSDSLPWJGVDSRYVNWLKERGIL
ERINAASKDYDATVFDIRKDGFVNISTSYKPIPSFQAGWHKSAYGNWWYQ
APDSTGEYAVGWNEIEGEWYYFNQTGILLQNQWKKWNNHWFYLTDSGASA
KNWKKIAGIWYYFNKENQMEIGWIQDKEQWYYLDVDGSMKTGWLQYMGQW
YYFAPSGEMKMGWVKDKETWYYMDSTGVMKTGEIEVAGQHYYLEDSGAMK
QGWHKKANDWYFYKTDGSRAVGWIKDKDKWYFLKENGQLLVNGKTPEGYT
VDSSGAWLVDVSIEKSATIKTTSHSEIKESKEVVKKDLENKETSQHESVT
MFSTSQDLTSSTSQSSETSVNKSESEQZ

ID309

(SEQ. ID. NO. 204)
ATGGAAATTAATGTGAGTAAATTAAGAACAGATTTGCCTCAAGTCGGCGT
GCAACCATATAGGCAAGTACACGCACACTCAACTGGGAATCCGCATTCAA
CCGTACAGAATGAAGCGGATTATCACTGGCCGAAAGACCCAGAATTAGGT
TTTTTCTCGCACATTGTTGGGAACGGTTGCATCATGCAGGTAGGACCTGT
TGATAATGGTGCCTGGGACGTTGGGGGCGGTTGGAATGCTGAGACCTATG
CAGCGGTTGAACTGATTGAAAGCCATTCAACCAAAGAAGAGTTCATGACG
GACTACCGCCTTTATATCGAACTCTTACGCAATCTAGCAGATGAAGCAGG
TTTGCCGAAAACGCTTGATACAGGGAGTTTAGCTGGAATTAAAACGCACG
AGTATTGCACGAATAACCAACCAAACAACCACTCAGACCACGTTGACCCT
TATCCATATCTTGCTAAATGGGGCATTAGCCGTGAGCAGTTTAAGCATGA
TATTGAGAACGGCTTGACGATTGAAACAGGCTGGCAGAAGAATGACACTG
GCTACTGGTACGTACATTCAGACGGCTCTTATCCAAAAGACAAGTTTGAG
AAAAATCAATGGCACTTGGTACTACTTTGACAGTTCAGGCTATATGCTTGC
AGACCGCTGGAGGAAGCACACAGACGGCAACTGGTACTGGTTCGACAACT
CAGGCGAAATGGCTACAGGCTGGAAGAAAATCGCTGATAAGTGGTACTAT
TTCAACGAAGAAGGTGCCATGAAGACAGGCTGGGTCAAGTACAAGGACAC
TTGGTACTACTTAGACGCTAAAGAAGGCGCCATGGTATCAAATGCCTTTA

TABLE 4-continued

TCCAGTCAGCGGACGGAACAGGCTGGTACTACCTCAAACCAGACGGAACA
CTGGCAGACAAGCCAGAATTCACAGTAGAGCCAGATGGCTTGATTACAGT
AAAATAA (SEQ. ID. NO. 192)
MEINVSKLRTDLPQVGVQPYRQVHAHSTGNPHSTVQNEADYHWRKDPELG
FFSHIVGNGCIMQVGPVDNGAWDVGGGWNAETYAAVELIESHSTKEEFMT
DYRLYIELLRNLADEAGLPKTLDTGSLAGIKTHEYCTNNQPNNHSDHVDP
YPYLAKWGISREQFKHDIENGLTIETGWQKNDTGYWYVHSDGSYPKDKFE
KINGTWYYFDSSGYMLADRWRKHTDGNWYWFDNSGEMATGWKKIADKWYY
FNEEGAMKTGWVKYKDTWYYLDAKEGAMVSNAFIQSADGTGWYYLKPDGT
LADKPEFTVEPDGLITVKZ

ID310

(SEQ. ID. NO. 205)
ATGGGCACAACAGGATTTACAATAATTGACTTAATTATCTTGATTTGTTT
ATTTACTTGCGGTGTTGGTTGCAGGTATCTATTTCTCTAAAAAAGAGATG
AAAGGAAAAGAGTTCTTTAAAGGAGATGGTTCGGTTCTTCGGTATGTTAC
TTCGGTATCCATTTTTGCCACAATGCTCAGTCCGATTTCCTTCTTGGGAC
TCGCTGGTAGCTCTTATGCAGGTAGCTGGATTTTATGGTTTGCTCAATTA
GGGATGGTAGTAGCTATTCCACTGACAATTCGTTTTATCTTACCTATCTT
TGCACGGATAGACATCGATACGGCATATGATTACTTGGATAAACGTTTTA
ATTCTAAAGCACTTCGTATTATTTCAGCACTCTTGTTTATTATTTATCAA
TTGGGACGTATGTCTATCATTATGTACCTCCCATCAGCTGGTTTATCAGT
ATTCAGAGGAATTGACATCAATATTTTGATTATTTTGATGGGTGTAGTTG
CAATTGTTTATTCTTATACTGGTGGTCTAAAATCCGTATTATGGACAGAC
TTTATTCAAGGTGTGATTCTGATTAGTGGTGTCGTTTTAGCTTTATTTGT
ACTGATTGCTAATATTAAAGGTGGCTTTGGTGCAGTAGCAGAAACATTAG
CAAACGGGAAATTCCTTGCTGCAAATGAAAAACTTTTCGATCCTAACTTG
CTTTCAAACTCCATCTTTTTAATTGTGATGGGTTCAGGCTTTACAATCTT
GTCTTCCTATGCTTCATCTCAAGATTTGGTTCAACGTTTTACTACAACAC
AAAATATTAAGAAACTTAATAAGATGTTGTTCACAAAGCCTGTTTTGTCA
CTTGCAACTGCAACAGTCTTTTACTTGATTGGTACAGGCTTGTACGTATT
CTATCAAGTACAAAATGCAGATAGTGCAGCTAGCAATATCCCTCAAGACC
AAATCTTTATGTACTTTATTGCATACCAGTTACCAGTAGGTATCACAGGT
TTGATCTTGGCAGCGATTTATGCAGCATCTCAATCAACTATTTCAACAGG
TTTGAACTCTGRTGCAACTTCATGGACATTGGATATTCAAGATGTCATTT
CTAAAAATATGTCAGACAATCGTCGTACGAAAATTGCACAATTCGTATCT
CTAGCAGTAGGTTTATTCTCAATTGGTGTTTCCATTGTCATGGCTCACTC
AGATATTAAATCTGCATACGAATGGTTCAATAGTTTCATGGGACTTGTAC
TTGGTCTACTTGGTGGTGTATTTATTCTTGGATTTGTTTCTAAAAAAGCA
AATAAACAAGGTGCTTATGCAGCGCTGATTGTATCAACCATCGTCATGGT

TABLE 4-continued

ATTTATTAAATACTTCCTTCCTCCAACAGCTGTTAGCTACTGGGCATATT
CATTGATTTCAATCTCTGTATCAGTAGTTTCAGGTTATATTGTATCTGTT
CTTACTGGAAATAAAGTATCTGCACCTAAATATACAACGATRCATGATAT
TACAGAAATTAAAGCGGATTCAAGTTGGGAAGTTCGTCACTAA (SEQ. ID. NO. 193)
MGTTGFTIIDLIILIVYLLAVLVAGIYFSKKEMKGKEFFKGDGSVPWYVT
SVSIFATMLSPISFLGLAGSSYAGSWILWFAQLGMVVAIPLTIRFILPIF
ARIDIDTAYDYLDKRFNSKALRIISALLFIIYQLGRMSIIMYLPSAGLSV
LTGIDINILIILMGVVAIVYSYTGGLKSVLWTDFIQGVILISGVVLALFV
LIANIKGGFGAVAETLANGKELAANEKLFDPNLLSNSIFLIVMGSGFTIL
SSYASSQDLVQRFTTTQNIKKLN14LFTNGVLSLATAIVFYLIGTGLYVF
YQVQNADSAASNIPQDQIFMYFIAYQLPVGITGLILAAIYAASQSTISTG
LNSVATSWTLDIQDVISKNMSDNRRTKIAQFVSLAVGLFSIGVSIVMAHS
DIKSAYEWFNSFMGLVLGLLGGVFILGFVSKKANKQGAYAALIVSTIVMV
FIKYFLPPTAVSYWAYSLISISVSVVSGYIVSVLTGNKVSAPKYTTIHDI
TEIKADSSWEVRHZ

ID311

(SEQ. ID. NO. 206)
ATGAAAATTAATAAAAAATATCTAGCAGGTTCAGTGGCAGTCCTTGCCCT
AAGTGTTTGTTCCTATGAGCTTGGTCGTCACCAAGCTGGTCAGGATAAGA
AAGAGTCTAATCGAGTTGCTTATATAGATGGTGATCAGGCTCGTCAAAAG
GCAGAAAACTTGACACCAGATGAAGTCAGTAAGAGGGAGGGGATCAACGC
CGAACAAATCCTCATCAAGATTACGGATCAAGGTTATGTGACCTCTCATG
GAGACCATTATCATTACTATAATGGCAAGCTCCCTTATGATGCCATCATC
AGTGAAGAGCTCCTCATGAAAGATCCGAATTATCAGTTGAAGGATTCAGA
CATTGTCAATGAAATCAAGGGTGGTTATGTCATCAAGGTAGACGGAAAAT
ACTATGTThCCTTAAGGATGCAGCTCATGCGGATAATATTCGGACAAAAG
AAGAGATTAAACGTCAGAAGCAGGAACGCAGTCATAATCACGGGTCAGGA
GCTAACGATCATGCAGTAGCTGCAGCCAGAGCCCAAGGACGCTATACAAC
GGATGATGGGTATATCTTCAATGCATCTGATATCATTGAGGACACGGGTG
ATGCTTATATCGTTCCTCACGGCGACCATTACCATTACATTCCTAAGAAT
GAGTTATCAGCTAGCGAGTTAGCTGCTGCAGAAOCCTATTGGAATGGGAA
GCAGGGATCTCGTCCTTCTTCAAGTTCTAGTTATAATGCAAATCCAGCTC
AACCAAGATTGTCAGAGAACCACAATCTGACTGTCACTCAAACTTATCAT
CAAAATCAAGGGGAAAACATTICAAGCCTTTTACGTGAATHGTATGCTAA
ACCCTTATCAGAACGCCCATTGGAATCTGATGGCCTTATTTTCGACCCAG
CGCAAATCACAAGTCGAACCCCCAGAGGTGTAGCTGTCCCTCATGGTAAC
CATTACCACTTTATCCCTTATGAACAAATCTCTGAATTGGAAAAACGAAT
TGCTCGTATTATTCCCCTTCGTTATCGTTCAAACCATTGGGTACCAGATT
CAAGACCAGAACAACCAAGTCCACAATCGACTCCGGAACCTAGTCCAAGT
CCGCAACCTGCACCAAATCCTCAACCAGCTCCAAGCAATCCAATTGATGA

TABLE 4-continued

GAAATTGGTCAAAGAAGCTGTTCGAAAAGTAGGCGATGGTTATGTCTTTG
AGGAGAATGGAGTTTCTCGTTATATCCCAGCCAAGGATCTTTCAGCAGAA
ACAGCAGCAGGCATTGATAGCAAACTGGCCAAGCAGGAAAGTTTATCTCA
TAAGCTAGGAGCTAAGAAAACTGACCTCCCATCTAGTGATCGAGAATTTT
ACAATAAGGCTTATGACTTACTAGCAAGAATTCACCAAGATTTACTTGAT
AATAAAGGTCGACAAGTTGATTTGAGGCTTTGGATAACCTGTTGGAACG
ACTCAAGGATGTCCCAAGTGATAAAGTCAAGTTAGTGGATGATATTCTTG
CCTTCTTAGCTCCGATTCGTCATCCAGAACGTTTAGGAAAACCAAATGCG
CAAATTACCTACACTGATGATGAGATTCAAGTAGCCAAGTTGGCAGGCAA
GTACACAACAGAAGACGGTTATATCTTTGATCCTCGTGATATAACCAGTG
ATGAGGGGATGCCTATGTAACTCCACATATGACCCATAGCCACTGGATT
AAAAAAGATAGTTTGTCTGAAGCTGAGAGAGCGGCAGCCCAGGCTTATGC
TAAAGAGAAAGGTTTGACCCCTCCTTCGACAGACCATCAGGATTCAGGAA
ATACTGAGGCAAAAGGAGCAGAAGCTATCTACAACCGCGTGAAAGCAGCT
AAGAAGGTGCCACTTGATCGTATGCCTTACAATCTTCAATATACTGTAGA
AGTCAAAAACGGTAGTTTAATCATACCTCATTATGACCATTACCATAACA
TCAAATTTGAGTGGTTTGACGAAGGCCTTTATGAGGCACCTAAGGGGTAT
ACTCTTGAGGATCTTTTGGCGACTGTCAAGTACTATGTCGAACATCCAAA
CGAACGTCCGCATTCAGATAATGGTTTTGGTAACGCTAGCGACCATGTTC
AAAGAAACAAAAATGGTCAAGCTGATACCAATCAAACGGAAAAACCAAGC
GAGGAGAAACCTCAGACAGAAAAACCTGAGGAAGAAACCCCTCGAGAAGA
GAAACCGCAAAGCGAGAAACCAGAGTCTCCAAAACCAACAGAGGAACCAG
AAGAATCACCAGAGGAATCAGAAGAACCTCAGGTCGAGACTGAAAAGGTT
GAAGAAAACTGAGAGAGGCTGAAGATTTACTTGGAAAAATCCAGGATCC
AATTATCAAGTCCAATGCCAAAGAGACTCTCACAGGATTAAAAAATAATT
TACTATTTGGCACCCAGGACAACAATACTATTATGGCAGAAGCTGAAAAA
CTATTGGCTTTATTAAAGGAGAGTAAGTAA (SEQ. ID. NO. 194)
MKINKKYLAGSVAVLALSVCSYELGRHQAGQDKKESNRVAYIDGDQAGQK
AENLTPDEVSKREGINAEQIVIKITDQGYVTSHGDHYHYYNGKVPYDAII
SEELLMKDPNYQLKDSDIVNEIKGGYVIKVDGKYYVYLKDAAHADNIRTK
EEIKRQKQERSHNHGSGANDHAVAAARAQGRYTTDDGYIFNASDIIEDTG
DAYIVPHGDHYYIPKNELSASELAAAEAYWNGKQGSRPSSSSSYNANPA
QPRLSENWNTTVTPTYHQNQGENISSLLRELYAKPLSERJVESDGLIFDP
AOITSRTARGVAVPHGNHYHFIPYEQMSELEKRIARIIPLRYRSNHWVPD
SRPEQPSPQSTPEPSPSPQPAP4PQPAPSNPIDEKLVKEAVRKVGDGYVF
EENGVSRYIPAKDLSAETAAGIDSKLAKQESLSHKLGAKKTDLPSSDREF
YNKAYDLLARIHQDLLDNKGRQVDFEALDNLLERLKDVPSDKVKLVDDIL
AFLAPIRHPERLGKPNAQITYTDDEIQVAKLAGKYTTEDGYIFDPRDITS
DEGDAYVTPHMTHSHWIKKDSLSEAERAAAQAYAKEKGLTPPSTDHQDSG

NTEAKGAEAIYNRNKAAKKVPLDRMPYNLQYTVEVKNGSLIIPHYDHYHN
IKFEWFDEGLYEAPKGYTLEDLLATVKYYVEHPNERPHSDNGFGNASDHV
QRNKNGQADTNQTEKPSEEKPQTEKPEEETPREEKPQSEKPESPKPTEEP
EESPEESEEPQVETEKVEEKLREAEDLLGKIQDPIIKSNAKETLTGLKNN
LLFGTQDNNTIMAEAEKLLALLKESKZ

ID312

(SEQ. ID. NO. 307)
ATGGAGGGATTGGTTAGAGTGCATTTATTGCCTGTATTTGGCGATTACAA
GCTATCTAAACTTACTACGCCTATTCTTCAACAGCAAGTAAACAAATGGG
CTGACAAGGCAAATAAAGGCGAAAAGGGGCATTTGCTAACTACTCTTTG
CTCCATAACATGAATAAGCGTATTTTGAAATATGGCGTAGCTATCCAGGT
AATACAATACAACCCAGCTAATGATGTCATCGTTCCACGCAAACAGCAAA
AAGAAAAGGCTGCTGTCAAATACTTAGACAACAAAGAATTAAAACAGTTT
CTTGATTATTTAGATGCTCTGGATCAATCAAATTATGAGAACTTATTTGA
TGTTGTTCTGTATAAGACTTTATTGGCCACTGGTTGCCGTATTAGTGAGG
CTCTGGCTCTTGAATGGTCTGATATTGACCTAGAAAGCGGTGTTATAGC
ATCAATAAGACACTAAACCGCTATCAGGAAATAAACTCACCTAAATCAAG
CGCTGGTTATCGTGATATACCAATAGACAAAGCCACATTACTTTTACTGA
AACAATACAAAAACCGTCAACAAATTCAGTCTTGGAAATTAGGCCGATCT
GAAACAGTTGTATTCTCTGTATTTACGGAGAAATATGCTTATGCTTGTAA
CTTACGCAAACGCCTAAATAAGCATTTTGATGCTGCTGGAGTAACTAACG
TATCATTTCATGGTTTCCGCCATACACATACTACTATGATGCTCTATGCT
CAGGTTAGCCCGAAAGATGTTCAGTATAGATTAGGCCACTCTAATTTAAT
GATCACTGAAAATACTTACTGGCATACTAACCAAGAGAATGCAAAAAAAG
CCGTCTCAAATTATGAAACAGCTATCAACAATTTATAA (SEQ. ID. NO. 195)
MEGLVRVHLLPVFGDYKLSKLTTPILQQQVNKWADKANKGEKGAFANYSL
LHNMNKRILKYGVAIQVIQYNPANDVIVPRKQQKEKAAVKYLDNKELKQF
LDYLDALDQSNYQNLFDVVLYKTLLATGCRISEALALEWSDIDLESGVIS
INKTLNRYQEINSPKSSAGYRDIPIDKATLLLLKQYKNRQQIQSWKLGRS
ETVVFSVFTEKYAYACNLRKRLNKHFDAAGVTNVSFHGFRHTHTTMMLYA
QVSPKDVQYRLGHSNLMITENTYWHTNQENAKKAVSNYETAINNLZ

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07722888B2). An electronic copy of the "Sequence Listing" will also be available from the USPTO upon request and payment of the fee set forth in 37 CFR 1.19(b)(3).

What is claimed is:

1. An isolated *Streptococcus pneumoniae* polypeptide comprising
    (a) the amino acid sequence of SEQ ID NO: 191; or
    (b) the amino acid sequence at least 99% identical to SEQ ID NO: 191.

2. A fusion protein comprising (a) the amino acid sequence of SEQ ID NO: 191; or
    (b) the amino acid sequence at least 99% identical to SEQ ID NO: 191.

3. An immunogenic and/or antigenic composition comprising the polypeptide of claim 1 and one or more excipients, diluents, or adjuvants.

4. The composition of claim 3, wherein said composition is an antigenic composition.

5. The composition of claim 3, wherein said composition is an immunogenic composition.

* * * * *